United States Patent
Bonfanti et al.

(10) Patent No.: US 11,407,715 B2
(45) Date of Patent: Aug. 9, 2022

(54) SUBSTITUTED INDOLINE DERIVATIVES AS DENGUE VIRAL REPLICATION INHIBITORS

(71) Applicants: JANSSEN PHARMACEUTICALS, INC., Titusville, NJ (US); KATHOLIEKE UNIVERSITEIT LEUVEN, Leuven (BE)

(72) Inventors: Jean-François Bonfanti, Issy-les-Moulineaux (FR); Bart Rudolf Romanie Kesteleyn, Beerse (BE); Dorothée Alice Marie-Eve Bardiot, Leuven (BE); Arnaud Didier M Marchand, Leuven (BE); Erwin Coesemans, Beerse (BE); Jérôme Michel Claude Fortin, Issy-les-Moulineaux (FR); Guillaume Jean Maurice Mercey, Issy-les-Moulineaux (FR); Pierre Jean-Marie Bernard Raboisson, Beerse (BE)

(73) Assignees: Janssen Pharmaceuticals, Inc., Titusville, NJ (US); Katholieke Universiteit Leuven, Leuven (BE)

( * ) Notice: Subject to any disclaimer, the term of this patent is extended or adjusted under 35 U.S.C. 154(b) by 5 days.

(21) Appl. No.: 16/612,670

(22) PCT Filed: May 18, 2018

(86) PCT No.: PCT/EP2018/063028
§ 371 (c)(1),
(2) Date: Nov. 11, 2019

(87) PCT Pub. No.: WO2018/215315
PCT Pub. Date: Nov. 29, 2018

(65) Prior Publication Data
US 2020/0255376 A1     Aug. 13, 2020

(30) Foreign Application Priority Data
May 22, 2017  (EP) .................................. 17172237

(51) Int. Cl.
*C07D 209/14*   (2006.01)
*A61P 31/14*    (2006.01)
*A61K 45/06*    (2006.01)

(52) U.S. Cl.
CPC ............ *C07D 209/14* (2013.01); *A61P 31/14* (2018.01); *A61K 45/06* (2013.01)

(58) Field of Classification Search
CPC .................................................. C07D 209/14
See application file for complete search history.

(56) References Cited

U.S. PATENT DOCUMENTS

| | | |
|---|---|---|
| 6,177,426 B1 | 1/2001 | Denney et al. |
| 7,601,735 B2 | 10/2009 | Tyms et al. |
| 8,143,259 B2 | 3/2012 | Colburn et al. |
| 8,299,056 B2 | 10/2012 | Bahmanyar et al. |
| 8,324,217 B2 | 12/2012 | Colburn et al. |
| 8,524,764 B2 | 9/2013 | Canales et al. |
| 8,884,030 B2 | 11/2014 | Canales et al. |
| 8,993,604 B2 | 3/2015 | Byrd et al. |
| 9,029,376 B2 | 5/2015 | Byrd et al. |
| 9,522,923 B2 | 12/2016 | Richards et al. |
| 9,944,598 B2 | 4/2018 | Kesteleyn et al. |
| 10,029,984 B2 | 7/2018 | Kesteleyn et al. |
| 10,064,870 B2 | 9/2018 | Rajagopalan et al. |
| 10,071,961 B2 | 9/2018 | Vandyck et al. |
| 10,117,850 B2 | 11/2018 | Griffioen et al. |
| 10,209,902 B1 | 2/2019 | Kesteleyn et al. |
| 10,323,026 B2 | 6/2019 | Ikeda et al. |
| 2005/0239821 A1 | 10/2005 | Neyts et al. |
| 2006/0194835 A1 | 8/2006 | Dugourd et al. |
| 2006/0211698 A1 | 9/2006 | Botyanszki et al. |
| 2008/0318338 A1 | 12/2008 | Kamal et al. |
| 2010/0048589 A1* | 2/2010 | Colburn .............. C07D 401/06 548/491 |
| 2013/0023532 A1 | 1/2013 | Casillas et al. |
| 2014/0213586 A1 | 7/2014 | Bardiot et al. |

(Continued)

FOREIGN PATENT DOCUMENTS

| JP | 2012-206959 A | 10/2012 |
|---|---|---|
| WO | 99-21559 A1 | 5/1999 |

(Continued)

OTHER PUBLICATIONS

Japanese Office Action dated Jun. 2, 2020 from Japanese Patent Appln. No. JP2017-243354 (English language translation).
ACS on STN Registry No. 931079-09-3, Apr. 20, 2007.
ACS on STN Registry No. 931007-71-5, Apr. 19, 2007.
ACS on STN Registry No. 930910-25-1, Apr. 19, 2007.
ACS on STN Registry No. 930724-99-5, Apr. 18, 2007.
ACS on STN Registry No. 930463-83-5, Apr. 17, 2007.
ACS on STN Registry No. 925399-60-6, Mar. 7, 2007.

(Continued)

*Primary Examiner* — Shawquia Jackson
(74) *Attorney, Agent, or Firm* — Burns & Levinson, LLP; Shawn P. Foley; Chris Lorenc

(57) ABSTRACT

The present invention concerns substituted indoline derivatives, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

21 Claims, No Drawings
Specification includes a Sequence Listing.

(56) References Cited

U.S. PATENT DOCUMENTS

| | | |
|---|---|---|
| 2016/0297810 A1 | 10/2016 | Bardiot et al. |
| 2017/0002006 A1 | 1/2017 | Corte et al. |
| 2017/0096429 A1 | 4/2017 | Corte et al. |
| 2017/0281633 A1 | 10/2017 | Boylan et al. |
| 2017/0281766 A1 | 10/2017 | Wiltzius |
| 2017/0283500 A1 | 10/2017 | Wiltzius et al. |
| 2017/0298017 A1 | 10/2017 | Kesteleyn et al. |
| 2018/0256544 A1 | 9/2018 | Kesteleyn et al. |
| 2018/0256545 A1 | 9/2018 | Kesteleyn et al. |
| 2018/0346419 A1 | 12/2018 | Kesteleyn et al. |
| 2019/0104738 A1 | 4/2019 | Narine et al. |
| 2019/0112266 A1 | 4/2019 | Kesteleyn et al. |
| 2019/0183931 A1 | 6/2019 | Bakker et al. |

FOREIGN PATENT DOCUMENTS

| | | |
|---|---|---|
| WO | 02089780 A2 | 11/2002 |
| WO | 03050295 A2 | 6/2003 |
| WO | 2006076529 A1 | 7/2006 |
| WO | 2009149054 A1 | 12/2009 |
| WO | 2010021878 A1 | 2/2010 |
| WO | 2010027500 A1 | 3/2010 |
| WO | 2010091413 A1 | 8/2010 |
| WO | 2011037643 A2 | 3/2011 |
| WO | 2011088303 A1 | 7/2011 |
| WO | 2011-120025 A1 | 9/2011 |
| WO | 2013045516 A1 | 4/2013 |
| WO | 2014154682 A1 | 10/2014 |
| WO | 2016050831 A1 | 4/2016 |
| WO | 2016050841 A1 | 4/2016 |
| WO | 2016053455 A1 | 4/2016 |
| WO | 2017046255 A1 | 3/2017 |
| WO | 2017046258 A1 | 3/2017 |
| WO | 2017079216 A1 | 5/2017 |
| WO | 2017167832 A1 | 10/2017 |
| WO | 2017167950 A1 | 10/2017 |
| WO | 2017167951 A1 | 10/2017 |
| WO | 2017167952 A1 | 10/2017 |
| WO | 2017167953 A1 | 10/2017 |
| WO | 2017171100 A1 | 10/2017 |
| WO | 2017173206 A1 | 10/2017 |
| WO | 2017173256 A1 | 10/2017 |
| WO | 2017173384 A1 | 10/2017 |
| WO | 2017173410 A1 | 10/2017 |
| WO | 2018178238 A1 | 10/2018 |
| WO | 2018178240 A1 | 10/2018 |
| WO | 20188215316 A1 | 11/2018 |

OTHER PUBLICATIONS

ACS on STN Registry No. 920950-24-9, Feb. 14, 2007.
ACS on STN Registry No. 920926-40-5, Feb. 14, 2007.
ACS on STN Registry No. 920888-80-8, Feb. 14, 2007.
ACS on STN Registry No. 920870-55-9, Feb. 14, 2007.
ACS on STN Registry No. 920827-69-6, Feb. 14, 2007.
ACS on STN Registry No. 920696-97-5, Feb. 13, 2007.
ACS on STN Registry No. 920694-81-1, Feb. 13, 2007.
ACS on STN Registry No. 920668-38-8, Feb. 13, 2007.
ACS on STN Registry No. 879164-92-8, Apr. 4, 2006.
ACS on STN Registry No. 878462-38-5, Mar. 29, 2006.
ACS on STN Registry No. 853320-15-7, Jun. 30, 2005.
PCT International Search Report and Written Opinion dated Aug. 21, 2018 in connection with PCT International Application No. PCT/EP2018/063028.
Prasad L. Polavarapu, et al., Intrinsic Rotation and Molecular Structure, Chirality 15: S143-S149 (2003).
Prevention, Dengue, Centers for Disease Control and Prevention (Sep. 27, 2012) https://www.cdc.govidengue/prevention/index.html, internet.
Lidia Moreira Lima et al.. Bioisosterism: A Useful Strategy for Molecular Modification and Drug Design, Current Medicinal Chemistry, Bentham Science Publishers Ltd. (2005) 12, pp. 23-49.
Ian Stansfield et al., Development of carboxylic acid replacements in indole-N-acetamide inhibitors of hepatitis C virus NS5B polymerase, Bioorganic & Medicinal Chemistry Letters 17 (2007) 5143-5149, ScienceDirect (2007), www.sciencedirect.com, internet.
Boltromeyuk V.V., Obshchaya khimiya (General Chemistry), Minsk, Vysheyshaya shkola, 2012, p. 65, (translation).
Nolff et al.. Burger's Medicinal Chemistry and Drug Discovery, 5th Ed. part 1, p. 975-977 (1995).
Banker, et al., (1996) Modern Pharmaceuticals, 3rd Edition, Revised and Expanded, p. 596.
Registry No. 924715-04-8, entered in STN on Mar. 4, 2007.
Registry No. 1012956-97-6, entered in STN on Apr. 8, 2008.
Registry No. 1277962-26-1, entered in STN on Apr. 10, 2011.
Registry No. 1386200-09-4, entered in STN on Aug. 3, 2012.
Registry No. 1386766-68-2, entered in STN on Aug. 6, 2012.
Registry No. 1388629-42-2, entered in STN on Aug. 9, 2012.
Registry No. 1388775-15-2, entered in STN on Aug. 9, 2012.
Registry No. 1388908-86-8, entered in STN on Aug. 14, 2012.
N.C.B.I.: "qHTS for inhibitors of binding or entry into cells for Marburg Virus," Pubchem Bioassay Record AID 540276, Jul. 2011, 13 pages, XP55641386, Retrieved from the Internet: https://pubchem.ncbi.nlm.nih.gov/bioassay/540276.
EP Search Report dated Nov. 19, 2019 from European Patent Appln. No. EP 19183201.3.
"Solvation," Wikipedia, at internet address: https://en.wikipedia.org/wiki/Solvation, web page last edited on Mar. 13, 2019, 6 pages.
Examination Report dated Jan. 7, 2020 from Indian Patent Appln. No. 201727014547.
Opposition filed in Ecuadorian Patent Application No. SENADI-2019-83621 (English language translation).
Opposition filed in Ecuadorian Patent Application No. SENADI-2019-83640 (English language translation).
Wiberg et al., "Temperature Dependence of Optical Rotation: α-Pinene, β-Pinene Pinane, Camphene, Camphor and Fenchone," The Journal of Physical Chemistry A 2004 108 (26), 5559-5563.

* cited by examiner

SUBSTITUTED INDOLINE DERIVATIVES AS DENGUE VIRAL REPLICATION INHIBITORS

CROSS-REFERENCE TO RELATED APPLICATIONS

This application is a U.S. national stage entry under 35 U.S.C. § 371 of PCT International Patent Application No. PCT/EP2018/063028, filed May 18, 2018, which claims priority to European Patent Application No. 17172237.4, filed May 22, 2017, the contents of which are incorporated herein by reference in their entirety.

The present invention relates to substituted indoline derivatives, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

BACKGROUND OF THE INVENTION

Flaviviruses, which are transmitted by mosquitoes or ticks, cause life-threatening infections in man, such as encephalitis and hemorrhagic fever. Four distinct, but closely related serotypes of the flavivirus dengue are known, so-called DENV-1, -2, -3, and -4. Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titers. In both primary and secondary infections, higher viral titers are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyper endemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome.

The mosquitoes that carry dengue, including *Aedes aegypti* and *Aedes albopictus* (tiger mosquito), are moving north on the globe. According to the United States (US) Centers for Disease Control and Prevention (CDC), both mosquitoes are currently omnipresent in southern Texas. The spread north of dengue-carrying mosquitoes is not confined to the US, but has also been observed in Europe.

Dengvaxia®, the dengue vaccine produced by Sanofi Pasteur was first approved in Mexico and has received in the meantime approval in more countries. Nevertheless, the vaccine leaves considerable room for improvement due to limited efficacy, especially against DENV-1 and -2, low efficacy in flavivirus-naïve subjects and the lengthy dosing schedule.

Despite these shortcomings, the vaccine is a game changer in endemic settings as it will offer protection to a large part of the population, but likely not to very young infants, who bear the largest burden of dengue. In addition, the dosing schedule and very limited efficacy in flavivirus-naïve subjects make it unsuitable and likely not worthwhile/cost-effective for travelers from non-endemic areas to dengue-endemic areas. The above mentioned shortcomings of the dengue vaccines are the reason why there is a need for a pre-exposure prophylactic dengue antiviral.

Furthermore, today, specific antiviral drugs for the treatment or prevention of dengue fever virus infection are not available. Clearly, there is still a great unmet medical need for therapeutics for the prevention or treatment of viral infections in animals, more in particular in humans and especially for viral infections caused by flaviviruses, more in particular Dengue virus. Compounds with good anti-viral potency, no or low levels of side-effects, a broad spectrum activity against multiple Dengue virus serotypes, a low toxicity and/or good pharmacokinetic or -dynamic properties are highly needed.

WO-2010/021878 discloses 2-phenylpyrrolidine and indoline derivatives as cold menthol receptor antagonists for treatment of inflammatory and central diseases. WO-2013/045516 discloses indole and indoline derivatives for use in the treatment of dengue viral infections.

The present invention now provides compounds, substituted indoline derivatives, which show high potent activity against all four (4) serotypes of the Dengue virus.

SUMMARY OF THE INVENTION

The present invention is based on the unexpected finding that at least one of the above-mentioned problems can be solved by the current compounds of the invention.

The present invention provides compounds which have been shown to possess potent antiviral activity against all four (4) serotypes currently known. The present invention furthermore demonstrates that these compounds efficiently inhibit proliferation of Dengue virus (DENV). Therefore, these compounds constitute a useful class of potent compounds that can be used in the treatment and/or prevention of viral infections in animals, mammals and humans, more specifically for the treatment and/or prevention of infections with Dengue viruses.

The present invention furthermore relates to the use of such compounds as medicines and to their use for the manufacture of medicaments for treating and/or preventing viral infections, in particular with viruses belonging to the family of the Dengue viruses in animals or mammals, more in particular in humans. The invention also relates to methods for the preparation of all such compounds and to pharmaceutical compositions comprising them in an effective amount.

The present invention also relates to a method of treatment or prevention of dengue viral infections in humans by the administration an effective amount of one or more such compounds, or a pharmaceutically acceptable salt thereof optionally in combination with one or more other medicines, like another antiviral agent, to a patient in need thereof.

One aspect of the invention is the provision of compounds of formula (I), including any stereochemically isomeric form thereof:

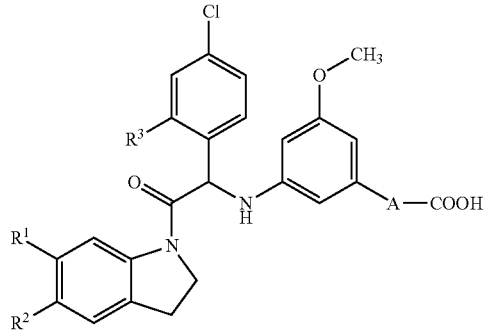

wherein
R¹ is trifluoromethyl, trifluoromethoxy, or chloro;
R² is hydrogen, fluoro, or methoxy;
R³ is hydrogen, or methoxy;
A represents —(CH$_2$)$_n$— wherein n is 3 or 4;
—O—(CH$_2$)$_n$— wherein n is 2 or 4;
—O—(CH$_2$)$_n$— wherein n is 3 and one or two CH$_2$ are substituted with one or two CH$_3$;

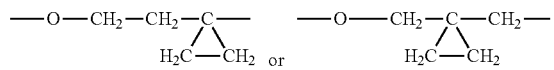

—CH$_2$—O—(CH$_2$)$_n$— wherein n is 2; or
—X—Y— wherein X is a —O—, —OCH$_2$—, or —NH—; and
Y is C$_{3-4}$cycloalkyl optionally substituted with fluoro, or
Y is bicyclo[1.1.1]pentanyl;
or a pharmaceutically acceptable salt, solvate or polymorph thereof.

Specifically above mentioned compounds are selected from the group comprising:

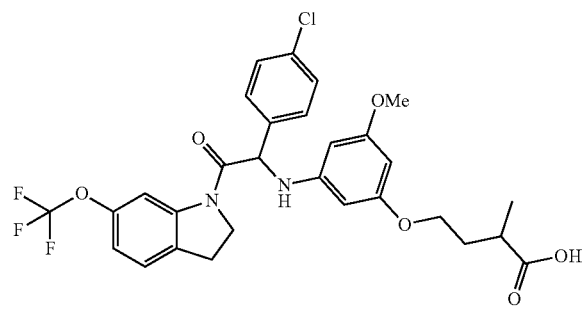

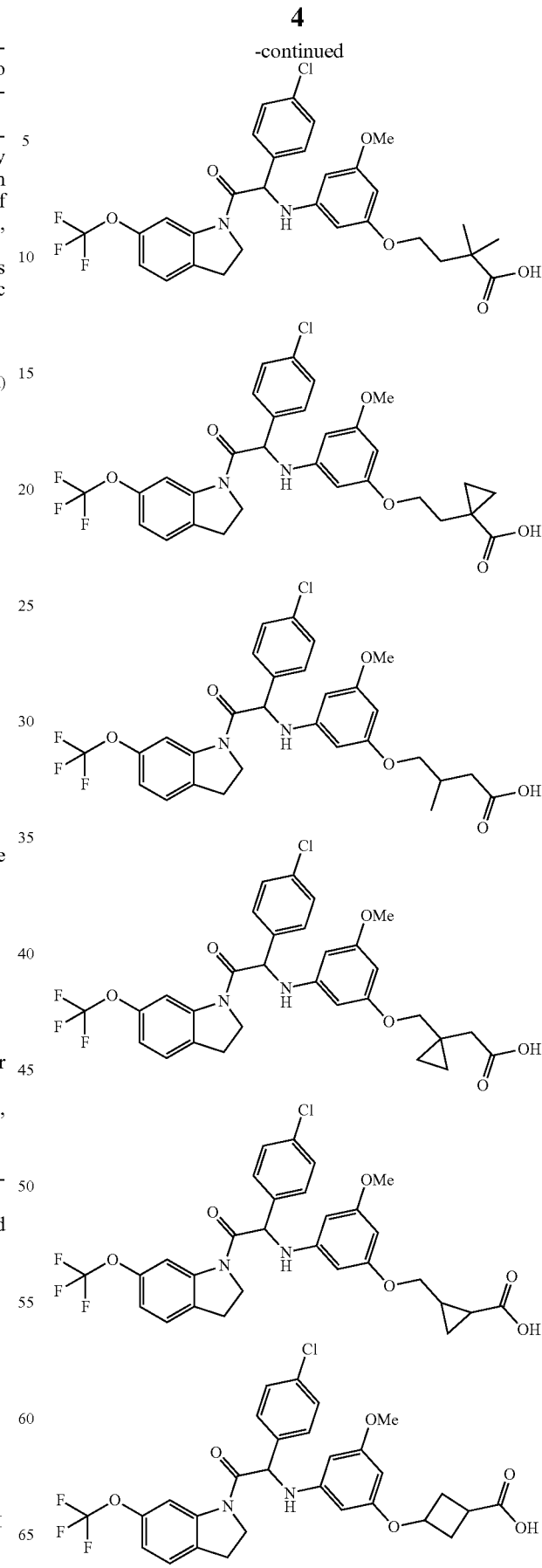

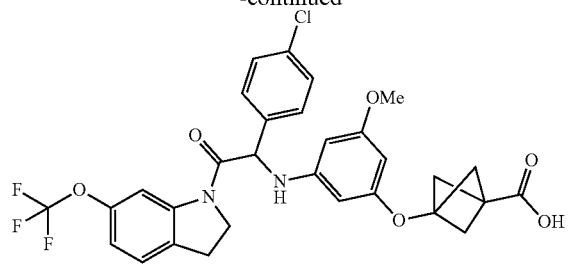
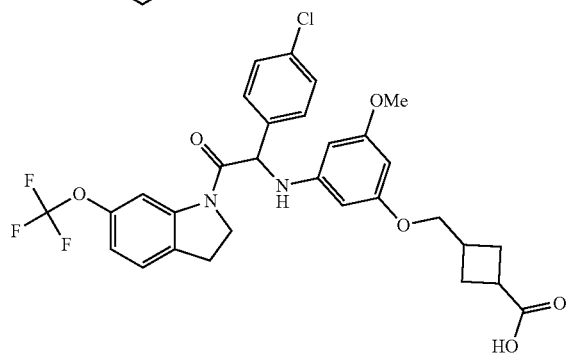
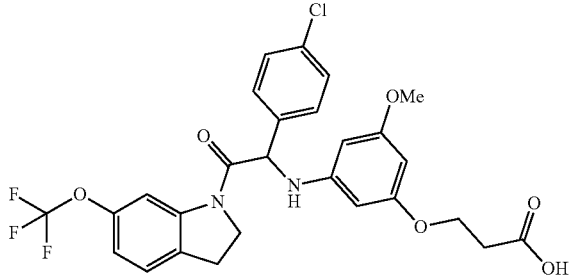
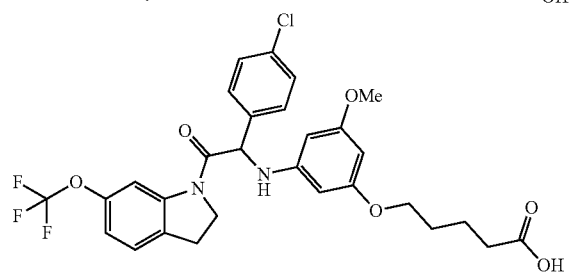
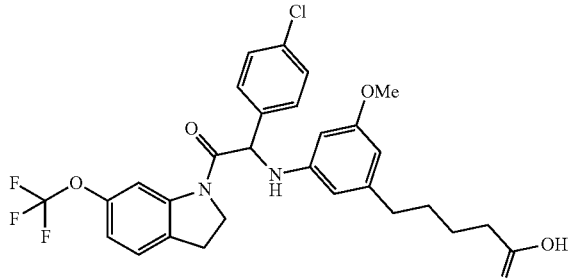
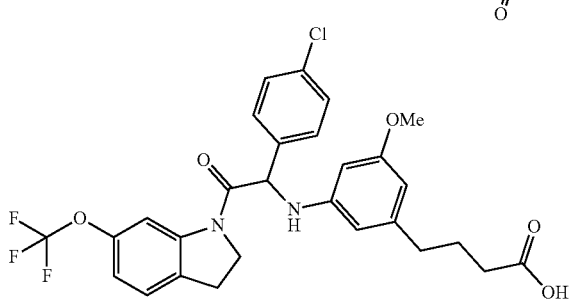
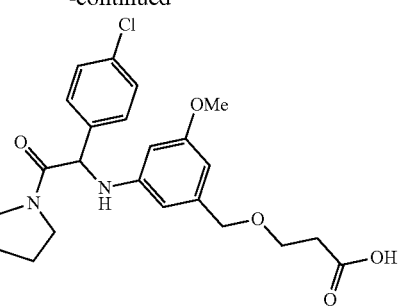
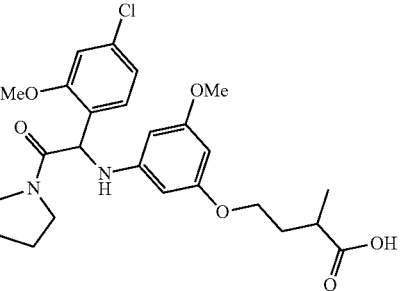
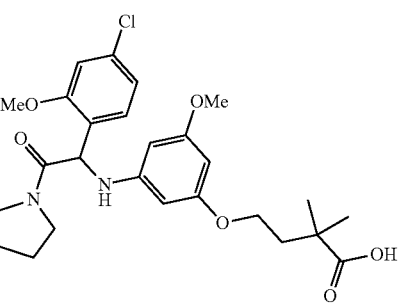
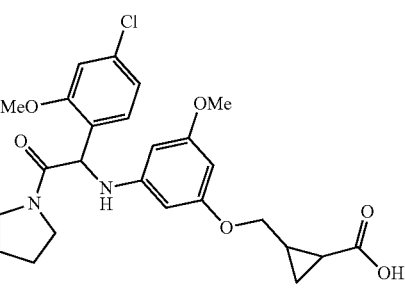
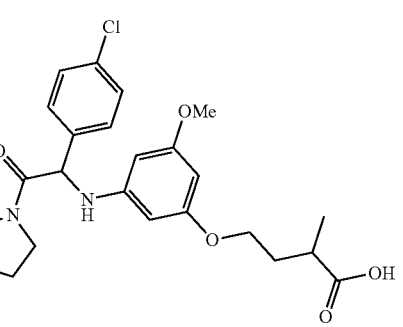

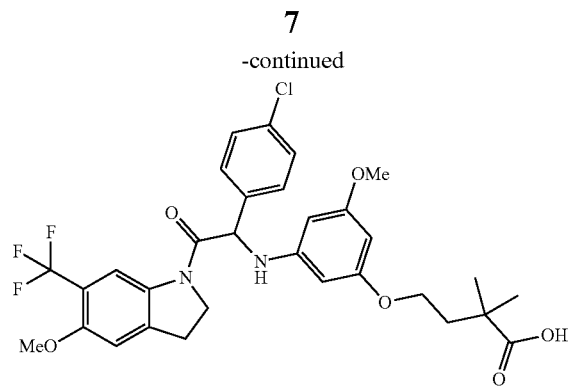
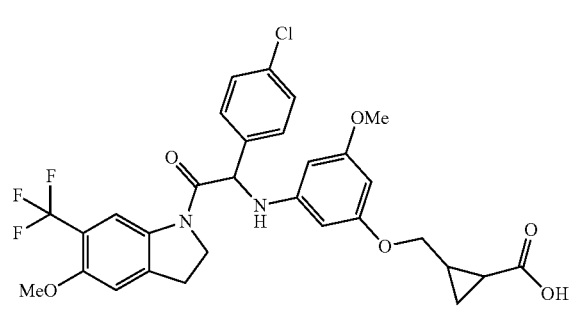
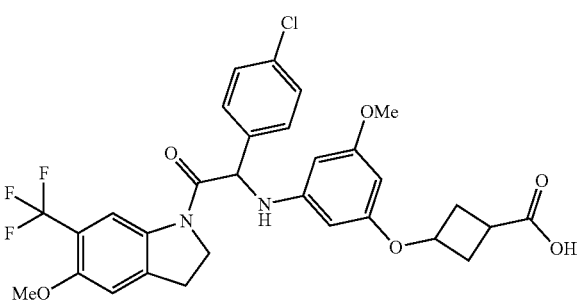
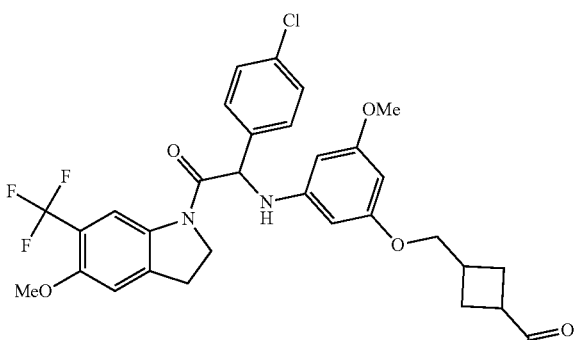
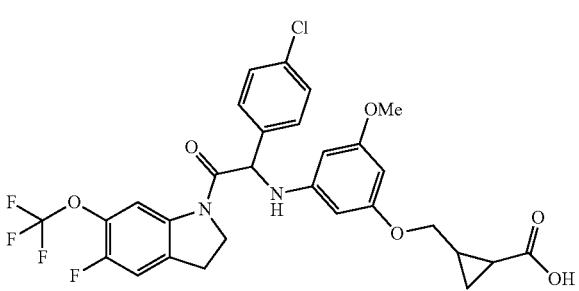

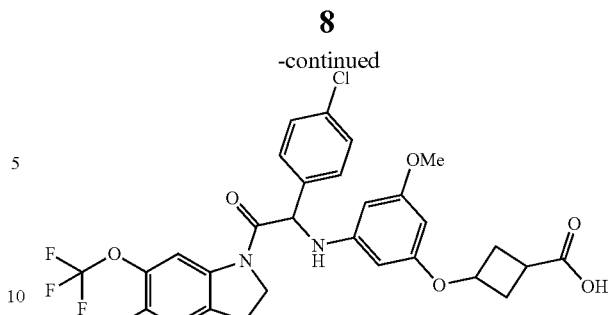
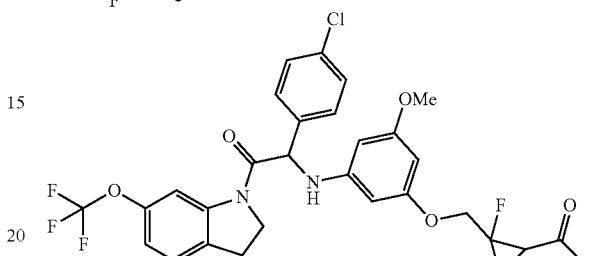
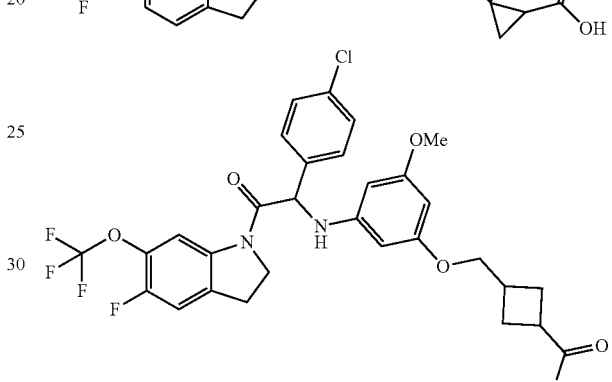
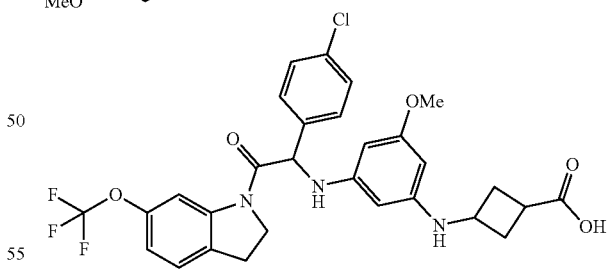

A first group of compounds are compounds of formula (I) wherein A represents —O—(CH$_2$)$_n$— wherein n is 3 or 4.

A second group of compounds are compounds of formula (I) wherein A represents —O—(CH$_2$)$_n$— wherein n is 2 or 4.

A third group of compounds are compounds of formula (I) wherein A represents —O—(CH$_2$)$_n$— wherein n is 3 and one or two CH$_2$ are substituted with one or two CH$_3$; or A represents

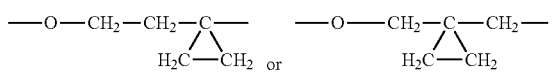

A fourth group of compounds are compounds of formula (I) wherein A represents —CH$_2$—O—(CH$_2$)$_n$— wherein n is 2.

A fifth group of compounds are compounds of formula (I) wherein A represents —X—Y— wherein X is a —O—, —OCH$_2$—, or —NH—; and Y is C$_{3-4}$cycloalkyl optionally substituted with fluoro.

A sixth group of compounds are compounds of formula (I) wherein A represents —X—Y— wherein X is a —O—, —OCH$_2$—, or —NH—; and Y is bicyclo[1.1.1]pentanyl.

A seventh group of compounds are compounds of formula (I) wherein R$^1$ is trifluoromethoxy, R$^2$ is hydrogen, and R$^3$ is hydrogen.

An eighth group of compounds are compounds of formula (I) wherein R$^1$ is trifluoromethoxy, R$^2$ is hydrogen, and R$^3$ is methoxy.

A ninth group of compounds are compounds of formula (I) wherein R$^1$ is trifluoromethyl, R$^2$ is methoxy, and R$^3$ is hydrogen.

A tenth group of compounds are compounds of formula (I) wherein R$^1$ is trifluoromethoxy, R$^2$ is fluoro, and R$^3$ is hydrogen.

An eleventh group of compounds are compounds of formula (I) wherein R$^1$ is chloro, R$^2$ is methoxy, and R$^3$ is hydrogen.

Part of the current invention is also a pharmaceutical composition comprising a compound mentioned above or a stereoisomeric form, a pharmaceutically acceptable salt, solvate or polymorph thereof together with one or more pharmaceutically acceptable excipients, diluents or carriers.

Pharmaceutically acceptable salts of said compounds include the acid addition and base salts thereof. Suitable acid addition salts are formed from acids which form non-toxic salts. Suitable base salts are formed from bases which form non-toxic salts.

The pharmaceutically acceptable acid salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-amino-salicylic, pamoic acid and the like acids.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral or rectal administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of the invention used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the terms "compound of formula (I)" and "intermediates of synthesis of formula (I)" are meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. Substituents on bivalent cyclic (partially) saturated radicals may have either the cis- or trans-configuration; for example if a compound contains a disubstituted cycloalkyl group, the substituents may be in the cis or trans configuration.

The term "stereoisomers" also includes any rotamers, also called conformational isomers, the compounds of formula (I) may form.

Therefore, the invention includes enantiomers, diastereomers, racemates, E isomers, Z isomers, cis isomers, trans isomers, rotamers, and any mixture thereof, whenever chemically possible.

The meaning of all those terms, i.e. enantiomers, diastereomers, racemates, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

Some of the compounds according to formula (I) may also exist in their tautomeric form. Such forms in so far as they may exist, although not explicitly indicated in the above formula (I) are intended to be included within the scope of the present invention.

The compounds of formula (I) of the present invention all have at least one asymmetric carbon atom as indicated in the FIGURE below by the carbon atom labelled with *:

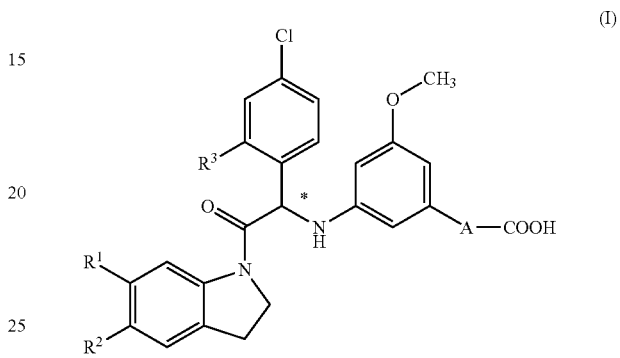

Due to the presence of said chiral center, a "compound of formula (I)" can be the (R)-enantiomer, the (S)-enantiomer, the racemic form, or any possible combination of the two individual enantiomers in any ratio. When the absolute configuration of an asymmetric carbon atom was not known, a relative stereochemistry descriptor was used: *R or *S (or R* and S*) to indicate the pure but unknown stereochemistry of the chiral center.

Since radical A allows for substituents introducing additional asymmetric carbon atoms, the compounds of formula (I) may have more than one asymmetric carbon atom. When the absolute stereochemistry of the more than one asymmetric carbon atoms was not determined, the relative stereochemistry was indicated using the relative stereochemistry descriptors *R and *S and where possible in combination with cis and trans when radical A contains a cyclic moiety.

In an aspect the present invention relates to a first group of compound of formula (I) wherein the compounds of formula (I) have the (−) specific rotation.

In a further aspect the present invention relates to a second ground of compounds of formula (I) wherein the compounds of formula (I) have the (+) specific rotation.

In an embodiment, the present invention relates to a compound of formula (I) having the (+) specific rotation wherein said compound is selected from the group consisting of compounds (1C), (1 D), (2A), (4C), (4D), (5A), (6AB), (6BB), (7B), (8B), (9B), (10B), (11B), (12B), (13B), (14A), (15B), (17C), (17D), (18B), (19AB), (19BB), (20C), (20D), (21B), (22AB), (22BB), (23B), (24B), (25B), (27B), (28AB), (28BB), (29AB), (29BB), (30A), (31A), (32B), (33C), and (33D).

EXAMPLES

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

LC/MS Method codes (Flow expressed in mL/min; column temperature (T) in ° C.; Run time in minutes).

| Method code | Instrument | Column | Mobile phase | Gradient | Flow Col T | Run time (min) |
|---|---|---|---|---|---|---|
| LC-A | Waters: Acquity ® UPLC ®-DAD-SQD | Waters: BEH C18 (1.7 μm, 2.1 × 50 mm) | A: 10 mM $CH_3COONH_4$ in 95% $H_2O$ + 5% $CH_3CN$ B: $CH_3CN$ | From 95% A to 5% A in 1.3 min, held for 0.7 min. | 0.8 mL/min 55° C. | 2 |
| LC-B | Waters: Acquity ® UPLC ®-DAD-SQD | Waters: HSS T3 (1.8 μm, 2.1 × 100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 mL/min 55° C. | 3.5 |
| LC-C | Waters: Acquity ® UPLC ®-DAD-Quattro Micro ™ | Waters: BEH C18 (1.7 μm, 2.1 × 100 mm) | A: $CH_3COONH_4$ 7 mM 95%/ $CH_3CN$ 5%, B: $CH_3CN$ | 84.2% A for 0.49 min, to 10.5% A in 2.18 min, held for 1.94 min, back to 84.2% A in 0.73 min, held for 0.73 min. | 0.343 mL/min 40° C. | 6.2 |
| LC-D | Waters: Acquity ® H-Class-DAD and SQD2TM | Waters BEH ® C18 (1.7 μm, 2.1 × 100 mm) | A: $CH_3COONH_4$ 7 mM 95%/ $CH_3CN$ 5%, B: $CH_3CN$ | 84.2% A/15.8% B to 10.5% A in 2.18 min, held for 1.96 min, back to 84.2% A/ 15.8% B in 0.73 min, held for 0.49 min. | 0.343 mL/min 40° C. | 6.1 |

SFC/MS Methods

The SFC measurement was performed using an Analytical Supercritical fluid chromatography (SFC) system composed by a binary pump for delivering carbon dioxide (CO2) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Analytical SFC/MS Methods (Flow expressed in mL/min; column temperature (T) in ° C.; Run time in minutes, Backpressure (BPR) in bars.

| Method code | column | mobile phase | gradient | Flow Col T | Run time BPR |
|---|---|---|---|---|---|
| SFC-A | Daicel Chiralpak ® OD3 column (3.0 μm, 150 × 4.6 mm) | A: $CO_2$ B: EtOH (+0.2% $iPrNH_2$) | 25% B hold 6 min, to 50% in 1 min hold 2.5 min | 2.5 40 | 9.5 110 |

-continued

| Method code | column | mobile phase | gradient | Flow Col T | Run time BPR |
|---|---|---|---|---|---|
| SFC-B | Daicel Chiralpak ® AD3 column (3.0 µm, 150 × 4.6 mm) | A: $CO_2$<br>B: EtOH (+0.2% iPrNH$_2$ + 3% H$_2$O) | 10%-50% B in 6 min, hold 3.5 min | 2.5<br>40 | 9.5<br>110 |
| SFC-C | Daicel Chiralpak ® AD3 column (3.0 µm, 150 × 4.6 mm) | A: $CO_2$<br>B: iPrOH (+0.2% iPrNH$_2$) | 10%-50% B in 6 min, hold 3.5 min | 2.5<br>40 | 9.5<br>110 |
| SFC-D | Daicel Chiralpak ® OD3 column (3.0 µm, 150 × 4.6 mm) | A: $CO_2$<br>B: EtOH (+0.2% iPrNH$_2$) | 10%-50% B in 6 min, hold 3.5 min | 2.5<br>40 | 9.5<br>110 |
| SFC-E | Daicel Chiralpak ® AD3 column (3.0 µm, 150 × 4.6 mm) | A: $CO_2$<br>B: EtOH (+0.2% iPrNH$_2$) | 10%-50% B in 6 min, hold 3.5 min | 2.5<br>40 | 9.5<br>110 |
| SFC-F | Daicel Chiralcel ® OJ-H column (5 µm, 150 × 4.6 mm) | A: $CO_2$<br>B: MeOH | 30% B hold 7 min, | 3<br>35 | 7<br>100 |
| SFC-G | Daicel Chiralcel ® OD-3 column (3 µm, 100 × 4.6 mm) | A: $CO_2$<br>B: iPrOH | 40% B hold 3 min, | 3.5<br>35 | 3<br>103 |
| SFC-H | Daicel Chiralcel ® OD-3 column (3 µm, 100 × 4.6 mm) | A: $CO_2$<br>B: MeoH | 40% B hold 3 min, | 3.5<br>35 | 3<br>103 |
| SFC-I | Daicel Chiralcel ® OD-3 column (3 µm, 100 × 4.6 mm) | A: $CO_2$<br>B: EtoH | 40% B hold 3 to 6 min, | 3.5<br>35 | 3 to 6<br>103 |
| SFC-J | Regis Whelk O1, S, S column (3 µm, 100 × 4.6 mm) | A: $CO_2$<br>B: MeOH | 40% B hold 3 min, | 3.5<br>35 | 3<br>103 |
| SFC-K | Daicel Chiralcel ® OD-H column (5 µm, 150 × 4.6 mm) | A: $CO_2$<br>B: iPrOH (+0.3% iPrNH$_2$) | 35% B hold 7 min, | 3<br>35 | 7<br>100 |
| SFC-L | Daicel Chiralcel ® AD-3 column (3 µm, 100 × 4.6 mm) | A: $CO_2$<br>B: EtOH | 45% B hold 3 min, | 3.5<br>35 | 3<br>103 |
| SFC-M | Daicel Chiralcel ® OD-H column (5 µm, 150 × 4.6 mm) | A: $CO_2$<br>B: MeOH | 40% B hold 7 min, | 3<br>35 | 7<br>100 |
| SFC-N | Daicel Chiralpak ® AD-3 column (3 µm, 100 × 4.6 mm) | A: $CO_2$<br>B: EtOH (+0.3% iPrNH$_2$) | 15% B hold 10 min, | 3.5<br>35 | 10<br>103 |
| SFC-O | Phenomenex Luxcellulose-2 column (3 µm, 100 × 4.6 mm) | A: $CO_2$<br>B: MeOH | 25% B hold 3 min, | 3.5<br>35 | 3<br>103 |
| SFC-P | Daicel Chiralcel ® OD-3 column (3 µm, 100 × 4.6 mm) | A: $CO_2$<br>B: MeOH | 30% B hold 3 min, | 3.5<br>35 | 3<br>103 |
| SFC-Q | Daicel Chiralcel ® AD-3 column (3 µm, 100 × 4.6 mm) | A: $CO_2$<br>B: iPrOH (+0.3% iPrNH$_2$) | 60% B hold 3 min, | 3.5<br>35 | 3<br>103 |
| SFC-R | Daicel Chiralcel ® OD-3 column (3 µm, 100 × 4.6 mm) | A: $CO_2$<br>B: EtOH | 50% B hold 3 to 6 min, | 3.5<br>35 | 3 to 6<br>103 |
| SFC-S | Daicel Chiralcel ® OD-H column (5 µm, 150 × 4.6 mm) | A: $CO_2$<br>B: EtOH (+0.3% iPrNH$_2$) | 50% B hold 7 min, | 3<br>35 | 7<br>100 |
| SFC-T | Regis Whelk O1, S, S column (3 µm, 100 × 4.6 mm) | A: $CO_2$<br>B: MeOH | 50% B hold 3 min, | 3.5<br>35 | 3<br>103 |

Melting Points

Values are either peak values or melt ranges, and are obtained with experimental uncertainties that are commonly associated with this analytical method.

DSC823e (Indicated as DSC)

For a number of compounds, melting points were determined with a DSC823e (Mettler-Toledo). Melting points were measured with a temperature gradient of 10° C./minute. Maximum temperature was 300° C.

Optical Rotations:

Optical rotations were measured on a Perkin-Elmer 341 polarimeter with a sodium lamp and reported as follows: [α]° (λ, c g/100 ml, solvent, T° C.).

$[\alpha]_\lambda^T = (100\alpha)/(l \times c)$: where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

Stereochemistry Note:
In the below examples, the stereochemistry indications *R and *S refer to a pure but unknown stereochemistry of the chiral centers.

| Abbreviations used in experimental part | | | |
|---|---|---|---|
| (M + H)+ MH+ | protonated molecular ion | iPrNH2 | isopropylamine |
| aq. | aqueous | iPrOH | 2-propanol |
| Boc | tert-butyloxycarbonyl | K2CO3 | potassium carbonate |
| Boc2O | di-tert-butyl dicarbonate | KNO3 | potassium nitrate |
| br | broad | LiAlH4 | lithium aluminium hydride |
| CH3CN | acetonitrile | m/z | mass-to-charge ratio |
| CHCl3 | chloroform | Me | methyl |
| CH2Cl2 | dichloromethane | MeOH | methanol |
| CH3OH | methanol | MgSO4 | magnesium sulfate |
| CO2 | carbon dioxide | min | minute(s) |
| CsCO3 | cesium carbonate | MTBE | methyl-tert-butylether |
| d | doublet | N2 | nitrogen |
| DCM | dichloromethane | Na2CO3 | sodium carbonate |
| DIEA | diisopropylethylamine | Na2SO4 | sodium sulfate |
| DIPE | diisopropyl ether | NaBH4 | sodium borohydride |
| DMA | dimethylacetamide | NaCl | sodium chloride |
| DMAP | 4-dimethylaminopyridine | NaHCO3 | sodium bicarbonate |
| DME | 1,2-dimethoxyethane | NaOH | sodium hydroxide |
| DMF | dimethylformamide | NH4Cl | ammonium chloride |
| DMSO | dimethyl sulfoxide | NH4HCO3 | ammonium bicarbonate |
| EDCl | 1-ethyl-3-(3-dimethylamino-propyl)carbodiimide | NMP | N-methylpyrrolidon |
| eq. | equivalent | q | quartet |
| Et2O | diethyl ether | rt or RT | room temperature |
| Et3N | triethylamine | SEMCl | 2-(trimethylsilyl)ethoxymethyl chloride |
| EtOAc | ethyl acetate | s | singlet |
| EtOH | ethanol | t | triplet |
| H2 | hydrogen | tBuOK | potassium tert-butanolaat |
| HNO3 | nitric acid | TEA | triethylamine |
| H2O | water | TFA | trifluoroacetic acid |
| H2SO4 | sulfuric acid | THF | tetrahydrofuran |
| HATU | O-(7-aza-1H-benzotriazol-1-yl)-N,N,N',N'-tetramethyl-uronium hexafluorophosphate - CAS [148893-10-1] | 2-Me-THF | 2-methyltetrahydrofuran |
| HCl | hydrochloric acid | TMSCl | trimethylsilyl chloride |
| HPLC | high performance liquid chromatography | TMSCF3 | trifluoromethyltrimethylsilane |

Example 1: Synthesis of 4-(3-((1-(4-chlorophenyl)-2-oxo-2-(6-(trifluoromethoxy)indolin-1-yl)ethyl)amino)-5-methoxyphenoxy)-2-methylbutanoic Acid (Compound 1) and Separation into Stereoisomers 1A, 1B, 1C and 1D

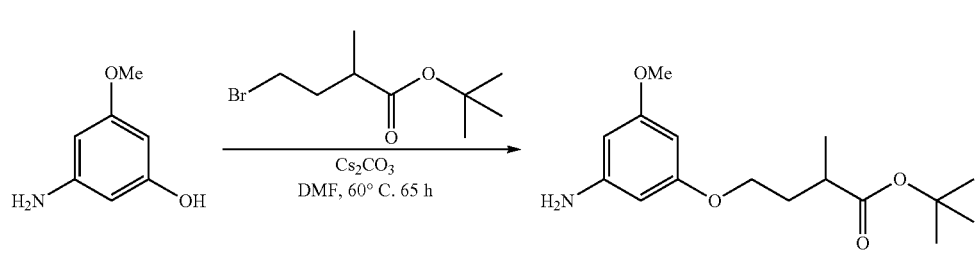

1a

-continued
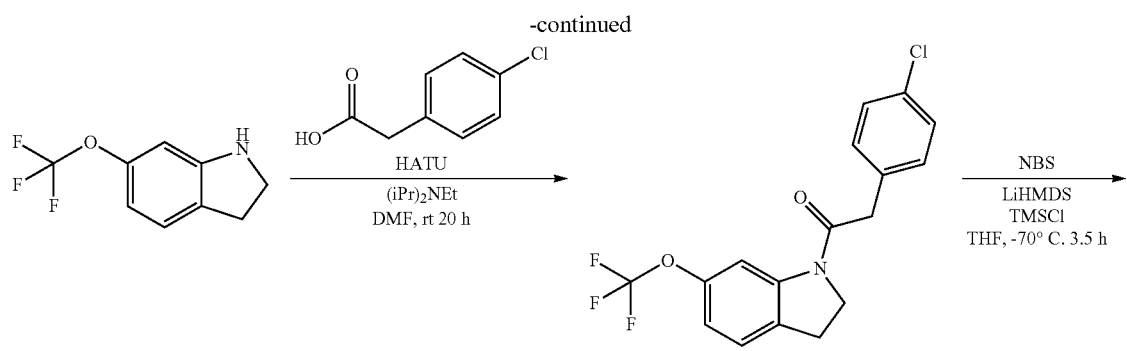
1b
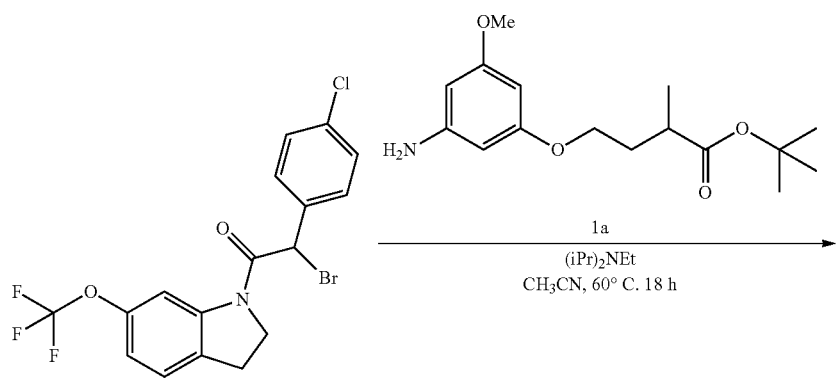
1c
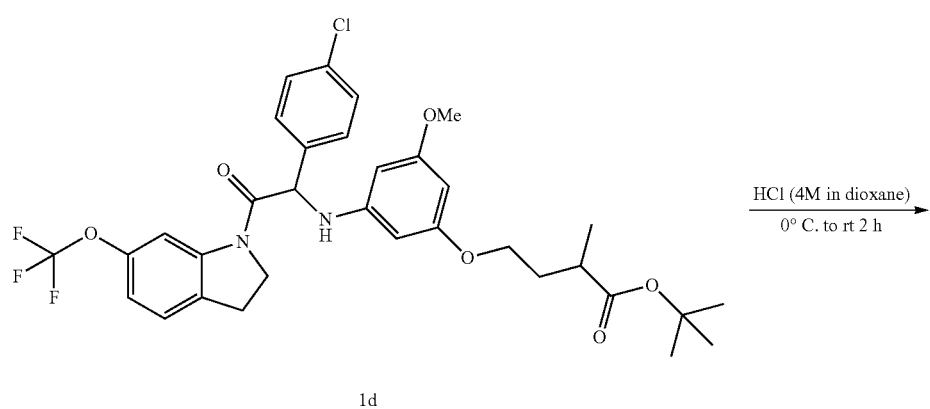
1d
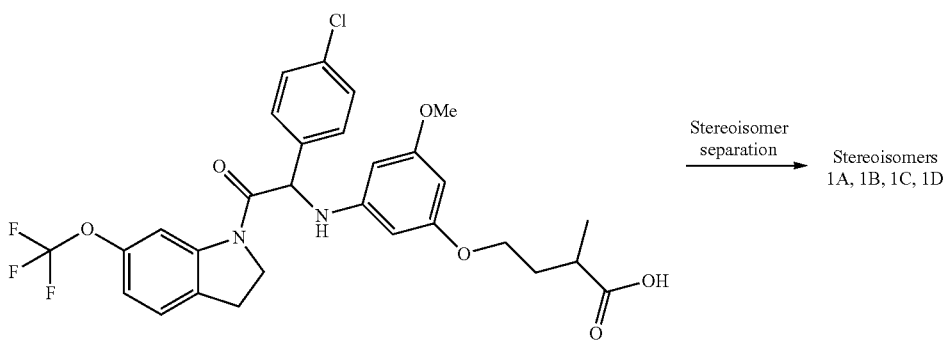
1

Synthesis of Intermediate 1a:

To a stirred solution of tert-butyl 4-bromo-2-methylbutanoate [CAS1210410-44-8] (1.0 g, 4.22 mmol) in DMF (15 mL) was added 3-amino-5-methoxyphenol [CAS 162155-27-3] (587 mg, 4.22 mmol) and $Cs_2CO_3$ (2.75 g, 8.43 mmol). The reaction was stirred at 60° C. for 65 h, and allowed to reach room temperature. The mixture was poured out into $H_2O$ (100 mL). The product was extracted with $CH_2Cl_2$ (2 times). The combined organic layers were dried over $MgSO_4$, filtered, and the solvent was evaporated under reduced pressure. The residue was purified by flash chromatography on silica gel (50 g) using a gradient of heptane/EtOAc from 100/0 to 50/50. The desired fractions were combined, evaporated under reduced pressure and co-evaporated with $CH_3CN$, yielding tert-butyl 4-(3-amino-5-methoxyphenoxy)-2-methylbutanoate 1a (440 mg).

Synthesis of Intermediate 1b:

A mixture of 6-(trifluoromethoxy)indoline [CAS 959235-95-1] (5 g, 24.6 mmol), 2-(4-chlorophenyl)acetic acid [CAS 1878-66-6] (4.2 g, 24.6 mmol), HATU (14.3 g, 36.9 mmol) and diisopropylethylamine (12.2 mL, 73.8 mmol) in DMF (60 mL) was stirred at room temperature for 20 h. The mixture was poured out slowly into stirring $H_2O$ (275 mL) and the resulting suspension was stirred for 50 minutes. The solids were filtered off and washed (4×) with $H_2O$. The solid residue was taken up in toluene (125 mL), filtered over a paper filter, and the filtrate was evaporated under reduced pressure. The solid residue was stirred up in $Et_2O$/heptane 2/1 (30 mL), filtered off, washed (3×) with $Et_2O$/heptane 1/1, and dried under vacuum at 50° C. to provide 2-(4-chlorophenyl)-1-(6-(trifluoromethoxy)indolin-1-yl)ethanone 1b (7.33 g).

Synthesis of Intermediate 1c:

At −70° C., under $N_2$ flow, LiHMDS 1M in THF (41.2 mL, 41.2 mmol) was added dropwise to a solution of 2-(4-chlorophenyl)-1-(6-(trifluoromethoxy)indolin-1-yl)ethanone 1b (7.33 g, 20.6 mmol) in 2-Me-THF (300 mL). The mixture was stirred for 50 min at −70° C. and trimethylsilyl chloride (4.21 mL, 33.0 mmol) was slowly added. Stirring was continued at −70° C. for 35 min and a solution of N-bromosuccinimide (4.03 g, 22.7 mmol) in THF (40 mL) and 2-Me-THF (60 mL) was added dropwise. After stirring for 3.5 h at −70° C., the reaction was quenched with a saturated solution of $NH_4Cl$ (300 mL). The mixture was allowed to reach room temperature. Water (50 mL) and brine (50 mL) were added. The mixture was extracted with diisopropyl ether (150 mL). The organic layer was separated, dried over $MgSO_4$, filtered, the solvent was evaporated under reduced pressure and co-evaporated with $CH_3CN$ to give 2-bromo-2-(4-chlorophenyl)-1-(6-(trifluoromethoxy)indolin-1-yl)ethanone 1c (7.87 g).

Synthesis of Intermediate 1d:

A mixture of 2-bromo-2-(4-chlorophenyl)-1-(6-(trifluoromethoxy)indolin-1-yl)ethanone 1c (850 mg, 1.96 mmol), tert-butyl 4-(3-amino-5-methoxyphenoxy)-2-methylbutanoate 1a (620 mg, 2.10 mmol) and diisopropylethylamine (506 µL, 2.93 mmol) in $CH_3CN$ (30 mL) was stirred at 60° C. for 18 h. The mixture was allowed to reach room temperature, and was poured out into water (125 mL). The product was extracted (2×) with $Et_2O$. The combined organic layers were washed with brine, dried over $MgSO_4$, filtered off, and evaporated under reduced pressure. The residue was purified by flash chromatography on silica gel (12 g) using a gradient of heptane/EtOAc/EtOH 100/0/0 to 40/45/15. The desired fractions were combined and evaporated under reduced pressure, and co-evaporated with dioxane to provide tert-butyl 4-(3-((1-(4-chlorophenyl)-2-oxo-2-(6-(trifluoromethoxy)indolin-1-yl)ethyl)amino)-5-methoxyphenoxy)-2-methylbutanoate 1d (1.27 g).

Synthesis of Compound 1 and Separation into Stereoisomers 1A, 1B, 1C and 1D:

A cooled (ice-bath) solution of tert-butyl 4-(3-((1-(4-chlorophenyl)-2-oxo-2-(6-(trifluoromethoxy)indolin-1-yl)ethyl)amino)-5-methoxyphenoxy)-2-methylbutanoate 1d (1.27 g, 1.96 mmol) in 4M HCl in dioxane (9 mL) was stirred at 0° C. for 20 min and at room temperature for 2 h. The precipitate was filtered off, washed (3×) with dioxane and the solid was air-dried to afford 4-(3-((1-(4-chlorophenyl)-2-oxo-2-(6-(trifluoromethoxy)indolin-1-yl)ethyl)amino)-5-methoxyphenoxy)-2-methylbutanoic acid as an HCl salt (Compound 1, 900 mg).

The 4 stereoisomers of Compound 1 (900 mg) were separated via preparative chiral SFC (Stationary phase: Chiralpak® Diacel AD 20×250 mm, mobile phase: $CO_2$, iPrOH+0.4% $iPrNH_2$). The product fractions were combined and evaporated under reduced pressure. The stereoisomers in the product fractions of the first two eluted peaks were not completely separated and required further separation via preparative chiral SFC (Stationary phase: Chiralpak® Diacel AD 20×250 mm, mobile phase: $CO_2$, EtOH+0.4% $iPrNH_2$). The product fractions were combined and evaporated under reduced pressure.

The first eluted stereoisomer was purified by flash chromatography on silica gel (12 g) with heptane/EtOAc/EtOH/HOAc gradient 100/0/0/0 to 40/45/14.7/0.3. The desired fractions were combined and evaporated under reduced pressure, and co-evaporated with $CH_3CN$. The product was lyophilized from a solvent mixture of $CH_3CN$ (2 mL) and $H_2O$ (1.2 mL) to provide Stereoisomer 1A (63 mg).

The second eluted stereoisomer was purified by flash chromatography on silica gel (12 g) with heptane/EtOAc/EtOH/HOAc gradient 100/0/0/0 to 40/45/14.7/0.3. The desired fractions were combined and evaporated, and co-evaporated with $CH_3CN$. The product was lyophilized from a solvent mixture of $CH_3CN$ (2 mL) and $H_2O$ (1.2 mL) to provide Stereoisomer 1B (79 mg).

The third eluted stereoisomer was purified via preparative HPLC (Stationary phase: RP XBridge® Prep C18 OBD—10 µm, 30×150 mm, mobile phase: 0.25% $NH_4HCO_3$ solution in water, $CH_3CN$). The desired fractions were combined and the organic volatiles were evaporated under reduced pressure. The residue was mixed with EtOAc (25 mL) and 1N HCl (0.5 mL). After stirring for 10 min, the layers were separated. The organic layer was isolated, washed with brine, dried over $MgSO_4$, filtered, evaporated under reduced pressure, and co-evaporated with $CH_3CN$. The residue was lyophilized from a solvent mixture of $CH_3CN$ (1.5 mL) and $H_2O$ (0.75 mL) to provide Stereoisomer 1C (62 mg).

The fourth eluted stereoisomer was purified by flash chromatography on silica gel (12 g) with heptane/EtOAc/EtOH/HOAc gradient 100/0/0/0 to 40/45/14.7/0.3. The desired fractions were combined and evaporated under reduced pressure, and co-evaporated with $CH_3CN$. The product was lyophilized from a solvent mixture of $CH_3CN$ (2 mL) and $H_2O$ (1.2 mL) to provide Stereoisomer 1D (105 mg)

Compound 1:

$^1$H NMR (400 MHz, DMSO-$d_6$) δ ppm 1.10 (dd, J=7.0, 1.3 Hz, 3H) 1.69 (dq, J=13.6, 6.7 Hz, 1H) 1.91-2.01 (m, 1H) 2.43-2.48 (m, 1H) 3.07-3.26 (m, 2H) 3.61 (s, 3H) 3.85 (br t, J=6.5 Hz, 2H) 4.04 (td, J=10.3, 7.2 Hz, 1H) 4.52 (td, J=10.2, 6.4 Hz, 1H) 5.56 (d, J=8.8 Hz, 1H) 5.75 (t, J=2.0 Hz, 1H) 5.89-5.98 (m, 2H) 6.43 (d, J=8.6 Hz, 1H) 7.01 (dd, J=8.3, 1.4 Hz, 1H) 7.33 (d, J=8.4 Hz, 1H) 7.40-7.47 (m, 2H) 7.51-7.58 (m, 2H) 8.03 (s, 1H) 12.16 (br s, 1H)

LC/MS (method LC-A): $R_t$ 1.14 min, MH$^+$ 593

Stereoisomer 1A:

$^1$H NMR (400 MHz, DMSO-d$_6$) δ ppm 1.10 (d, J=7.0 Hz, 3H) 1.69 (dq, J=13.5, 6.6 Hz, 1H) 1.91-2.01 (m, 1H) 2.46-2.48 (m, 1H) 3.08-3.27 (m, 2H) 3.61 (s, 3H) 3.85 (t, J=6.6 Hz, 2H) 4.04 (td, J=10.3, 6.9 Hz, 1H) 4.45-4.57 (m, 1H) 5.55 (d, J=8.8 Hz, 1H) 5.75 (t, J=2.0 Hz, 1H) 5.92-5.96 (m, 2H) 6.43 (d, J=8.8 Hz, 1H) 7.01 (dd, J=8.3, 1.7 Hz, 1H) 7.33 (d, J=8.4 Hz, 1H) 7.40-7.46 (m, 2H) 7.55 (d, J=8.6 Hz, 2H) 8.03 (s, 1H) 12.16 (br s, 1H) LC/MS (method LC-A): $R_t$ 1.15 min, MH$^+$ 593

$[α]_D^{20}$: −37.6° (c 0.415, DMF)

Chiral SFC (method SFC-A): $R_t$ 3.52 min, MH$^+$ 593 chiral purity 100%.

Stereoisomer 1B:

$^1$H NMR (400 MHz, DMSO-d$_6$) δ ppm 1.09 (d, J=7.0 Hz, 3H) 1.69 (dq, J=13.6, 6.6 Hz, 1H) 1.91-2.01 (m, 1H) 2.44-2.48 (m, 1H) 3.08-3.27 (m, 2H) 3.61 (s, 3H) 3.79-3.90 (m, 2H) 4.04 (td, J=10.4, 7.2 Hz, 1H) 4.52 (td, J=10.2, 6.6 Hz, 1H) 5.55 (d, J=8.8 Hz, 1H) 5.75 (t, J=2.0 Hz, 1H) 5.92-5.97 (m, 2H) 6.43 (d, J=8.8 Hz, 1H) 7.01 (dd, J=8.1, 1.5 Hz, 1H) 7.33 (d, J=8.1 Hz, 1H) 7.44 (d, J=7.8 Hz, 2H) 7.55 (d, J=7.2 Hz, 2H) 8.03 (s, 1H) 12.16 (br s, 1H)

LC/MS (method LC-A): $R_t$ 1.15 min, MH$^+$ 593

$[α]_D^{20}$: −65.3° (c 0.455, DMF)

Chiral SFC (method SFC-A): $R_t$ 4.15 min, MH$^+$ 593 chiral purity 97.1%.

Stereoisomer 1C:

$^1$H NMR (400 MHz, DMSO-d$_6$) δ ppm 1.11 (d, J=7.0 Hz, 3H) 1.70 (dq, J=13.5, 6.5 Hz, 1H) 1.90-2.03 (m, 1H) 2.44-2.49 (m, 1H) 3.07-3.25 (m, 2H) 3.62 (s, 3H) 3.86 (t, J=6.6 Hz, 2H) 3.98-4.11 (m, 1H) 4.46-4.57 (m, 1H) 5.56 (d, J=8.6 Hz, 1H) 5.76 (t, J=2.1 Hz, 1H) 5.90-5.99 (m, 2H) 6.44 (d, J=8.8 Hz, 1H) 7.01 (dd, J=7.9, 1.8 Hz, 1H) 7.34 (d, J=8.4 Hz, 1H) 7.44 (d, J=8.4 Hz, 2H) 7.55 (d, J=7.8 Hz, 2H) 8.04 (s, 1H) 12.18 (br s, 1H)

LC/MS (method LC-A): $R_t$ 1.15 min, MH$^+$ 593

$[α]_D^{20}$: +35.2° (c 0.455, DMF)

Chiral SFC (method SFC-A): $R_t$ 2.84 min, MH$^+$ 593 chiral purity 99.3%.

Stereoisomer 1D:

$^1$H NMR (400 MHz, DMSO-d$_6$) δ ppm 1.10 (d, J=7.0 Hz, 3H) 1.70 (dq, J=13.5, 6.6 Hz, 1H) 1.92-2.02 (m, 1H) 2.46-2.49 (m, 1H) 3.09-3.29 (m, 2H) 3.62 (s, 3H) 3.80-3.92 (m, 2H) 4.05 (td, J=10.5, 7.0 Hz, 1H) 4.53 (td, J=10.4, 6.5 Hz, 1H) 5.56 (d, J=8.8 Hz, 1H) 5.76 (t, J=2.0 Hz, 1H) 5.93-5.97 (m, 2H) 6.44 (d, J=8.6 Hz, 1H) 7.01 (dd, J=8.1, 1.5 Hz, 1H) 7.34 (d, J=8.1 Hz, 1H) 7.40-7.47 (m, 2H) 7.56 (d, J=8.4 Hz, 2H) 8.04 (s, 1H) 12.17 (br s, 1H)

LC/MS (method LC-A): $R_t$ 1.15 min, MH$^+$ 593

$[α]_D^{20}$: +64.3° (c 0.42, DMF)

Chiral SFC (method SFC-A): $R_t$ 2.65 min, MH$^+$ 593 chiral purity 98.1%.

Example 2: Synthesis of 4-(3-((1-(4-chlorophenyl)-2-oxo-2-(6-(trifluoromethoxy)indolin-1-yl)ethyl)amino)-5-methoxyphenoxy)-2,2-dimethylbutanoic Acid (Compound 2) and Chiral Separation into Enantiomers 2A and 2B

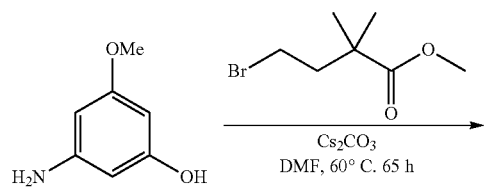

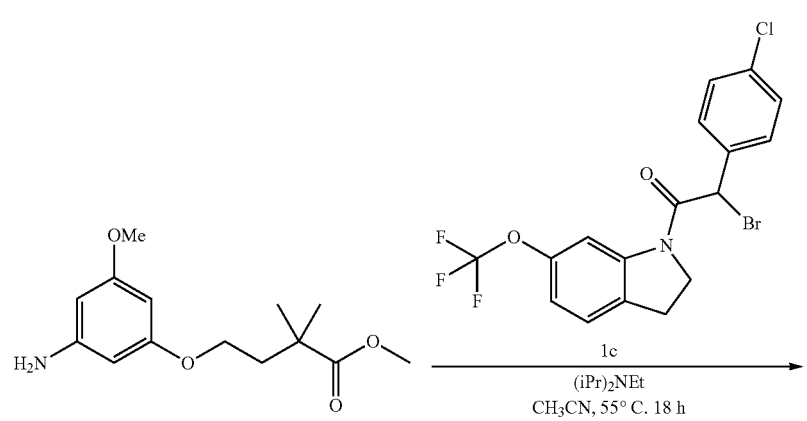

2a

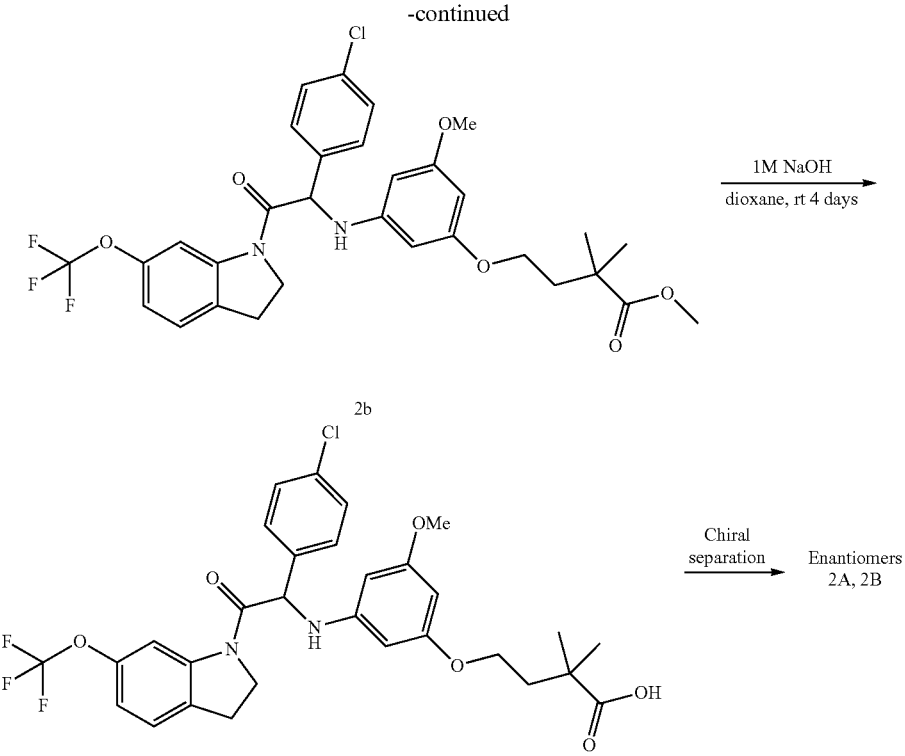

Synthesis of Intermediate 2a:

To a stirred solution of methyl 4-bromo-2,2-dimethylbutanoate [CAS 4833-99-2] (2.5 g, 12 mmol) in DMF (35 mL) was added 3-amino-5-methoxyphenol [CAS 162155-27-3] (1.66 g, 12 mmol) and $Cs_2CO_3$ (7.79 g, 23.9 mmol). The reaction was stirred at 60° C. for 65 h, and allowed to reach room temperature. The mixture was poured out into $H_2O$ (150 mL). The product was extracted with $CH_2Cl_2$. The organic layer was dried over $MgSO_4$, filtered, and the solvent was evaporated under reduced pressure. The residue was purified by flash chromatography on silica gel (25 g) using a gradient of heptane/$CH_2Cl_2$/MeOH 100/0/0 to 0/100/0 to 0/99/1. The desired fractions were combined, evaporated under reduced pressure and co-evaporated with toluene. The solids were dried under vacuum at 50° C. to provide methyl 4-(3-amino-5-methoxyphenoxy)-2,2-dimethylbutanoate 2a (440 mg).

Synthesis of Intermediate 2b:

A mixture of 2-bromo-2-(4-chlorophenyl)-1-(6-(trifluoromethoxy)indolin-1-yl)ethanone 1c (1.57 g, 3.61 mmol), methyl 4-(3-amino-5-methoxyphenoxy)-2,2-dimethylbutanoate 2a (970 mg, 3.63 mmol) and diisopropylethylamine (961 μL, 5.58 mmol) in $CH_3CN$ (25 mL) was stirred at 55° C. for 18 h. The mixture was allowed to reach room temperature, and poured out into water (125 mL). The product was extracted (2×) with $Et_2O$. The combined organic layers were dried over $MgSO_4$, filtered, and evaporated under reduced pressure. The residue was purified by flash chromatography on silica gel (40 g) using a gradient of heptane/EtOAc/EtOH 100/0/0 to 40/45/15. The desired fractions were combined and evaporated under reduced pressure, and co-evaporated with dioxane to provide methyl 4-(3-(((1-(4-chlorophenyl)-2-oxo-2-(6-(trifluoromethoxy)indolin-1-yl)ethyl)amino)-5-methoxyphenoxy)-2-methylbutanoate 2b (2.24 g).

Synthesis of Compound 2 and Separation into Enantiomers 2A and 2B:

1M NaOH in water (9 mL, 9 mmol) was added to a stirring solution of methyl 4-(3-(((1-(4-chlorophenyl)-2-oxo-2-(6-(trifluoromethoxy)indolin-1-yl)ethyl)amino)-5-methoxyphenoxy)-2-methylbutanoate 2b (2.24 g, 3.61 mmol) in dioxane (15 mL). The reaction mixture was stirred at room temperature for 4 days. 1N HCl (10 mL) was added slowly. After stirring for 20 min, the product was extracted with $Et_2O$. The organic layer was separated, dried over $MgSO_4$, filtered, and evaporated under reduced pressure. The residue (2.9 g) was purified by flash chromatography on silica gel (80 g) with heptane/EtOAc/EtOH/HOAc gradient 100/0/0/0 to 40/45/14.7/0.3. The desired fractions were combined, evaporated under reduced pressure, and co-evaporated with diisopropyl ether. The residue (1.6 g) was further purified via preparative HPLC (Stationary phase: RP XBridge® Prep C18 OBD—10 μm, 50×150 mm, mobile phase: 0.5% $NH_4Ac$ solution in water+10% $CH_3CN$, MeOH). The product fractions were combined, and the organic volatiles were evaporated under reduced pressure. The residue was partitioned between 2-Me-THF (300 mL) and brine. The organic layer was dried over $MgSO_4$, filtered and evaporated under reduced pressure. The residue was further purified by flash chromatography on silica gel (12 g) with heptane/EtOAc/EtOH/HOAc gradient 100/0/0/0 to 0/75/24.5/0.5 to 40/45/14.7/0.3. The product fractions were combined and evaporated under reduced pressure. The foamy solid was dried under vacuum at 45° C. to provide 4-(3-(((1-(4-chlorophenyl)-2-oxo-2-(6-(trifluoromethoxy)indolin-1-yl)ethyl)amino)-5-methoxyphenoxy)-2,2-dimethylbutanoic acid (Compound 2, 0.97 g) as a racemic mixture.

The enantiomers of Compound 2 (800 mg) were separated via preparative chiral SFC (Stationary phase: Chiralpak® Diacel AD 20×250 mm, mobile phase: $CO_2$, EtOH+0.4% iPrNH$_2$). The product fractions were combined and evaporated under reduced pressure. The first eluted product was mixed with EtOAc (15 mL), water (5 mL) and 1N HCl (1 mL). After stirring for 15 minutes, the layers were separated. The organic layer was dried over $MgSO_4$, filtered, evaporated under reduced pressure, and co-evaporated with MeOH. The residue was triturated with water (4 mL) and MeOH (1.5 mL) while cooling on an ice-bath. The solids were filtered off, washed (4×) with $H_2O$/MeOH 4/1, and dried under vacuum at 45° C. to provide Enantiomer 2A (292 mg). The second eluted product was mixed with EtOAc (15 mL), water (5 mL) and 1N HCl (1 mL). After stirring for 30 minutes, the layers were separated. The organic layer was dried over $MgSO_4$, filtered, evaporated under reduced pressure, and co-evaporated with MeOH. The residue was triturated with water (4 mL) and MeOH (1.5 mL) while cooling on an ice-bath. The solids were filtered off, washed (4×) with $H_2O$/MeOH 2/1, and dried under vacuum at 45° C. to provide Enantiomer 2B (342 mg).

Compound 2:
$^1$H NMR (400 MHz, DMSO-d$_6$) δ ppm 1.13 (d, J=2.6 Hz, 6H) 1.87 (t, J=7.2 Hz, 2H) 3.08-3.27 (m, 2H) 3.61 (s, 3H) 3.85 (t, J=7.2 Hz, 2H) 4.04 (td, J=10.4, 7.2 Hz, 1H) 4.52 (td, J=10.2, 6.2 Hz, 1H) 5.54 (d, J=8.8 Hz, 1H) 5.74 (t, J=2.0 Hz, 1H) 5.90-5.96 (m, 2H) 6.43 (d, J=8.6 Hz, 1H) 7.01 (dd, J=8.3, 1.4 Hz, 1H) 7.33 (d, J=8.1 Hz, 1H) 7.39-7.48 (m, 2H) 7.50-7.60 (m, 2H) 8.03 (s, 1H) 12.19 (br s, 1H)

LC/MS (method LC-A): R$_t$ 1.22 min, MH$^+$ 607

Enantiomer 2A:
$^1$H NMR (400 MHz, DMSO-d$_6$) δ ppm 1.13 (d, J=2.6 Hz, 6H) 1.87 (t, J=7.3 Hz, 2H) 3.08-3.27 (m, 2H) 3.61 (s, 3H) 3.85 (t, J=7.2 Hz, 2H) 3.97-4.12 (m, 1H) 4.52 (td, J=10.3, 6.5 Hz, 1H) 5.54 (d, J=8.6 Hz, 1H) 5.74 (t, J=2.1 Hz, 1H) 5.90-5.96 (m, 2H) 6.43 (d, J=8.6 Hz, 1H) 7.01 (dd, J=8.1, 1.5 Hz, 1H) 7.33 (d, J=8.1 Hz, 1H) 7.39-7.49 (m, 2H) 7.55 (d, J=8.6 Hz, 2H) 8.03 (s, 1H) 12.20 (br s, 1H)

LC/MS (method LC-A): R$_t$ 1.23 min, MH$^+$ 607

$[\alpha]_D^{20}$: +49.6° (c 0.56, DMF)

Chiral SFC (method SFC-B): R$_t$ 6.47 min, MH$^+$ 607 chiral purity 100%.

Enantiomer 2B:
$^1$H NMR (400 MHz, DMSO-d$_6$) δ ppm 1.13 (d, J=2.6 Hz, 6H) 1.87 (t, J=7.2 Hz, 2H) 3.08-3.28 (m, 2H) 3.61 (s, 3H) 3.85 (t, J=7.2 Hz, 2H) 4.04 (td, J=10.3, 7.3 Hz, 1H) 4.52 (td, J=10.3, 6.5 Hz, 1H) 5.54 (d, J=8.8 Hz, 1H) 5.74 (t, J=2.0 Hz, 1H) 5.90-5.96 (m, 2H) 6.43 (d, J=8.6 Hz, 1H) 7.01 (dd, J=8.1, 1.5 Hz, 1H) 7.33 (d, J=8.1 Hz, 1H) 7.41-7.46 (m, 2H) 7.55 (m, J=8.6 Hz, 2H) 8.03 (s, 1H) 12.20 (br s, 1H)

LC/MS (method LC-A): R$_t$ 1.23 min, MH$^+$ 607

$[\alpha]_D^{20}$: −49.2° (c 0.445, DMF)

Chiral SFC (method SFC-B): R$_t$ 7.18 min, MH$^+$ 607 chiral purity 98.8%.

Example 3: Synthesis of 4-(3-((1-(4-chlorophenyl)-2-oxo-2-(6-(trifluoromethoxy)indolin-1-yl)ethyl)amino)-5-methoxyphenoxy)-2,2-dimethylbutanoic Acid (Compound 3)

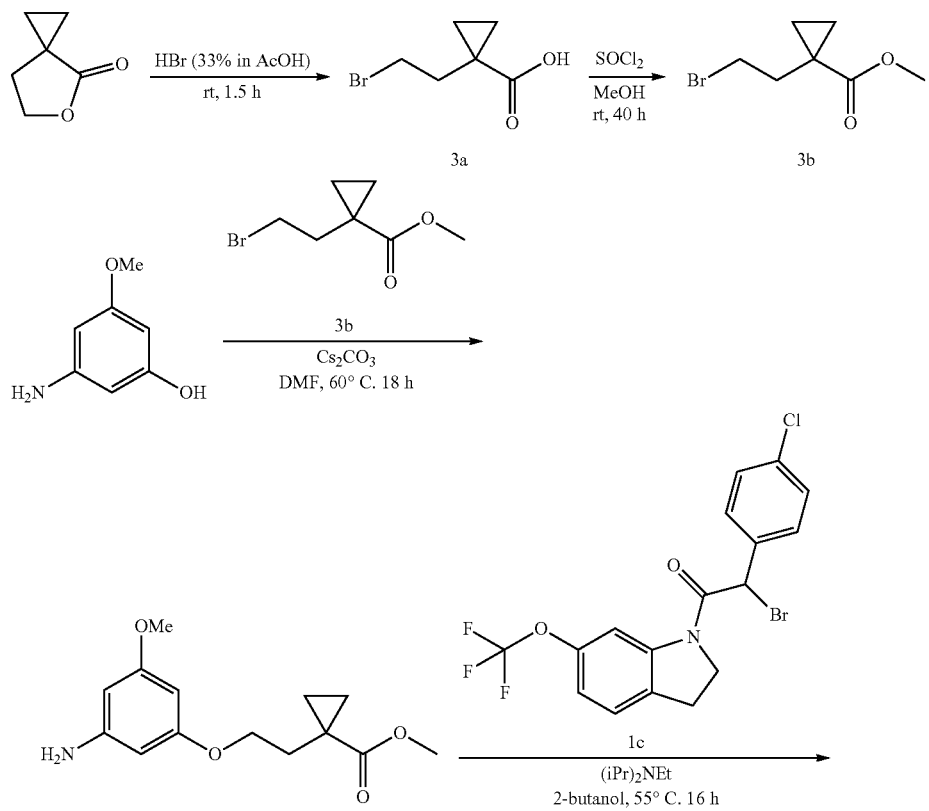

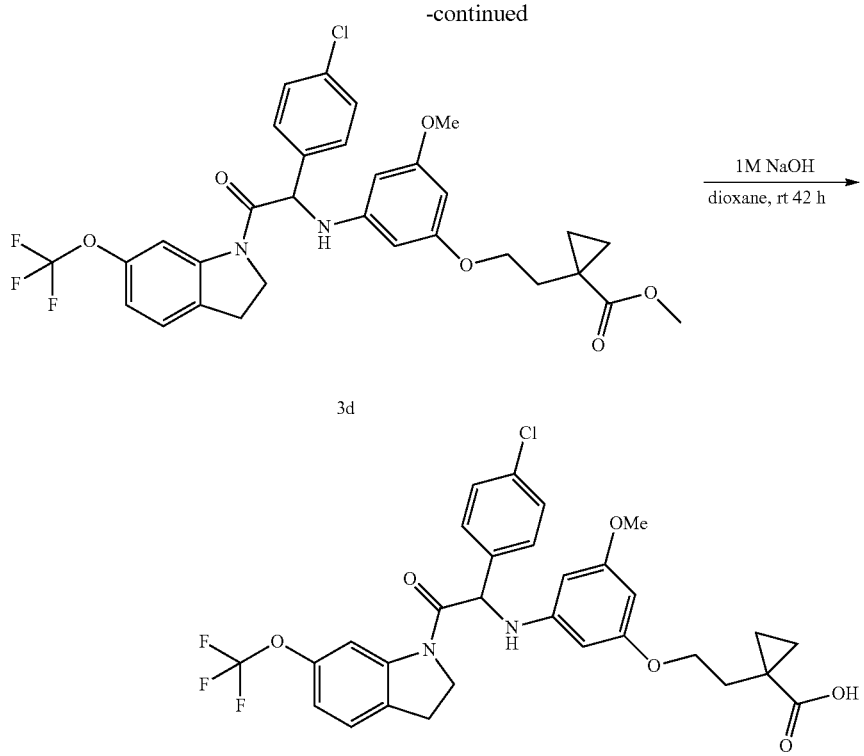

Synthesis of Intermediate 3a:

5-Oxaspiro[2.4]heptan-4-one (930 mg, 8.29 mmol) was mixed with a solution of 33% HBr in AcOH (8 mL). The reaction mixture was stirred at room temperature for 1.5 h, and poured out into ice-water (50 mL). After stirring for 10 min, the product was filtered off, washed (5×) with water and dried under vacuum at 45° C. to provide 1-(2-bromoethyl)cyclopropane-1-carboxylic acid 3a (753 mg).

Synthesis of Intermediate 3b:

A solution of 1-(2-bromoethyl)cyclopropane-1-carboxylic acid 3a (540 mg, 2.8 mmol) in MeOH (11 mL) was stirred under $N_2$-atm while cooling on an ice-bath. Thionyl chloride (304 μL, 4.2 mmol) was added dropwise. The reaction mixture was stirred at room temperature for 40 h. The solvents were evaporated under reduced pressure, and co-evaporated with $CH_3CN$ to provide methyl 1-(2-bromoethyl)cyclopropane-1-carboxylate 3b (380 mg).

Synthesis of Intermediate 3c:

To a stirred solution of methyl 1-(2-bromoethyl)cyclopropane-1-carboxylate 3b (380 mg, 1.84 mmol) in DMF (10 mL) was added 3-amino-5-methoxyphenol [CAS 162155-27-3] (250 mg, 1.80 mmol) and $Cs_2CO_3$ (1.17 g, 3.59 mmol). The reaction was stirred at 60° C. for 18 h, and allowed to reach room temperature. The mixture was poured out into $H_2O$ (60 mL). The product was extracted (2×) with $Et_2O$. The combined organic layers were washed with brine, dried over $MgSO_4$, filtered, and the solvent was evaporated under reduced pressure and co-evaporated with toluene. The residue was purified by flash chromatography on silica gel (12 g) using a gradient of heptane/$CH_2Cl_2$/MeOH 100/0/0 to 0/100/0 to 0/99/1. The product fractions were combined, evaporated under reduced pressure and co-evaporated with $CH_3CN$ to provide methyl 1-(2-(3-amino-5-methoxyphenoxy)ethyl)cyclopropane-1-carboxylate 3c (220 mg).

Synthesis of Intermediate 3d:

A mixture of 2-bromo-2-(4-chlorophenyl)-1-(6-(trifluoromethoxy)indolin-1-yl)ethanone 1c (320 mg, 0.736 mmol), methyl 1-(2-(3-amino-5-methoxyphenoxy)ethyl)cyclopropane-1-carboxylate 3c (220 mg, 0.829 mmol) and diisopropylethylamine (254 μL, 1.47 mmol) in 2-butanol (7.5 mL) was stirred at 55° C. for 16 h. The mixture was allowed to reach room temperature, and poured out into water (25 mL). The product was extracted (2×) with $Et_2O$. The combined organic layers were washed with brine, dried over $MgSO_4$, filtered, and evaporated under reduced pressure. The residue was purified by flash chromatography on silica gel (12 g) using a gradient of heptane/EtOAc/EtOH 100/0/0 to 60/30/10. The product fractions were combined and evaporated under reduced pressure, and co-evaporated with dioxane to provide methyl 1-(2-(3-((1-(4-chlorophenyl)-2-oxo-2-(6-(trifluoromethoxy)indolin-1-yl)ethyl)amino)-5-methoxyphenoxy)ethyl)cyclopropane-1-carboxylate 3d (456 mg).

Synthesis of Compound 3:

1M NaOH in water (1.84 mL, 1.84 mmol) was added to a stirring solution of methyl 1-(2-(3-((1-(4-chlorophenyl)-2-oxo-2-(6-(trifluoromethoxy)indolin-1-yl)ethyl)amino)-5-methoxyphenoxy)ethyl)cyclopropane-1-carboxylate 3d (0.456 mg, 0.737 mmol) in dioxane (3 mL). The reaction mixture was stirred at room temperature under $N_2$-atm for 42 h. Water (15 mL) and 1N HCl (2 mL) were added. After stirring for 10 min, the product was filtered off, washed (3×) with water and dried under vacuum at 45° C. the residue was purified via preparative HPLC (Stationary phase: RP XBridge® Prep C18 OBD—10 μm, 30×150 mm, mobile phase: 0.25% $NH_4HCO_3$ solution in water, $CH_3CN$). The product fractions were combined and the organic solvents were evaporated. The remaining aqueous solution was extracted (2×) with Et$_2$O. The combined organic layers were washed with brine, dried over MgSO$_4$, filtered, evaporated under reduced pressure, and co-evaporated with MeOH. The resulting foam was stirred up in H$_2$O/MeOH 3/1 (4 mL), filtered off, washed (3×) with H$_2$O/MeOH 3/1, and dried under vacuum at 45° C. to provide 1-(2-(3-((1-(4-chlorophenyl)-2-oxo-2-(6-(trifluoromethoxy)indolin-1-yl)ethyl)amino)-5-methoxyphenoxy)ethyl)cyclopropane-1-carboxylic acid (Compound 3, 255 mg) as a racemic mixture.
Compound 3:
$^1$H NMR (400 MHz, DMSO-d$_6$) δ ppm 0.73-0.84 (m, 2H) 1.00-1.11 (m, 2H) 1.81-1.91 (m, 2H) 3.07-3.26 (m, 2H) 3.62 (s, 3H) 3.97 (t, J=7.3 Hz, 2H) 4.05 (td, J=10.3, 7.3 Hz, 1H) 4.52 (td, J=10.2, 6.6 Hz, 1H) 5.55 (d, J=8.6 Hz, 1H) 5.77 (t, J=2.1 Hz, 1H) 5.90-5.98 (m, 2H) 6.42 (d, J=8.6 Hz, 1H) 7.00 (dd, J=8.1, 1.5 Hz, 1H) 7.33 (d, J=8.1 Hz, 1H) 7.39-7.49 (m, 2H) 7.55 (d, J=8.4 Hz, 2H) 8.03 (s, 1H) 12.19 (br s, 1H)

LC/MS (method LC-B): R$_t$ 2.19 min, MH$^+$ 605

Example 4: Synthesis of 4-(3-((1-(4-chlorophenyl)-2-oxo-2-(6-(trifluoromethoxy)indolin-1-yl)ethyl)amino)-5-methoxyphenoxy)-3-methylbutanoic Acid (Compound 4) and Separation into Stereoisomers 4A, 4B, 4C and 4D

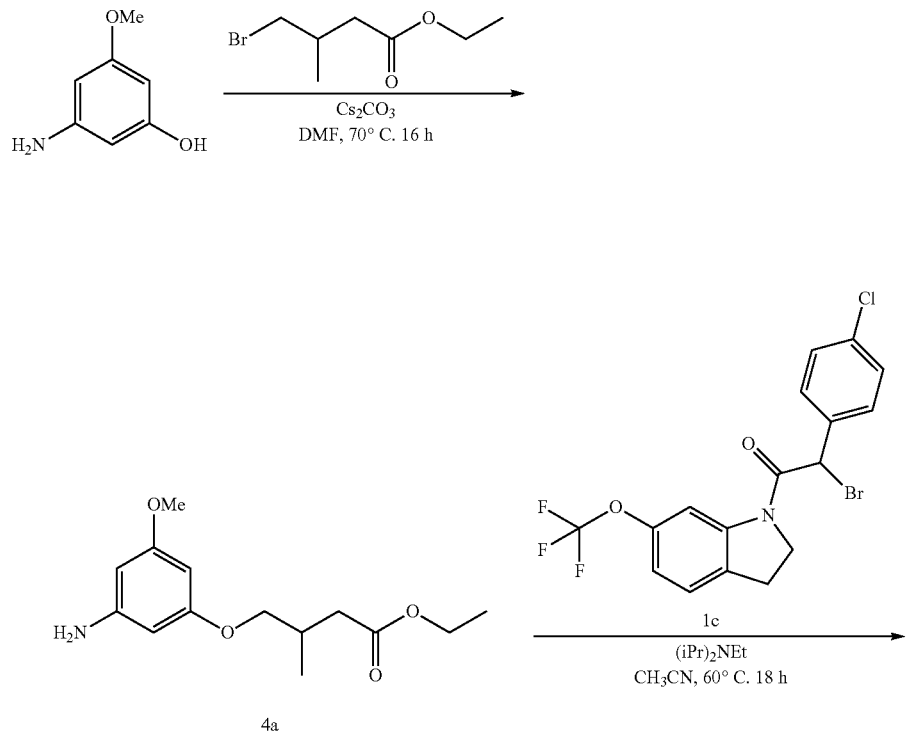

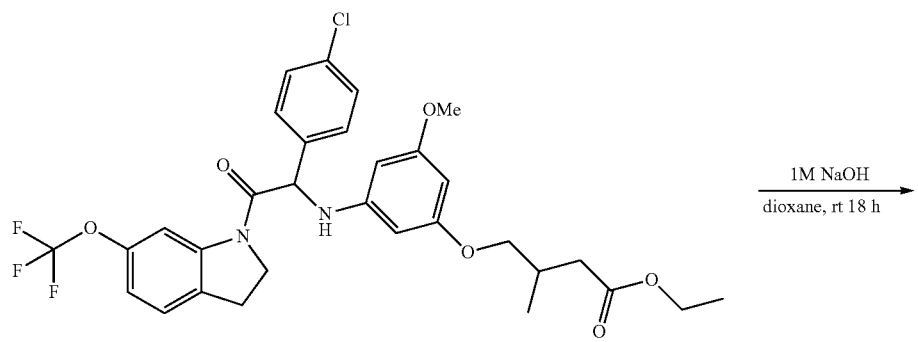

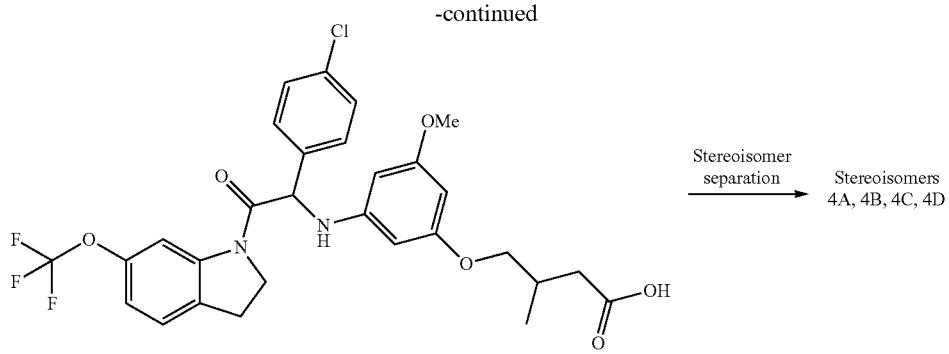

4

Synthesis of Intermediate 4a:

To a stirred solution of ethyl 4-bromo-3-methylbutanoate [CAS 56703-10-7] (1.0 g, 4.78 mmol) in DMF (15 mL) was added 3-amino-5-methoxyphenol [CAS 162155-27-3] (666 mg, 4.78 mmol) and $Cs_2CO_3$ (3.12 g, 9.57 mmol). The reaction was stirred at 70° C. for 16 h, and allowed to reach room temperature. The mixture was poured out into $H_2O$ (75 mL). The product was extracted (2×) with $Et_2O$. The combined organic layers were washed with brine, dried over $MgSO_4$, filtered, and the solvent was evaporated under reduced pressure. The residue was purified by flash chromatography on silica gel (25 g) using a gradient of heptane/EtOAc from 100/0 to 50/50. The product fractions were combined, evaporated under reduced pressure and co-evaporated with $CH_3CN$, yielding ethyl 4-(3-amino-5-methoxyphenoxy)-3-methylbutanoate 4a (430 mg).

Synthesis of Intermediate 4b:

A mixture of 2-bromo-2-(4-chlorophenyl)-1-(6-(trifluoromethoxy)indolin-1-yl)ethanone 1c (430 mg, 1.15 mmol), ethyl 4-(3-amino-5-methoxyphenoxy)-3-methylbutanoate 4a (430 mg, 1.61 mmol) and diisopropylethylamine (396 μL, 2.30 mmol) in $CH_3CN$ (15 mL) was stirred at 60° C. for 18 h under $N_2$ atmosphere. The mixture was allowed to reach room temperature, and was poured out into water (75 mL). The product was extracted (2×) with $Et_2O$. The combined organic layers were washed with brine, dried over $MgSO_4$, filtered, and evaporated under reduced pressure. The residue was purified by flash chromatography on silica gel (12 g) using a gradient of heptane/EtOAc/EtOH 100/0/0 to 40/45/15. The product fractions were combined and evaporated under reduced pressure, and co-evaporated with EtOH to provide ethyl 4-(3-((1-(4-chlorophenyl)-2-oxo-2-(6-(trifluoromethoxy)indolin-1-yl)ethyl)amino)-5-methoxyphenoxy)-3-methylbutanoate 4b (714 mg).

Synthesis of Compound 4 and Separation into Stereoisomers 4A, 4B, 4C and 4D:

1M NaOH in water (2.9 mL, 2.9 mmol) was added to a stirring solution of ethyl 4-(3-((1-(4-chlorophenyl)-2-oxo-2-(6-(trifluoromethoxy)indolin-1-yl)ethyl)amino)-5-methoxyphenoxy)-3-methylbutanoate 4b (714 mg, 1.15 mmol) in a solvent mixture of dioxane (5 mL) and EtOH (2 mL). The reaction mixture was stirred at room temperature for 18 h. 1N HCl (3 mL) was added slowly. After stirring for 2 min, the product was extracted (2×) with $Et_2O$. The combined organic layers were separated, dried over $MgSO_4$, filtered, and evaporated under reduced pressure. The residue was purified by flash chromatography on silica gel (40 g) using a gradient of heptane/EtOAc/EtOH/HOAc 100/0/0/0 to 40/45/14.7/0.3. The product fractions were combined and evaporated under reduced pressure. The residue was stirred up in $Et_2O$ (5 mL). The solids were filtered off, washed (3×) with $Et_2O$, and dried under vacuum at 50° C. to provide 4-(3-((1-(4-chlorophenyl)-2-oxo-2-(6-(trifluoromethoxy)indolin-1-yl)ethyl)amino)-5-methoxyphenoxy)-3-methylbutanoic acid (Compound 4, 290 mg) as a racemic mixture.

The 4 stereoisomers of Compound 4 (274 mg) were separated via preparative chiral SFC (Stationary phase: Chiralpak® Diacel AD 20×250 mm, mobile phase: $CO_2$, iPrOH+0.4% $iPrNH_2$). The product fractions were combined and evaporated under reduced pressure. The stereoisomers in the product fractions of the second and the third eluted peaks were not completely separated and required further separation via preparative chiral SFC (Stationary phase: Chiralpak® Diacel AD 20×250 mm, mobile phase: $CO_2$, EtOH+0.4% $iPrNH_2$). The product fractions were combined and evaporated under reduced pressure. The 4 stereoisomers were solidified by lyophilization from a solvent mixture of $CH_3CN$ and water to provide Stereoisomers 4A (72 mg), 4B (35 mg), 4C (35 mg) and 4D (67 mg).

Compound 4:

$^1$H NMR (400 MHz, DMSO-$d_6$) δ ppm 0.96 (d, J=6.6 Hz, 3H) 2.05-2.15 (m, 1H) 2.16-2.28 (m, 1H) 2.39 (dd, J=15.4, 5.5 Hz, 1H) 3.08-3.27 (m, 2H) 3.62 (s, 3H) 3.65-3.75 (m, 2H) 4.05 (td, J=10.4, 7.2 Hz, 1H) 4.43-4.59 (m, 1H) 5.56 (d, J=8.8 Hz, 1H) 5.76 (t, J=2.0 Hz, 1H) 5.93 (t, J=1.8 Hz, 1H) 5.97 (s, 1H) 6.43 (d, J=8.8 Hz, 1H) 7.01 (dd, J=8.1, 1.5 Hz, 1H) 7.33 (d, J=8.1 Hz, 1H) 7.43 (d, J=7.8 Hz, 2H) 7.55 (d, J=8.4 Hz, 2H) 8.03 (br s, 1H) 12.10 (br s, 1H)

LC/MS (method LC-B): $R_t$ 2.07 min, MH$^+$ 593

Stereoisomer 4A:

$^1$H NMR (400 MHz, DMSO-$d_6$) δ ppm 0.96 (d, J=6.8 Hz, 3H) 2.05-2.13 (m, 1H) 2.22 (dq, J=13.1, 6.6 Hz, 1H) 2.33-2.40 (m, 1H) 3.06-3.21 (m, 2H) 3.62 (s, 3H) 3.65-3.76 (m, 2H) 4.05 (td, J=10.4, 7.2 Hz, 1H) 4.52 (td, J=10.1, 6.4 Hz, 1H) 5.56 (d, J=8.8 Hz, 1H) 5.76 (t, J=2.0 Hz, 1H) 5.93 (t, J=1.9 Hz, 1H) 5.97 (t, J=1.7 Hz, 1H) 6.43 (d, J=8.6 Hz, 1H) 7.00 (dd, J=8.1, 1.5 Hz, 1H) 7.33 (d, J=8.1 Hz, 1H) 7.43 (m, J=8.6 Hz, 2H) 7.55 (m, J=8.6 Hz, 2H) 8.03 (br s, 1H) 11.51 (br s, 1H)

LC/MS (method LC-B): $R_t$ 2.04 min, MH$^+$ 593

$[\alpha]_D^{20}$: −59.6° (c 0.245, DMF)

Chiral SFC (method SFC-C): $R_t$ 5.84 min, MH$^+$ 593 chiral purity 100%.

Stereoisomer 4B:

$^1$H NMR (400 MHz, DMSO-$d_6$) δ ppm 0.96 (d, J=6.6 Hz, 3H) 2.07-2.14 (m, 1H) 2.22 (dq, J=13.2, 6.5 Hz, 1H) 2.38

(dd, J=15.2, 5.5 Hz, 1H) 3.02-3.23 (m, 2H) 3.62 (s, 3H) 3.65-3.76 (m, 2H) 4.04 (td, J=10.3, 7.3 Hz, 1H) 4.52 (td, J=10.5, 6.2 Hz, 1H) 5.56 (d, J=8.8 Hz, 1H) 5.76 (t, J=2.0 Hz, 1H) 5.93 (t, J=1.8 Hz, 1H) 5.97 (t, J=1.7 Hz, 1H) 6.43 (d, J=8.6 Hz, 1H) 7.00 (dd, J=8.0, 1.4 Hz, 1H) 7.33 (d, J=8.1 Hz, 1H) 7.41-7.46 (m, 2H) 7.55 (m, J=8.4 Hz, 2H) 8.03 (br s, 1H) 12.00 (br s, 1H)

LC/MS (method LC-B): $R_t$ 2.04 min, MH+ 593

$[\alpha]_D^{20}$: −47.5° (c 0.255, DMF)

Chiral SFC (method SFC-C): $R_t$ 6.34 min, MH+ 593 chiral purity 98.0%.

Stereoisomer 4C:

$^1$H NMR (400 MHz, DMSO-$d_6$) δ ppm 0.96 (d, J=6.6 Hz, 3H) 2.06-2.14 (m, 1H) 2.22 (dq, J=13.3, 6.4 Hz, 1H) 2.37 (dd, J=15.3, 5.6 Hz, 1H) 3.08-3.22 (m, 2H) 3.62 (s, 3H) 3.66-3.74 (m, 2H) 4.04 (td, J=10.5, 7.0 Hz, 1H) 4.52 (td, J=10.2, 6.6 Hz, 1H) 5.56 (d, J=8.8 Hz, 1H) 5.76 (t, J=2.1 Hz, 1H) 5.93 (t, J=1.7 Hz, 1H) 5.97 (t, J=1.8 Hz, 1H) 6.44 (d, J=8.8 Hz, 1H) 7.01 (dd, J=8.1, 1.5 Hz, 1H) 7.33 (d, J=8.1 Hz, 1H) 7.44 (m, J=8.6 Hz, 2H) 7.55 (m, J=8.6 Hz, 2H) 8.03 (br s, 1H) 10.85-12.62 (m, 1H)

LC/MS (method LC-B): $R_t$ 2.04 min, MH+ 593

$[\alpha]_D^{20}$: +47.7° (c 0.26, DMF)

Chiral SFC (method SFC-C): $R_t$ 6.31 min, MH+ 593 chiral purity 100%.

Stereoisomer 4D:

$^1$H NMR (360 MHz, DMSO-$d_6$) δ ppm 0.96 (d, J=7.0 Hz, 3H) 2.06-2.15 (m, 1H) 2.17-2.28 (m, 1H) 2.38 (dd, J=15.4, 5.5 Hz, 1H) 3.07-3.26 (m, 2H) 3.62 (s, 3H) 3.65-3.76 (m, 2H) 4.05 (td, J=10.2, 7.3 Hz, 1H) 4.52 (td, J=10.3, 6.4 Hz, 1H) 5.57 (d, J=8.8 Hz, 1H) 5.76 (t, J=2.0 Hz, 1H) 5.93 (t, J=1.5 Hz, 1H) 5.97 (t, J=1.5 Hz, 1H) 6.46 (d, J=8.4 Hz, 1H) 7.01 (dd, J=8.2, 1.6 Hz, 1H) 7.33 (d, J=8.4 Hz, 1H) 7.44 (m, J=8.4 Hz, 2H) 7.55 (m, J=8.4 Hz, 2H) 8.03 (br s, 1H) 11.95 (br s, 1H)

LC/MS (method LC-B): $R_t$ 2.04 min, MH+ 593

$[\alpha]_D^{20}$: +60.7° (c 0.285, DMF)

Chiral SFC (method SFC-C): $R_t$ 7.58 min, MH+ 593 chiral purity 100%.

Example 5: Synthesis of 2-(1-((3-((1-(4-chlorophenyl)-2-oxo-2-(6-(trifluoro-methoxy)indolin-1-yl)ethyl)amino)-5-methoxyphenoxy)methyl)cyclopropyl)acetic Acid (Compound 5) and Chiral Separation into Enantiomers 5A and 5B

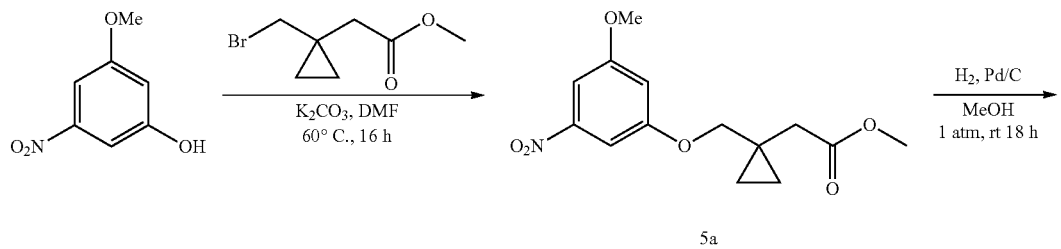

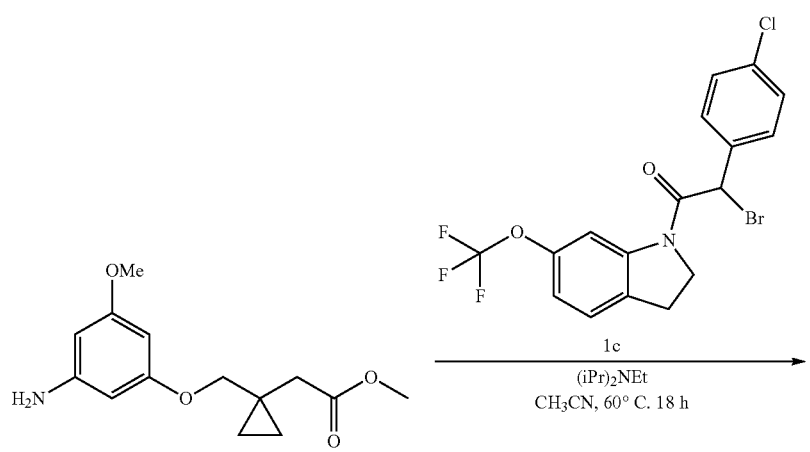

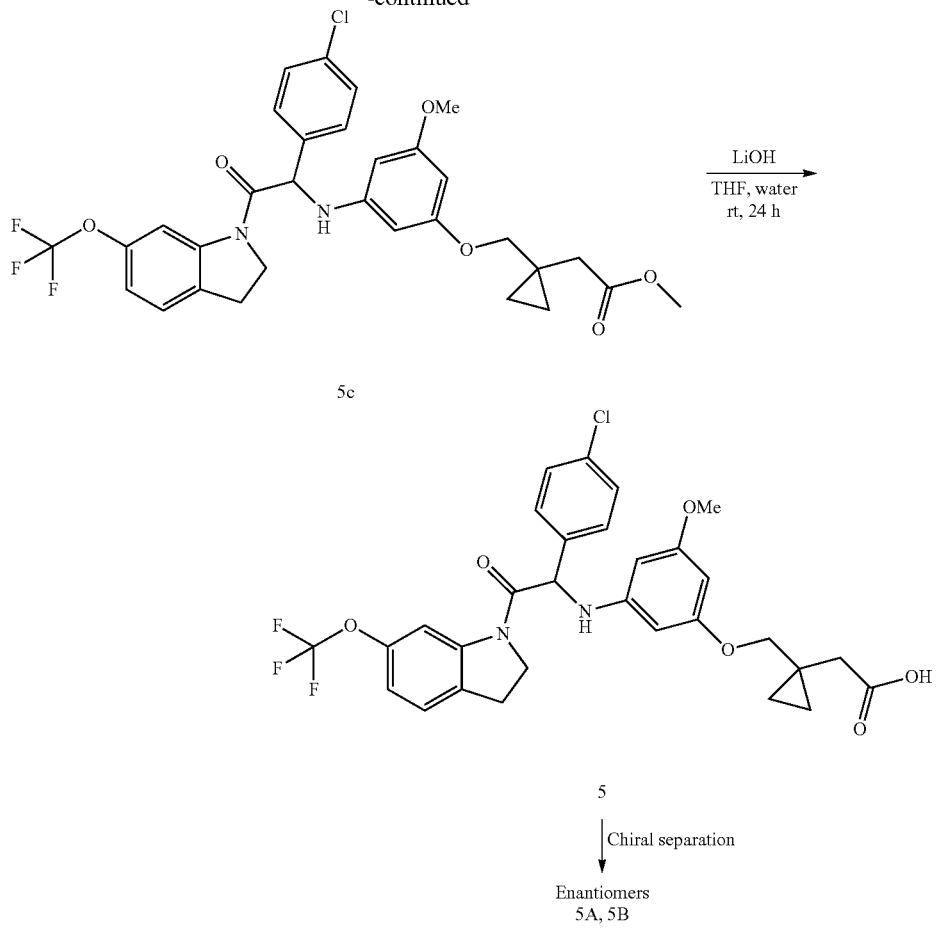

Synthesis of Intermediate 5a:

Methyl 2-(1-(bromomethyl)cyclopropyl)acetate [855473-50-6] (306 mg, 1.478 mmol) was added dropwise to a solution of 3-methoxy-5-nitrophenol [7145-49-5] (250 mg, 1.478 mmol) and K$_2$CO$_3$ (306 mg, 2.217 mmol) in DMF (2.5 mL). The mixture was stirred at 60° C. for 16 h. The reaction was cooled to 0° C., and diluted with water and ice. The mixture was extracted with EtOAc. The organic layer was washed with water, dried over MgSO$_4$, filtered and the solvent was concentrated under reduced pressure to give methyl 2-(1-((3-methoxy-5-nitrophenoxy)methyl)cyclopropyl)acetate 5a. The yield was considered as quantitative. The compound was used as such in the next step.

Synthesis of Intermediate 5b:

A solution of methyl 2-(1-((3-methoxy-5-nitrophenoxy)methyl)cyclopropyl)acetate 5a (520 mg, 1.761 mmol) in MeOH (8 mL), containing a catalytic amount of 10% Pd/C (300 mg, 0.282 mmol) was hydrogenated under atmospheric pressure of H$_2$ at room temperature for 18 h. The catalyst was removed by filtration over a short pad of Celite® and the filter cake was rinsed several times with EtOAc. The combined filtrates were evaporated to give methyl 2-(1-((3-amino-5-methoxyphenoxy)methyl)cyclopropyl)acetate 5b (390 mg), which was used without further purification in the next step.

Synthesis of Intermediate 5c:

A mixture of 2-bromo-2-(4-chlorophenyl)-1-(6-(trifluoromethoxy)indolin-1-yl)ethanone 1c (250 mg, 0.575 mmol), methyl 2-(1-((3-amino-5-methoxy-phenoxy)methyl)cyclopropyl)acetate 5b (184 mg, 0.575 mmol) and diisopropylethylamine (200 μL, 1.15 mmol) in CH$_3$CN (7.5 mL) was stirred at 60° C. for 18 h. The solvent was concentrated under reduced pressure. Ice/water was added and the mixture was extracted with EtOAc. The organic layer was washed with water, dried over MgSO$_4$, filtered, and concentrated under reduced pressure. The residue was purified by column chromatography on silica gel (30 μm, 24 g, heptane/EtOAc 75/25). The product fractions were combined and evaporated under reduced pressure. The residue was crystallized from CH$_3$CN/diisopropyl ether and dried to give methyl 2-(1-((3-((1-(4-chlorophenyl)-2-oxo-2-(6-(trifluoro-methoxy)indolin-1-yl)ethyl)amino)-5-methoxyphenoxy)methyl)cyclopropyl)acetate 5c (206 mg).

Synthesis of Compound 5 and Separation into Enantiomers 5A and 5B:

LiOH monohydrate (63 mg, 1.502 mmol) in water (1.63 mL) was added dropwise to a solution of methyl 2-(1-((3-((1-(4-chlorophenyl)-2-oxo-2-(6-(trifluoromethoxy)-indolin-1-yl)ethyl)amino)-5-methoxyphenoxy)methyl)cyclopropyl)acetate 5c (186 mg, 0.3 mmol) in THF (3.7 mL). The reaction mixture was stirred at room temperature for 24 h. 3N HCl was added to acidify the reaction mixture, and the aqueous solution was extracted with EtOAc. The combined organic layers were dried over MgSO$_4$, filtered, and concentrated under reduced pressure. The residue was crystallized from CH$_3$CN/diisopropyl ether and dried to give 2-(1-((3-((1-(4-chlorophenyl)-2-oxo-2-(6-(trifluoromethoxy)indolin-1-yl)ethyl)amino)-5-methoxyphenoxy)methyl)cyclopropyl)acetic acid (Compound 5, 115 mg). the separation of the enantiomers of Compound 5 (71 mg) was performed via preparative chiral SFC (Stationary phase: Chiralpak® Diacel AD 20×250 mm, mobile phase: $CO_2$, EtOH+0.4% $iPrNH_2$). For both enantiomers, the product fractions were combined and evaporated under reduced pressure. The residues were partitioned between water and $Et_2O$. The mixtures were acidified to pH 1-2 by the addition of 1N HCl and the layers were separated. The aqueous layer was extracted again with $Et_2O$. The combined organic layers were dried over $MgSO_4$, filtered, and evaporated under reduced pressure. The residues were dried under vacuum at 50° C. to provide Enantiomer 5A (22 mg) and Enantiomer 5B (23 mg) as off-white powders.

Compound 5:
$^1$H NMR (500 MHz, DMSO-$d_6$) δ ppm 0.49-0.55 (m, 4H) 2.33 (s, 2H) 2.99-3.25 (m, 2H) 3.62 (s, 3H) 3.73 (s, 2H) 4.05 (td, J=10.40, 7.25 Hz, 1H) 4.52 (td, J=10.25, 6.31 Hz, 1H) 5.57 (d, J=9.14 Hz, 1H) 5.74 (s, 1H) 5.92 (s, 1H) 5.95 (s, 1H) 6.45 (d, J=9.14 Hz, 1H) 7.02 (br d, J=9.14 Hz, 1H) 7.34 (d, J=8.20 Hz, 1H) 7.44 (d, J=8.20 Hz, 2H) 7.55 (d, J=8.51 Hz, 3H) 8.03 (s, 1H) 12.01 (br s, 1H)

LC/MS (method LC-C): $R_t$ 3.18 min, MH$^+$ 605
MP=111° C.

Enantiomer 5A:
$^1$H NMR (360 MHz, DMSO-$d_6$) δ ppm 0.46-0.58 (m, 4H) 2.33 (s, 2H) 3.04-3.27 (m, 2H) 3.61 (s, 3H) 3.72 (s, 2H) 4.05 (td, J=10.2, 7.3 Hz, 1H) 4.52 (td, J=10.2, 6.6 Hz, 1H) 5.57 (d, J=9.1 Hz, 1H) 5.74 (t, J=2.0 Hz, 1H) 5.92 (t, J=1.6 Hz, 1H) 5.94-5.97 (m, 1H) 6.45 (d, J=8.8 Hz, 1H) 7.01 (dd, J=8.1, 1.5 Hz, 1H) 7.33 (d, J=8.4 Hz, 1H) 7.44 (d, J=8.4 Hz, 2H) 7.51-7.59 (m, 2H) 8.03 (s, 1H) 12.12 (br s, 1H)

LC/MS (method LC-A): $R_t$ 1.15 min, MH$^+$ 605

$[α]_D^{20}$: +37.0° (c 0.135, DMF)

Chiral SFC (method SFC-E): $R_t$ 5.84 min, MH$^+$ 605 chiral purity 100%.

Enantiomer 5B:
$^1$H NMR (360 MHz, DMSO-$d_6$) δ ppm 0.46-0.57 (m, 4H) 2.33 (s, 2H) 3.05-3.26 (m, 2H) 3.61 (s, 3H) 3.72 (s, 2H) 4.05 (td, J=10.4, 7.3 Hz, 1H) 4.52 (td, J=10.3, 6.4 Hz, 1H) 5.57 (d, J=8.8 Hz, 1H) 5.74 (t, J=2.0 Hz, 1H) 5.92 (t, J=1.8 Hz, 1H) 5.94-5.97 (m, 1H) 6.45 (d, J=8.8 Hz, 1H) 7.01 (dd, J=8.2, 1.6 Hz, 1H) 7.33 (d, J=8.1 Hz, 1H) 7.44 (d, J=8.4 Hz, 2H) 7.50-7.61 (m, 2H) 8.03 (s, 1H) 12.11 (br s, 1H)

LC/MS (method LC-A): $R_t$ 1.15 min, MH$^+$ 605

$[α]_D^{20}$: −48.8° (c 0.16, DMF)

Chiral SFC (method SFC-E): $R_t$ 6.53 min, MH$^+$ 605 chiral purity 100%.

Example 6A: Synthesis of (1R*,2R*)-2-((3-((1-(4-chlorophenyl)-2-oxo-2-(6-(trifluoromethoxy)indolin-1-yl)ethyl)amino)-5-methoxyphenoxy)methyl)-cyclopropanecarboxylic Acid (Compound 6A) and Separation into Stereoisomers 6AA and 6AB

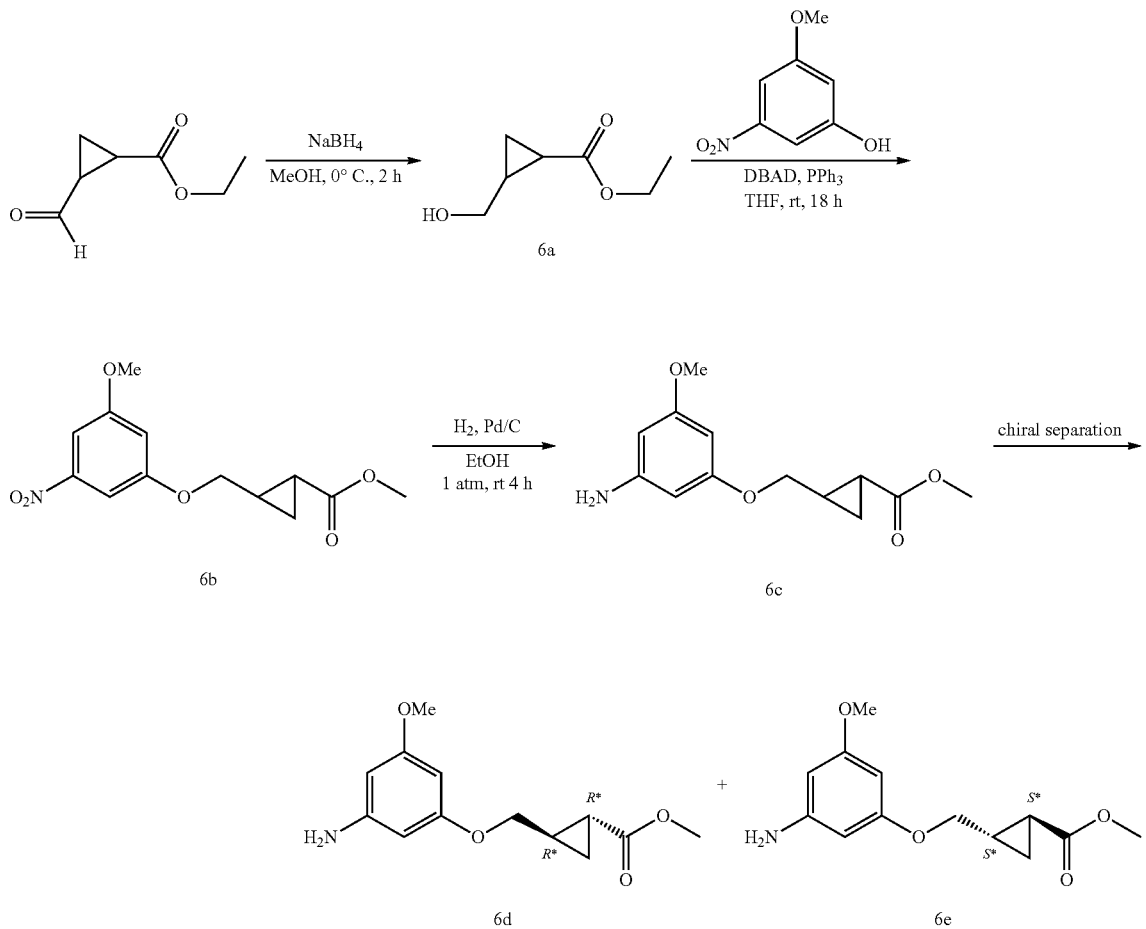

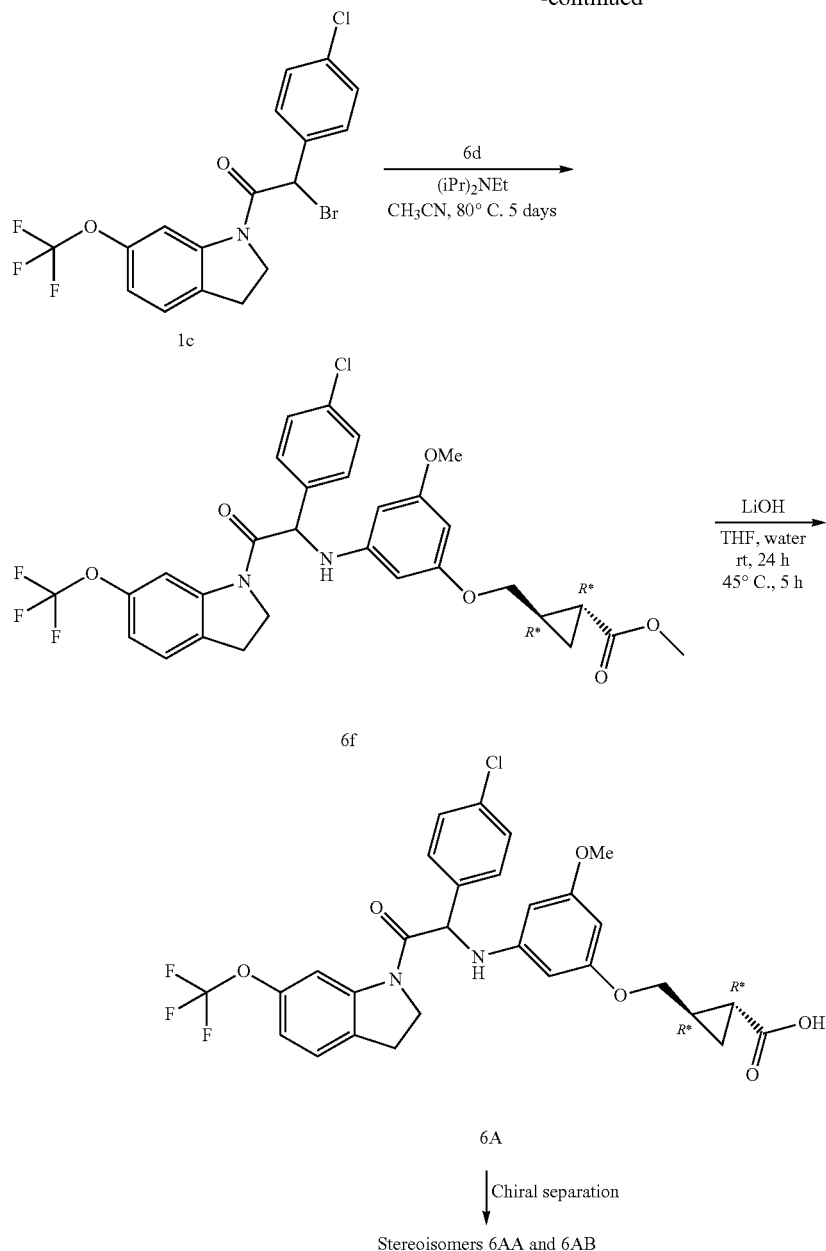

Synthesis of Intermediate 6a:

To a solution of ethyl 2-formylcyclopropanecarboxylate [20417-61-2] (9 mL, 67.996 mmol) in MeOH (200 mL) was added portionwise NaBH$_4$ (5.15 g, 133.993 mmol) at 0° C. and the mixture was stirred at 0° C. for 2 h. CH$_2$Cl$_2$ and water were added. The layers were separated; the aqueous layer was extracted with CH$_2$Cl$_2$ and the combined organic layers were dried over MgSO$_4$, filtered and concentrated under reduced pressure to give ethyl 2-(hydroxymethyl) cyclopropanecarboxylate 6a (9.15 g). The compound was used as such in the next step.

Synthesis of Intermediate 6b:

Di-tert-butyl azodicarboxylate (4.8 g, 20.809 mmol) was added portionwise to a solution of 3-methoxy-5-nitrophenol [7145-49-5] (3.2 g, 18.917 mmol), ethyl 2-(hydroxymethyl) cyclopropanecarboxylate 6a (3 g, 20.809 mmol), and PPh$_3$ (5.46 g, 20.809 mmol) in THF (150 mL). The reaction was stirred at room temperature under N$_2$ for 18 h. The solution was concentrated under reduced pressure. The crude residue was purified by preparative LC (irregular SiOH 20-45 μm, 220 g, heptane/EtOAc from 85/15 to 75/25). The pure fractions were combined and concentrated under reduced pressure to give methyl 2-((3-methoxy-5-nitrophenoxy) methyl)cyclopropanecarboxylate 6b (1.4 g).

Synthesis of Intermediate 6c and Chiral Separation into Enantiomers 6d and 6e:

A solution of methyl 2-((3-methoxy-5-nitrophenoxy) methyl)cyclopropanecarboxylate 6b (1.3 g, 4.402 mmol) in EtOH (65 mL) containing a catalytic amount of 10% Pd/C (750 mg, 0.704 mmol) was hydrogenated under atmospheric pressure of H$_2$ at room temperature for 4 h. The catalyst was removed by filtration over a short pad of Celite® and the filter cake was rinsed several times with EtOAc. The combined filtrates were evaporated. The crude residue was purified by preparative LC (Irregular SiOH 20-45 µm, 40 g, heptane/EtOAc 80/20). The pure fractions were combined and the solvent was evaporated to dryness to give methyl 2-((3-amino-5-methoxyphenoxy)methyl)cyclopropanecarboxylate 6c (780 mg). The enantiomers were separated via chiral SFC (Stationary phase: Chiralpak® AD-H 5 µm 250×30 mm, mobile phase: 80% $CO_2$, 20% EtOH) to give the first eluted enantiomer 6d (trans R*,R*, 344 mg, $[\alpha]_D^{20}$: −78.6° (c 0.257, DMF)) and the second eluted enantiomer 6e (trans S*,S*, 371 mg, $[\alpha]_D^{20}$: +74.5° (c 0.251, DMF)).

Synthesis of Intermediate 6f:

A mixture of 2-bromo-2-(4-chlorophenyl)-1-(6-(trifluoromethoxy)indolin-1-yl)ethanone 1c (376 mg, 0.864 mmol), (1R*,2R*)-methyl 2-((3-amino-5-methoxyphenoxy)methyl)cyclopropanecarboxylatemethoxyphenoxy)methyl)cyclopropyl)acetate 6d (344 mg, 1.297 mmol) and diisopropylethylamine (298 µL, 1.729 mmol) in $CH_3CN$ (12 mL) was stirred at 80° C. for 5 days. The solvent was concentrated under reduced pressure. Ice/water was added and the mixture was extracted with EtOAc. The organic layer was washed with water, dried over $MgSO_4$, filtered, and concentrated under reduced pressure. The residue was purified by column chromatography on silica gel (25-30 µm, 40 g, heptane/EtOAc 80/20). The product fractions were combined and evaporated under reduced pressure to give (1R*,2R*)-methyl 2-((3-((1-(4-chlorophenyl)-2-oxo-2-(6-(trifluoromethoxy)indolin-1-yl)ethyl)amino)-5-methoxyphenoxy)methyl)-cyclopropanecarboxylate 6f (500 mg).

Synthesis of Compound 6A and Chiral Separation into Stereoisomers 6AA and 6AB:

LiOH monohydrate (169 mg, 4.039 mmol) in water (10 mL) was added dropwise to a solution of (1R*,2R*)-methyl 2-((3-((1-(4-chlorophenyl)-2-oxo-2-(6-(trifluoromethoxy)indolin-1-yl)ethyl)amino)-5-methoxyphenoxy)methyl)cyclopropanecarboxylate 6f (500 mg, 0.808 mmol) in THF (10 mL). The reaction mixture was stirred at room temperature for 18 h and at 45° C. for 5 h. 3N HCl was added to acidify the solution, and the mixture was extracted with EtOAc. The combined organic layers were dried over $MgSO_4$, filtered, and concentrated under reduced pressure. The residue was purified by column chromatography on silica gel (20-45 µm, 40 g, heptane/EtOAc 80/20). The product fractions were combined and evaporated under reduced pressure to give (1R*,2R*)-2-((3-((1-(4-chlorophenyl)-2-oxo-2-(6-(trifluoromethoxy)indolin-1-yl)ethyl)amino)-5-methoxyphenoxy)methyl)cyclopropanecarboxylic acid (Compound 6A, 780 mg). The two stereoisomers were separated via chiral SFC (Stationary phase: Chiralcel® OD-H 5 µm 250×30 mm, mobile phase: 55% $CO_2$, 45% iPrOH) to give, after solidification from heptane/diisopropyl ether, the first eluted Stereoisomer 6AA (123 mg) and the second eluted Stereoisomer 6AB (125 mg).

Stereoisomer 6AA:

$^1$H NMR (500 MHz, DMSO-$d_6$) δ ppm 0.75-0.96 (m, 1H) 1.00-1.07 (m, 1H) 1.44-1.57 (m, 1H) 1.57-1.70 (m, 1H) 3.09-3.27 (m, 2H) 3.62 (s, 3H) 3.69 (br dd, J=10.25, 7.72 Hz, 1H) 3.80-3.95 (m, 1H) 4.00-4.09 (m, 1H) 4.39-4.65 (m, 1H) 5.57 (br d, J=8.51 Hz, 1H) 5.76 (s, 1H) 5.95 (s, 1H) 5.97 (s, 1H) 6.46 (br d, J=8.83 Hz, 1H) 7.02 (br d, J=8.20 Hz, 1H) 7.34 (d, J=8.20 Hz, 1H) 7.44 (d, J=8.51 Hz, 2H) 7.55 (br d, J=8.20 Hz, 2H) 8.04 (br s, 1H) 12.02 (br s, 1H)

LC/MS (method LC-C): $R_t$ 2.95 min, MH$^+$ 591

$[\alpha]_D^{20}$: −78.0° (c 0.282, DMF)

Chiral SFC (method SFC-G): $R_t$ 1.08 min, MH$^+$ 591 chiral purity 99.82%.

Stereoisomer 6AB:

$^1$H NMR (500 MHz, DMSO-$d_6$) δ ppm 0.79-0.90 (m, 1H) 1.00-1.08 (m, 1H) 1.43-1.57 (m, 1H) 1.57-1.72 (m, 1H) 2.95-3.27 (m, 2H) 3.62 (s, 3H) 3.63-3.78 (m, 1H) 3.78-3.98 (m, 1H) 4.00-4.09 (m, 1H) 4.29-4.65 (m, 1H) 5.57 (br d, J=8.83 Hz, 1H) 5.76 (br s, 1H) 5.95 (s, 1H) 5.96 (s, 1H) 6.46 (br d, J=8.51 Hz, 1H) 7.01 (br d, J=7.57 Hz, 1H) 7.34 (br d, J=7.88 Hz, 1H) 7.44 (br d, J=7.88 Hz, 2H) 7.55 (br d, J=7.88 Hz, 2H) 8.04 (br s, 1H) 11.88 (br s, 1H)

LC/MS (method LC-C): $R_t$ 2.95 min, MH$^+$ 591

$[\alpha]_D^{20}$: +12.9° (c 0.272, DMF)

Chiral SFC (method SFC-G): $R_t$ 1.87 min, MH$^+$ 591 chiral purity 99.55%.

Example 6B: Synthesis of ((1 S*,2S*)-2-((3-((1-(4-chlorophenyl)-2-oxo-2-(6-(trifluoromethoxy)indolin-1-yl)ethyl)amino)-5-methoxyphenoxy)methyl)-cyclopropanecarboxylic Acid (Compound 6B) and Separation into Stereoisomers 6BA and 6BB

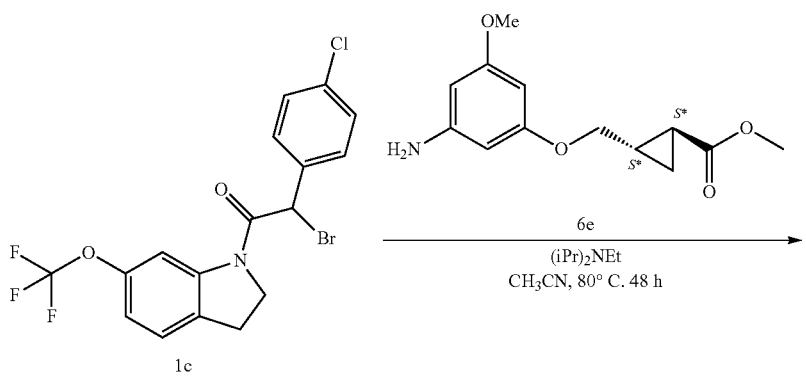

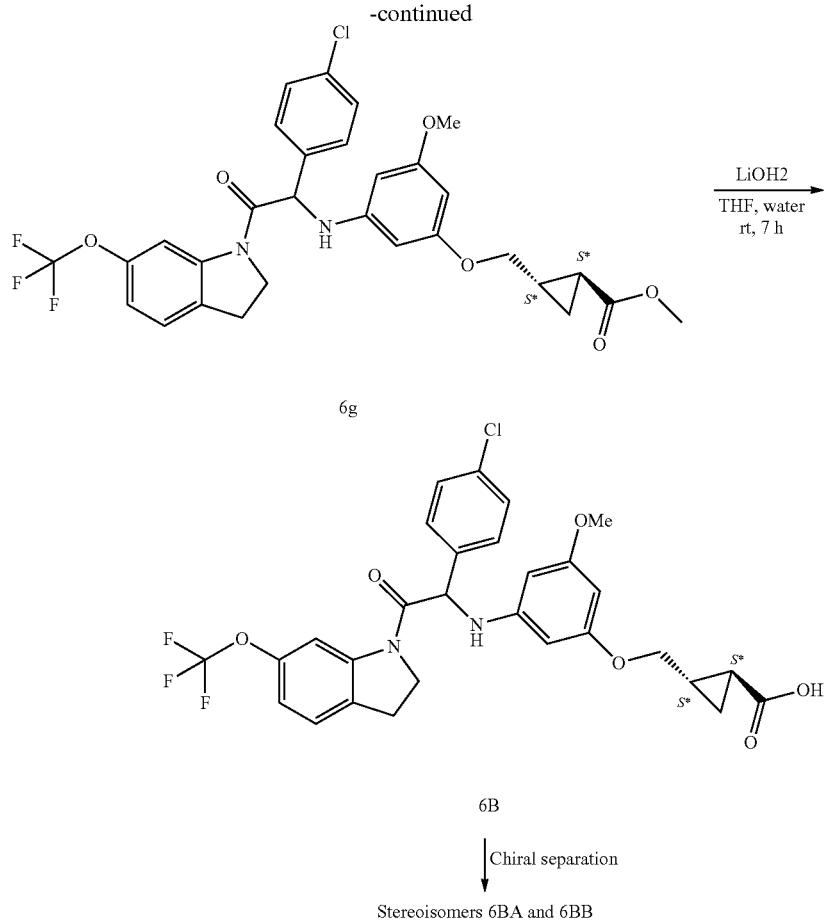

Synthesis of Intermediate 6g:

A mixture of 2-bromo-2-(4-chlorophenyl)-1-(6-(trifluoromethoxy)indolin-1-yl)ethanone 1c (405 mg, 0.932 mmol), (1S*,2S*)-methyl 2-((3-amino-5-methoxyphenoxy)methyl)cyclopropanecarboxylatemethoxyphenoxy)methyl)cyclopropyl)acetate 6e (371 mg, 1.398 mmol) and diisopropylethylamine (321 μL, 1.864 mmol) in CH₃CN (12 mL) was stirred at 80° C. for 48 h. The solvent was concentrated under reduced pressure. Ice/water was added and the mixture was extracted with EtOAc. The organic layer was washed with water, dried over MgSO₄, filtered, and concentrated under reduced pressure. The residue was purified by column chromatography on silica gel (25-30 μm, 40 g, heptane/EtOAc 80/20). The product fractions were combined and evaporated under reduced pressure to give (1S*,2S*)-methyl 2-((3-((1-(4-chlorophenyl)-2-oxo-2-(6-(trifluoromethoxy)indolin-1-yl)ethyl)amino)-5-methoxyphenoxy)methyl)-cyclopropanecarboxylate 6g (580 mg).

Synthesis of Compound 6B and Chiral Separation into Stereoisomers 6BA and 6BB:

LiOH monohydrate (203 mg, 4.846 mmol) in water (10 mL) was added dropwise to a solution of (1S*,2S*)-methyl 2-((3-((1-(4-chlorophenyl)-2-oxo-2-(6-(trifluoromethoxy)indolin-1-yl)ethyl)amino)-5-methoxyphenoxy)methyl)-cyclopropanecarboxylate 6g (600 mg, 0.969 mmol) in THF (10 mL). The reaction mixture was stirred at room temperature for 7 h. 3N HCl was added to acidify the solution, and the mixture was extracted with EtOAc. The combined organic layers were dried over MgSO₄, filtered, and concentrated under reduced pressure. The residue was purified by column chromatography on silica gel (20-45 μm, 40 g, heptane/EtOAc 80/20). The product fractions were combined and evaporated under reduced pressure to give (1S*,2S*)-2-((3-((1-(4-chlorophenyl)-2-oxo-2-(6-(trifluoromethoxy)indolin-1-yl)ethyl)amino)-5-methoxyphenoxy)methyl)cyclopropanecarboxylic acid (Compound 6B, 348 mg). The two stereoisomers were separated via chiral SFC (Stationary phase: Chiralcel® OD-H 5 μm 250×30 mm, mobile phase: 55% CO₂, 45% iPrOH) to give, after solidification from heptane/diisopropyl ether, the first eluted Stereoisomer 6BA (109 mg) and the second eluted Stereoisomer 6BB (102 mg).

Stereoisomer 6BA:

$^1$H NMR (500 MHz, DMSO-$d_6$) δ ppm 0.73-0.98 (m, 1H) 0.98-1.08 (m, 1H) 1.49-1.58 (m, 1H) 1.58-1.71 (m, 1H) 3.00-3.27 (m, 2H) 3.61 (s, 3H) 3.68 (dd, J=10.40, 7.57 Hz, 1H) 3.84 (dd, J=10.56, 6.15 Hz, 1H) 4.00-4.08 (m, 1H) 4.50-4.57 (m, 1H) 5.57 (d, J=8.83 Hz, 1H) 5.75 (s, 1H) 5.95 (s, 1H) 5.96 (s, 1H) 6.46 (br d, J=8.83 Hz, 1H) 7.01 (br d, J=7.25 Hz, 1H) 7.33 (d, J=7.88 Hz, 1H) 7.44 (d, J=8.51 Hz, 2H) 7.55 (d, J=8.51 Hz, 2H) 8.03 (s, 1H) 12.26 (br s, 1H)

LC/MS (method LC-D): $R_t$ 2.82 min, MH⁺ 591

$[α]_D^{20}$: −12.5° (c 0.28, DMF)

Chiral SFC (method SFC-G): $R_t$ 1.10 min, no MH⁺, chiral purity 100%.

Stereoisomer 6BB:

$^1$H NMR (500 MHz, DMSO-$d_6$) δ ppm 0.78-0.95 (m, 1H) 1.00-1.08 (m, 1H) 1.48-1.59 (m, 1H) 1.59-1.68 (m, 1H) 2.91-3.25 (m, 2H) 3.61 (s, 3H) 3.68 (br dd, J=10.40, 7.57 Hz, 1H) 3.84 (dd, J=10.56, 6.15 Hz, 1H) 4.00-4.09 (m, 1H) 4.30-4.58 (m, 1H) 5.57 (d, J=8.83 Hz, 1H) 5.75 (s, 1H) 5.95 (s, 1H), 5.96 (s, 1H) 6.45 (br d, J=8.83 Hz, 1H) 7.01 (br d, J=7.88 Hz, 1H) 7.33 (d, J=8.20 Hz, 1H) 7.44 (d, J=8.20 Hz, 2H) 7.55 (d, J=8.20 Hz, 2H) 8.03 (s, 1H) 12.11 (br s, 1H)

LC/MS (method LC-D): R$_t$ 2.81 min, MH$^+$ 591

[α]$_D^{20}$: +81.4° (c 0.28, DMF)

Chiral SFC (method SFC-G): R$_t$ 1.87 min, no MH$^+$, chiral purity 99.02%.

Example 7: Synthesis of (1r,3r)-3-(3-((1-(4-chlorophenyl)-2-oxo-2-(6-(trifluoromethoxy)indolin-1-yl)ethyl)amino)-5-methoxyphenoxy)cyclobutenecarboxylic Acid (Compound 7) and Separation into Enantiomers 7A and 7B

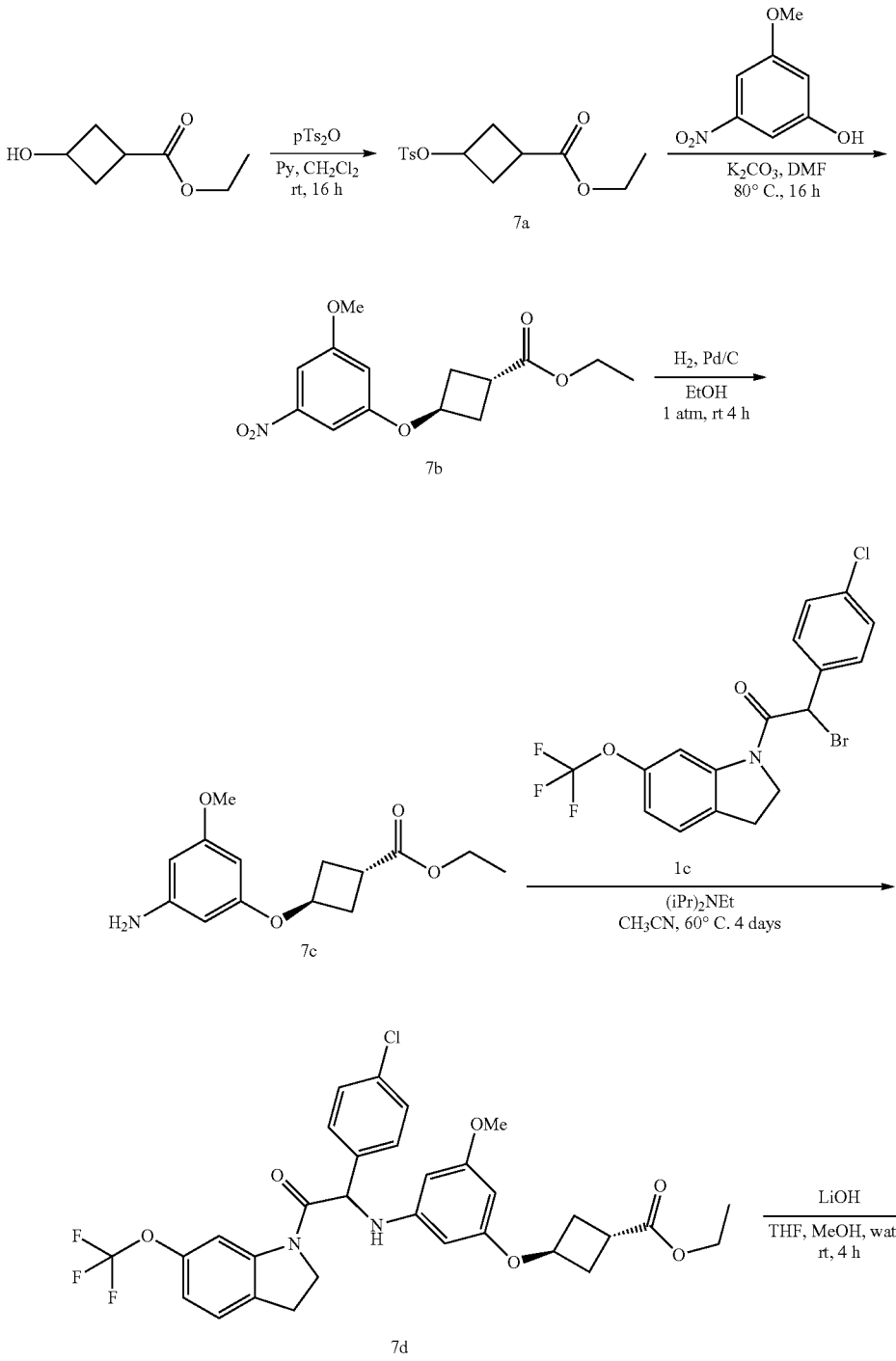

-continued

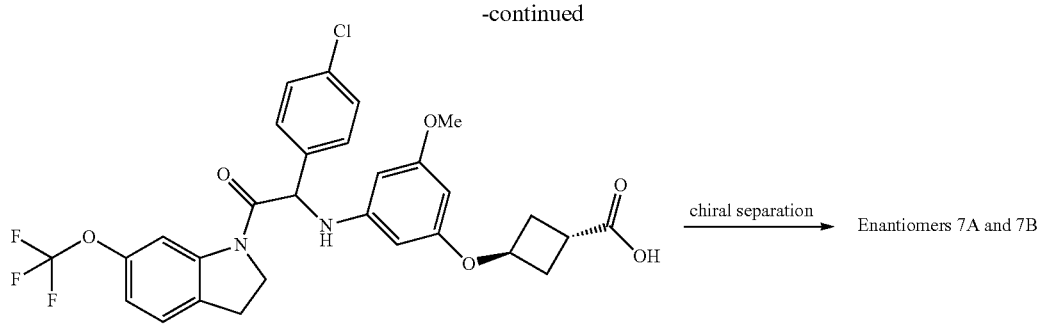

7

Synthesis of Intermediate 7a:

Under a $N_2$ flow, to a solution of ethyl 3-hydroxycyclobutanecarboxylate [17205-02-6] (1 g, 6.936 mmol) in $CH_2Cl_2$ (30 mL) were added pyridine (0.838 mL) and tosyl anhydride (2.49 g, 7.63 mmol). The mixture was stirred overnight at room temperature. The mixture was concentrated under vacuum, suspended in diethyl ether (200 mL) and washed with 0.5 M hydrochloric acid (2×60 mL), a saturated solution of sodium hydrogen carbonate (2×60 mL), water (60 mL) and brine (50 mL). The solution was dried over sodium sulfate, filtered and concentrated under reduced pressure to yield ethyl 3-(tosyloxy)cyclobutanecarboxylate 7a (2.0 g).

Synthesis of Intermediate 7b:

Ethyl 3-(tosyloxy)cyclobutanecarboxylate 7a (1.94 g, 6.504 mmol) was added dropwise to a mixture of 3-methoxy-5-nitrophenol [7145-49-5] (1.0 g, 5.912 mmol) and $K_2CO_3$ (981 mg, 7.095 mmol) in DMF (10 mL). The mixture was stirred at 80° C. for 16 h. The mixture was diluted with water and extracted with EtOAc. The organic layer was washed with water, dried over $MgSO_4$, filtered and the solvent was evaporated under reduced pressure. Purification was performed by flash chromatography on silica gel (15-40 μm, 80 g, heptane/EtOAc 95/5 to 85/15). The pure fractions were combined and evaporated to dryness to give (1r,3r)-ethyl 3-(3-methoxy-5-nitrophenoxy)cyclobutanecarboxylate 7b (1.1 g).

Synthesis of Intermediate 7c:

A solution of (1r,3r)-ethyl 3-(3-methoxy-5-nitrophenoxy)cyclobutanecarboxylate 7b (1.1 g, 3.725 mmol) in EtOH (20 mL) containing a catalytic amount of 10% Pd/C (396 mg, 0.373 mmol) was hydrogenated under atmospheric pressure of $H_2$ at room temperature for 4 h. The catalyst was removed by filtration over a short pad of Celite® and the filter cake was rinsed several times with MeOH. The combined filtrates were evaporated under reduced pressure to give (1r,3r)-ethyl 3-(3-amino-5-methoxyphenoxy)cyclobutanecarboxylate 7c (920 mg). The compound was used as such in the next step.

Synthesis of Intermediate 7d:

A mixture of 2-bromo-2-(4-chlorophenyl)-1-(6-(trifluoromethoxy)indolin-1-yl)ethanone 1c (1.072 g, 2.467 mmol), (1r,3r)-ethyl 3-(3-amino-5-methoxy-phenoxy)cyclobutanecarboxylate 7c (720 mg, 2.714 mmol) and diisopropylethylamine (850 μL, 4.934 mmol) in $CH_3CN$ (32 mL) was stirred at 60° C. for 4 days. The mixture was diluted with water and extracted with EtOAc. The organic layer was washed with 1N HCl and brine, dried over $MgSO_4$, filtered and the solvent was evaporated under vacuum to give (1r,3r)-ethyl 3-(3-((1-(4-chlorophenyl)-2-oxo-2-(6-(trifluoromethoxy)indolin-1-yl)ethyl)amino)-5-methoxyphenoxy)cyclobutanecarboxylate 7d (1.6 g), which was used as such in the next step.

Synthesis of Compound 7 and Chiral Separation into Enantiomers 7A and 7B:

At 0° C., LiOH monohydrate (325 mg, 7.75 mmol) was added portionwise to a solution of (1r,3r)-ethyl 3-(3-((1-(4-chlorophenyl)-2-oxo-2-(6-(trifluoromethoxy)-indolin-1-yl)ethyl)amino)-5-methoxyphenoxy)cyclobutanecarboxylate 7d (1.6 g, 2.585 mmol) in THF/water/MeOH (1/1/1) (30 mL). The reaction mixture was stirred at room temperature for 4 h. The mixture was diluted with water and 3N HCl was added to acidify the solution. The mixture was extracted with EtOAc. The combined organic layers were dried over $MgSO_4$, filtered, and concentrated under reduced pressure. The residue was purified by column chromatography on silica gel (15-40 μm, 80 g, $CH_2Cl_2$/MeOH 100/0 to 98/2). The product fractions were combined and evaporated under reduced pressure to give (1r,3r)-3-(3-((1-(4-chlorophenyl)-2-oxo-2-(6-(trifluoromethoxy)indolin-1-yl)ethyl)amino)-5-methoxyphenoxy)cyclobutene-carboxylic acid (Compound 7, 1.16 g). The two enantiomers were separated via chiral SFC (Stationary phase: Chiralcel® OD-H 5 μm 250×30 mm, mobile phase: 55% $CO_2$, 45% MeOH) to give, after solidification from heptane/diisopropyl ether, the first eluted Enantiomer 7A (358 mg) and the second eluted Enantiomer 7B (388 mg).

Compound 7:

$^1$H NMR (500 MHz, DMSO-$d_6$) δ ppm 2.19-2.30 (m, 2H) 2.57 (qd, J=6.8, 3.6 Hz, 2H) 2.95-3.05 (m, 1H) 3.08-3.27 (m, 2H) 3.61 (s, 3H) 4.03 (td, J=10.4, 7.3 Hz, 1H) 4.53 (td, J=10.4, 6.3 Hz, 1H) 4.68 (quin, J=6.7 Hz, 1H) 5.54 (d, J=8.5 Hz, 1H) 5.62 (s, 1H) 5.85 (s, 1H) 5.92 (s, 1H) 6.53 (d, J=8.5 Hz, 1H) 7.01 (br d, J=7.9 Hz, 1H) 7.33 (d, J=8.2 Hz, 1H) 7.45 (d, J=8.2 Hz, 2H) 7.55 (d, J=8.5 Hz, 2H) 8.04 (s, 1H) 12.34 (br s, 1H)

LC/MS (method LC-C): $R_t$ 2.95 min, MH$^+$ 591

Enantiomer 7A:

$^1$H NMR (500 MHz, DMSO-$d_6$) δ ppm 2.20-2.28 (m, 2H) 2.53-2.60 (m, 2H) 2.95-3.04 (m, 1H) 3.07-3.26 (m, 2H) 3.60 (s, 3H) 4.03 (td, J=10.4, 7.3 Hz, 1H) 4.52 (td, J=10.2, 6.3 Hz, 1H) 4.67 (t, J=6.8 Hz, 1H) 5.53 (d, J=8.5 Hz, 1H) 5.61 (t, J=2.0 Hz, 1H) 5.84 (s, 1H) 5.91 (s, 1H) 6.52 (d, J=8.5 Hz, 1H) 7.01 (dd, J=8.2, 1.6 Hz, 1H) 7.33 (d, J=8.2 Hz, 1H) 7.44 (d, J=8.5 Hz, 2H) 7.55 (d, J=8.5 Hz, 2H) 8.03 (s, 1H) 12.24-12.40 (m, 1H)

LC/MS (method LC-C): $R_t$ 2.96 min, MH$^+$ 591

$[\alpha]_D^{20}$: −41.6° (c 0.298, DMF)

Chiral SFC (method SFC-H): $R_t$ 1.25 min, MH$^+$ 591, chiral purity 100%.

Enantiomer 7B:

$^1$H NMR (500 MHz, DMSO-$d_6$) δ ppm 2.19-2.28 (m, 2H) 2.57 (qd, J=6.8, 3.9 Hz, 2H) 2.95-3.04 (m, 1H) 3.08-3.25 (m, 2H) 3.60 (s, 3H) 4.03 (td, J=10.5, 7.1 Hz, 1H) 4.53 (td, J=10.4, 6.3 Hz, 1H) 4.67 (quin, J=6.7 Hz, 1H) 5.53 (d, J=8.5 Hz, 1H) 5.61 (t, J=2.0 Hz, 1H) 5.84 (s, 1H) 5.91 (s, 1H) 6.52 (d, J=8.5 Hz, 1H) 7.01 (dd, J=8.0, 1.4 Hz, 1H) 7.33 (d, J=8.2 Hz, 1H) 7.44 (d, J=8.5 Hz, 2H) 7.55 (d, J=8.5 Hz, 2H) 8.03 (s, 1H) 12.32 (br s, 1H)

LC/MS (method LC-C): $R_t$ 2.95 min, MH+ 591

$[\alpha]_D^{20}$: +43.7° (c 0.332, DMF)

Chiral SFC (method SFC-H): $R_t$ 2.05 min, MH+ 591, chiral purity 100%.

Example 8: Synthesis of (1s,3s)-3-(3-((1-(4-chlorophenyl)-2-oxo-2-(6-(trifluoromethoxy)indolin-1-yl)ethyl)amino)-5-methoxyphenoxy)cyclobutene-Carboxylic Acid (Compound 8) and Separation into Enantiomers 8A and 8B

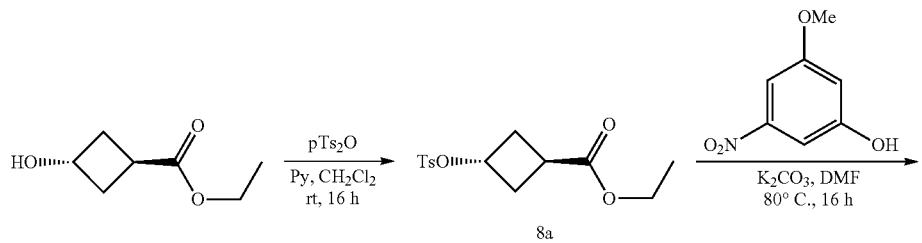

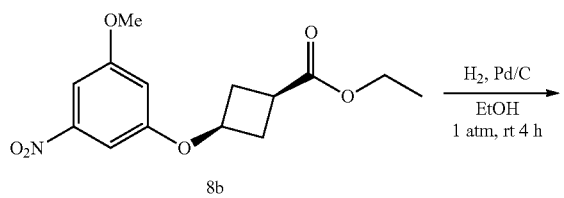

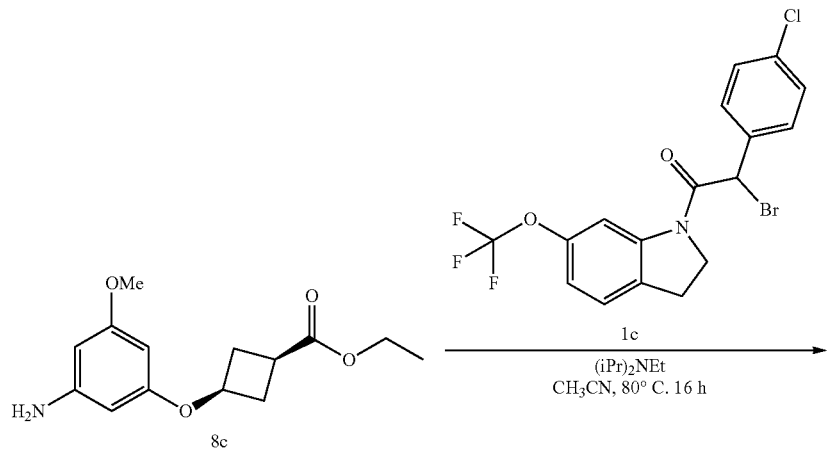

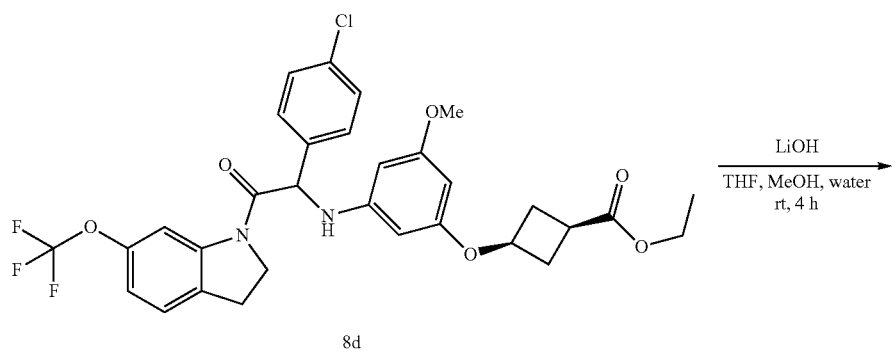

-continued

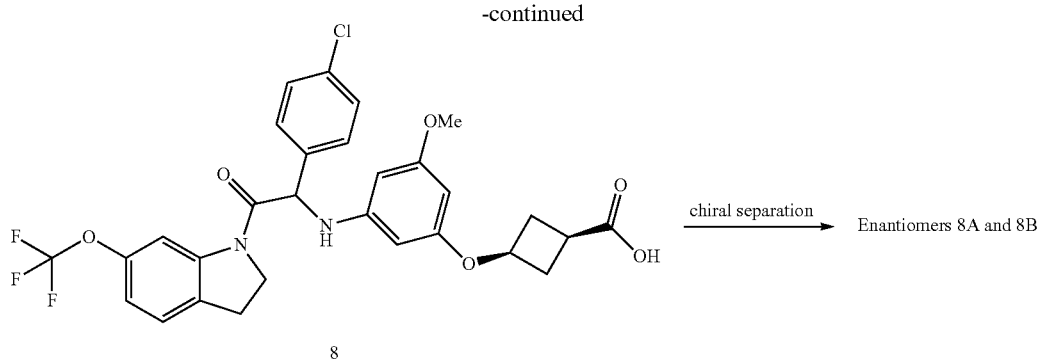

8

Synthesis of Intermediate 8a:
Under a N₂ flow, to a solution of (1r,3r)-ethyl 3-hydroxycyclobutanecarboxylate [160351-88-2] (1.86 g, 12.901 mmol) in CH₂Cl₂ (50 mL) were added pyridine (1.56 mL) and tosyl anhydride (4.63 g, 14.192 mmol). The mixture was stirred for 6 h at room temperature. The mixture was concentrated under vacuum, suspended in diethyl ether (200 mL) and washed with 0.5 M hydrochloric acid (2×60 mL), a saturated solution of sodium hydrogen carbonate (2×60 mL), water (60 mL) and brine (50 mL), and then dried over sodium sulfate, filtered and concentrated under reduced pressure to yield (1r,3r)-ethyl 3-(tosyloxy)cyclobutanecarboxylate 8a (3.97 g). The compound was used as such in the next step.

Synthesis of Intermediate 8b:
(1r,3r)-ethyl 3-(tosyloxy)cyclobutanecarboxylate 8a (3.85 g, 12.904 mmol) was added dropwise to a mixture of 3-methoxy-5-nitrophenol [7145-49-5] (1.98 g, 11.73 mmol) and K₂CO₃ (1.95 g, 14.07 mmol) in DMF (20 mL). The mixture was stirred at 80° C. for 16 h. The mixture was diluted with water and extracted with EtOAc. The organic layer was washed with water, dried over MgSO₄, filtered and the solvent was evaporated under reduced pressure. Purification was performed by flash chromatography on silica gel (15-40 µm, 120 g, heptane/EtOAc 95/5 to 85/15) The pure fractions were combined and evaporated to dryness to give (1s,3s)-ethyl 3-(3-methoxy-5-nitrophenoxy)cyclobutanecarboxylate 8b (2.04 g).

Synthesis of Intermediate 8c:
A solution of (1s,3s)-ethyl 3-(3-methoxy-5-nitrophenoxy)cyclobutanecarboxylate 8b (2.04 g, 6.908 mmol) in EtOH (50 mL) containing a catalytic amount of 10% Pd/C (735 mg, 0.691 mmol) was hydrogenated under atmospheric pressure of H₂ at room temperature for 4 h. The catalyst was removed by filtration over a short pad of Celite® and the filter cake was rinsed several times with EtOH. The combined filtrates were evaporated under reduced pressure to give (1s,3s)-ethyl 3-(3-amino-5-methoxyphenoxy)cyclobutanecarboxylate 8c (1.8 g). The compound was used as such in the next step.

Synthesis of Intermediate 8d:
A mixture of 2-bromo-2-(4-chlorophenyl)-1-(6-(trifluoromethoxy)indolin-1-yl)ethanone 1c (1.5 g, 3.462 mmol), (1s,3s)-ethyl 3-(3-amino-5-methoxyphenoxy)cyclobutanecarboxylate 8c (870 mg, 3.462 mmol) and diisopropylethylamine (1.19 mL, 6.924 mmol) in CH₃CN (30 mL) was stirred at 80° C. for 16 h. The mixture was diluted with water and extracted with EtOAc. The organic layer was washed with 1N HCl and brine, dried over MgSO₄, filtered and the solvent was evaporated under vacuum. The compound was crystallized from CH₃CN/Et₂O to give intermediate 8 (fraction 1, 820 mg). The filtrate was concentrated under reduced pressure to give another batch of crude intermediate 8 (fraction 2, 1 g).

The reaction was duplicated starting from 692 mg (1.592 mmol) of 1c (using the same reaction conditions as described above). The reaction product was crystallized from Et₂O to give intermediate 8 (fraction 3, 400 mg). The filtrate was concentrated under reduced pressure to give another batch of intermediate 8 (fraction 4, 600 mg). Fractions 2 and 4 were combined and purified by flash chromatography on silica gel (15-40 µm, 80 g, heptane/EtOAc 90/10 to 70/30) The pure fractions were combined and evaporated to dryness to give fraction 5 (250 mg). Fractions 1, 3 and 5 were combined and dried to give (1s,3s)-ethyl 3-(3-((1-(4-chlorophenyl)-2-oxo-2-(6-(trifluoromethoxy)indolin-1-yl)ethyl)amino)-5-methoxyphenoxy)cyclobutanecarboxylate 8d (1.53 g).

Synthesis of Compound 8 and Chiral Separation into Enantiomers 8A and 8B:
At 0° C., LiOH monohydrate (318 mg, 7.58 mmol) was added portionwise to a solution of (1s,3s)-ethyl 3-(3-((1-(4-chlorophenyl)-2-oxo-2-(6-(trifluoromethoxy)-indolin-1-yl)ethyl)amino)-5-methoxyphenoxy)cyclobutanecarboxylate 8d (1.53 g, 2.529 mmol) in THF/water/MeOH (1/1/1) (30 mL). The reaction mixture was stirred at room temperature for 4 h. The mixture was diluted with water and 3N HCl was added to acidify the solution. The mixture was extracted with EtOAc. The combined organic layers were dried over MgSO₄, filtered, and concentrated under reduced pressure. The residue was purified by column chromatography on silica gel (15-40 µm, 40 g, CH₂Cl₂/MeOH 100/0 to 98.5/1.5). The pure fractions were combined and evaporated under reduced pressure to give (1s,3s)-3-(3-((1-(4-chlorophenyl)-2-oxo-2-(6-(trifluoromethoxy)indolin-1-yl)ethyl)amino)-5-methoxyphenoxy)cyclobutanecarboxylic acid (Compound 8, 1.26 g). The two enantiomers were separated via chiral SFC (Stationary phase: Chiralcel® OD-H 5 µm 250×20 mm, mobile phase: 55% CO₂, 45% EtOH) to give, after solidification from ether/diisopropyl ether, the first eluted Enantiomer 8A (442 mg) and the second eluted Enantiomer 8B (433 mg).

Compound 8:
$^1$H NMR (500 MHz, DMSO-d₆) δ ppm 2.03-2.13 (m, 2H) 2.57-2.66 (m, 2H) 2.66-2.76 (m, 1H) 3.08-3.26 (m, 2H) 3.61 (s, 3H) 4.04 (td, J=10.2, 7.3 Hz, 1H) 4.44-4.58 (m, 2H) 5.54 (d, J=8.5 Hz, 1H) 5.66 (s, 1H) 5.87 (s, 1H) 5.94 (s, 1H) 6.49 (d, J=8.5 Hz, 1H) 7.02 (br d, J=8.2 Hz, 1H) 7.34 (d, J=8.2 Hz, 1H) 7.45 (d, J=8.2 Hz, 2H) 7.55 (d, J=8.2 Hz, 2H) 8.04 (s, 1H) 12.27 (br s, 1H)

LC/MS (method LC-C): $R_t$ 2.90 min, MH$^+$ 591

Enantiomer 8A:

$^1$H NMR (500 MHz, DMSO-d$_6$) δ ppm 2.01-2.14 (m, 2H) 2.55-2.72 (m, 3H) 3.08-3.24 (m, 2H) 3.61 (s, 3H) 4.04 (td, J=10.4, 7.3 Hz, 1H) 4.41-4.57 (m, 2H) 5.54 (d, J=8.8 Hz, 1H) 5.66 (s, 1H) 5.86 (s, 1H) 5.93 (s, 1H) 6.48 (br d, J=8.8 Hz, 1H) 7.01 (br d, J=8.2 Hz, 1H) 7.33 (d, J=8.2 Hz, 1H) 7.44 (d, J=8.5 Hz, 2H) 7.55 (d, J=8.2 Hz, 2H) 8.03 (s, 1H)

LC/MS (method LC-C): $R_t$ 2.90 min, MH$^+$ 591

$[α]_D^{20}$: −47.1° (c 0.274, DMF)

Chiral SFC (method SFC-I): $R_t$ 1.18 min, MH$^+$ 591, chiral purity 100%.

Enantiomer 8B:

$^1$H NMR (500 MHz, DMSO-d$_6$) δ ppm 2.02-2.13 (m, 2H) 2.55-2.70 (m, 3H) 3.06-3.25 (m, 2H) 3.61 (s, 3H) 4.04 (td, J=10.2, 7.3 Hz, 1H) 4.39-4.57 (m, 2H) 5.54 (d, J=8.8 Hz, 1H) 5.66 (s, 1H) 5.86 (s, 1H) 5.93 (s, 1H) 6.48 (br d, J=8.8 Hz, 1H) 7.01 (br d, J=7.9 Hz, 1H) 7.33 (d, J=8.2 Hz, 1H) 7.44 (d, J=8.2 Hz, 2H) 7.55 (d, J=8.5 Hz, 2H) 8.03 (s, 1H)

LC/MS (method LC-C): $R_t$ 2.91 min, MH$^+$ 591

$[α]_D^{20}$: +40.0° (c 0.25, DMF)

Chiral SFC (method SFC-I): $R_t$ 2.16 min, MH$^+$ 591, chiral purity 100%.

Example 9: Synthesis of 3-((3-((1-(4-chlorophenyl)-2-oxo-2-(6-(trifluoromethoxy)-indolin-1-yl)ethyl)amino)-5-methoxyphenoxy)methyl)bicyclo[1.1.1]pentane-1-Carboxylic Acid (Compound 9) and Chiral Separation into Enantiomers 9A and 9B

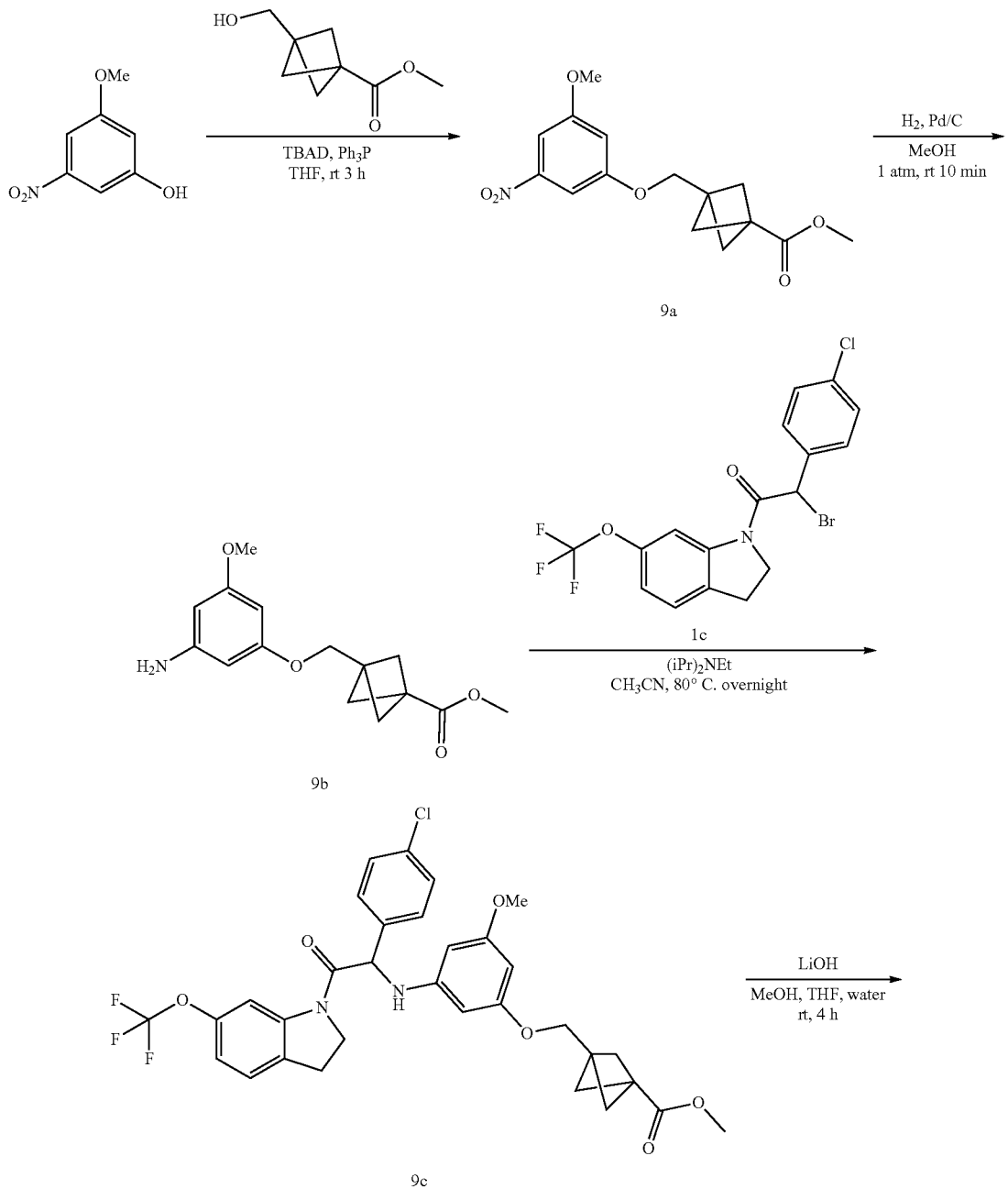

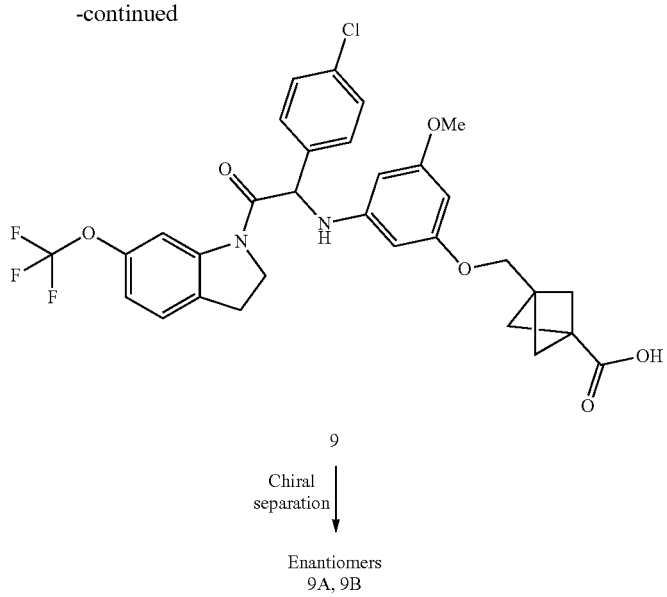

9
Chiral separation ↓
Enantiomers
9A, 9B

Synthesis of Intermediate 9a:

3-Methoxy-5-nitrophenol [7145-49-5] (1.1 g, 6.4 mmol), di-tert-butyl azodicarboxylate (TBAD, 1.65 g, 7.04 mmol) and triphenylphosphine (2.35 g, 8.96 mmol) were dissolved in dry THF (25 mL) at room temperature under $N_2$ atmosphere. A solution of methyl 3-(hydroxylmethyl)bicyclo[1.1.1]pentane-1-carboxylate [180464-87-3] (1.0 g, 6.4 mmol) in dry THF (5 mL) was added dropwise (exothermic). The reaction mixture was stirred at room temperature for 3 h. The solvent was evaporated under reduced pressure and the residual yellow oil was purified by column chromatography on silica gel (100 g) using a gradient of EtOAc:EtOH(3:1)/heptane 0/100 to 50/50. The product fractions were combined and evaporated under reduced pressure. The residue was triturated with a small amount of $Et_2O$. The solid was filtered off and washed with a small amount of $Et_2O$ and dried under vacuum at 50° C. to give methyl 3-((3-methoxy-5-nitrophenoxy)methyl)bicyclo[1.1.1]pentane-1-carboxylate 9a (1.06 g).

Synthesis of Intermediate 9b:

A solution of methyl 3-((3-methoxy-5-nitrophenoxy)methyl)bicyclo[1.1.1]pentane-1-carboxylate 9a (1.06 g, 3.44 mmol) in MeOH (150 mL) containing a catalytic amount of 10% Pd/C (366 mg, 0.34 mmol) was hydrogenated under atmospheric pressure of $H_2$ at room temperature for 10 min. The catalyst was removed by filtration over a short pad of Celite® under $N_2$-atmosphere and the filter cake was rinsed several times with MeOH. The combined filtrates were evaporated to give methyl 3-((3-amino-5-methoxyphenoxy)methyl)bicyclo[1.1.1]pentane-1-carboxylate 9b (961 mg) as a black oil which was used without further purification in the next step.

Synthesis of Intermediate 9c:

A mixture of 2-bromo-2-(4-chlorophenyl)-1-(6-(trifluoromethoxy)indolin-1-yl)ethanone 1c (1.16 g, 2.67 mmol), methyl 3-((3-amino-5-methoxyphenoxy)methyl)bicyclo[1.1.1]pentane-1-carboxylate 9b (961 mg, 3.47 mmol) and diisopropylethylamine (689 µL, 4.0 mmol) in $CH_3CN$ (50 mL) was stirred at 80° C. overnight. The solvent was evaporated under reduced pressure and the residue was dissolved in $CH_2Cl_2$. The organic solution was washed with 1N HCl and water, dried over $MgSO_4$, filtered, and evaporated under reduced pressure. The residue was purified by column chromatography on silica gel (100 g) using a gradient of EtOAc:EtOH(3:1)/heptane 0/100 to 50/50. The product fractions were combined and evaporated under reduced pressure. The residue was suspended in a small amount of heptane/EtOAc 10/1 and the solid was filtered off and washed with a small amount of heptane. The solids were dried under vacuum at 50° C. to give methyl 3-((3-((1-(4-chlorophenyl)-2-oxo-2-(6-(trifluoromethoxy)indolin-1-yl)ethyl)amino)-5-methoxyphenoxy)methyl)bicyclo[1.1.1]pentane-1-carboxylate 9c (1.21 g) as a white powder.

Synthesis of Compound 9 and Separation into Enantiomers 9A and 9B:

LiOH (92 mg, 3.84 mmol) was added to a solution of methyl 3-((3-((1-(4-chlorophenyl)-2-oxo-2-(6-(trifluoromethoxy)indolin-1-yl)ethyl)amino)-5-methoxyphenoxy)methyl)bicyclo[1.1.1]pentane-1-carboxylate 9c (1.21 g, 1.92 mmol) in a solvent mixture of MeOH (20 mL), THF (40 mL) and water (20 mL). The reaction mixture was stirred at room temperature for 4 h. 1N HCl (1 mL) was added and the organic volatiles were evaporated under reduced pressure. The residual aqueous mixture was diluted with water, acidified with 1N HCl to pH 2, and extracted twice with $Et_2O$. The combined organic layers were dried over $MgSO_4$, filtered, and evaporated under reduced pressure. The residue was dried under vacuum at 50° C. to give 3-((3-((1-(4-chlorophenyl)-2-oxo-2-(6-(trifluoro-methoxy)indolin-1-yl)ethyl)amino)-5-methoxyphenoxy)methyl)bicyclo[1.1.1]pentane-1-carboxylic acid (Compound 9, 1.06 g) as a pale yellow solid.

The enantiomers of Compound 9 (994 mg) were separated by preparative chiral SFC (Stationary phase: Chiralcel® Diacel OD 20×250 mm, mobile phase: $CO_2$, EtOH+0.4% $iPrNH_2$). The product fractions were combined and evaporated under reduced pressure. The first eluted product was partitioned between EtOAc and water. 1N HCl was added and the layers were separated. The aqueous layer was extracted again with EtOAc. The combined organic layers were dried over $MgSO_4$, filtered, evaporated under reduced pressure and dried under vacuum at 50° C. to give Enantiomer 9A (353 mg). The second eluted product was partitioned between EtOAc and water. 1N HCl was added and the layers were separated. The aqueous layer was extracted again with EtOAc. The combined organic layers were dried over MgSO$_4$, filtered, evaporated under reduced pressure and dried under vacuum at 50° C. to give Enantiomer 9B (193 mg).

Compound 9:

$^1$H NMR (360 MHz, DMSO-d$_6$) δ ppm 1.92 (s, 6H) 3.06-3.27 (m, 2H) 3.62 (s, 3H) 3.87 (s, 2H) 4.06 (td, J=10.3, 7.1 Hz, 1H) 4.52 (td, J=10.2, 6.6 Hz, 1H) 5.58 (d, J=8.8 Hz, 1H) 5.75 (t, J=2.0 Hz, 1H) 5.92-5.97 (m, 2H) 6.46 (d, J=9.1 Hz, 1H) 7.01 (dd, J=8.2, 1.6 Hz, 1H) 7.34 (d, J=8.1 Hz, 1H) 7.41-7.47 (m, 2H) 7.51-7.58 (m, 2H) 8.03 (br s, 1H) 12.37 (br s, 1H)

LC/MS (method LC-A): R$_t$ 1.09 min, MH$^+$ 617

Enantiomer 9A:

$^1$H NMR (360 MHz, DMSO-d$_6$) δ ppm 1.92 (s, 6H) 3.07-3.25 (m, 2H) 3.61 (s, 3H) 3.87 (s, 2H) 3.98-4.11 (m, 1H) 4.51 (td, J=10.2, 6.4 Hz, 1H) 5.57 (d, J=8.8 Hz, 1H) 5.75 (t, J=2.0 Hz, 1H) 5.92-5.96 (m, 2H) 6.46 (d, J=9.1 Hz, 1H) 7.01 (dd, J=8.1, 1.5 Hz, 1H) 7.33 (d, J=8.1 Hz, 1H) 7.44 (d, J=8.4 Hz, 2H) 7.50-7.59 (m, 2H) 8.03 (br s, 1H) 12.37 (br s, 1H)

LC/MS (method LC-B): R$_t$ 1.91 min, MH$^+$ 617

$[α]_D^{20}$: −43.6° (c 0.5, DMF)

Chiral SFC (method SFC-D): R$_t$ 5.26 min, MH$^+$ 617 chiral purity 98.6%.

Enantiomer 9B:

$^1$H NMR (360 MHz, DMSO-d$_6$) δ ppm 1.93 (s, 6H) 3.08-3.25 (m, 2H) 3.62 (s, 3H) 3.88 (s, 2H) 4.00-4.11 (m, 1H) 4.52 (td, J=10.2, 6.6 Hz, 1H) 5.58 (d, J=8.8 Hz, 1H) 5.76 (t, J=1.8 Hz, 1H) 5.92-5.98 (m, 2H) 6.47 (d, J=8.8 Hz, 1H) 7.01 (dd, J=8.1, 1.5 Hz, 1H) 7.33 (d, J=8.4 Hz, 1H) 7.44 (d, J=8.4 Hz, 2H) 7.51-7.60 (m, 2H) 8.04 (br s, 1H) 12.38 (br s, 1H)

LC/MS (method LC-B): R$_t$ 1.91 min, MH$^+$ 617

$[α]_D^{20}$: +42.2° (c 0.41, DMF)

Chiral SFC (method SFC-D): R$_t$ 6.47 min, MH$^+$ 617 chiral purity 99.5%.

Example 10: Synthesis of (1s,3s)-3-((3-((1-(4-chlorophenyl)-2-oxo-2-(6-(trifluoro-methoxy)indolin-1-yl)ethyl)amino)-5-methoxyphenoxy)methyl)cyclobutenecarboxylic Acid (Compound 10) and Chiral Separation into Enantiomers 10A and 10B

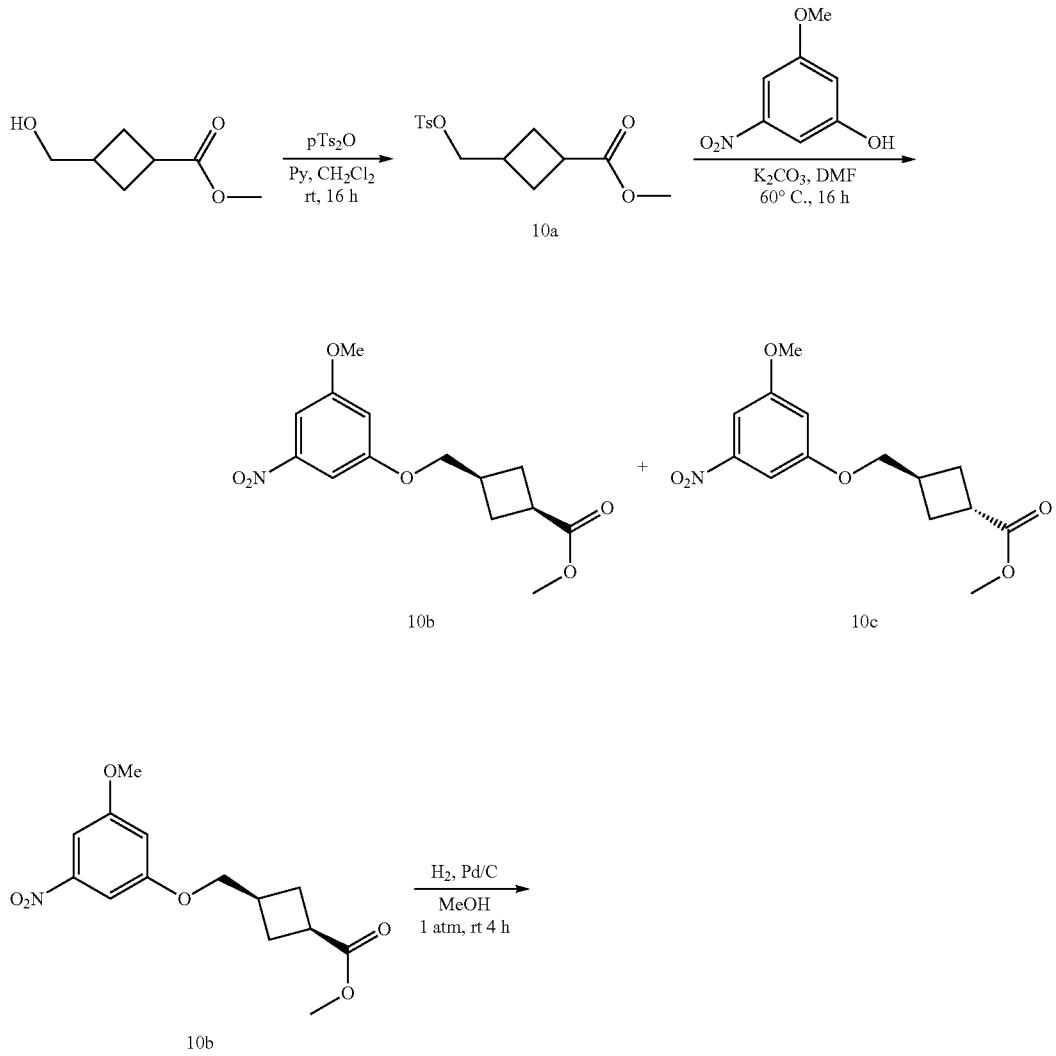

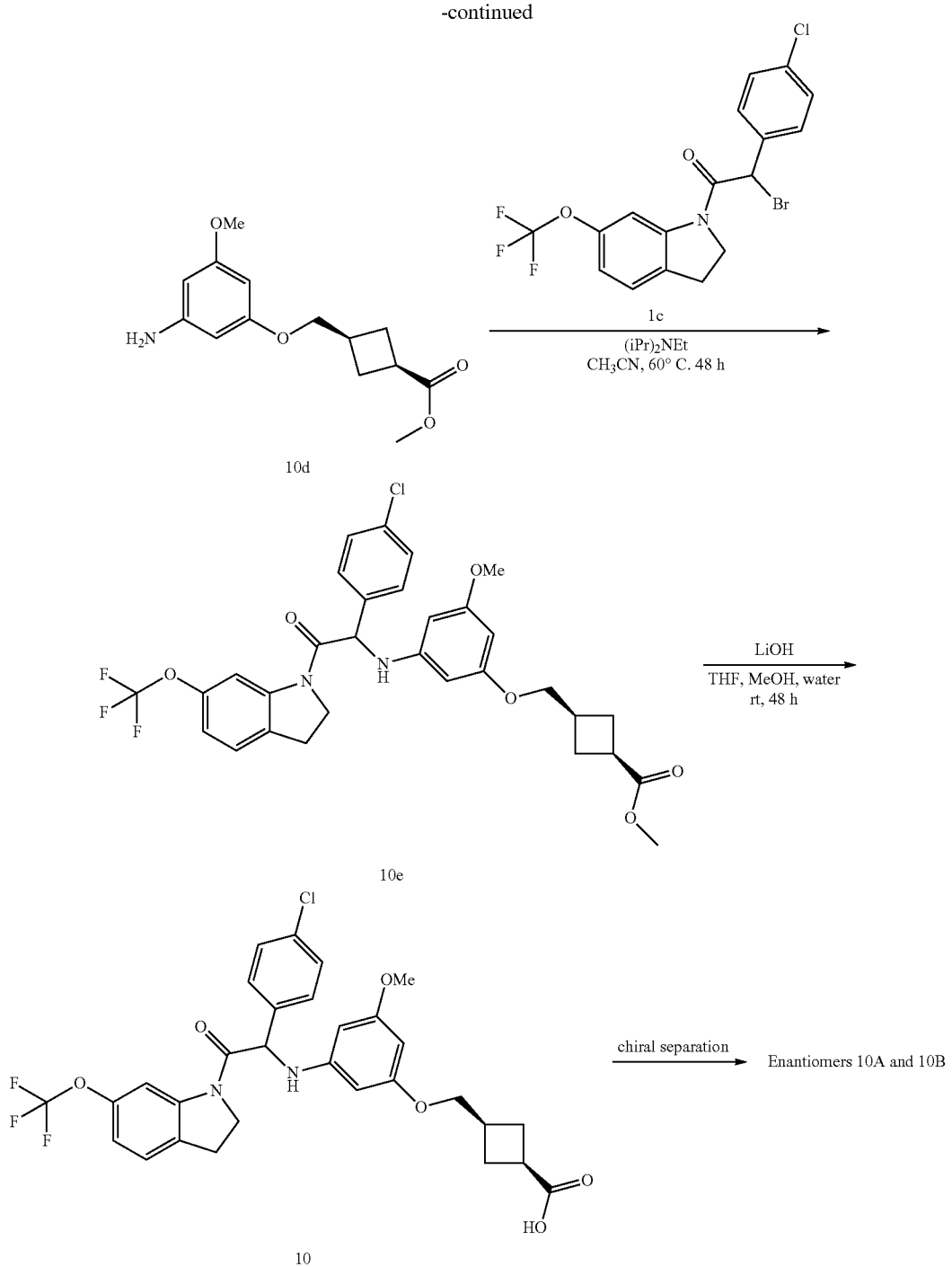

Synthesis of Intermediate 10a:

Under a $N_2$ flow, to a solution of methyl 3-(hydroxymethyl)cyclobutanecarboxylate [89941-55-9] (1.4 g, 9.71 mmol) in $CH_2Cl_2$ (20 mL) were added pyridine (1.17 mL) and tosyl anhydride (3.49 g, 10.682 mmol). The mixture was stirred for 16 h at room temperature. The mixture was concentrated under vacuum, suspended in diethyl ether (200 mL) and washed with 0.5 M hydrochloric acid (2×50 mL), a saturated solution of sodium hydrogen carbonate (2×50 mL), and brine (50 mL). The mixture was dried over sodium sulfate, filtered and concentrated under reduced pressure to yield methyl 3-((tosyloxy)methyl)cyclobutanecarboxylate 10a (2.15 g). The compound was used as such in the next step.

Synthesis of Intermediates 10b and 10c:

3-((tosyloxy)methyl)cyclobutanecarboxylate 10a (2.15 g, 7.206 mmol) was added dropwise to a mixture of 3-methoxy-5-nitrophenol [7145-49-5] (1.22 g, 7.206 mmol) and $K_2CO_3$ (1.5 g, 10.809 mmol) in DMF (14 mL). The mixture was stirred at 60° C. for 16 h. The mixture was diluted with water and extracted with EtOAc. The organic layer was washed with water, dried over $MgSO_4$, filtered and the solvent was evaporated under reduced pressure. Purification was performed by flash chromatography on silica gel (15-40 μm, 80 g, heptane/EtOAc 85/15 to 80/20). The pure fractions were combined and evaporated to dryness. The stereoisomers were separated via chiral SFC (Stationary phase: Chiralpack® AD-H 5 μm 250×30 mm, mobile phase: 55% $CO_2$, 45% MeOH) to give (1s,3s)-methyl 3-((3-methoxy-5-nitrophenoxy)methyl)cyclobutanecarboxylate 10b (541 mg) and (1r,3r)-methyl 3-((3-methoxy-5-nitrophenoxy)methyl)cyclobutanecarboxylate 10c (428 mg).

Synthesis of Intermediate 10d:

A solution of (1s,3s)-methyl 3-((3-methoxy-5-nitrophenoxy)methyl)cyclobutane-carboxylate 10b (530 mg, 1.795 mmol) in MeOH (10 mL) containing a catalytic amount of 10% Pd/C (191 mg, 0.179 mmol) was hydrogenated under atmospheric pressure of $H_2$ at room temperature for 4 h. The catalyst was removed by filtration over a short pad of Celite® and the filter cake was rinsed several times with MeOH. The combined filtrates were evaporated under reduced pressure to give (1s,3s)-methyl 3-((3-amino-5-methoxyphenoxy)methyl)cyclobutanecarboxylate 10d (480 mg). The compound was used as such in the next step.

Synthesis of Intermediate 10e:

A mixture of 2-bromo-2-(4-chlorophenyl)-1-(6-(trifluoromethoxy)indolin-1-yl)ethanone 1c (580 mg, 1.334 mmol), (1s,3s)-methyl 3-((3-amino-5-methoxyphenoxy)methyl)cyclobutanecarboxylate 10d (460 mg, 1.734 mmol) and diisopropylethylamine (460 μL, 2.667 mmol) in $CH_3CN$ (10 mL) was stirred at 60° C. for 48 h. The mixture was concentrated under reduced pressure and taken-up with EtOAc. The organic layer was washed with 1N HCl and water, dried over $MgSO_4$, filtered and the solvent was evaporated under vacuum to give, after crystallization from $Et_2O$/diisopropyl ether (1s,3s)-methyl 3-((3-((1-(4-chlorophenyl)-2-oxo-2-(6-(trifluoromethoxy)indolin-1-yl)ethyl)amino)-5-methoxyphenoxy)methyl)cyclobutene-carboxylate 10e (625 mg).

Synthesis of Compound 10 and Chiral Separation into Enantiomers 10A and 10B:

At 0° C., LiOH monohydrate (127 mg, 3.029 mmol) was added portionwise to a solution of (1s,3s)-methyl 3-((3-((1-(4-chlorophenyl)-2-oxo-2-(6-(trifluoromethoxy)-indolin-1-yl)ethyl)amino)-5-methoxyphenoxy)methyl)cyclobutanecarboxylate 10e (625 mg, 1.01 mmol) in THF/water/MeOH (1/1/1) (15 mL). The reaction mixture was stirred at room temperature for 48 h. The mixture was cooled to 0° C. and was diluted with water. 3N HCl was added to acidify the solution and the mixture was extracted with EtOAc. The combined organic layers were dried over $MgSO_4$, filtered, and concentrated under reduced pressure. The residue was crystallized from $Et_2O$/diisopropyl ether to give (1s,3s)-3-((3-((1-(4-chlorophenyl)-2-oxo-2-(6-(trifluoromethoxy)indolin-1-yl)ethyl)amino)-5-methoxyphenoxy)methyl)cyclobutene-carboxylic acid (Compound 10, 440 mg). The two enantiomers were separated via chiral SFC (Stationary phase: Whelk® O1 (S,S) 5 μm 250×21.1 mm, mobile phase: 58% $CO_2$, 42% MeOH) to give, after solidification from heptane/diisopropyl ether/ether, the first eluted Enantiomer 10A (116 mg) and the second eluted Enantiomer 10B (119 mg).

Compound 10:

$^1$H NMR (500 MHz, DMSO-$d_6$) δ ppm 1.87-1.99 (m, 2H) 2.18-2.30 (m, 2H) 2.53-2.61 (m, 1H) 2.97 (quin, J=8.9 Hz, 1H) 3.08-3.27 (m, 2H) 3.62 (s, 3H) 3.78 (br d, J=6.3 Hz, 2H) 4.05 (td, J=10.4, 7.2 Hz, 1H) 4.52 (td, J=10.3, 6.5 Hz, 1H) 5.57 (d, J=8.8 Hz, 1H) 5.72-5.78 (m, 1H) 5.94 (s, 2H) 6.45 (br d, J=8.8 Hz, 1H) 6.95-7.06 (m, 1H) 7.34 (d, J=8.2 Hz, 1H) 7.44 (d, J=8.2 Hz, 2H) 7.55 (d, J=8.5 Hz, 2H) 8.04 (s, 1H) 12.08 (br s, 1H)

LC/MS (method LC-D): $R_t$ 2.94 min, $MH^+$ 605

MP=128° C.

Enantiomer 10A:

$^1$H NMR (500 MHz, DMSO-$d_6$) δ ppm 1.84-1.97 (m, 2H) 2.15-2.30 (m, 2H) 2.53-2.61 (m, 1H) 2.94 (quin, J=8.9 Hz, 1H) 3.07-3.25 (m, 2H) 3.61 (s, 3H) 3.77 (br d, J=6.3 Hz, 2H) 4.05 (td, J=10.4, 6.9 Hz, 1H) 4.52 (td, J=10.3, 6.1 Hz, 1H) 5.57 (d, J=8.8 Hz, 1H) 5.74 (t, J=1.9 Hz, 1H) 5.93 (s, 2H) 6.44 (d, J=8.8 Hz, 1H) 7.01 (dd, J=8.0, 1.4 Hz, 1H) 7.33 (d, J=8.2 Hz, 1H) 7.44 (d, J=8.5 Hz, 2H) 7.55 (d, J=8.2 Hz, 2H) 8.03 (s, 1H)

LC/MS (method LC-C): $R_t$ 3.08 min, $MH^+$ 605

$[\alpha]_D^{20}$: −44.0 (c 0.314, DMF)

Chiral SFC (method SFC-J): $R_t$ 1.63 min, $MH^+$ 605, chiral purity 100%.

Enantiomer 10B:

$^1$H NMR (500 MHz, DMSO-$d_6$) δ ppm 1.85-1.97 (m, 2H) 2.17-2.28 (m, 2H) 2.53-2.58 (m, 1H) 2.94 (quint, J=8.8 Hz, 1H) 3.07-3.24 (m, 2H) 3.61 (s, 3H) 3.72-3.82 (m, 2H) 4.05 (td, J=10.4, 7.3 Hz, 1H) 4.52 (td, J=10.4, 6.9 Hz, 1H) 5.57 (d, J=8.8 Hz, 1H) 5.72-5.77 (m, 1H) 5.93 (s, 2H) 6.44 (d, J=8.8 Hz, 1H) 7.01 (dd, J=8.0, 1.4 Hz, 1H) 7.33 (d, J=7.9 Hz, 1H) 7.44 (d, J=8.5 Hz, 2H) 7.55 (d, J=8.2 Hz, 2H) 8.03 (s, 1H)

LC/MS (method LC-C): $R_t$ 3.08 min, $MH^+$ 605

$[\alpha]_D^{20}$: +45.5° (c 0.308, DMF)

Chiral SFC (method SFC-J): $R_t$ 2.14 min, $MH^+$ 605, chiral purity 99.57%.

Example 11: Synthesis of (1r,3r)-3-((3-((1-(4-chlorophenyl)-2-oxo-2-(6-(trifluoromethoxy)indolin-1-yl)ethyl)amino)-5-methoxyphenoxy)methyl)cyclobutene-Carboxylic Acid (Compound 11) and Chiral Separation into Enantiomers 11A and

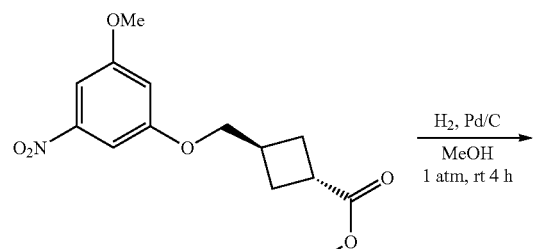

10c

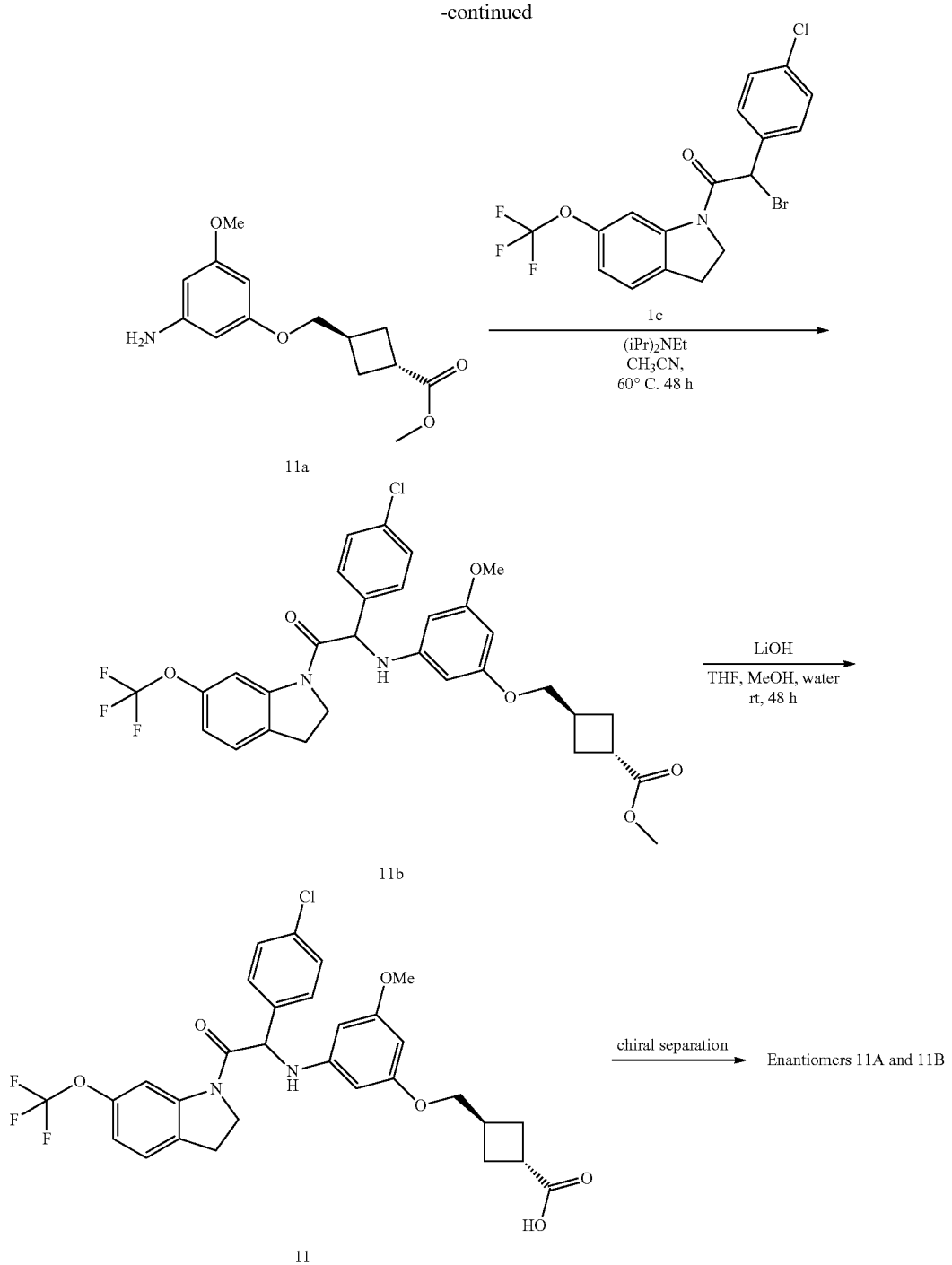

Synthesis of Intermediate 11a:

A solution of (1r,3r)-methyl 3-((3-methoxy-5-nitrophenoxy)methyl)cyclobutene-carboxylate 10c (410 mg, 1.388 mmol) in MeOH (10 mL) containing a catalytic amount of 10% Pd/C (148 mg, 0.139 mmol) was hydrogenated under atmospheric pressure of $H_2$ at room temperature for 4 h. The catalyst was removed by filtration over a short pad of Celite® and the filter cake was rinsed several times with MeOH. The combined filtrates were evaporated under reduced pressure to give (1r,3r)-methyl 3-((3-amino-5-methoxyphenoxy)methyl)cyclobutanecarboxylate 11a (370 mg). The compound was used as such in the next step.

Synthesis of Intermediate 11b:

A mixture of 2-bromo-2-(4-chlorophenyl)-1-(6-(trifluoromethoxy)indolin-1-yl)ethanone 1c (460 mg, 1.058 mmol), (1r,3r)-methyl 3-((3-amino-5-methoxyphenoxy)methyl)cyclobutanecarboxylate 11a (365 mg, 1.376 mmol) and diisopropylethylamine (365 µL, 2.117 mmol) in $CH_3CN$ (8 mL) was stirred at 60° C. for 48 h. The mixture was concentrated under reduced pressure and taken-up with EtOAc. The organic layer was washed with 1N HCl and water, dried over MgSO₄, filtered and the solvent was evaporated under vacuum to give, after crystallization from Et₂O/diisopropyl ether (1r,3r)-methyl 3-((3-((1-(4-chlorophenyl)-2-oxo-2-(6-(trifluoromethoxy)indolin-1-yl)ethyl)amino)-5-methoxyphenoxy)methyl)cyclobutanecarboxylate 11b (515 mg).
Synthesis of Compound 11 and Chiral Separation into Enantiomers 11A and 11B:

At 0° C., LiOH monohydrate (105 mg, 2.496 mmol) was added portionwise to a solution of ((1r,3r)-methyl 3-((3-((1-(4-chlorophenyl)-2-oxo-2-(6-(trifluoromethoxy)-indolin-1-yl)ethyl)amino)-5-methoxyphenoxy)methyl)cyclobutanecarboxylate 11b (515 mg, 0.832 mmol) in THF/water/MeOH (1/1/1) (15 mL). The reaction mixture was stirred at room temperature for 48 h. The mixture was cooled to 0° C. and was diluted with water. 3N HCl was added to acidify the solution and the mixture was extracted with EtOAc. The combined organic layers were dried over MgSO₄, filtered, and concentrated under reduced pressure. The residue was purified by flash chromatography on silica gel (15-40 µm, 24 g, CH₂Cl₂/CH₃OH 100/0 to 98/2). The pure fractions were combined and evaporated to dryness to give (1r,3r)-3-((3-((1-(4-chlorophenyl)-2-oxo-2-(6-(trifluoromethoxy)indolin-1-yl)ethyl)amino)-5-methoxyphenoxy)methyl)cyclobutanecarboxylic acid (Compound 11, 460 mg). The two enantiomers were separated via chiral SFC (Stationary phase: Whelk® O1 (S,S) 5 µm 250×21.1 mm, mobile phase: 58% CO₂, 42% MeOH) to give, after crystallization from ether/diisopropyl ether, the first eluted Enantiomer 11A (121 mg) and the second eluted Enantiomer 11B (120 mg).
Compound 11:
¹H NMR (500 MHz, DMSO-d₆) δ ppm 1.92-2.04 (m, 2H) 2.21-2.31 (m, 2H) 2.57-2.62 (m, 1H) 3.04-3.26 (m, 3H) 3.63 (s, 3H) 3.88 (br d, J=6.9 Hz, 2H) 4.00-4.11 (m, 1H) 4.47-4.58 (m, 1H) 5.57 (d, J=8.8 Hz, 1H) 5.78 (s, 1H) 5.96 (br d, J=9.7 Hz, 2H) 6.45 (br d, J=8.8 Hz, 1H) 7.02 (br d, J=8.2 Hz, 1H) 7.34 (d, J=8.2 Hz, 1H) 7.45 (d, J=8.2 Hz, 2H) 7.55 (d, J=8.5 Hz, 2H) 8.04 (s, 1H) 12.12 (br s, 1H)
LC/MS (method LC-D): $R_t$ 2.95 min, MH⁺ 605
Enantiomer 11A:
¹H NMR (500 MHz, DMSO-d₆) δ ppm 1.94-2.03 (m, 2H) 2.21-2.31 (m, 2H) 2.55-2.62 (m, 1H) 3.04-3.25 (m, 3H) 3.62 (s, 3H) 3.87 (d, J=7.3 Hz, 2H) 4.04 (td, J=10.4, 6.9 Hz, 1H) 4.52 (td, J=10.2, 6.3 Hz, 1H) 5.57 (d, J=8.8 Hz, 1H) 5.78 (t, J=1.9 Hz, 1H) 5.94 (s, 1H) 5.96 (s, 1H) 6.45 (d, J=8.5 Hz, 1H) 7.01 (dd, J=8.2, 1.6 Hz, 1H) 7.33 (d, J=8.2 Hz, 1H) 7.44 (d, J=8.5 Hz, 2H) 7.55 (d, J=8.5 Hz, 2H) 8.03 (s, 1H) 12.12 (br s, 1H)
LC/MS (method LC-C): $R_t$ 3.08 min, MH⁺ 605
$[α]_D^{20}$: −43.3° (c 0.319, DMF)
Chiral SFC (method SFC-J): $R_t$ 1.73 min, MH⁺ 605, chiral purity 100%.
Enantiomer 11B:
¹H NMR (500 MHz, DMSO-d₆) δ ppm 1.92-2.02 (m, 2H) 2.21-2.32 (m, 2H) 2.55-2.62 (m, 1H) 3.04-3.25 (m, 3H) 3.62 (s, 3H) 3.87 (d, J=6.9 Hz, 2H) 4.05 (td, J=10.3, 7.1 Hz, 1H) 4.52 (td, J=10.3, 6.5 Hz, 1H) 5.57 (d, J=8.8 Hz, 1H) 5.78 (t, J=1.9 Hz, 1H) 5.94 (s, 1H) 5.96 (s, 1H) 6.45 (br d, J=8.8 Hz, 1H) 7.01 (br d, J=8.2 Hz, 1H) 7.33 (d, J=8.2 Hz, 1H) 7.44 (d, J=8.5 Hz, 2H) 7.55 (d, J=8.5 Hz, 2H) 8.03 (s, 1H) 12.16 (br s, 1H)
LC/MS (method LC-C): $R_t$ 3.08 min, MH⁺ 605
$[α]_D^{20}$: +45.5° (c 0.323, DMF)
Chiral SFC (method SFC-J): $R_t$ 2.36 min, MH⁺ 605, chiral purity 99.61%.

Example 12: Synthesis of 3-(3-((1-(4-chlorophenyl)-2-oxo-2-(6-(trifluoromethoxy)indolin-1-yl)ethyl)amino)-5-methoxyphenoxy)propanoic Acid (Compound 12) and Chiral Separation into Enantiomers 12A and 12B

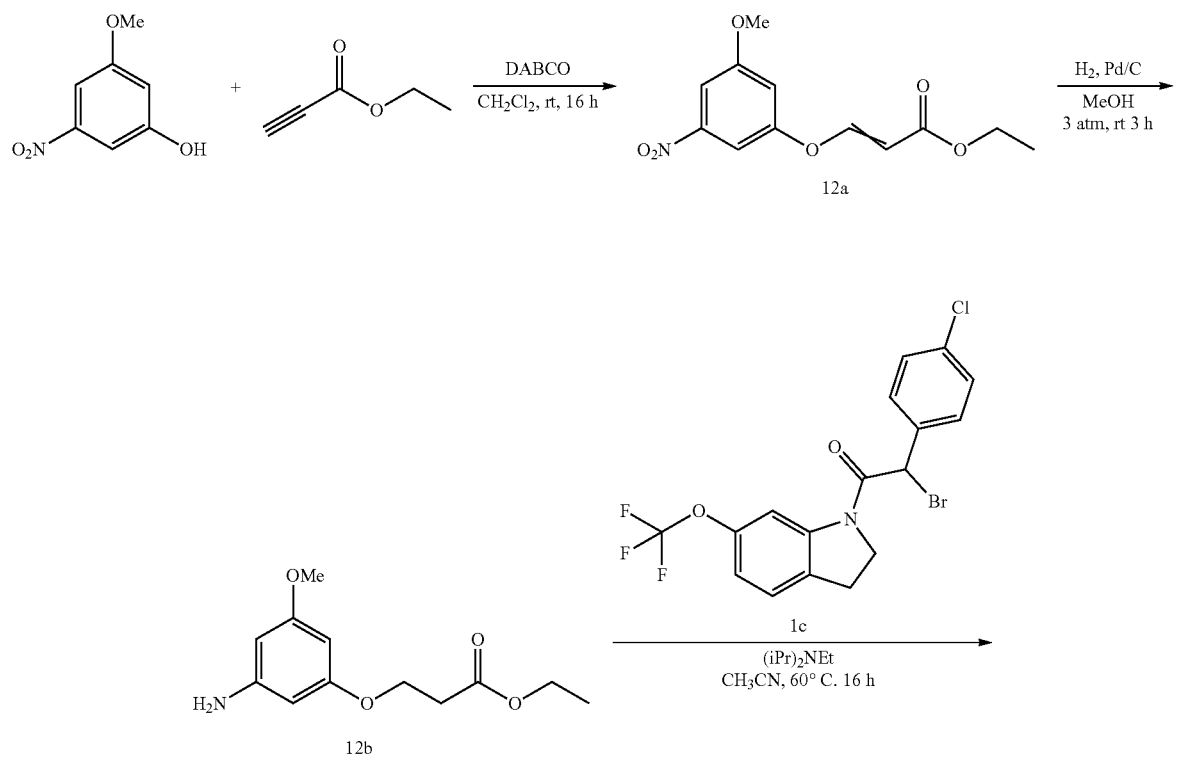

-continued

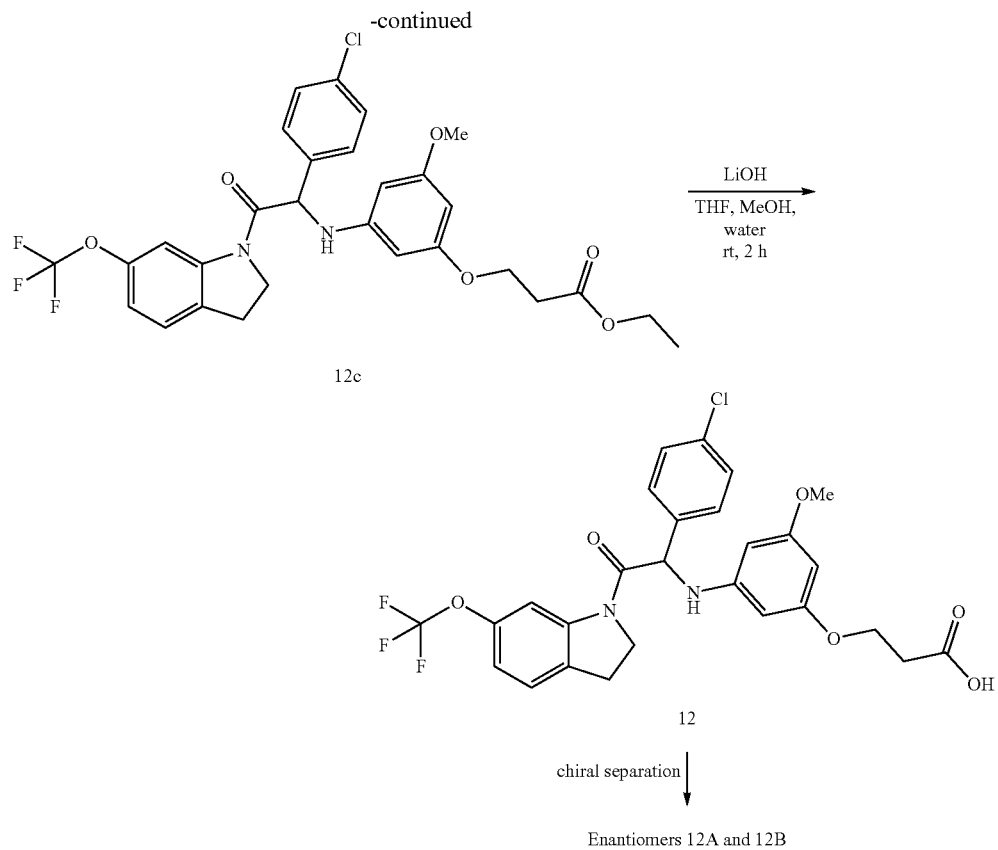

chiral separation

Enantiomers 12A and 12B

Synthesis of Intermediate 12a:

1,4-diazabicyclo[2.2.2]octane (66 mg, 0.591 mmol) was added to a solution of 3-methoxy-5-nitrophenol [7145-49-5] (2.0 g, 11.825 mmol), ethylacetylenecarboxylate (1.2 mL, 11.825 mmol) in $CH_2Cl_2$ (20 mL). The mixture was stirred at room temperature for 16 h. The mixture was poured out into water and the layers were decanted. The organic layer was washed with water, brine, dried over $MgSO_4$, filtered and the solvent was evaporated under reduced pressure to give ethyl 3-(3-methoxy-5-nitrophenoxy)acrylate 12a (3.22 g, E/Z mixture).

Synthesis of Intermediate 12b:

A mixture of ethyl 3-(3-methoxy-5-nitrophenoxy)acrylate 12a (3.2 g, 11.97 mmol) and Pd/C (10%) (2.5 g, 2.395 mmol) in $CH_3OH$ (100 mL) was hydrogenated under a pressure of 3 bar for 3 h. The catalyst was removed by filtration through a pad of Celite®. The filter cake was rinsed with $CH_3OH$ and the combined filtrates were concentrated under reduced pressure. Purification was performed by flash chromatography on silica gel (15-40 μm, 80 g, heptane/ EtOAc 75/25). The pure fractions were combined and evaporated to dryness to give ethyl 3-(3-amino-5-methoxyphenoxy)propanoate 12b (1.8 g).

Synthesis of Intermediate 12c:

A mixture of 2-bromo-2-(4-chlorophenyl)-1-(6-(trifluoromethoxy)indolin-1-yl)ethanone 1c (1.0 g, 2.301 mmol), ethyl 3-(3-amino-5-methoxyphenoxy)-propanoate 12b (716 mg, 2.991 mmol) and diisopropylethylamine (793 μL, 4.602 mmol) in $CH_3CN$ (29 mL) was stirred at 60° C. for 16 h. The mixture was concentrated under reduced pressure and taken-up with EtOAc. The organic layer was washed with 1N HCl and water, dried over $MgSO_4$, filtered and the solvent was evaporated under vacuum. Purification was performed by flash chromatography on silica gel (15-40 μm, 80 g, heptane/ EtOAc 75/25). The pure fractions were combined and evaporated to dryness to give 3-(3-((1-(4-chlorophenyl)-2-oxo-2-(6-(trifluoromethoxy)indolin-1-yl)ethyl)amino)-5-methoxyphenoxy)propanoic acid 12c (660 mg).

Synthesis of Compound 12 and Chiral Separation into Enantiomers 12A and 12B:

At 0° C., LiOH monohydrate (79 mg, 1.889 mmol) was added portionwise to a solution of 3-(3-((1-(4-chlorophenyl)-2-oxo-2-(6-(trifluoromethoxy)indolin-1-yl)ethyl) amino)-5-methoxyphenoxy)propanoic acid 12c (560 mg, 0.944 mmol) in THF/water/MeOH (1/1/1) (15 mL). The reaction mixture was stirred at room temperature for 2 h. The mixture was cooled to 0° C. and was diluted with water. 3N HCl was added to acidify the solution. The mixture was extracted with EtOAc. The combined organic layers were dried over $MgSO_4$, filtered, and concentrated under reduced pressure. The residue was purified via reverse phase (Stationary phase: YMC-DispoPack AT ODS-25: 120 g, mobile phase: Gradient from 75% $NH_4HCO_3$ 0.2%, 25% $CH_3CN$ to 35% $NH_4HCO_3$ 0.2%, 65% $CH_3CN$). The pure fractions were combined and evaporated to dryness to give 3-(3-((1-(4-chlorophenyl)-2-oxo-2-(6-(trifluoromethoxy)indolin-1-yl)ethyl)amino)-5-methoxyphenoxy)propanoic acid (Compound 12, 126 mg). The two enantiomers were separated on a 70 mg batch via chiral SFC (Stationary phase: Chiralcel® OD-H 5 μm 250×20 mm, mobile phase: 65% $CO_2$, 35% iPrOH (+0.3% $iPrNH_2$) to give, after freeze-drying in a mixture of $CH_3CN$ (2 mL)/water (8 mL), the first eluted Enantiomer 12A (30 mg) and the second eluted Enantiomer 12B (35 mg).

Compound 12:

¹H NMR (400 MHz, DMSO-d₆) δ ppm 2.56 (t, J=6.1 Hz, 2H) 3.04-3.26 (m, 2H) 3.61 (s, 3H) 3.95-4.11 (m, 3H) 4.43-4.61 (m, 1H) 5.56 (d, J=8.6 Hz, 1H) 5.74 (s, 1H) 5.94 (br d, J=7.1 Hz, 2H) 6.46 (d, J=9.1 Hz, 1H) 7.00 (br d, J=8.1 Hz, 1H) 7.33 (d, J=8.1 Hz, 1H) 7.43 (d, J=8.1 Hz, 2H) 7.55 (d, J=8.6 Hz, 2H) 8.03 (s, 1H)

LC/MS (method LC-C): $R_t$ 2.84 min, MH⁺ 565

Enantiomer 12A:

¹H NMR (500 MHz, DMSO-d₆) δ ppm 2.62 (br t, J=6.0 Hz, 2H) 3.09-3.24 (m, 2H) 3.62 (s, 3H) 4.00-4.10 (m, 3H) 4.47-4.57 (m, 1H) 5.58 (d, J=8.8 Hz, 1H) 5.75 (s, 1H) 5.95 (br d, J=6.6 Hz, 2H) 6.49 (br d, J=8.8 Hz, 1H) 7.02 (br d, J=8.2 Hz, 1H) 7.34 (d, J=8.2 Hz, 1H) 7.44 (d, J=8.5 Hz, 2H) 7.55 (d, J=8.5 Hz, 2H) 8.04 (s, 1H) 12.04-12.63 (m, 1H)

LC/MS (method LC-C): $R_t$ 2.83 min, MH⁺ 565

$[\alpha]_D^{20}$: −47.3° (c 0.275, DMF)

Chiral SFC (method SFC-K): $R_t$ 2.50 min, MH⁺ 565, chiral purity 100%.

Enantiomer 12B:

¹H NMR (500 MHz, DMSO-d₆) δ ppm 2.58-2.67 (m, 2H) 3.08-3.25 (m, 2H) 3.62 (s, 3H) 3.99-4.12 (m, 3H) 4.52 (td, J=10.3, 6.1 Hz, 1H) 5.58 (s, 1H) 5.75 (s, 1H) 5.95 (br d, J=6.6 Hz, 2H) 6.50 (br s, 1H) 7.02 (br d, J=7.9 Hz, 1H) 7.34 (d, J=8.2 Hz, 1H) 7.44 (d, J=8.5 Hz, 2H) 7.55 (d, J=8.5 Hz, 2H) 8.04 (s, 1H) 12.35 (br s, 1H)

LC/MS (method LC-C): $R_t$ 2.83 min, MH⁺ 565

$[\alpha]_D^{20}$: +41.8° (c 0.297, DMF)

Chiral SFC (method SFC-K): $R_t$ 4.34 min, MH⁺ 565, chiral purity 99.1%.

Example 13: Synthesis of 5-(3-((1-(4-chlorophenyl)-2-oxo-2-(6-(trifluoromethoxy)-indolin-1-yl)ethyl)amino)-5-methoxyphenoxy)pentanoic acid (Compound 13) and Chiral Separation into Enantiomers 13A and 13B

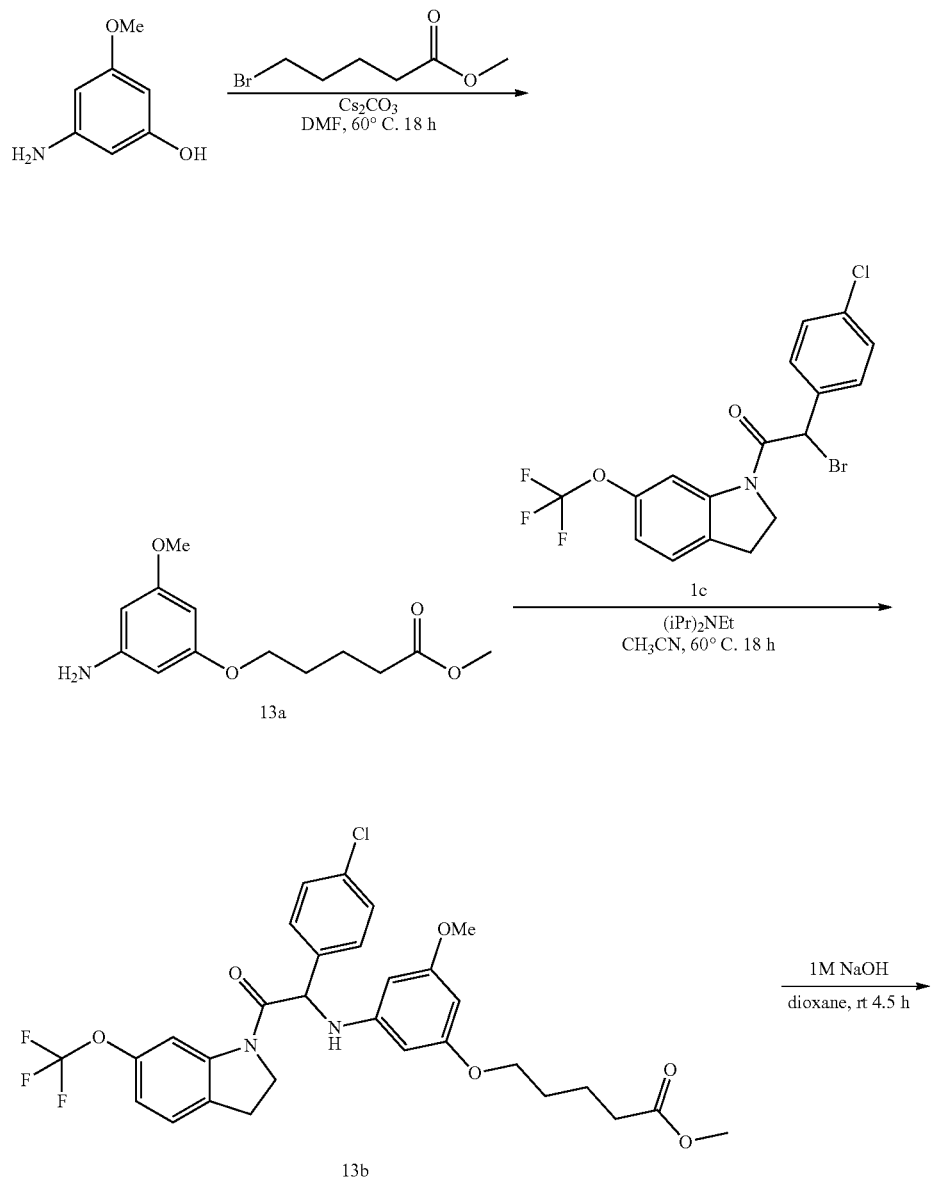

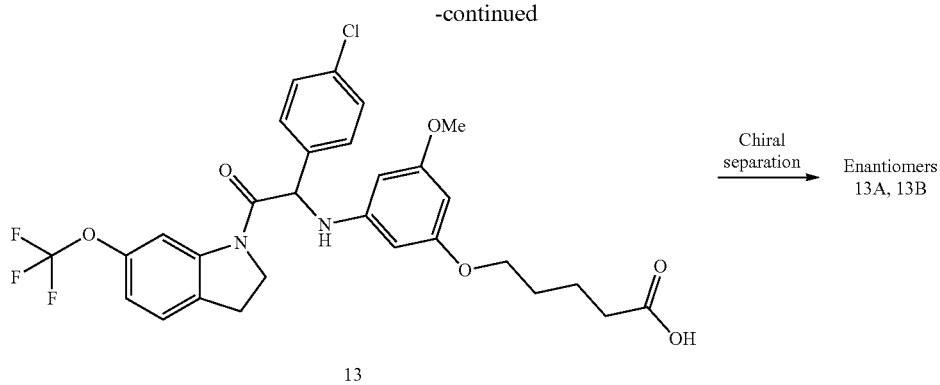

13

Synthesis of Intermediate 13a:

To a stirred solution of methyl 5-bromo-valerate [CAS 5454-83-1] (1.06 mL, 7.19 mmol) in DMF (25 mL) was added 3-amino-5-methoxyphenol [CAS 162155-27-3](1.0 g, 7.19 mmol) and $Cs_2CO_3$ (4.68 g, 14.4 mmol). The reaction was stirred at 60° C. for 18 h, and allowed to reach room temperature. The mixture was poured out into $H_2O$ (125 mL). The product was extracted (2×) with $CH_2Cl_2$. The combined organic layers were dried over $MgSO_4$, filtered, and the solvent was evaporated under reduced pressure. The residue was purified by flash chromatography on silica gel (25 g) using a gradient of heptane/EtOAc 100/0 to 50/50. The product fractions were combined, evaporated under reduced pressure and co-evaporated with $CH_3CN$. The product were dried under vacuum at 45° C. to provide methyl 5-(3-amino-5-methoxyphenoxy)pentanoate 13a (200 mg).

Synthesis of Intermediate 13b:

A mixture of 2-bromo-2-(4-chlorophenyl)-1-(6-(trifluoromethoxy)indolin-1-yl)ethanone 1c (340 mg, 0.78 mmol), methyl 5-(3-amino-5-methoxyphenoxy)pentanoate 13a (198 mg, 0.78 mmol) and diisopropylethylamine (270 µL, 1.56 mmol) in $CH_3CN$ (30 mL) was stirred at 60° C. for 18 h. The mixture was allowed to reach room temperature, and was poured out into water (150 mL). The product was extracted (2×) with $Et_2O$. The combined organic layers were washed with brine, dried over $MgSO_4$, filtered, and evaporated under reduced pressure. The residue was purified by flash chromatography on silica gel (40 g) using a gradient of heptane/EtOAc/EtOH 100/0/0 to 40/45/15. The product fractions were combined and evaporated under reduced pressure, and co-evaporated with dioxane to provide methyl 5-(3-((1-(4-chlorophenyl)-2-oxo-2-(6-(trifluoromethoxy)indolin-1-yl)ethyl)amino)-5-methoxyphenoxy)pentanoate 13b (475 mg).

Synthesis of Compound 13 and Separation into Enantiomers 13A and 13B:

1M NaOH in water (1.96 mL, 1.96 mmol) was added to a stirring solution of methyl 5-(3-((1-(4-chlorophenyl)-2-oxo-2-(6-(trifluoromethoxy)indolin-in-1-yl)ethyl)amino)-5-methoxyphenoxy)pentanoate 13b (475 mg, 0.78 mmol) in dioxane (5 mL). The reaction mixture was stirred at room temperature for 4.5 h. the reaction mixture was diluted with water (20 mL) 1N HCl (2.1 mL). After stirring for 10 min, the product was extracted with 2-Me-THF. The organic layer was separated, dried over $MgSO_4$, filtered, and evaporated under reduced pressure. The residue was purified by flash chromatography on silica gel (40 g) with a gradient of heptane/EtOAc/EtOH/HOAc 100/0/0/0 to 40/45/14.7/0.3. The product fractions were combined and evaporated under reduced pressure to a residual volume of ~7.5 mL, allowing precipitation of the reaction product. The solids were filtered off, washed (3×) with EtOAc/heptane 1/3 and dried under vacuum at 45° C. to provide 5-(3-((1-(4-chlorophenyl)-2-oxo-2-(6-(trifluoromethoxy)indolin-11-yl)ethyl)amino)-5-methoxyphenoxy)pentanoic acid (Compound 13, 139 mg) as a racemic mixture. The enantiomers of Compound 13 (112 mg) were separated via preparative chiral SFC (Stationary phase: Chiralpak® Diacel OD 20×250 mm, mobile phase: $CO_2$, EtOH+0.4% $iPrNH_2$). The fractions containing the first eluted product were combined, evaporated under reduced pressure, and co-evaporated with $CH_3CN$. The residue was lyophilized from a solvent mixture of $CH_3CN$ (1.5 mL) and water (1 mL) to provide Enantiomer 13A (39 mg). The fractions containing the second eluted product were combined, evaporated under reduced pressure, and evaporated with $CH_3CN$. The residue was lyophilized from $CH_3CN$ (1.75 mL) and water (1.25 mL) to provide Enantiomer 13B (33 mg).

Compound 13

$^1$H NMR (400 MHz, DMSO-$d_6$) δ ppm 1.55-1.69 (m, 4H) 2.25 (t, J=7.0 Hz, 2H) 3.07-3.26 (m, 2H) 3.62 (s, 3H) 3.83 (t, J=5.9 Hz, 2H) 4.05 (td, J=10.4, 7.2 Hz, 1H) 4.52 (td, J=10.3, 6.4 Hz, 1H) 5.56 (d, J=8.8 Hz, 1H) 5.75 (t, J=2.0 Hz, 1H) 5.91-5.97 (m, 2H) 6.42 (d, J=8.8 Hz, 1H) 7.01 (dd, J=8.3, 1.7 Hz, 1H) 7.33 (d, J=8.1 Hz, 1H) 7.38-7.48 (m, 2H) 7.55 (d, J=8.6 Hz, 2H) 8.03 (br s, 1H) 12.01 (s, 1H)

LC/MS (method LC-A): $R_t$ 1.13 min, MH$^+$ 593

Enantiomer 13A:

$^1$H NMR (400 MHz, DMSO-$d_6$) δ ppm 1.55-1.69 (m, 4H) 2.24 (t, J=7.0 Hz, 2H) 3.07-3.26 (m, 2H) 3.62 (s, 3H) 3.83 (t, J=5.9 Hz, 2H) 4.05 (td, J=10.5, 7.3 Hz, 1H) 4.52 (td, J=10.3, 6.4 Hz, 1H) 5.56 (d, J=8.8 Hz, 1H) 5.75 (t, J=2.1 Hz, 1H) 5.92-5.96 (m, 2H) 6.42 (d, J=8.6 Hz, 1H) 7.01 (dd, J=8.1, 1.5 Hz, 1H) 7.33 (d, J=8.1 Hz, 1H) 7.39-7.48 (m, 2H) 7.55 (d, J=8.6 Hz, 2H) 8.03 (br s, 1H) 12.02 (br s, 1H)

LC/MS (method LC-B): $R_t$ 2.08 min, MH$^+$ 593

$[α]_D^{20}$: −48.6° (c 0.43, DMF)

Chiral SFC (method SFC-D): $R_t$ 5.27 min, MH$^+$ 593 chiral purity 100%.

Enantiomer 13B:

$^1$H NMR (400 MHz, DMSO-$d_6$) δ ppm 1.55-1.69 (m, 4H) 2.24 (t, J=7.2 Hz, 2H) 3.04-3.25 (m, 2H) 3.62 (s, 3H) 3.83 (t, J=5.9 Hz, 2H) 4.05 (td, J=10.4, 7.2 Hz, 1 H) 4.52 (td, J=10.3, 6.2 Hz, 1H) 5.56 (d, J=8.8 Hz, 1H) 5.75 (t, J=2.0 Hz, 1H) 5.92-5.96 (m, 2H) 6.42 (d, J=8.8 Hz, 1H) 7.01 (dd, J=8.1, 1.5 Hz, 1H) 7.33 (d, J=8.1 Hz, 1H) 7.42-7.46 (m, 2H) 7.55 (d, J=8.6 Hz, 2H) 8.03 (br s, 1H) 12.00 (br s, 1H)
LC/MS (method LC-B): $R_t$ 2.08 min, MH+ 593
$[\alpha]_D^{20}$: +48.3° (c 0.42, DMF)
Chiral SFC (method SFC-D): $R_t$ 6.94 min, MH+ 593 chiral purity 100%.
Example 14: Synthesis of 5-(3-((1-(4-chlorophenyl)-2-oxo-2-(6-(trifluoro-methoxy)indolin-1-yl)ethyl)amino)-5-methoxyphenyl)pentanoic acid (Compound 14) and Chiral Separation into Enantiomers 14A and 14B
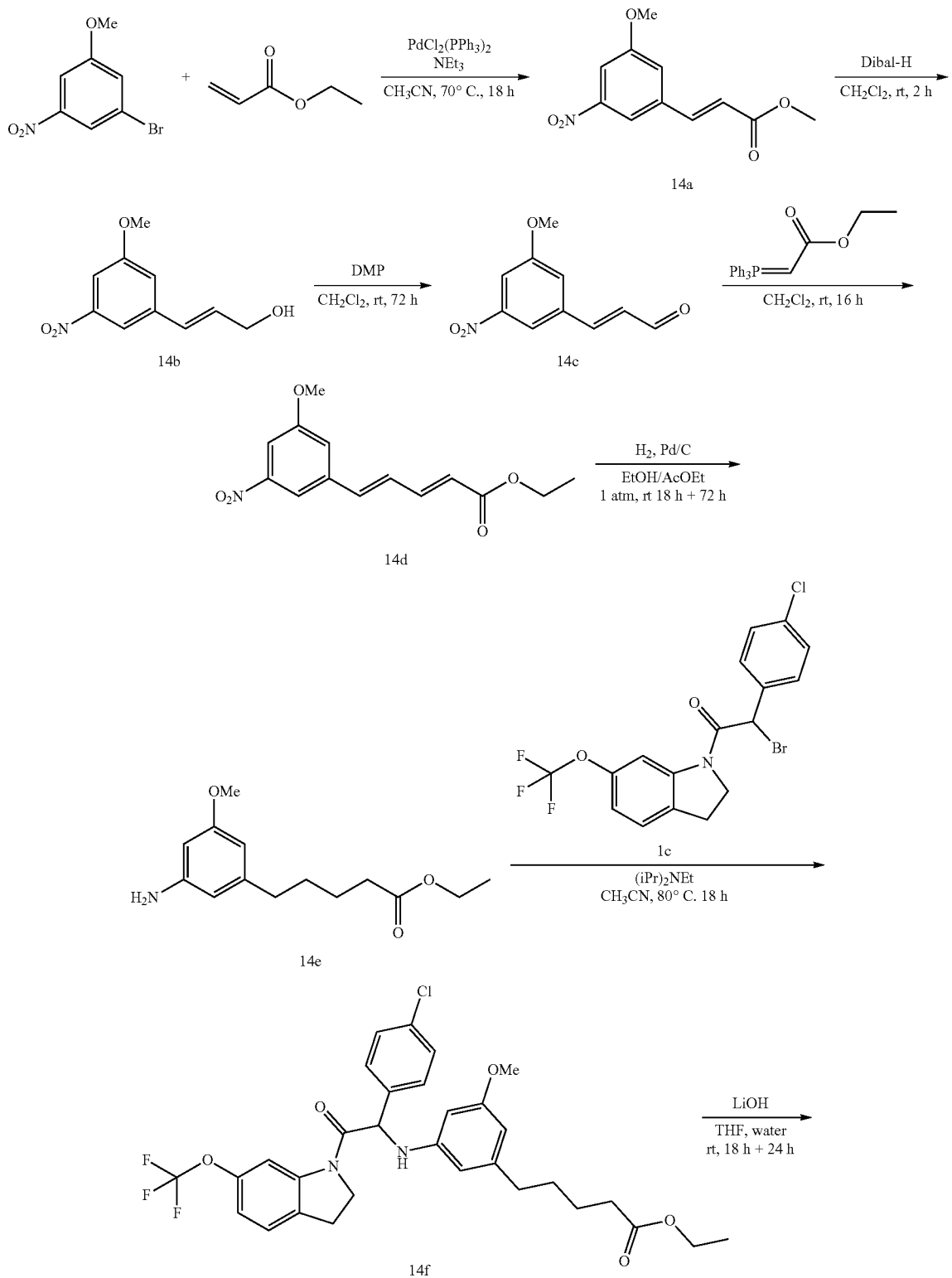

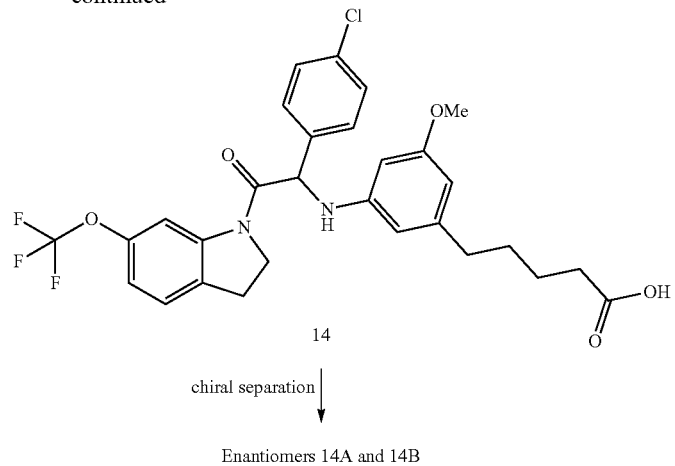

Enantiomers 14A and 14B

Synthesis of Intermediate 14a:

In a sealed tube under N₂ atmosphere, PdCl₂(PPh₃)₂ (1.5 g, 2.2 mmol) was added to a degased solution of 1-bromo-3-methoxy-5-nitrobenzene [CAS 16618-67-0](5.0 g, 22 mmol), methyl acrylate (6.0 mL, 67 mmol) in CH₃CN (45 ml) and triethylamine (12 mL). The reaction was stirred at 70° C. for 18 h. The mixture was concentrated under reduced pressure. The residue was purified by flash chromatography on silica gel (30 µm, 120 g, heptane/EtOAc gradient from 90/10 to 75/25) to give (E)-methyl 3-(3-methoxy-5-nitrophenyl)acrylate 14a (2.0 g).

Synthesis of Intermediate 14b:

Under N₂ at 0° C., diisobutyl aluminumhydride (1M in CH₂Cl₂) (20 mL, 20 mmol) was added dropwise to a solution of (E)-methyl 3-(3-methoxy-5-nitrophenyl)acrylate 14a (2.4 g, 10.12 mmol) in CH₂Cl₂ (65 ml). The reaction was slowly warmed to room temperature and stirred for 2 h. The mixture was quenched with HCl (3N) and extracted with CH₂Cl₂. The organic layer was dried over MgSO₄, filtered and concentrated under reduced pressure to give (E)-3-(3-methoxy-5-nitrophenyl)prop-2-en-1-ol 14b (2.1 g). The compound was used as such in the next step.

Synthesis of Intermediate 14c:

Under N₂ at 0° C., Dess-Martin Periodinane (24 mL, 11.04 mmol) was slowly added to a solution of (E)-3-(3-methoxy-5-nitrophenyl)prop-2-en-1-ol 14b (2.1 g, 10.04 mmol) in CH₂Cl₂ (64 mL) and the mixture was stirred at room temperature for 72 h. Water was added and the mixture was filtered. The filtrate was extracted with CH₂Cl₂, dried over MgSO₄ and evaporated until dryness to give (E)-3-(3-methoxy-5-nitrophenyl)acrylaldehyde 14c (2.5 g). The compound was used as such in the next step.

Synthesis of Intermediate 14d:

Under N₂, (carbethoxymethylene)triphenylphosphorane (5.0 g, 14.48 mmol) was added in one portion to a mixture of (E)-3-(3-methoxy-5-nitrophenyl)acrylaldehyde 14c (2.5 g, 9.65 mmol, 80% pure) in CH₂Cl₂ (62 mL) and stirred at room temperature for 16 h. The mixture was concentrated under reduced pressure. The residue was purified by flash chromatography on silica gel (30 µm, 80 g, heptane/EtOAc gradient from 85/15 to 60/30) to give (2E,4E)-ethyl 5-(3-methoxy-5-nitrophenyl)penta-2,4-dienoate 14d (2.1 g). The compound was used as such in the next step.

Synthesis of Intermediate 14e:

A mixture of (2E,4E)-ethyl 5-(3-methoxy-5-nitrophenyl)penta-2,4-dienoate 14d (1.9 g, 6.85 mmol) in EtOH (40 mL) and EtOAc (6.7 mL) was hydrogenated under an atmospheric pressure of H₂ for 18 h with Pd/C (10%) (0.73 g, 0.69 mmol) as a catalyst. The catalyst was removed by filtration through a pad of Celite®. The Celite® was washed with EtOAc and the combined filtrates were concentrated under vacuum. The residue was hydrogenated again in EtOH (40 mL) and EtOAc (6.7 mL) under an atmospheric pressure of H₂ for 72 h with Pd/C (10%) (0.73 g, 0.69 mmol) as a catalyst. The catalyst was removed by filtration through a pad of Celite®. The Celite® was washed with EtOAc and the combined filtrates were concentrated under vacuum to give ethyl 5-(3-amino-5-methoxyphenyl)pentanoate 14e (1.4 g). The compound was used as such in the next step.

Synthesis of Intermediate 14f:

A mixture of 2-bromo-2-(4-chlorophenyl)-1-(6-(trifluoromethoxy)indolin-1-yl)ethanone 1c (1.6 g, 3.71 mmol), ethyl 5-(3-amino-5-methoxyphenyl)pentanoate 14e (1.4 g, 5.57 mmol) and diisopropylethylamine (1.3 mL, 7.43 mmol) in CH₃CN (19 mL) was stirred at 80° C. for 18 h. The mixture was taken up with EtOAc, and washed with 0.5 N HCl (twice) and water. The organic layer was dried over MgSO₄, filtered and the solvent was evaporated under vacuum. Purification was performed by flash chromatography on silica gel (30 µm, 40 g, heptane/EtOAc from 85/15 to 75/25) to give ethyl 5-(3-((1-(4-chlorophenyl)-2-oxo-2-(6-(trifluoromethoxy)indolin-1-yl)ethyl)amino)-5-methoxyphenyl)pentanoate 14f (1.8 g). The compound was used as such in the next step.

Synthesis of Compound 14 and Chiral Separation into Enantiomers 14A and 14B:

A solution of LiOH monohydrate (0.62 g, 15 mmol) in water (16 mL) was added to a solution of ethyl 5-(3-((1-(4-chlorophenyl)-2-oxo-2-(6-(trifluoromethoxy)indolin-1-yl)ethyl)amino)-5-methoxyphenyl)pentanoate 14f (1.8 g, 2.98 mmol) in THF (36 mL). The mixture was stirred at room temperature for 18 h. LiOH monohydrate (0.62 g, 15 mmol) was added again and the mixture was stirred at room temperature for 24 h. The solution was acidified with HCl (3N) and extracted with EtOAc. The organic layer was dried over MgSO₄, filtered and concentrated under reduced pressure. The residue was purified by flash chromatography on silica gel (30 µm, 40 g, CH₂Cl₂/MeOH 100/0 to 98/2) to give 5-(3-((1-(4-chlorophenyl)-2-oxo-2-(6-(trifluoromethoxy)indolin-1-yl)ethyl)amino)-5-methoxyphenyl)pentanoic acid (compound 14, 920 mg). The enantiomers were separated via chiral SFC (Stationary phase: Chiralpak® AD-H 5 µm 250×30 mm, mobile phase: 55% CO₂, 45% EtOH) to give, after solidification from pentane/Et₂O, the first eluted Enantiomer 14A (248 mg) and the second eluted Enantiomer 14B (263 mg).

Compound 14:
¹H NMR (500 MHz, DMSO-d₆) δ ppm 1.47 (br s, 4H) 2.15-2.22 (m, 2H) 2.34-2.43 (m, 2H) 3.07-3.26 (m, 2H) 3.62 (s, 3H) 3.92-4.14 (m, 1H) 4.40-4.64 (m, 1H) 5.56 (br d, J=8.83 Hz, 1H) 6.00 (s, 1H) 6.13 (br s, 1H) 6.20 (s, 1H) 6.37 (br d, J=8.51 Hz, 1H) 7.01 (br d, J=7.88 Hz, 1H) 7.33 (br d, J=7.88 Hz, 1H) 7.44 (br d, J=8.20 Hz, 2H) 7.56 (br d, J=8.20 Hz, 2H) 8.04 (br s, 1H) 12.01 (br s, 1H)

LC/MS (method LC-C): $R_t$ 3.18 min, MH⁺ 577

Enantiomer 14A:
¹H NMR (500 MHz, DMSO-d₆) δ ppm 1.40-1.61 (m, 4H) 2.14-2.24 (m, 2H) 2.33-2.42 (m, 2H) 3.06-3.23 (m, 2H) 3.62 (s, 3H) 3.92-4.18 (m, 1H) 4.40-4.59 (m, 1H) 5.40-5.69 (m, 1H) 6.00 (s, 1H) 6.13 (s, 1H) 6.20 (s, 1H) 6.30-6.47 (m, 1H) 6.91-7.12 (m, 1H) 7.28-7.38 (m, 1H) 7.44 (d, J=8.20 Hz, 2H) 7.56 (d, J=8.51 Hz, 2H) 7.95-8.29 (m, 1H) 11.99 (br s, 1H)

LC/MS (method LC-C): $R_t$ 3.21 min, MH⁺ 577

$[α]_D^{20}$: +55.8° (c 0.312, DMF)

Chiral SFC (method SFC-L): $R_t$ 1.32 min, no MH⁺, chiral purity 100%.

Enantiomer 14B:
¹H NMR (500 MHz, DMSO-d₆) δ ppm 1.40-1.53 (m, 4H) 2.15-2.25 (m, 2H) 2.32-2.44 (m, 2H) 3.00-3.27 (m, 2H) 3.62 (s, 3H) 3.95-4.18 (m, 1H) 4.44-4.79 (m, 1H) 5.57 (d, J=8.83 Hz, 1H) 6.00 (s, 1H) 6.13 (s, 1H) 6.20 (s, 1H) 6.37 (br d, J=8.83 Hz, 1H) 7.02 (br d, J=7.25 Hz, 1H) 7.34 (d, J=8.20 Hz, 1H) 7.44 (d, J=8.20 Hz, 2H) 7.56 (d, J=8.51 Hz, 2H) 8.04 (s, 1H) 12.00 (m, 1H)

LC/MS (method LC-C): $R_t$ 3.20 min, MH⁺ 577

$[α]_D^{20}$: −53.7° (c 0.326, DMF)

Chiral SFC (method SFC-L): $R_t$ 1.74 min, no MH⁺, chiral purity 100%.

Example 15: Synthesis of 4-(3-((1-(4-chlorophenyl)-2-oxo-2-(6-(trifluoromethoxy)indolin-1-yl)ethyl)amino)-5-methoxyphenyl)butanoic Acid (Compound 15) and Chiral Separation into Enantiomers 15A and 15B

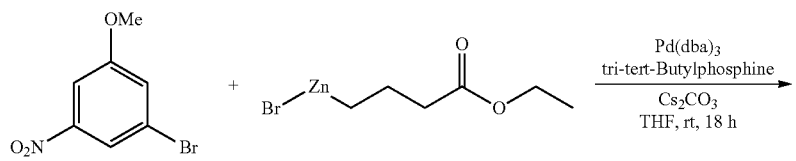

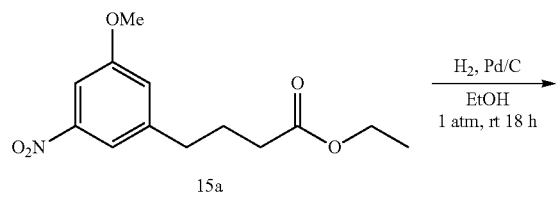

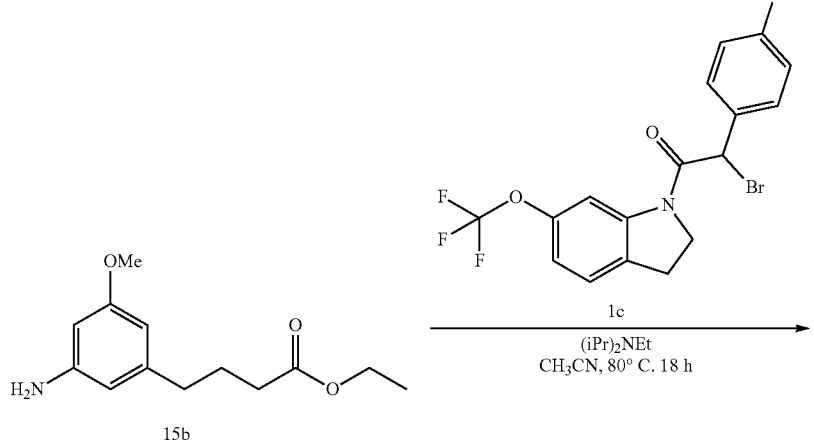

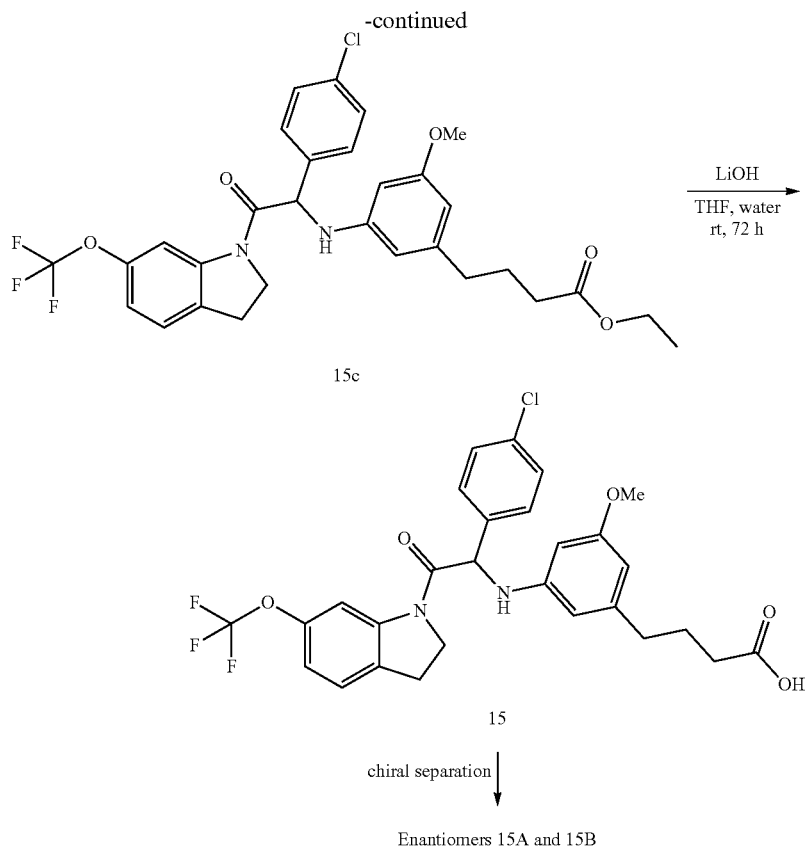

15c

15 chiral separation

Enantiomers 15A and 15B

Synthesis of Intermediate 15a:

4-ethoxy-4-oxobutylzinc bromide (5.2 mL, 2.6 mmol) and $Pd_2(dba)_3$ (0.20 g, 0.22 mmol) were added to a degased solution of 1-bromo-3-methoxy-5-nitrobenzene [CAS 16618-67-0] (0.5 g, 2.2 mmol), tri-tert-butylphosphine (87 mg, 0.43 mmol) and $Cs_2CO_3$ (1.4 g, 4.3 mmol) in THF (8.8 mL). The reaction was stirred at room temperature for 18 h under $N_2$ atmosphere. The mixture was concentrated under reduced pressure. The residue was purified by flash chromatography on silica gel (30 μm, 80 g, heptane/EtOAc from 95/5 to 80/20) to give ethyl 4-(3-methoxy-5-nitrophenyl) butanoate 15a (370 mg).

Synthesis of Intermediate 15b:

A mixture of ethyl 4-(3-methoxy-5-nitrophenyl)butanoate 15a (0.37 g, 1.38 mmol) in EtOH (8.1 mL) was hydrogenated under an atmospheric pressure of $H_2$ for 18 h with Pd/C (10%) (0.15 g, 0.14 mmol) as a catalyst. The catalyst was removed by filtration through a pad of Celite®. The Celite® was washed with EtOAc and the filtrate was concentrated under vacuum to give ethyl 4-(3-amino-5-methoxyphenyl)butanoate 15b (350 mg). The compound was used as such in the next step.

Synthesis of Intermediate 15c:

A mixture of 2-bromo-2-(4-chlorophenyl)-1-(6-(trifluoromethoxy)indolin-1-yl)ethanone 1c (0.43 g, 0.98 mmol), ethyl 4-(3-amino-5-methoxyphenyl)butanoate 15b (0.35 g, 1.48 mmol) and diisopropylethylamine (0.34 mL, 2.0 mmol) in $CH_3CN$ (5.1 mL) was stirred at 80° C. for 18 h. The mixture was taken up with EtOAc, and washed with 0.5 N HCl (twice) and water. The organic layer was dried over $MgSO_4$, filtered and the solvent was evaporated under vacuum. Purification was performed by flash chromatography on silica gel (30 μm, 40 g, heptane/EtOAc from 85/15 to 75/25) to give ethyl 4-(3-((1-(4-chlorophenyl)-2-oxo-2-(6-(trifluoromethoxy)indolin-1-yl)ethyl)amino)-5-methoxyphenyl)butanoate 15c (340 mg).

Synthesis of Compound 15 and Chiral Separation into Enantiomers 15A and 15B:

Under $N_2$, a solution of LiOH monohydrate (0.12 g, 2.9 mmol) in water (3.1 mL) was added to a solution of ethyl 4-(3-((1-(4-chlorophenyl)-2-oxo-2-(6-(trifluoromethoxy)indolin-1-yl)ethyl)amino)-5-methoxyphenyl)butanoate 15c (0.34 g, 0.58 mmol) in THF (7 mL). The mixture was stirred at room temperature for 72 h. The solution was acidified with HCl (3N) and extracted with EtOAc. The organic layer was dried over $MgSO_4$, filtered and concentrated under reduced pressure. The residue was purified by flash chromatography on silica gel (30 μm, 24 g, $CH_2Cl_2$/MeOH 100/0 to 98/2) to give, after solidification from $Et_2O$, 4-(3-((1-(4-chlorophenyl)-2-oxo-2-(6-(trifluoromethoxy)indolin-1-yl) ethyl)amino)-5-methoxyphenyl)butanoic acid (compound 15, 285 mg). The enantiomers were separated via chiral SFC (Stationary phase: Chiralcel® OD-H 5 μm 250×30 mm, mobile phase: 65% $CO_2$, 35% MeOH) to give, after solidification from $Et_2O$, the first eluted Enantiomer 15A (75 mg) and the second eluted Enantiomer 15B (85 mg).

Compound 15:

$^1$H NMR (500 MHz, DMSO-$d_6$) δ ppm 1.66-1.86 (m, 2H) 2.11-2.26 (m, 2H) 2.32-2.44 (m, 2H) 3.03-3.26 (m, 2H) 3.62 (s, 3H) 4.04 (td, J=10.32, 7.09 Hz, 1H) 4.52 (td, J=10.32, 6.15 Hz, 1H) 5.56 (d, J=8.83 Hz, 1H) 6.00 (s, 1H) 6.14 (s, 1H) 6.21 (s, 1H) 6.38 (d, J=8.83 Hz, 1H) 7.01 (dd, J=8.20, 1.26 Hz, 1H) 7.33 (d, J=8.20 Hz, 1H) 7.38-7.50 (m, 2H) 7.56 (d, J=8.20 Hz, 2H) 8.03 (s, 1H) 12.01 (s, 1H)

LC/MS (method LC-D): R$_t$ 2.96 min, MH$^+$ 563
Enantiomer 15A:
$^1$H NMR (500 MHz, DMSO-d$_6$) δ ppm 1.56-1.87 (m, 2H) 2.11-2.21 (m, 2H) 2.35-2.42 (m, 2H) 3.02-3.22 (m, 2H) 3.62 (s, 3H) 3.97-4.18 (m, 1H) 4.39-4.61 (m, 1H) 5.56 (d, J=8.59 Hz, 1H) 5.99 (s, 1H) 6.13 (s, 1H) 6.20 (s, 1H) 6.37 (br d, J=9.09 Hz, 1H) 7.00 (br d, J=8.59 Hz, 1H) 7.33 (d, J=8.08 Hz, 1H) 7.43 (d, J=8.59 Hz, 2H) 7.55 (d, J=8.59 Hz, 2H) 8.03 (s, 1H) 11.99 (br s, 1H)

LC/MS (method LC-C): R$_t$ 3.08 min, MH$^+$ 563

[α]$_D^{20}$: −59.0° (c 0.293, DMF)

Chiral SFC (method SFC-M): R$_t$ 2.19 min, no MH$^+$, chiral purity 99.31%.

Enantiomer 15B:
$^1$H NMR (500 MHz, DMSO-d$_6$) δ ppm 1.60-1.86 (m, 2H) 2.10-2.21 (m, 2H) 2.35-2.42 (m, 2H) 3.02-3.23 (m, 2H) 3.62 (s, 3H) 3.82-4.26 (m, 1H) 4.36-4.71 (m, 1H) 5.56 (d, J=9.09 Hz, 1H) 5.99 (s, 1H) 6.13 (s, 1H) 6.20 (s, 1H) 6.37 (d, J=9.09 Hz, 1H) 7.00 (br d, J=8.59 Hz, 1H) 7.33 (d, J=8.08 Hz, 1H) 7.43 (d, J=8.59 Hz, 2H) 7.55 (d, J=8.59 Hz, 2H) 8.03 (s, 1H) 11.97 (br s, 1H)

LC/MS (method LC-C): R$_t$ 3.08 min, MH$^+$ 563

[α]$_D^{20}$: +48.0° (c 0.225, DMF)

Chiral SFC (method SFC-M): R$_t$ 3.73 min, no MH$^+$, chiral purity 99.61%.

Example 16: Synthesis of 3-((3-((1-(4-chlorophenyl)-2-oxo-2-(6-(trifluoromethoxy)-indolin-1-yl)ethyl)amino)-5-methoxybenzyl)oxy)propanoic Acid (Compound 16)

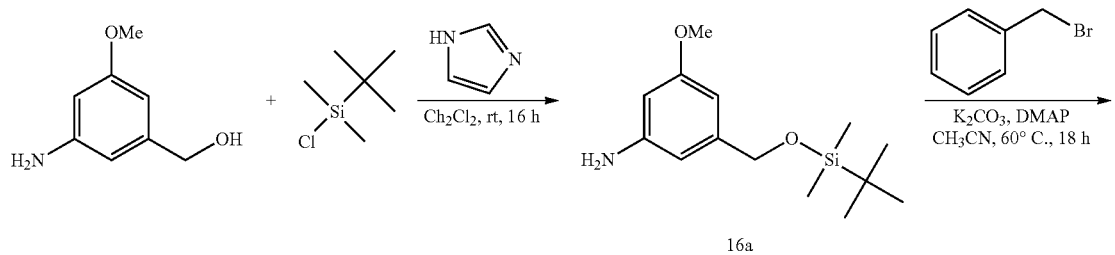

16a

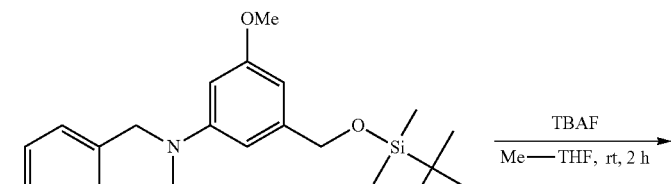

16b

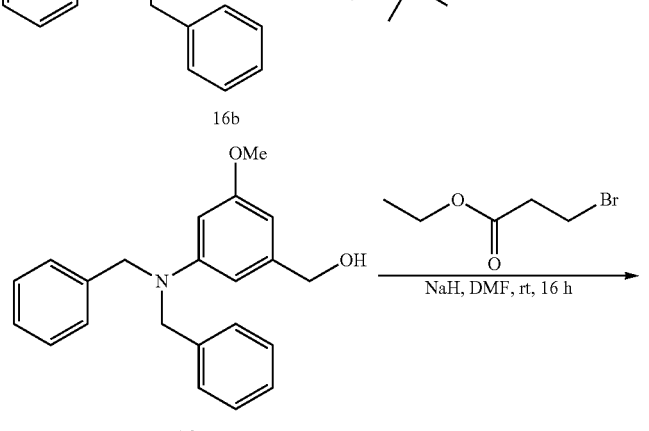

16c

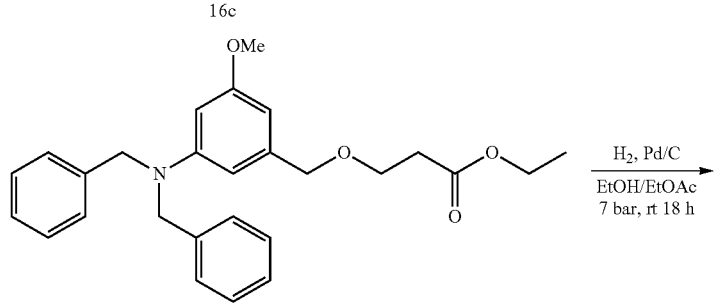

16d

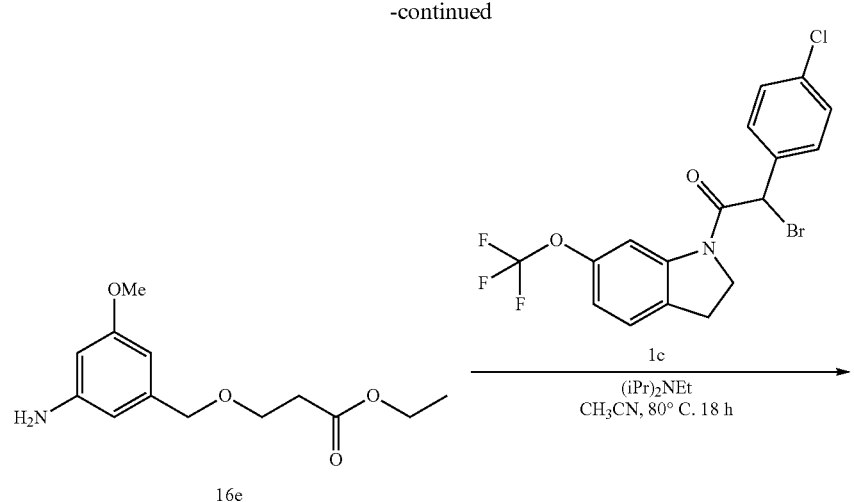
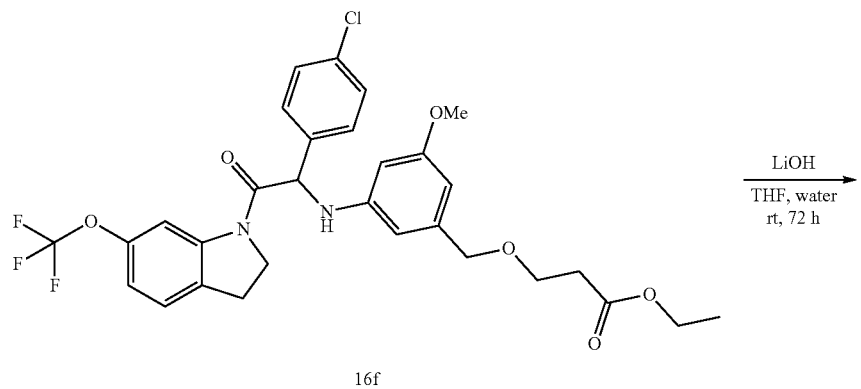
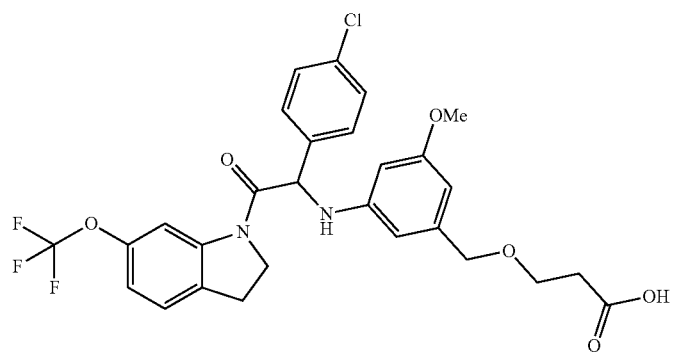

Synthesis of Intermediate 16a:

Tert-butyldimethylsilyl chloride (6.1 g, 40.48 mmol) was added to a solution of (3-amino-5-methoxyphenyl)methanol [1261566-52-2] (3.1 g, 20.24 mmol) and imidazole (4.13 g, 60.71 mmol) in $CH_2Cl_2$ (130 mL) at room temperature. The reaction was stirred at room temperature for 16 h, quenched with water and extracted with $CH_2Cl_2$. The organic layer was separated, washed with water and brine, dried over $MgSO_4$, filtered and evaporated to dryness. The residue was purified by flash chromatography on silica gel (30 μm, 120 g, heptane/EtOAc from 85/15 to 65/35). The pure fractions were combined and evaporated to dryness to give 3-(((tert-butyldimethylsilyl)oxy)methyl)-5-methoxyaniline 16a (3.4 g). The compound was used as such in the next step.

Synthesis of Intermediate 16b:

A mixture of benzyl bromide (3.8 mL, 31.8 mmol), 3-(((tert-butyldimethylsilyl)oxy)-methyl)-5-methoxyaniline 16a (3.4 g, 12.71 mmol), $K_2CO_3$ (5.27 g, 38.14 mmol) and DMAP (155 mg, 1.27 mmol) in $CH_3CN$ (66 mL) was stirred at 60° C. for 18 h. The mixture was filtered and the filtrate was concentrated under reduced pressure. The residue was purified by flash chromatography on silica gel (30 μm, 120 g, heptane/EtOAc from 100/0 to 90/10). The pure fractions were combined and evaporated to dryness to give N,N-dibenzyl-3-(((tert-butyldimethylsilyl)oxy)methyl)-5-methoxyaniline 16b (6 g).

Synthesis of Intermediate 16c:

TBAF (1M in THF) (15.3 mL, 15.3 mmol) was added to a solution of N,N-dibenzyl-3-(((tert-butyldimethylsilyl)oxy)methyl)-5-methoxyaniline 16b (5.69 g, 12.71 mmol) in Me-THF (64 mL). The mixture was stirred at room temperature for 2 h. The mixture was diluted with EtOAc, washed 3 times with brine and with an aqueous saturated solution of $NaHCO_3$, dried over $MgSO_4$, filtered and concentrated under reduced pressure. The residue was purified by flash chromatography on silica gel (30 μm, 120 g, heptane/EtOAc from 85/15 to 75/25). The pure fractions were combined and evaporated to dryness to give (3-(dibenzylamino)-5-methoxyphenyl)methanol 16 c (4.1 g).

Synthesis of Intermediate 16d:

Ethyl 3-bromopropionate (0.126 mL, 0.99 mmol) added dropwise to a solution of (3-(dibenzylamino)-5-methoxyphenyl)methanol 16c (300 mg, 0.90 mmol), NaH (60% dispersion in mineral oil) (40 mg, 0.99 mmol) in DMF (7.0 ml). The reaction was stirred at room temperature for 16 h. After dilution with EtOAc, the crude material was washed with brine (5×). The organic layer was dried over $MgSO_4$ and evaporated to dryness. Purification was performed by flash chromatography on silica gel (30 μm, 24 g, heptane/EtOAc from 85/15 to 75/25). The pure fractions were combined and evaporated to dryness to give ethyl 3-((3-(dibenzylamino)-5-methoxybenzyl)oxy)propanoate 16d (97 mg).

Synthesis of Intermediate 16e:

A mixture of ethyl 3-((3-(dibenzylamino)-5-methoxybenzyl)oxy)propanoate 16d (97 mg, 0.22 mmol) in EtOH (1.3 mL) and EtOAc (0.66 mL) was hydrogenated under a pressure of 7 bar of $H_2$ at room temperature for 18 h with Pd/C (10%) (24 mg, 0.022 mmol) as a catalyst. The catalyst was removed by filtration through a pad of Celite®. The Celite® was washed with EtOAc and the filtrate was concentrated under reduced pressure to give ethyl 3-((3-amino-5-methoxybenzyl)oxy)-propanoate 16e (52 mg).

Synthesis of Intermediate 16f:

A mixture of 2-bromo-2-(4-chlorophenyl)-1-(6-(trifluoromethoxy)indolin-1-yl)ethanone 1c (74 mg, 0.17 mmol), ethyl 3-((3-amino-5-methoxybenzyl)oxy)-propanoate 16e (52 mg, 0.21 mmol) and diisopropylethylamine (59 μL, 0.34 mmol) in $CH_3CN$ (0.89 mL) was stirred at 80° C. for 18 h. The mixture was concentrated under reduced pressure. Purification was performed by flash chromatography on silica gel (30 μm, 12 g, heptane/EtOAc from 85/15 to 75/25). The pure fractions were combined and evaporated to dryness to give ethyl 3-((3-((1-(4-chlorophenyl)-2-oxo-2-(6-(trifluoromethoxy)indolin-1-yl)ethyl)amino)-5-methoxybenzyl)oxy)propanoate 16f (48 mg).

Synthesis of Compound 16:

A solution of LiOH monohydrate (33 mg, 0.79 mmol) in water (0.43 mL) was added to a solution of ethyl 3-((3-((1-(4-chlorophenyl)-2-oxo-2-(6-(trifluoromethoxy)-indolin-1-yl)ethyl)amino)-5-methoxybenzyl)oxy)propanoate 16f (48 mg, 0.079 mmol) in THF (0.97 mL). The mixture was stirred at room temperature for 72 h. The solution was acidified with HCl (3N) and extracted with EtOAc. The organic layer was dried over $MgSO_4$, filtered and concentrated under reduced pressure. The residue was purified by flash chromatography on silica gel (30 μm, 12 g, $CH_2Cl_2$/MeOH 100/0 to 98/2). A second purification was performed via reverse phase chromatography (Stationary phase: YMC-actus Triart-C18 10 μm 30×150 mm, mobile phase: Gradient from 65% $NH_4HCO_3$ 0.2%, 35% $CH_3CN$ to 25% $NH_4HCO_3$ 0.2%, 75% $CH_3CN$). The pure fractions were combined and evaporated to dryness to give, after freeze-drying in $CH_3CN$/water, 3-((3-((1-(4-chlorophenyl)-2-oxo-2-(6-(trifluoromethoxy)indolin-1-yl)ethyl)amino)-5-methoxybenzyl)oxy)propanoic acid (compound 16, 5 mg).

Compound 16:

$^1$H NMR (400 MHz, DMSO-$d_6$) δ ppm 2.34-2.42 (m, 2H) 3.03-3.23 (m, 2H) 3.49-3.59 (m, 2H) 3.63 (s, 3H) 3.97-4.21 (m, 2H) 4.27 (s, 2H) 4.49-4.57 (m, 1H) 5.58 (d, J=8.59 Hz, 1H) 6.11 (s, 1H) 6.21 (s, 1H) 6.33 (s, 1H) 6.48 (br d, J=8.59 Hz, 1H) 7.00 (br d, J=8.59 Hz, 1H) 7.33 (d, J=8.08 Hz, 1H) 7.43 (d, J=8.59 Hz, 2H) 7.56 (d, J=8.59 Hz, 2H) 8.03 (s, 1H)

LC/MS (method LC-C): $R_t$ 2.84 min, MH$^+$ 579

Example 17: Synthesis of 4-(3-((1-(4-chloro-2-methoxyphenyl)-2-oxo-2-(6-(trifluoromethoxy)indolin-1-yl)ethyl)amino)-5-methoxyphenoxy)-2-methylbutanoic acid (Compound 17) and Separation into Stereoisomers 17A, 17B, 17C and 17D

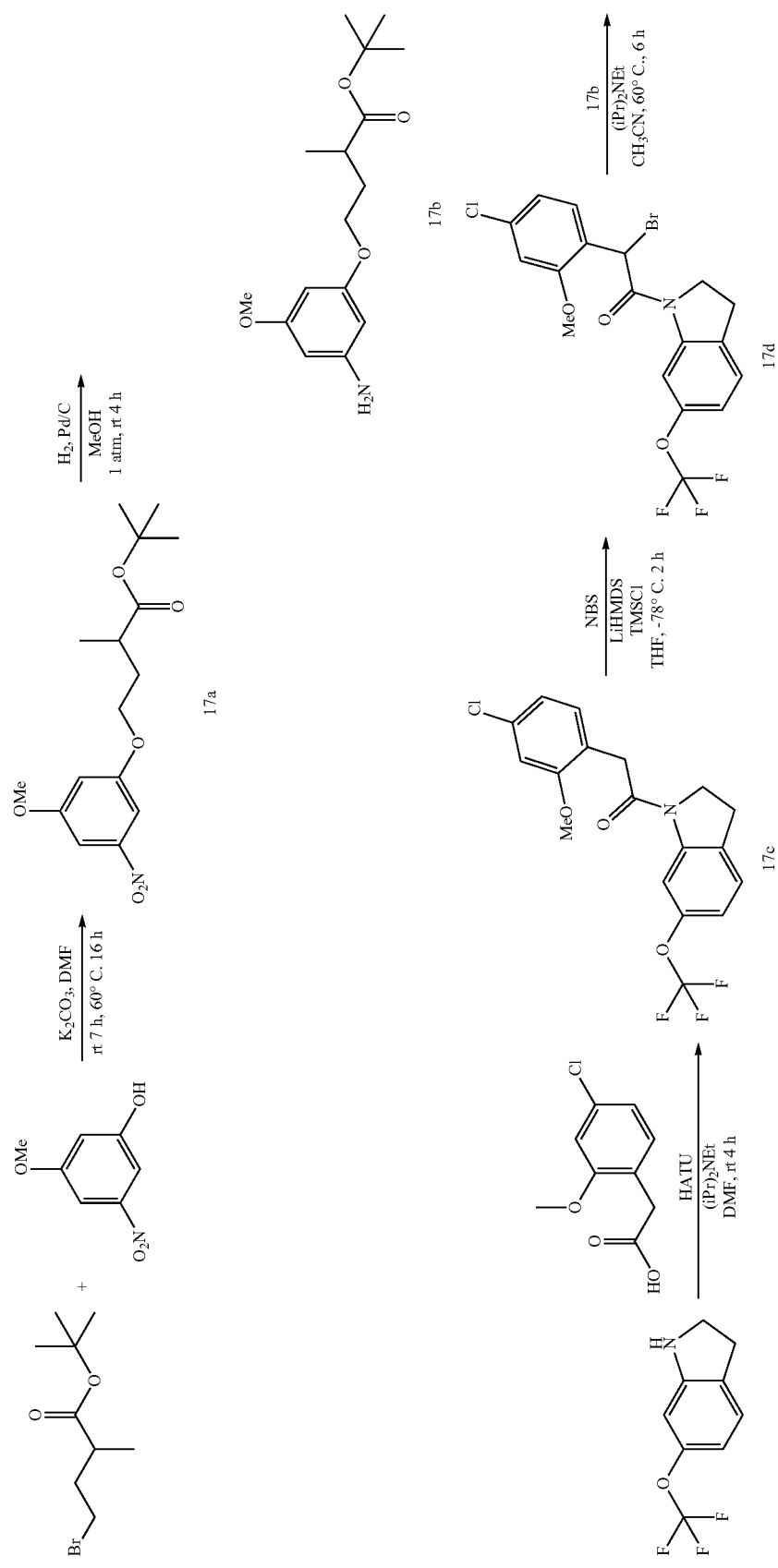

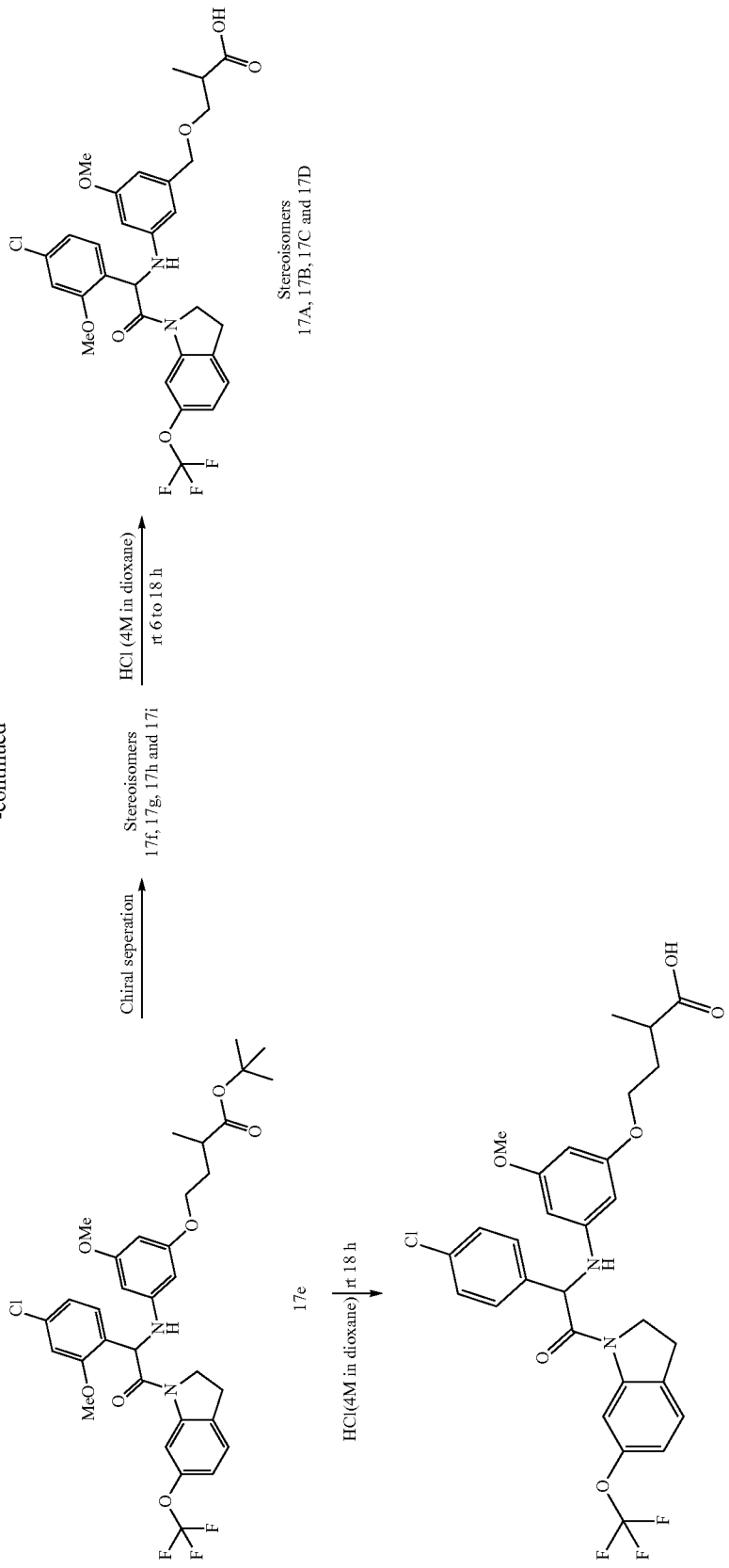

Synthesis of Intermediate 17a:

Tert-butyl 4-bromo-2-methylbutanoate [CAS 1210410-44-8 (3.9 g, 16.446 mmol) was added dropwise to a mixture of 3-methoxy-5-nitrophenol [7145-49-5] (2.78 g, 16.446 mmol) and $K_2CO_3$ (3.409 g, 24.669 mmol) in DMF (25 mL). The mixture was stirred at room temperature for 7 h and at 60° C. for 16 h. after cooling to 0° C., the mixture was diluted with water and ice and extracted with EtOAc. The organic layer was washed with water, dried over $MgSO_4$, filtered and the solvent was evaporated to dryness. The crude residue was purified by flash chromatography on silica gel (20-45 µm, 80 g, mobile phase: heptane/EtOAc 75/25). The pure fractions were combined and the solvent was evaporated under reduced pressure to give tert-butyl 4-(3-methoxy-5-nitrophenoxy)-2-methylbutanoate 17a (2.59 g).

Synthesis of Intermediate 17b:

A mixture of tert-butyl 4-(3-methoxy-5-nitrophenoxy)-2-methylbutanoate 17a (2.9 g, 8.913 mmol) in MeOH (50 mL) was hydrogenated under an atmospheric pressure of $H_2$ for 4 h with Pd/C (10%) (1.52 g, 1.426 mmol) as a catalyst. The catalyst was removed by filtration through a pad of Celite®. The Celite® was washed with EtOAc and the filtrate was concentrated under reduced pressure. The mixture was purified by flash chromatography on silica gel (20-45 µm, 40 g, mobile phase: heptane/EtOAc 85/15). The pure fractions were combined and the solvent was evaporated until dryness to give tert-butyl 4-(3-amino-5-methoxyphenoxy)-2-methylbutanoate 17b (2.29 g).

Synthesis of Intermediate 17c:

A mixture of 6-(trifluoromethoxy)indoline [CAS 959235-95-1] (2.5 g, 12.3 mmol), 2-(4-chloro-2-methoxyphenyl) acetic acid [CAS 170737-95-8] (2.47 g, 12.3 mmol), HATU (7 g, 18.5 mmol) and diisopropylethylamine (6.1 mL, 36.9 mmol) in DMF (40 mL) was stirred at room temperature for 4 h. Water and EtOAc were added. The organic layer was separated, washed with water, dried over $MgSO_4$, filtered and the solvent was evaporated under reduced pressure. The residue was purified by chromatography on silica gel (15-40 µm, 80 g, heptane/EtOAc 85/15). The pure fractions were combined and the solvent was concentrated under reduced pressure to give, after crystallization from $CH_3CN$/heptane, 2-(4-chloro-2-methoxyphenyl)-1-(6-(trifluoromethoxy)indolin-1-yl)ethanone 17c (4.3 g).

Synthesis of Intermediate 17d:

At −78° C., under a $N_2$ flow, LiHMDS 1M in THF (19.7 mL, 19.7 mmol) was added dropwise to a mixture of 2-(4-chloro-2-methoxyphenyl)-1-(6-(trifluoromethoxy)indolin-1-yl)ethanone 17c (3.8 g, 9.8 mmol) in THF (50 mL). TMSCl (1.5 mL, 11.8 mmol) was added dropwise. The mixture was stirred for 15 min at −78° C. and a solution of N-bromosuccinimide (1.9 g, 10.8 mmol) in THF (35 mL) was added dropwise. After stirring for 2 h at −78° C., the reaction was quenched with a saturated solution of $NH_4Cl$. The mixture was extracted with EtOAc. The organic layer was separated, dried over $MgSO_4$, filtered and the solvent was evaporated under reduced pressure to give 2-bromo-2-(4-chloro-2-methoxyphenyl)-1-(6-(trifluoromethoxy)indolin-1-yl)ethanone 17d (4.5 g). The compound was used as such in the next step.

Synthesis of Intermediate 17e and Separation into Stereoisomers 17f, 17g, 17h and 17i:

A mixture of 2-bromo-2-(4-chloro-2-methoxyphenyl)-1-(6-(trifluoromethoxy)indolin-1-yl)ethanone 17d (2 g, 4.304 mmol), tert-butyl 4-(3-amino-5-methoxyphenoxy)-2-methylbutanoate 17b (763 mg, 2.583 mmol) and diisopropylethylamine (1.5 mL, 8.608 mmol) in $CH_3CN$ (70 mL) was stirred at 60° C. for 6 h. The mixture was cooled to 0° C., diluted water and ice, and extracted with EtOAc. The organic layer was washed with water, dried over $MgSO_4$, filtered and the solvent was evaporated under reduced pressure. Purification was performed by flash chromatography on silica gel (25-30 µm, 40 g, heptane/EtOAc 80/20). A second purification was performed by flash chromatography on silica gel (25-30 µm, 40 g, heptane/EtOAc 85/15). The pure fractions were combined and evaporated to dryness to give tert-butyl 4-(3-((1-(4-chloro-2-methoxyphenyl)-2-oxo-2-(6-(trifluoromethoxy)indolin-1-yl)ethyl)amino)-5-methoxyphenoxy)-2-methylbutanoate 17e (787 mg). The stereoisomers were separated via chiral SFC (Stationary phase: Chiralpak® AD-H 5 µm 250×30 mm, mobile phase: 83% $CO_2$, 17% EtOH) to give a mixture of 17f and 17g (348 mg), and pure 17h (164 mg) and 17i (184 mg). 17f and 17g were further separated via chiral SFC (Stationary phase: Chiralpak® AD-H 5 µm 250×30 mm, mobile phase: 88% $CO_2$, 12% EtOH) to give 17f (145 mg) and 17g (140 mg).

Synthesis of Compound 17:

A mixture of tert-butyl 4-(3-((1-(4-chloro-2-methoxyphenyl)-2-oxo-2-(6-(trifluoromethoxy)indolin-1-yl)ethyl)amino)-5-methoxyphenoxy)-2-methylbutanoate 17e (180 mg, 0.265 mmol) in HCl (4M in dioxane) (3 mL) was stirred at room temperature for 18 h. The mixture was concentrated under reduced pressure. 5 mL of triethylamine was added and the solution was evaporated under vacuum. Purification was performed by flash chromatography on silica gel (30 µm, 12 g, $CH_2Cl_2$/MeOH from 99/1 to 96/4). The pure fractions were combined and evaporated to dryness (m=115 mg). The residue was solidified in pentane/diisopropyl ether and few drops of $CH_3CN$ to give 4-(3-((1-(4-chloro-2-methoxyphenyl)-2-oxo-2-(6-(trifluoromethoxy)indolin-1-yl)ethyl)amino)-5-methoxyphenoxy)-2-methylbutanoic acid (Compound 17, 75 mg).

Synthesis of Stereoisomer 17A:

A mixture of 17f (145 mg, 0.214 mmol) in HCl (4M in dioxane) (5 mL) was stirred at room temperature for 6 h. The mixture was concentrated under reduced pressure. 5 mL of $Et_3N$ was added and the solution was evaporated under vacuum. Purification was performed by flash chromatography on silica gel (15-40 µm, 12 g, $CH_2Cl_2$/MeOH from 99.5/0.5 to 95/5). The pure fractions were combined and evaporated to dryness (m=93 mg). The residue was solidified from pentane/diisopropyl ether and few drops of $CH_3CN$ to give Stereoisomer 17A (64 mg).

Synthesis of Stereoisomer 17B:

A mixture of 17g (135 mg, 0.199 mmol) in HCl (4M in dioxane) (5 mL) was stirred at room temperature for 18 h. The mixture was concentrated under reduced pressure. 5 mL of $Et_3N$ was added and the solution was evaporated under vacuum. Purification was performed by flash chromatography on silica gel (15-40 µm, 12 g, $CH_2Cl_2$/MeOH from 99.5/0.5 to 95/5). The pure fractions were combined and evaporated to dryness (m=65 mg). The residue was solidified from pentane/diisopropyl ether and few drops of $CH_3CN$ to give Stereoisomer 17B (38 mg).

Synthesis of Stereoisomer 17C:

A mixture of 17h (162 mg, 0.239 mmol) in HCl (4M in dioxane) (5 mL) was stirred at room temperature for 6 h. The mixture was concentrated under reduced pressure. 5 mL of $Et_3N$ was added and the solution was evaporated under vacuum. Purification was performed by flash chromatography on silica gel (15-40 µm, 12 g, $CH_2Cl_2$/MeOH from 99.5/0.5 to 95/5). The pure fractions were combined and evaporated to dryness (m=85 mg). The residue was solidified from pentane/diisopropyl ether and few drops of $CH_3CN$ to give Stereoisomer 17C (68 mg).

Synthesis of Stereoisomer 17D:

A mixture of 17i (179 mg, 0.264 mmol) in HCl (4M in dioxane) (5 mL) was stirred at room temperature for 6 h. The mixture was concentrated under reduced pressure. 5 mL of Et$_3$N was added and the solution was evaporated under vacuum. Purification was performed by flash chromatography on silica gel (15-40 μm, 24 g, CH$_2$Cl$_2$/MeOH from 99.5/0.5 to 95/5). The pure fractions were combined and evaporated to dryness (m=98 mg). The residue was solidified from pentane/diisopropyl ether and few drops of CH$_3$CN to give Stereoisomer 17D (54 mg).

Compound 17:

$^1$H NMR (500 MHz, DMSO-d$_6$) δ ppm 1.11 (br d, J=6.62 Hz, 3H) 1.54-1.82 (m, 1H) 1.82-2.07 (m, 1H) 3.10-3.22 (m, 2H) 3.62 (s, 3H) 3.77-3.87 (m, 2H) 3.91 (s, 3H) 3.96-4.18 (m, 1H) 4.30-4.43 (m, 1H) 5.60 (br d, J=8.20 Hz, 1H) 5.76 (br s, 1H) 5.87 (s 1H) 5.88 (s, 1H) 6.46 (br d, J=8.51 Hz, 1H) 6.98-7.6 (m, 2H) 7.15 (br s, 1H) 7.28-7.44 (m, 2H) 8.03 (br s, 1H) 12.20 (br s, 1H) (1H missing CH CO$_2$H under DMSO)

LC/MS (method LC-C): R$_t$ 3.16 min, MH$^+$ 623

Stereoisomer 17A:

$^1$H NMR (400 MHz, DMSO-d$_6$) δ ppm 1.10 (br d, J=7.07 Hz, 3H) 1.59-1.82 (m, 1H) 1.82-2.04 (m, 1H) 3.04-3.24 (m, 2H) 3.61 (s, 3H) 3.71-3.87 (m, 2H) 3.90 (s, 3H) 3.96-4.21 (m, 1H) 4.32-4.56 (m, 1H) 5.59 (br d, J=8.59 Hz, 1H) 5.75 (s, 1H) 5.85 (s, 1H) 5.87 (s, 1H) 6.44 (br d, J=8.59 Hz, 1H) 6.98-7.05 (m, 2H) 7.14 (s, 1H) 7.22-7.53 (m, 2H) 8.02 (br s, 1H) 12.19 (br s, 1H) (1H missing CH CO$_2$H under DMSO)

LC/MS (method LC-D): R$_t$ 3.07 min, MH$^+$ 623

[α]$_D^{20}$: −18.4° (c 0.305, DMF)

Chiral SFC (method SFC-N): R$_t$ 4.75 min, MH$^+$ 623, chiral purity 99.3%.

Stereoisomer 17B:

$^1$H NMR (400 MHz, DMSO-d$_6$) δ ppm 1.09 (br d, J=6.57 Hz, 3H) 1.64-1.83 (m, 1H) 1.83-2.09 (m, 1H) 3.00-3.23 (m, 2H) 3.61 (s, 3H) 3.68-3.86 (m, 2H) 3.90 (m, 3H) 3.96-4.21 (m, 1H) 4.26-4.56 (m, 1H) 5.59 (br d, J=8.08 Hz, 1H) 5.75 (br s, 1H) 5.86 (s, 1H) 5.87 (s, 1H) 6.44 (br d, J=8.59 Hz, 1H) 6.97-7.06 (m, 2H) 7.14 (s, 1H) 7.26-7.34 (m, 2H) 8.02 (br s, 1H) 12.20 (br s, 1H) (1H missing CH CO$_2$H under DMSO)

LC/MS (method LC-D): R$_t$ 3.03 min, MH$^+$ 623

[α]$_D^{20}$: −51.0° (c 0.298, DMF)

Chiral SFC (method SFC-N): R$_t$ 5.90 min, MH$^+$ 623, chiral purity 97.94%.

Stereoisomer 17C:

$^1$H NMR (400 MHz, DMSO-d$_6$) δ ppm 1.09 (d, J=6.57 Hz, 3H) 1.61-1.84 (m, 1H) 1.88-2.02 (m, 1H) 3.07-3.26 (m, 2H) 3.61 (s, 3H) 3.76-3.88 (m, 2H) 3.90 (s, 3H) 3.97-4.18 (m, 1H) 4.27-4.45 (m, 1H) 5.59 (brd, J=8.59 Hz, 1H) 5.75 (s, 1H) 5.86 (br s, 1H) 5.87 (br s, 1H) 6.39-6.49 (m, 1H) 6.97-7.02 (m, 1H) 7.02-7.05 (m, 1H) 7.14 (d, J=2.02 Hz, 1H) 7.29-7.32 (m, 1H) 7.32-7.37 (m, 1H) 8.02 (s, 1H) 12.19 (br s, 1H) (1H missing CH CO$_2$H under DMSO)

LC/MS (method LC-C): R$_t$ 3.16 min, MH$^+$ 623

[α]$_D^{20}$: +41.6° (c 0.257, DMF)

Chiral SFC (method SFC-N): R$_t$ 6.86 min, MH$^+$ 623, chiral purity 98.89%.

Stereoisomer 17D:

$^1$H NMR (500 MHz, DMSO-d$_6$) δ ppm 1.11 (d, J=6.94 Hz, 3H) 1.70 (dq, J=13.44, 6.55 Hz, 1H) 1.97 (dq, J=13.64, 6.80 Hz, 1H) 3.09-3.26 (m, 2H) 3.62 (s, 3H) 3.85 (br t, J=6.31 Hz, 2H) 3.91 (s, 3H) 3.97-4.09 (m, 1H) 4.31-4.47 (m, 1H) 5.60 (br d, J=8.51 Hz, 1H) 5.76 (s, 1H) 5.86 (br s, 1H) 5.88 (br s, 1H) 6.45 (br d, J=8.51 Hz, 1H) 7.00-7.08 (m, 2H) 7.15 (d, J=1.26 Hz, 1H) 7.32 (d, J=8.20 Hz, 1H) 7.34 (br d, J=8.20 Hz, 1H) 8.03 (br s, 1H) 12.18 (br s, 1H) (1H missing CH CO$_2$H under DMSO)

LC/MS (method LC-C): R$_t$ 3.15 min, MH$^+$ 623

[α]$_D^{20}$: +15.8° (c 0.297, DMF)

Chiral SFC (method SFC-N): R$_t$ 8.14 min, MH$^+$ 623, chiral purity 98.6%.

Example 18: Synthesis of 4-(3-((1-(4-chloro-2-methoxyphenyl)-2-oxo-2-(6-(trifluoromethoxy)indolin-1-yl)ethyl)amino)-5-methoxyphenoxy)-2,2-dimethylbutanoic acid (Compound 18) and Chiral Separation into Enantiomers 18A and 18B

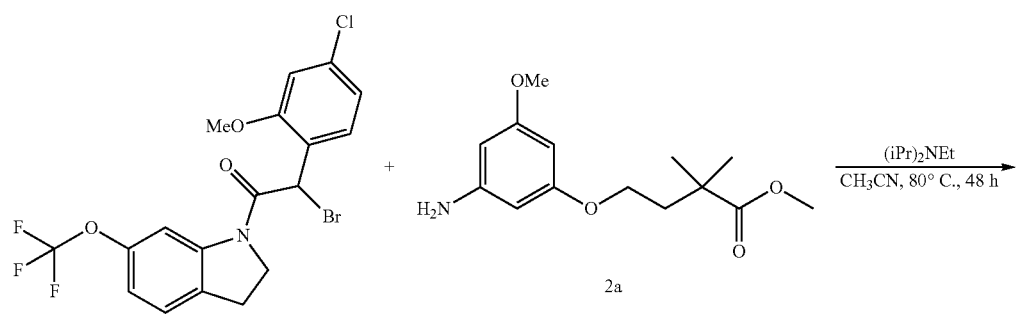

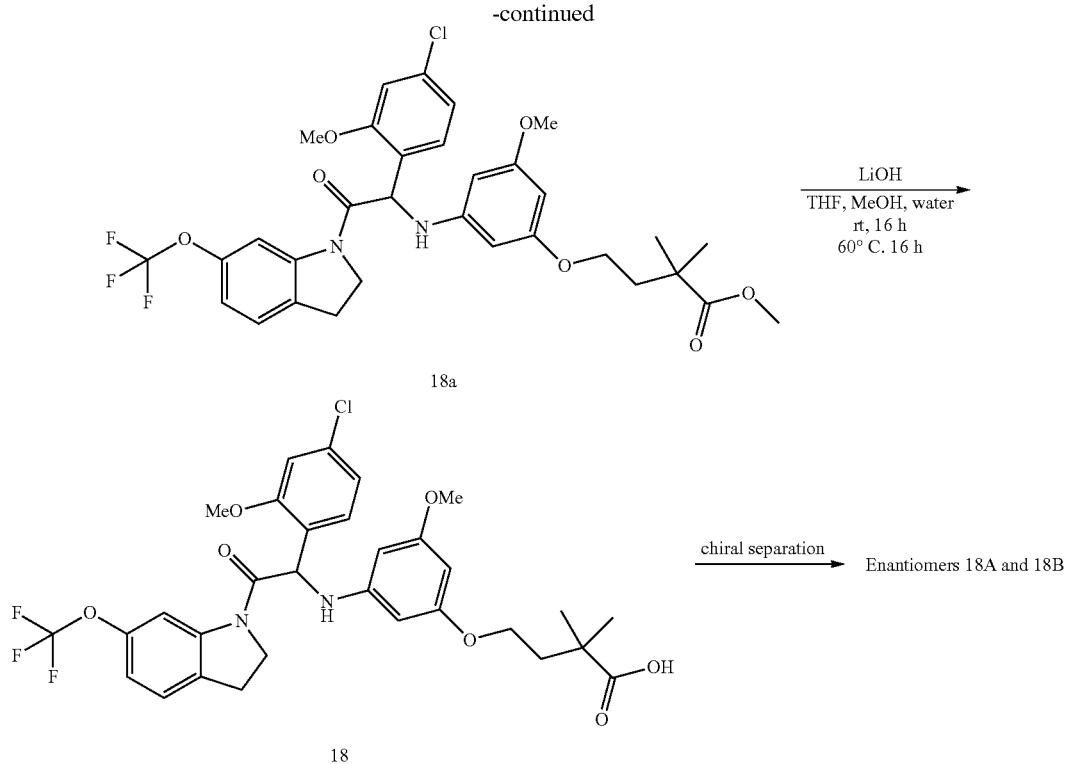

Synthesis of Intermediate 18a:

A mixture of 2-bromo-2-(4-chloro-2-methoxyphenyl)-1-(6-(trifluoromethoxy)indolin-1-yl)ethanone 17d (800 mg, 1.291 mmol), methyl 4-(3-amino-5-methoxyphenoxy)-2,2-dimethylbutanoate 2a (518 mg, 1.937 mmol) and diisopropylethylamine (445 µL, 2.583 mmol) in $CH_3CN$ (6 mL) was stirred at 80° C. for 48 h. The mixture was concentrated to dryness. The residue was taken up with EtOAc, washed with 1N HCl (twice), and with water. The organic layer was dried over $MgSO_4$, filtered and the solvent was evaporated under vacuum to give methyl 4-(3-((1-(4-chloro-2-methoxyphenyl)-2-oxo-2-(6-(trifluoromethoxy)indolin-1-yl)ethyl)amino)-5-methoxyphenoxy)-2,2-dimethylbutanoate 18a (950 mg). The compound was used as such in the next step.

Synthesis of Compound 18 and Chiral Separation into Enantiomers 18A and 18B:

At 0° C., LiOH monohydrate (184 mg, 4.38 mmol) was added portionwise to a solution of methyl 4-(3-((1-(4-chloro-2-methoxyphenyl)-2-oxo-2-(6-(trifluoro-methoxy)indolin-1-yl)ethyl)amino)-5-methoxyphenoxy)-2,2-dimethylbutanoate 18a (950 mg, 1.459 mmol) in THF/MeOH/water (1/1/1) (30 mL). The mixture was stirred at room temperature for 16 h, and then at 60° C. for 16 h. The mixture was diluted with water and extracted with EtOAc. The aqueous layer was slowly acidified to pH 5-6 with 3N HCl and extracted with EtOAc. The combined organic layers were dried over $MgSO_4$, filtered and the solvent was evaporated under vacuum. Purification was performed by flash chromatography on silica gel (15-40 µm, 40 g, $CH_2Cl_2/CH_3OH$, from 100/0 to 99/1). The pure fractions were combined and evaporated to dryness (m=350 mg). A small portion of the residue was crystallized from $Et_2O$/diisopropyl ether. The precipitate was filtered off and dried to give 4-(3-((1-(4-chloro-2-methoxyphenyl)-2-oxo-2-(6-(trifluoromethoxy)indolin-1-yl)ethyl)amino)-5-methoxyphenoxy)-2,2-dimethylbutanoic acid (Compound 18, 25 mg). The remaining amount (290 mg) was used for chiral separation. The enantiomers were separated via chiral SFC (Stationary phase: Chiralcel® OD-H 5 µm 250×30 mm, mobile phase: 75% $CO_2$, 25% MeOH) to give, after solidification from heptane/diisopropyl ether, the first eluted Enantiomer 18A (68 mg) and the second eluted Enantiomer 18B (70 mg).

Compound 18:

$^1$H NMR (500 MHz, DMSO-$d_6$) δ ppm 1.14 (d, J=2.2 Hz, 6H) 1.87 (t, J=7.1 Hz, 2H) 3.09-3.26 (m, 2H) 3.61 (s, 3H) 3.80-3.88 (m, 2H) 3.90 (s, 3H) 3.98-4.07 (m, 1H) 4.33-4.42 (m, 1H) 5.60 (d, J=8.5 Hz, 1H) 5.74 (s, 1H) 5.85 (s, 1H) 5.87 (s, 1H) 6.44 (d, J=8.5 Hz, 1H) 6.98-7.06 (m, 2H) 7.15 (d, J=1.6 Hz, 1H) 7.33 (dd, J=11.7, 8.2 Hz, 2H) 8.03 (s, 1H) 12.23 (br s, 1H)

LC/MS (method LC-C): $R_t$ 3.40 min, MH$^+$ 637

MP=138° C.

Enantiomer 18A:

$^1$H NMR (500 MHz, DMSO-$d_6$) δ ppm 1.14 (d, J=2.2 Hz, 6H) 1.87 (br t, J=7.1 Hz, 2H) 3.09-3.25 (m, 2H) 3.61 (s, 3H) 3.81-3.87 (m, 2H) 3.90 (s, 3H) 3.98-4.07 (m, 1H) 4.33-4.42 (m, 1H) 5.59 (d, J=8.5 Hz, 1H) 5.74 (s, 1H) 5.84 (s, 1H) 5.87 (s, 1H) 6.44 (br d, J=8.5 Hz, 1H) 6.98-7.06 (m, 2H) 7.14 (d, J=1.9 Hz, 1H) 7.33 (dd, J=10.7, 8.5 Hz, 2H) 8.02 (s, 1H) 11.94-12.35 (m, 1H)

LC/MS (method LC-C): $R_t$ 3.40 min, MH$^+$ 637

$[α]_D^{20}$: −30.2° (c 0.315, DMF)

Chiral SFC (method SFC-O): $R_t$ 1.31 min, no MH$^+$, chiral purity 100%.

Enantiomer 18B:

$^1$H NMR (500 MHz, DMSO-$d_6$) δ ppm 1.13 (d, J=2.5 Hz, 6H) 1.87 (t, J=7.3 Hz, 2H) 3.10-3.25 (m, 2H) 3.61 (s, 3H) 3.80-3.87 (m, 2H) 3.90 (s, 3H) 4.02 (td, J=10.2, 7.1 Hz, 1H) 4.33-4.41 (m, 1H) 5.59 (d, J=8.8 Hz, 1H) 5.73-5.76 (m, 1H) 5.84 (s, 1H) 5.87 (s, 1H) 6.44 (d, J=8.5 Hz, 1H) 6.97-7.08

(m, 2H) 7.14 (d, J=1.9 Hz, 1H) 7.33 (dd, J=11.2, 8.4 Hz, 2H) 8.02 (s, 1H) 11.92-12.44 (m, 1H)

LC/MS (method LC-C): R$_t$ 3.40 min, MH$^+$ 637

[α]$_D^{20}$: +28.0° (c 0.354, DMF)

Chiral SFC (method SFC-O): R$_t$ 1.60 min, no MH$^+$, chiral purity 99.45%.

Example 19A: Synthesis of (1R*,2R*)-2-((3-((1-(4-chloro-2-methoxyphenyl)-2-oxo-2-(6-(trifluoromethoxy)indolin-1-yl)ethyl)amino)-5-methoxyphenoxy)methyl)-cyclopropanecarboxylic acid (Compound 19A) and Separation into Stereoisomers 19AA and 19AB was cooled to 0° C. and was diluted with water and ice. The mixture was extracted with EtOAc. The organic layer was washed with water, dried over MgSO$_4$, filtered and the solvent was evaporated to dryness. The compound was purified by flash chromatography on silica gel (25-30 μm, 24 g, heptane/EtOAc 80/20). The pure fractions were combined and the solvent was removed under reduced pressure to give (1R*,2R*)-methyl 2-((3-((1-(4-chloro-2-methoxyphenyl)-2-oxo-2-(6-(trifluoromethoxy)indolin-1-yl)ethyl)amino)-5-methoxyphenoxy)methyl)-cyclopropanecarboxylate 19a (306 mg).

Synthesis of Compound 19A and Separation into Stereoisomers 19AA and 19AB:

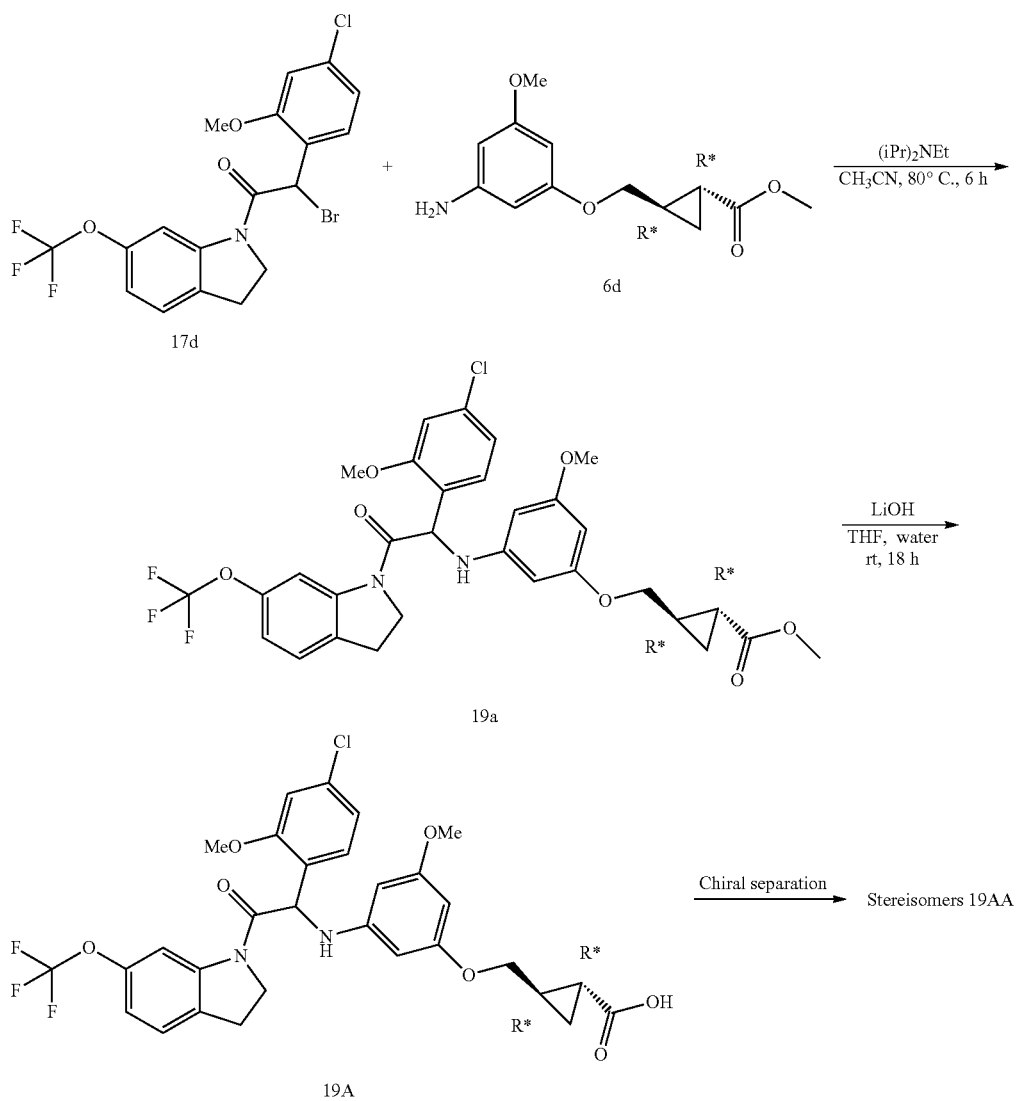

Synthesis of Intermediate 19a:

A mixture of 2-bromo-2-(4-chloro-2-methoxyphenyl)-1-(6-(trifluoromethoxy)indolin-1-yl)ethanone 17d (0.37 g, 0.796 mmol), (1R*,2R*)-methyl 2-((3-amino-5-methoxyphenoxy)methyl)cyclopropanecarboxylatemethoxyphenoxy)methyl)cyclopropyl)acetate 6d (0.317 g, 1.194 mmol) and diisopropylethylamine (0.274 mL, 1.593 mmol) in CH$_3$CN (10 mL) was stirred at 80° C. for 6 h. The reaction A solution of LiOH monohydrate (77 mg, 1.826 mmol) in water (5 mL) was added to a solution of (1R*,2R*)-methyl 2-((3-((1-(4-chloro-2-methoxyphenyl)-2-oxo-2-(6-(trifluoromethoxy)indolin-1-yl)ethyl)amino)-5-methoxyphenoxy)methyl)-cyclopropanecarboxylate 19a (237 mg, 0.365 mmol) in THF (5 mL). The mixture was stirred at room temperature for 18 h and concentrated under vacuum. The compound was purified by flash chromatography on silica gel (20-45 μm, 24 g, CH$_2$Cl$_2$/MeOH 99.5/0.5 to 98/2). The pure fractions were combined and concentrated under reduced pressure to give (1R*,2R*)-2-((3-((1-(4-chloro-2-methoxyphenyl)-2-oxo-2-(6-(trifluoromethoxy)indolin-1-yl)ethyl)amino)-5-methoxyphenoxy)methyl)cyclopropanecarboxylic acid (Compound 19A, 170 mg). The stereoisomers were separated via chiral SFC (Stationary phase: Chiralcel® OD-H 5 μm 250×30 mm, mobile phase: 65% CO$_2$, 35% MeOH) to give, after solidification from CH$_3$CN/diisopropyl ether/heptane the first eluted Stereoisomer 19AA (67 mg) and the second eluted Stereoisomer 19AB (59 mg).

Stereoisomer 19AA:

$^1$H NMR (500 MHz, DMSO-d$_6$) δ ppm 0.85-0.95 (m, 1H) 0.99-1.08 (m, 1H) 1.55 (dt, J=8.12, 4.30 Hz, 1H) 1.57-1.67 (m, 1H) 3.10-3.25 (m, 2H) 3.61 (s, 3H) 3.64-3.73 (m, 1H) 3.83 (br dd, J=10.40, 6.31 Hz, 1H) 3.90 (s, 3H) 3.98-4.08 (m, 1H) 4.29-4.44 (m, 1H) 5.60 (br d, J=8.51 Hz, 1H) 5.76 (s, 1H) 5.87 (s, 2H) 6.45 (br d, J=8.83 Hz, 1H) 6.96-7.07 (m, 2H) 7.14 (d, J=1.26 Hz, 1H) 7.31 (d, J=8.51 Hz, 1H) 7.32-7.38 (m, 1H) 8.02 (br s, 1H) 12.23 (br s, 1H)

LC/MS (method LC-D): R$_t$ 2.84 min, MH$^+$ 621

[α]$_D^{20}$: −65.6° (c 0.25, DMF)

Chiral SFC (method SFC-P): R$_t$ 1.44 min, no MH$^+$, chiral purity 100%.

Stereoisomer 19AB:

$^1$H NMR (500 MHz, DMSO-d$_6$) δ ppm 0.87-0.95 (m, 1H) 0.99-1.07 (m, 1H) 1.50-1.57 (m, 1H) 1.59-1.70 (m, 1H) 3.09-3.24 (m, 2H) 3.61 (s, 3H) 3.63-3.72 (m, 1H) 3.85 (br dd, J=10.40, 6.31 Hz, 1H) 3.90 (s, 3H) 3.99-4.09 (m, 1H) 4.30-4.44 (m, 1H) 5.60 (br d, J=8.51 Hz, 1H) 5.76 (s, 1H) 5.87 (s, 2H) 6.45 (br d, J=8.51 Hz, 1H) 7.00-7.09 (m, 2H) 7.14 (d, J=1.26 Hz, 1H) 7.30 (d, J=8.51 Hz, 1H) 7.34 (br d, J=8.20 Hz, 1H) 8.02 (br s, 1H) 12.26 (br s, 1H)

LC/MS (method LC-D): R$_t$ 2.85 min, MH$^+$ 621

[α]$_D^{20}$: +37.1 (c 0.28, DMF)

Chiral SFC (method SFC-P): R$_t$ 2.20 min, no MH$^+$, chiral purity 99.84%.

Example 19B: Synthesis of (1S*,2S*)-2-((3-((1-(4-chloro-2-methoxyphenyl)-2-oxo-2-(6-(trifluoromethoxy)indolin-1-yl)ethyl)amino)-5-methoxyphenoxy)methyl)-cyclopropanecarboxylic Acid (Compound 19B) and Separation into Stereoisomers 19BA and 19BB

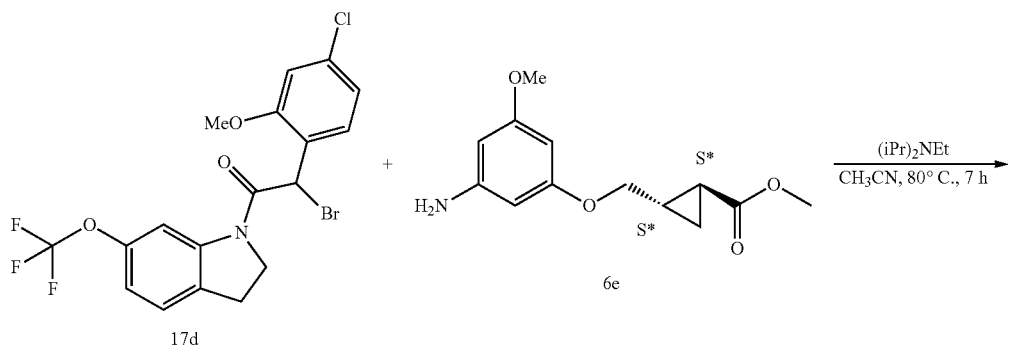

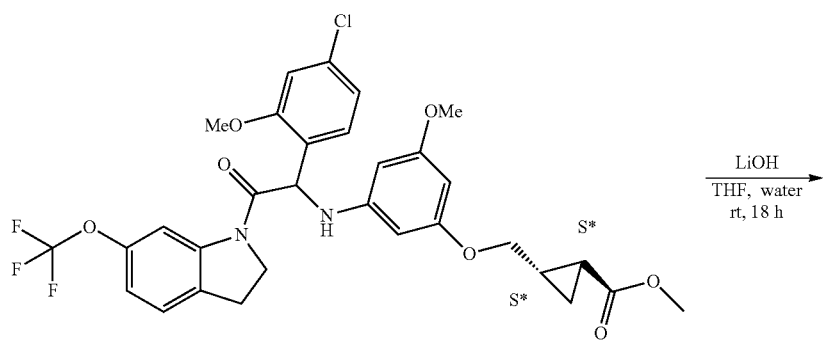

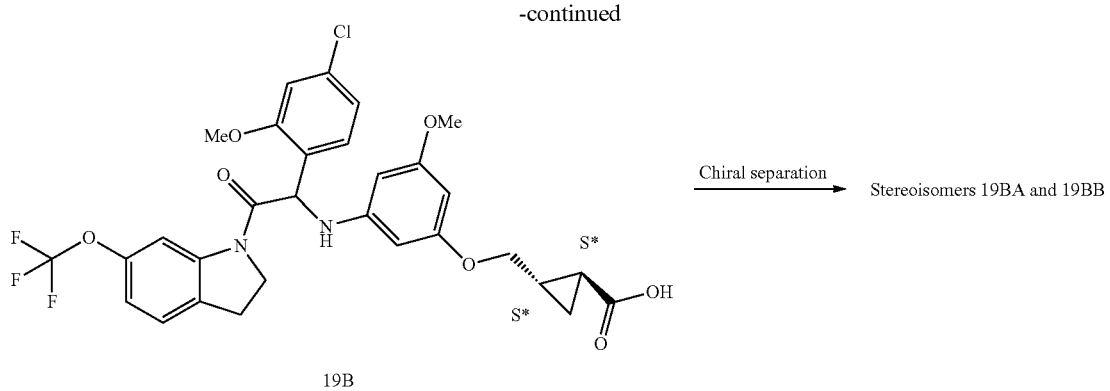

19B

Chiral separation → Stereoisomers 19BA and 19BB

Synthesis of Intermediate 19b:

A mixture of 2-bromo-2-(4-chloro-2-methoxyphenyl)-1-(6-(trifluoromethoxy)indolin-1-yl)ethanone 17d (0.39 g, 0.839 mmol), (1S*,2S*)-methyl 2-((3-amino-5-methoxyphenoxy)methyl)cyclopropanecarboxylatemethoxyphenoxy)methyl)cyclopropyl)acetate 6e (0.334 g, 1.259 mmol) and diisopropylethylamine (0.289 mL, 1.679 mmol) in CH$_3$CN (10 mL) was stirred at 80° C. for 7 h. The reaction was cooled to 0° C. and was diluted with water and ice. The mixture was extracted with EtOAc. The organic layer was washed with water, dried over MgSO$_4$, filtered and the solvent was evaporated to dryness. The compound was purified by flash chromatography on silica gel (25-30 μm, 24 g, heptane/EtOAc 80/20). The pure fractions were combined and the solvent was removed under reduced pressure to give (1 S*,2S*)-methyl 2-((3-((1-(4-chloro-2-methoxyphenyl)-2-oxo-2-(6-(trifluoromethoxy)indolin-1-yl)ethyl)amino)-5-methoxyphenoxy)methyl)-cyclopropanecarboxylate 19b (308 mg).

Synthesis of Compound 19B and Separation into Stereoisomers 19BA and 19BB:

A solution of LiOH monohydrate (98 mg, 2.334 mmol) in water (5 mL) was added to a solution of (1S*,2S*)-methyl 2-((3-((1-(4-chloro-2-methoxyphenyl)-2-oxo-2-(6-(trifluoromethoxy)indolin-1-yl)ethyl)amino)-5-methoxyphenoxy)methyl)-cyclopropanecarboxylate 19b (303 mg, 0.467 mmol) in THF (5 mL). The mixture was stirred at room temperature for 18 h and then concentrated under vacuum. The compound was purified by flash chromatography on silica gel (20-45 μm, 24 g, CH$_2$Cl$_2$/MeOH 100/0 to 98/2). The pure fractions were combined and concentrated under reduced pressure to give (1S*,2S*)-2-((3-((1-(4-chloro-2-methoxyphenyl)-2-oxo-2-(6-(trifluoromethoxy)indolin-1-yl)ethyl)amino)-5-methoxyphenoxy)methyl)-cyclopropanecarboxylic acid (Compound 19B, 250 mg). The stereoisomers were separated via chiral SFC (Stationary phase: Chiralcel® OD-H 5 μm 250×30 mm, mobile phase: 65% CO$_2$, 35% MeOH) to give, after solidification from CH$_3$CN/diisopropyl ether/heptane the first eluted Stereoisomer 19BA (97 mg) and the second eluted Stereoisomer 19BB (103 mg).

Stereoisomer 19BA:

$^1$H NMR (400 MHz, DMSO-d$_6$) δ ppm 0.85-0.95 (m, 1H) 0.95-1.09 (m, 1H) 1.54 (dt, J=8.34, 4.42 Hz, 1H) 1.55-1.66 (m, 1H) 3.09-3.25 (m, 2H) 3.61 (s, 3H) 3.66 (dd, J=10.36, 7.33 Hz, 1H) 3.85 (dd, J=10.61, 6.06 Hz, 1H) 3.89 (s, 3H) 3.96-4.12 (m, 1H) 4.26-4.43 (m, 1H) 5.59 (d, J=8.59 Hz, 1H) 5.76 (s, 1H) 5.87 (s, 1H) 5.88 (s, 1H) 6.44 (d, J=9.09 Hz, 1H) 6.93-7.06 (m, 2H) 7.14 (d, J=2.02 Hz, 1H) 7.30 (d, J=8.08 Hz, 1H) 7.34 (d, J=8.08 Hz, 1H) 8.02 (s, 1H) 12.20 (br s, 1H)

LC/MS (method LC-D): R$_t$ 2.84 min, MH$^+$ 621

$[α]_D^{20}$: −47.6° (c 0.271, DMF)

Chiral SFC (method SFC-P): R$_t$ 1.48 min, no MH$^+$, chiral purity 100%.

Stereoisomer 19BB:

$^1$H NMR (400 MHz, DMSO-d$_6$) δ ppm 0.85-0.97 (m, 1H) 0.98-1.07 (m, 1H) 1.51-1.58 (m, 1H) 1.55-1.67 (m, 1H) 3.07-3.25 (m, 2H) 3.61 (s, 3H) 3.65-3.74 (m, 1H) 3.83 (br dd, J=10.36, 5.81 Hz, 1H) 3.90 (s, 3H) 3.97-4.14 (m, 1H) 4.30-4.42 (m, 1H) 5.60 (br d, J=8.59 Hz, 1H) 5.76 (s, 1H) 5.87 (s, 2H) 6.44 (br d, J=8.59 Hz, 1H) 6.98-7.07 (m, 2H) 7.14 (d, J=1.52 Hz, 1H) 7.30 (d, J=8.08 Hz, 1H) 7.33 (br d, J=8.08 Hz, 1H) 8.02 (s, 1H) 12.24 (br s, 1H)

LC/MS (method LC-D): R$_t$ 2.84 min, MH$^+$ 621

$[α]_D^{20}$: +56.8° (c 0.264, DMF)

Chiral SFC (method SFC-P): R$_t$ 2.12 min, no MH$^+$, chiral purity 99.59%.

Example 20: Synthesis of 4-(3-((1-(4-chlorophenyl)-2-(5-methoxy-6-(trifluoro-methyl)indolin-1-yl)-2-oxoethyl)amino)-5-methoxyphenoxy)-2-methylbutanoic Acid (Compound 20) and Separation into Stereoisomers 20A, 20B, 20C and 20D

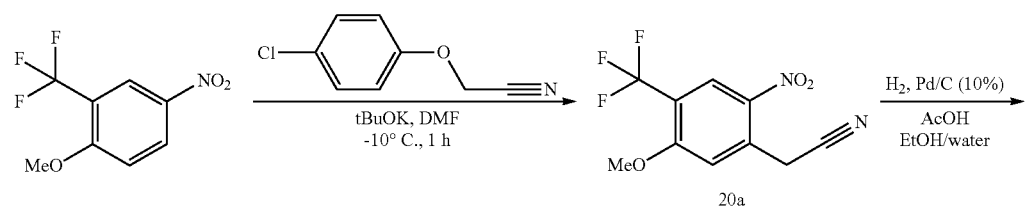

20a

-continued
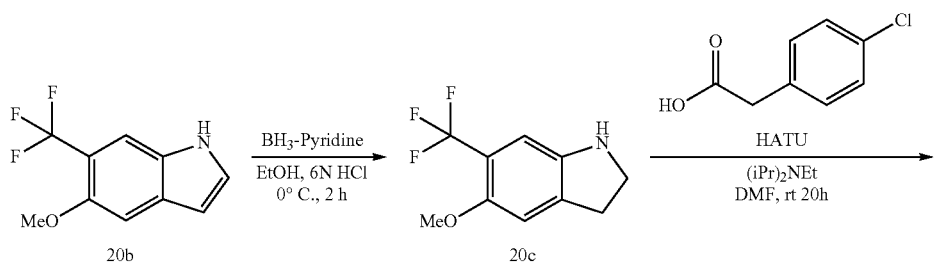
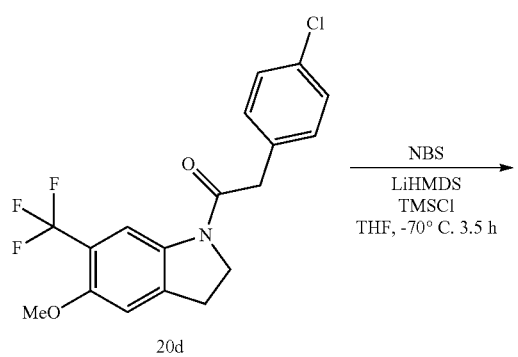
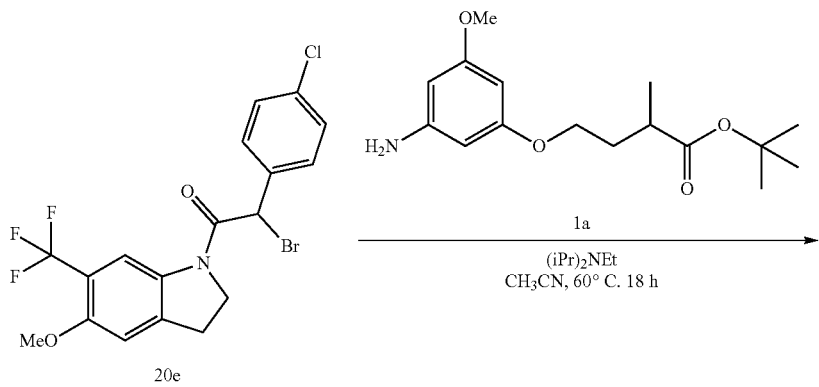
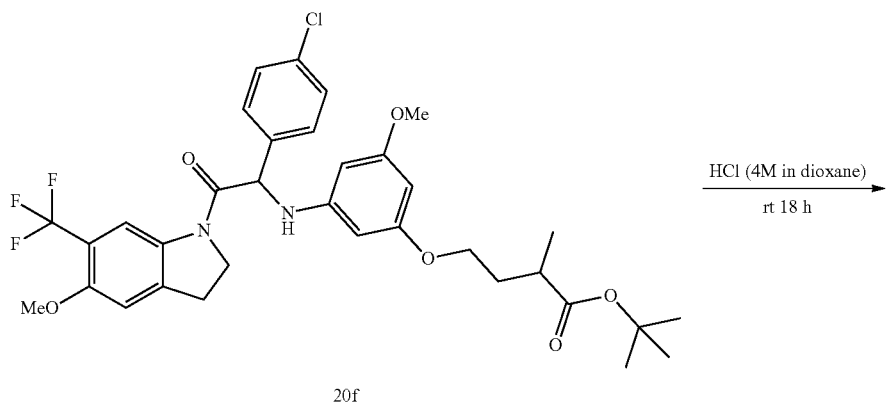

-continued

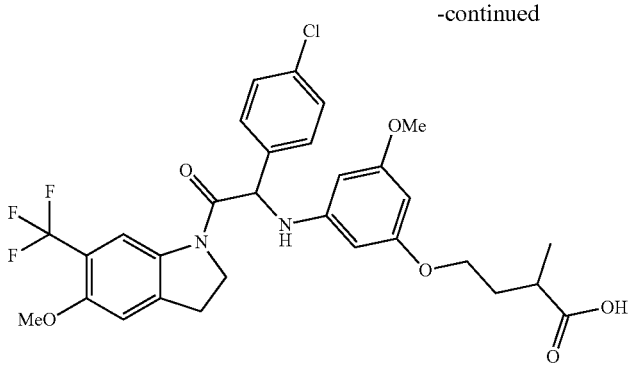

20

Stereoisomer separation → Stereoisomer 20A, 20B, 20C, 20D

Synthesis of Intermediate 20a:

A mixture of 1-methoxy-4-nitro-2-(trifluoromethyl)benzene [CAS 654-76-2] (24.5 g, 110.8 mmol) and 4-chlorophenoxyacetonitrile [CAS 3598-13-8] (20.4 g, 121.9 mmol) in DMF (100 mL) was added dropwise over 30 min to a stirred solution of tBuOK (27.35 g, 243.7 mmol) in DMF (100 mL) at −10° C. After addition, the purple solution was maintained at −10° C. for 1 h. 500 mL of ice-water and 500 mL of 6N HCl were added and the precipitate was filtered off, washed with water and dried under reduced pressure to afford 40.4 g of 2-(5-methoxy-2-nitro-4-(trifluoromethyl)-phenyl)acetonitrile 20a (used as such in the next step).

Synthesis of Intermediate 20b:

A solution of 2-(5-methoxy-2-nitro-4-(trifluoromethyl) phenyl)acetonitrile 20a (26 g, 99.9 mmol) in ethanol/water (9/1) (500 mL) and AcOH (5.2 mL) was hydrogenated for 1 h under a pressure of 3.5 Bar with 10% Pd/C (15.3 g) as the catalyst. The reaction mixture was filtered through a pad of Celite® and the filter cake was washed with a solvent mixture of $CH_2Cl_2$ and $CH_3OH$. The combined filtrates were concentrated under reduced pressure. The residue was filtered through a glass filter charged with silica 60-200 μm using heptane/EtOAc 80/20 as the eluent. The fractions containing the expected compound were combined and the solvent was concentrated under reduced pressure to give 5-methoxy-6-(trifluoromethyl)-1H-indole 20b (15.6 g).

Synthesis of Intermediate 20c:

At 0° C., $BH_3$-Pyridine (23.5 mL, 232.4 mmol) was added dropwise to a solution of 5-methoxy-6-(trifluoromethyl)-1H-indole 20b (10 g, 46.5 mmol) in EtOH (60 mL). 6N HCl (140 mL) was slowly added while maintaining the temperature below 10° C. The mixture was stirred at 0° C. for 2 h. Water (200 mL) was added and the mixture was basified to pH 8-9 with a concentrated aqueous solution of NaOH (the reaction temperature was kept below 20° C.). The precipitate was filtered off, washed with water (twice) and co-evaporated under reduced pressure with toluene to give 5-methoxy-6-(trifluoromethyl)indoline 20c (9 g).

Synthesis of Compound 20 and Separation into Stereoisomers 20A, 20B, 20C and 20D:

Compound 20 (330 mg) was obtained following the procedures described for the synthesis of Compound 1 starting from intermediate 20c. The 4 Stereoisomers 20A (50 mg), 20B (18 mg), 20C (68 mg) and 20D (32 mg) were obtained, in this elution order, via two subsequent chiral SFC separations: (Stationary phase: Chiralpak® AD-H 5 μm 250×30 mm, mobile phase: 40% $CO_2$, 60% iPrOH) and (Stationary phase: Chiralcel® OJ-H 5 μm 250×20 mm, mobile phase: 60% $CO_2$, 40% MeOH); followed by individual purification by flash chromatography on silica gel (15-40 μm, 12 g, $CH_2Cl_2$/MeOH 99.5/0.5 to 90/10) and subsequent solidification from $CH_3CN$/diisopropyl ether/heptane.

Stereoisomer 20A:

$^1$H NMR (400 MHz, DMSO-$d_6$) δ ppm 1.10 (d, J=7.07 Hz, 3H) 1.60-1.72 (m, 1H) 1.90-2.01 (m, 1H) 3.20-3.32 (m, 2H) 3.61 (s, 3H) 3.79-3.90 (m, 5H) 3.93-4.09 (m, 1H) 4.42-4.53 (m, 1H) 5.53 (br d, J=8.59 Hz, 1H) 5.74 (s, 1H) 5.93 (br s, 1H) 5.95 (br s, 1H) 6.38 (br d, J=9.09 Hz, 1H) 7.23 (s, 1H) 7.43 (br d, J=8.08 Hz, 2H) 7.55 (br d, J=8.08 Hz, 2H) 8.33 (s, 1H) 12.16 (br s 1H) (1H missing CH $CO_2H$ under DMSO)

LC/MS (method LC-C): $R_t$ 2.95 min, MH$^+$ 607

$[α]_D^{20}$: −40.9° (c 0.257, DMF)

Chiral SFC (method SFC-Q): $R_t$ 1.07 min, MH$^+$ 607, chiral purity 100%.

Stereoisomer 20B:

$^1$H NMR (400 MHz, DMSO-$d_6$) δ ppm 1.09 (d, J=6.94 Hz, 3H) 1.69 (dq, J=13.52, 6.53 Hz, 1H) 1.88-2.11 (m, 1H) 3.08-3.28 (m, 2H) 3.53-3.66 (m, 3H) 3.79-3.90 (m, 5H) 3.92-4.11 (m, 1H) 3.92-4.11 (m, 1H) 4.32-4.67 (m, 1H) 5.54 (d, J=8.51 Hz, 1H) 5.75 (s, 1H) 5.93 (s, 1H) 5.95 (s, 1H) 6.30-6.45 (m, 1H) 7.23 (s, 1H) 7.43 (d, J=8.20 Hz, 2H) 7.55 (d, J=8.20 Hz, 2H) 8.33 (s, 1H) 12.05 (br s, 1H) (1H missing CH $CO_2H$ under DMSO)

LC/MS (method LC-C): $R_t$ 2.95 min, MH$^+$ 607

$[α]_D^{20}$: −50.00 (c 0.266, DMF)

Chiral SFC (method SFC-Q): $R_t$ 1.07 min, MH$^+$ 607, chiral purity 100%.

Stereoisomer 20C:

$^1$H NMR (400 MHz, DMSO-$d_6$) δ ppm 1.09 (br d, J=6.94 Hz, 3H) 1.52-1.83 (m, 1H) 1.86-2.06 (m, 1H) 3.07-3.28 (m, 2H) 3.61 (s, 3H) 3.73-3.91 (m, 5H) 3.94-4.04 (m, 1H) 4.37-4.58 (m, 1H) 5.54 (br d, J=8.51 Hz, 1H) 5.75 (s, 1H) 5.93 (s, 1H) 5.95 (s, 1H) 6.39 (br d, J=8.51 Hz, 1H) 7.23 (s, 1H) 7.43 (br d, J=8.20 Hz, 2H) 7.55 (br d, J=8.20 Hz, 2H) 8.33 (s, 1H) 12.13 (br s, 1H) (1H missing CH $CO_2H$ under DMSO)

LC/MS (method LC-C): $R_t$ 2.95 min, MH$^+$ 607

$[α]_D^{20}$: +26.0° (c 0.288, DMF)

Chiral SFC (method SFC-Q): $R_t$ 1.56 min, MH$^+$ 607, chiral purity 99.68%.

Stereoisomer 20D:

$^1$H NMR (400 MHz, DMSO-$d_6$) δ ppm 1.09 (d, J=7.07 Hz, 3H) 1.60-1.75 (m, 1H) 1.85-1.99 (m, 1H) 3.11-3.27 (m, 2H) 3.61 (s, 3H) 3.77-3.91 (m, 5H) 3.93-4.05 (m, 1H) 4.44-4.56 (m, 1H) 5.54 (br d, J=8.59 Hz, 1H) 5.74 (s, 1H) 5.93 (br s, 1H) 5.95 (br s, 1H) 6.38 (br d, J=8.59 Hz, 1H)

7.23 (s, 1H) 7.43 (d, J=8.59 Hz, 2H) 7.55 (br d, J=8.08 Hz, 2H) 8.33 (s, 1H) 12.22 (br s, 1H) (1H missing CH CO$_2$H under DMSO)

LC/MS (method LC-C): R$_t$ 2.96 min, MH$^+$ 607

$[\alpha]_D^{20}$: +57.4° (c 0.27, DMF)

Chiral SFC (method SFC-Q): R$_t$ 2.19 min, MH$^+$ 607, chiral purity 100%.

Example 21: Synthesis of 4-(3-((1-(4-chlorophenyl)-2-(5-methoxy-6-(trifluoro-methyl)indolin-1-yl)-2-oxoethyl)amino)-5-methoxyphenoxy)-2,2-dimethylbutanoic acid (Compound 21) and Chiral Separation into Enantiomers 21A and 21B

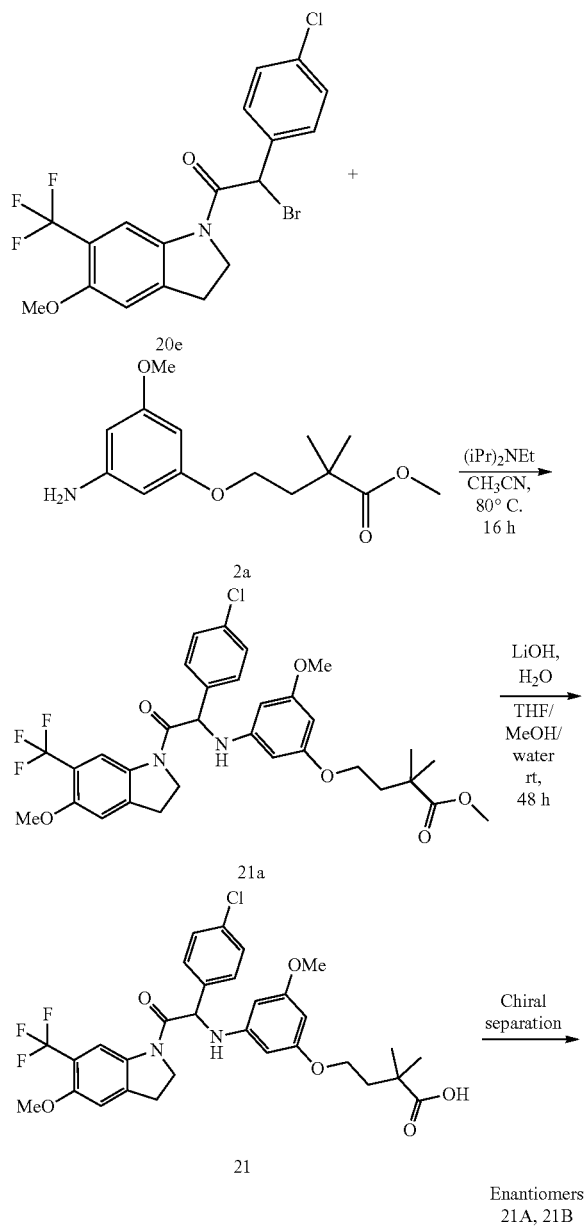

Synthesis of Intermediate 21a:

A mixture of 2-bromo-2-(4-chlorophenyl)-1-(5-methoxy-6-(trifluoromethyl)indolin-1-yl)ethanone 20e (904 mg, 2.014 mmol), methyl 4-(3-amino-5-methoxyphenoxy)-2,2-dimethylbutanoate 2a (700 mg, 2.619 mmol) and diisopropylethylamine (694 µL, 4.029 mmol) in CH$_3$CN (10 mL) was stirred at 80° C. for 16 h. The mixture was concentrated under reduced pressure. The residue was taken up with EtOAc. The organic layer was dried over MgSO$_4$, filtered and the solvent was evaporated to give methyl 4-(3-((1-(4-chlorophenyl)-2-(5-methoxy-6-(trifluoromethyl)indolin-1-yl)-2-oxoethyl)amino)-5-methoxyphenoxy)-2,2-dimethylbutanoate 21a (1.58 g), which was used as such in the next step.

Synthesis of Compound 21 and Chiral Separation into Enantiomers 21A and 21B:

At 0° C., LiOH monohydrate (254 mg, 6.046 mmol) was added to a solution of methyl 4-(3-((1-(4-chlorophenyl)-2-(5-methoxy-6-(trifluoromethyl)indolin-1-yl)-2-oxoethyl)amino)-5-methoxyphenoxy)-2,2-dimethylbutanoate 21a (1.28 g, 2.015 mmol) in THF/MeOH/water (15 mL). The mixture was warmed to room temperature and stirred for 48 h. The mixture was cooled to 0° C. and water was added. The mixture was acidified to pH 4-5 with 3N HCl and extracted with EtOAc. The combined organic layers were dried over MgSO$_4$, filtered and the solvent was evaporated. Purification was performed by flash chromatography on silica gel (15-µm, 40 g, CH$_2$Cl$_2$/CH$_3$OH: 100/0 to 98/2). The fractions containing expected compound were combined and evaporated to dryness. A second purification was performed via Reverse phase (Stationary phase: YMC-actus Triart-C18 10 µm 30×150 mm, mobile phase: Gradient from 70% aqueous NH$_4$HCO$_3$ 0.2%, 30% CH$_3$CN to 0% aqueous NH$_4$HCO$_3$ 0.2%, 100% CH$_3$CN). The pure fractions were combined and concentrated under vacuum to give 4-(3-((1-(4-chlorophenyl)-2-(5-methoxy-6-(trifluoromethyl)indolin-1-yl)-2-oxoethyl)amino)-5-methoxyphenoxy)-2,2-dimethylbutanoic acid (Compound 21, 455 mg). The enantiomers were separated via chiral SFC (Stationary phase: Chiralcel® OD-H 5 µm 250×30 mm, mobile phase: 55% CO$_2$, 45% MeOH) to give, after solidification from heptane/diisopropyl ether, the first eluted Enantiomer 21A (106 mg) and the second eluted Enantiomer 21B (103 mg).

Compound 21:

$^1$H NMR (500 MHz, DMSO-d$_6$) δ ppm 1.13 (d, J=3.8 Hz, 6H) 1.87 (t, J=7.3 Hz, 2H) 3.14-3.30 (m, 2H) 3.61 (s, 3H) 3.84 (m, 5H) 3.98 (td, J=10.4, 7.3 Hz, 1H) 4.51 (td, J=10.3, 6.1 Hz, 1H) 5.52 (d, J=8.5 Hz, 1H) 5.73 (t, J=1.9 Hz, 1H) 5.92 (s, 1H) 5.94 (s, 1H) 6.39 (d, J=8.5 Hz, 1H) 7.23 (s, 1H) 7.43 (d, J=8.5 Hz, 2H) 7.55 (d, J=8.5 Hz, 2H) 8.33 (s, 1H) 12.23 (br s, 1H)

LC/MS (method LC-C): R$_t$ 3.19 min, MH$^+$ 621

Enantiomer 21A:

$^1$H NMR (500 MHz, DMSO-d$_6$) δ ppm 1.08-1.15 (m, 6H) 1.85 (t, J=7.3 Hz, 2H) 3.13-3.30 (m, 2H) 3.55-3.65 (m, 3H) 3.80-3.89 (m, 5H) 3.98 (td, J=10.4, 7.3 Hz, 1H) 4.52 (td, J=10.4, 6.3 Hz, 1H) 5.54 (d, J=8.8 Hz, 1H) 5.73 (t, J=1.9 Hz, 1H) 5.92 (s, 1H) 5.95 (s, 1H) 6.38 (d, J=8.5 Hz, 1H) 7.23 (s, 1H) 7.43 (d, J=8.5 Hz, 2H) 7.56 (d, J=8.5 Hz, 2H) 8.34 (s, 1H)

LC/MS (method LC-C): R$_t$ 3.21 min, MH$^+$ 621

$[\alpha]_D^{20}$: −41.7° (c 0.254, DMF)

Chiral SFC (method SFC-H): R$_t$ 1.23 min, MH$^+$ 621, chiral purity 100%.

Enantiomer 21B:

$^1$H NMR (500 MHz, DMSO-d$_6$) δ ppm 1.08-1.16 (m, 6H) 1.86 (t, J=7.1 Hz, 2H) 3.15-3.29 (m, 2H) 3.61 (s, 3H) 3.80-3.90 (m, 5H) 3.98 (td, J=10.2, 7.3 Hz, 1H) 4.52 (td, J=10.4, 6.3 Hz, 1H) 5.53 (d, J=8.5 Hz, 1H) 5.70-5.75 (m, 1H) 5.92 (s, 1H) 5.95 (s, 1H) 6.38 (d, J=8.5 Hz, 1H) 7.23 (s, 1H) 7.43 (d, J=8.5 Hz, 2H) 7.56 (d, J=8.5 Hz, 2H) 8.34 (s, 1H)

LC/MS (method LC-C): $R_t$ 3.21 min, MH+ 621

$[\alpha]_D^{20}$: +44.0° (c 0.275, DMF)

Chiral SFC (method SFC-H): $R_t$ 2.38 min, MH+ 621, chiral purity 100%.

Example 22A: Synthesis of (1R*,2R*)-2-((3-((1-(4-chlorophenyl)-2-(5-methoxy-6-(trifluoromethyl)indolin-1-yl)-2-oxoethyl)amino)-5-methoxyphenoxy)methyl)-cyclopropanecarboxylic Acid (Compound 22A) and Separation into Stereoisomers 22AA and 22AB

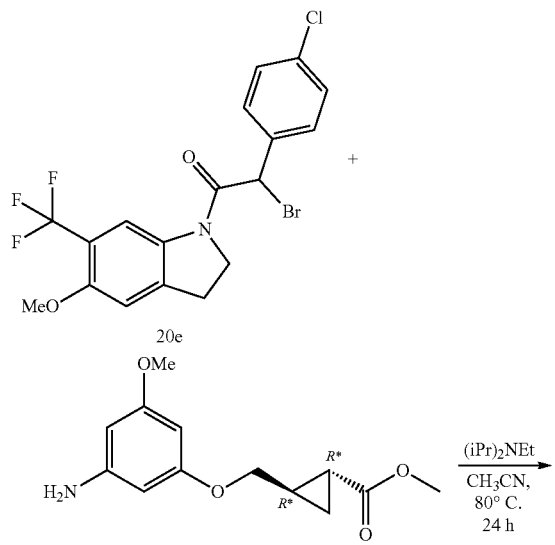

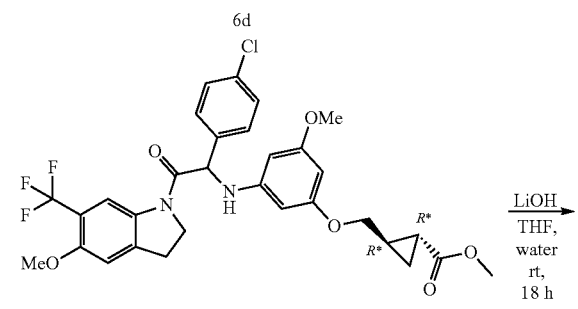

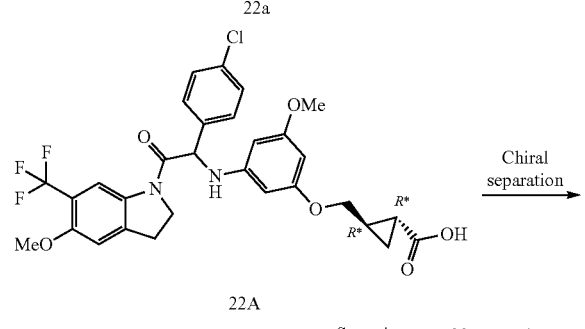

Stereoisomers 22AA and 22AB

Synthesis of Compound 22A and Separation into Stereoisomers 22AA and 22AB:

Compound 22A (284 mg) was synthesized from intermediate 20e using the procedures described for the synthesis of Compound 6A. The two stereoisomers were separated via chiral SFC (Stationary phase: Chiralcel® OD-H 5 μm 250× 30 mm, mobile phase: 50% $CO_2$, 50% EtOH) to give, after solidification from pentane/diisopropyl ether, the first eluted Stereoisomers 22AA (79 mg) and the second eluted Stereoisomers 22AB (74 mg).

Stereoisomers 22AA:

$^1$H NMR (500 MHz, DMSO-$d_6$) δ ppm 0.85-0.93 (m, 1H) 1.00-1.08 (m, 1H) 1.54 (dt, J=8.12, 4.30 Hz, 1H) 1.60-1.68 (m, 1H) 3.12-3.26 (m, 2H) 3.61 (s, 3H) 3.68 (dd, J=10.40, 7.57 Hz, 1H) 3.79-3.90 (m, 4H) 3.93-4.05 (m, 1H) 4.50 (td, J=10.40, 6.31 Hz, 1H) 5.55 (d, J=8.51 Hz, 1H) 5.75 (s, 1H) 5.94 (s, 1H) 5.96 (s, 1H) 6.39 (d, J=8.83 Hz, 1H) 7.23 (s, 1H) 7.43 (d, J=8.51 Hz, 2H) 7.55 (d, J=8.51 Hz, 2H) 8.33 (s, 1H) 12.23 (br s, 1H)

LC/MS (method LC-C): $R_t$ 2.80 min, MH+ 605

$[\alpha]_D^{20}$: −75.0° (c 0.3, DMF)

Chiral SFC (method SFC-R): $R_t$ 0.86 min, no MH+, chiral purity 100%.

Stereoisomers 22AB:

$^1$H NMR (500 MHz, DMSO-$d_6$) δ ppm 0.88 (br t, J=9.30 Hz, 1H) 1.02 (dt, J=8.43, 4.45 Hz, 1H) 1.47-1.58 (m, 1H) 1.59-1.68 (m, 1H) 3.13-3.28 (m, 2H) 3.61 (s, 3H) 3.64-3.72 (m, 1H) 3.84 (s, 4H) 3.92-4.06 (m, 1H) 4.50 (td, J=10.32, 6.15 Hz, 1H) 5.55 (d, J=8.83 Hz, 1H) 5.75 (s, 1H) 5.95 (s, 1H) 5.96 (s, 1H) 6.39 (d, J=8.83 Hz, 1H) 7.23 (s, 1H) 7.43 (d, J=8.51 Hz, 2H) 7.55 (d, J=8.51 Hz, 2H) 8.33 (s, 1H) 12.08 (br s, 1H)

LC/MS (method LC-D): $R_t$ 2.69 min, MH+ 605

$[\alpha]_D^{20}$: +10.0° (c 0.281, DMF)

Chiral SFC (method SFC-R): $R_t$ 1.84 min, no MH+, chiral purity 100%.

Example 22B: Synthesis of (1 S*,2S*)-2-((3-((1-(4-chlorophenyl)-2-(5-methoxy-6-(trifluoromethyl)indolin-1-yl)-2-oxoethyl)amino)-5-methoxyphenoxy)methyl)-cyclopropanecarboxylic Acid (Compound 22B) and Separation into Stereoisomers 22BA and 22BB

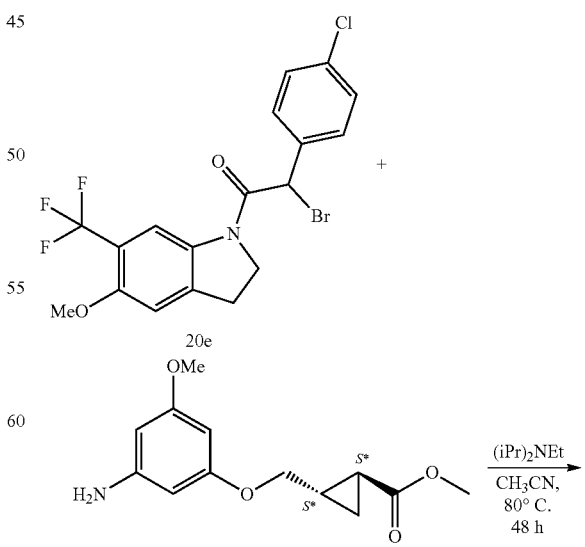

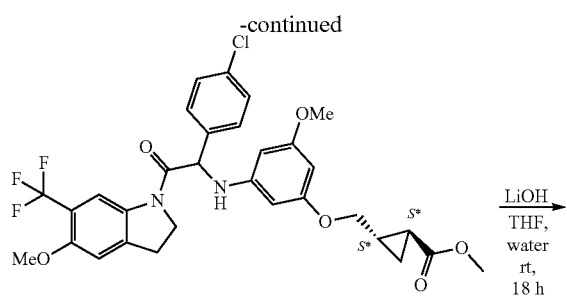

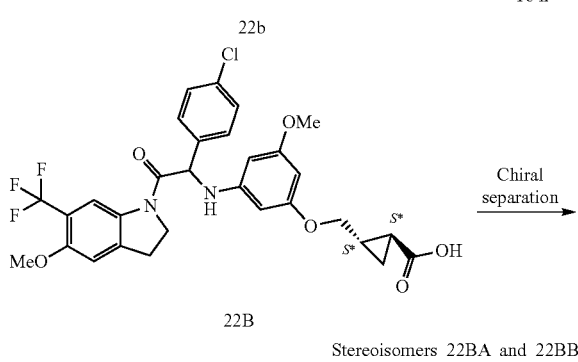

Stereoisomers 22BA and 22BB

Synthesis of Compound 22B and Separation into Stereoisomers 22BA and 22BB:

Compound 22B (257 mg) was synthesized from intermediate 20e using the procedure described for the synthesis of Compound 6B. The two stereoisomers were separated via chiral SFC (Stationary phase: Chiralcel® OD-H 5 μm 250× 30 mm, mobile phase: 50% CO$_2$, 50% EtOH) to give, after solidification from pentane/diisopropyl ether, the first eluted stereoisomers 22BA (49 mg) and the second eluted stereoisomers 22BB (61 mg).

Stereoisomers 22BA:
$^1$H NMR (500 MHz, DMSO-d$_6$) δ ppm 0.83-1.00 (m, 1H) 0.98-1.09 (m, 1H) 1.54 (dt, J=8.35, 4.33 Hz, 1H) 1.58-1.70 (m, 1H) 3.13-3.28 (m, 2H) 3.61 (s, 3H) 3.68 (dd, J=10.09, 7.57 Hz, 1H) 3.78-3.89 (m, 4H) 3.95-4.05 (m, 1H) 4.50 (td, J=10.25, 6.31 Hz, 1H) 5.55 (d, J=8.83 Hz, 1H) 5.75 (s, 1H) 5.95 (br s, 1H) 5.96 (br s, 1H) 6.39 (br d, J=8.83 Hz, 1H) 7.23 (s, 1H) 7.43 (d, J=8.51 Hz, 2H) 7.55 (d, J=8.51 Hz, 2H) 8.33 (s, 1H) 12.24 (br s, 1H)
LC/MS (method LC-D): R$_t$ 2.68 min, MH$^+$ 605
[α]$_D^{20}$: −9.3° (c 0.291, DMF)
Chiral SFC (method SFC-S): R$_t$ 1.48 min, MH$^+$ 605, chiral purity 100%.

Stereoisomers 22BB:
$^1$H NMR (500 MHz, DMSO-d$_6$) δ ppm 0.82-0.95 (m, 1H) 1.04-1.06 (m, 1H) 1.55 (dt, J=8.28, 4.22 Hz, 1H) 1.58-1.68 (m, 1H) 3.13-3.28 (m, 2H) 3.61 (s, 3H) 3.68 (dd, J=10.40, 7.25 Hz, 1H) 3.81-3.88 (m, 4H) 3.95-4.02 (m, 1H) 4.46-4.55 (m, 1H) 5.54 (d, J=8.83 Hz, 1H) 5.75 (s, 1H) 5.94 (s, 1H) 5.96 (s, 1H) 6.39 (d, J=9.14 Hz, 1H) 7.23 (s, 1H) 7.43 (d, J=8.51 Hz, 2H) 7.55 (d, J=8.51 Hz, 2H) 8.33 (s, 1H) 12.20 (br s, 1H)
LC/MS (method LC-C): R$_t$ 2.80 min, MH$^+$ 605
[α]$_D^{20}$: +80.0° (c 0.275, DMF)
Chiral SFC (method SFC-S): R$_t$ 3.12 min, MH$^+$ 605, chiral purity 99.55%.

Example 23: Synthesis of (1s,3s)-3-(3-((1-(4-chlorophenyl)-2-(5-methoxy-6-(trifluoromethyl)indolin-1-yl)-2-oxoethyl)amino)-5-methoxyphenoxy)cyclobutene-carboxylic Acid (Compound 23) and Chiral Separation into Enantiomers 23A and 23B

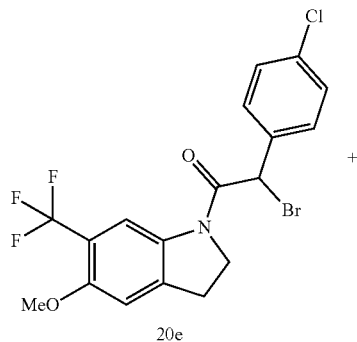

20e

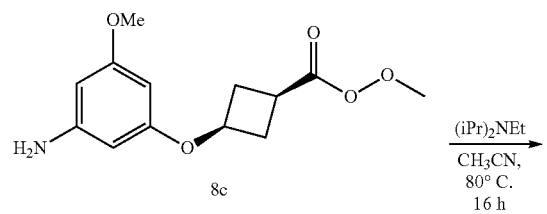

-continued

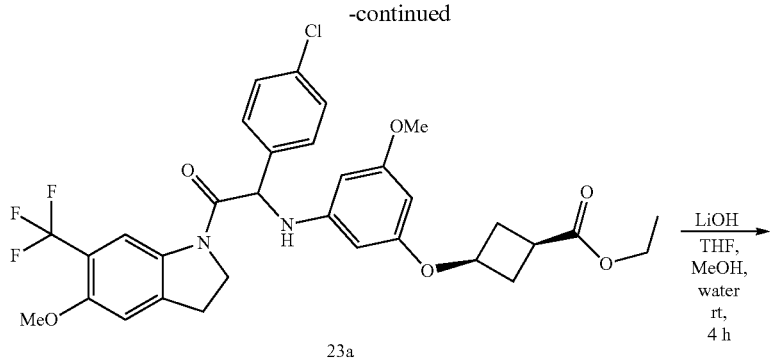

23a

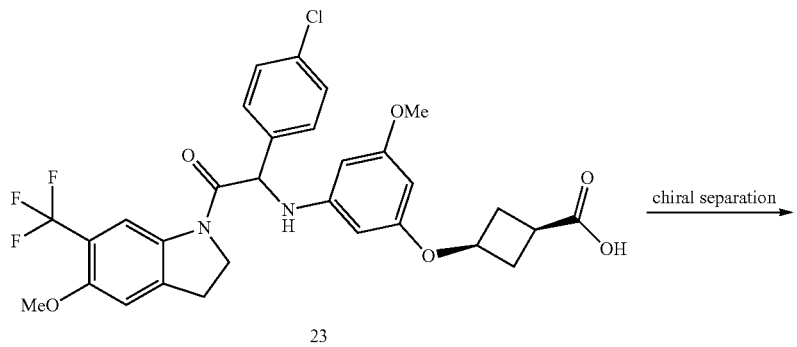

23

Enantiomers 23A and 23B

Synthesis of Compound 23 and Chiral Separation into Enantiomers 23A and 23B:

Compound 23A (280 mg) was synthesized from intermediate 20e using the procedures described for the synthesis of Compound 8. The two enantiomers were separated via chiral SFC (Stationary phase: Chiralcel® OD-H 5 μm 250×30 mm, mobile phase: 45% CO₂, 55% EtOH) to give, after solidification from heptane/diisopropyl ether, the first eluted Enantiomer 23A (60 mg) and the second eluted Enantiomer 23B (71 mg).

Compound 23:

¹H NMR (500 MHz, DMSO-d₆) δ ppm 2.02-2.15 (m, 2H) 2.58-2.65 (m, 2H) 2.66-2.75 (m, 1H) 3.14-3.29 (m, 2H) 3.61 (s, 3H) 3.84 (s, 3H) 3.98 (td, J=10.4, 7.3 Hz, 1H) 4.42-4.57 (m, 2H) 5.51 (d, J=8.5 Hz, 1H) 5.65 (t, J=1.9 Hz, 1H) 5.86 (s, 1H) 5.93 (s, 1H) 6.42 (d, J=8.5 Hz, 1H) 7.23 (s, 1H) 7.44 (d, J=8.5 Hz, 2H) 7.55 (d, J=8.5 Hz, 2H) 8.34 (s, 1H) 12.11-12.40 (m, 1H)

LC/MS (method LC-C): $R_t$ 2.76 min, MH⁺ 605

Enantiomer 23A:

¹H NMR (500 MHz, DMSO-d₆) δ ppm 2.02-2.15 (m, 2H) 2.57-2.65 (m, 2H) 2.66-2.75 (m, 1H) 3.14-3.28 (m, 2H) 3.61 (s, 3H) 3.84 (s, 3H) 3.98 (td, J=10.3, 7.1 Hz, 1H) 4.42-4.56 (m, 2H) 5.51 (d, J=8.5 Hz, 1H) 5.65 (t, J=2.0 Hz, 1H) 5.86 (s, 1H) 5.93 (s, 1H) 6.42 (d, J=8.5 Hz, 1H) 7.23 (s, 1H) 7.44 (d, J=8.5 Hz, 2H) 7.55 (d, J=8.5 Hz, 2H) 8.34 (s, 1H) 12.02-12.49 (m, 1H)

LC/MS (method LC-C): $R_t$ 2.75 min, MH⁺ 605

$[\alpha]_D^{20}$: −38.1° (c 0.307, DMF)

Chiral SFC (method SFC-R): $R_t$ 0.84 min, MH⁺ 605, chiral purity 100%.

Enantiomer 23B:

¹H NMR (500 MHz, DMSO-d₆) δ ppm 2.02-2.15 (m, 2H) 2.56-2.75 (m, 3H) 3.14-3.27 (m, 2H) 3.61 (s, 3H) 3.84 (s, 3H) 3.93-4.04 (m, 1H) 4.43-4.57 (m, 2H) 5.51 (br d, J=8.5 Hz, 1H) 5.65 (s, 1H) 5.86 (s, 1H) 5.93 (s, 1H) 6.42 (br d, J=8.5 Hz, 1H) 7.23 (s, 1H) 7.44 (br d, J=8.5 Hz, 2H) 7.55 (br d, J=8.5 Hz, 2H) 8.34 (s, 1H) 12.07-12.47 (m, 1H)

LC/MS (method LC-C): $R_t$ 2.76 min, MH⁺ 605

$[\alpha]_D^{20}$: +36.9° (c 0.309, DMF)

Chiral SFC (method SFC-R): $R_t$ 1.86 min, MH⁺ 605, chiral purity 100%.

Example 24: Synthesis of (1s,3s)-3-((3-((1-(4-chlorophenyl)-2-(5-methoxy-6-(trifluoromethyl)indolin-1-yl)-2-oxoethyl)amino)-5-methoxyphenoxy)methyl)-cyclobutanecarboxylic Acid (Compound 24) and Chiral Separation into Enantiomers 24A and 24B

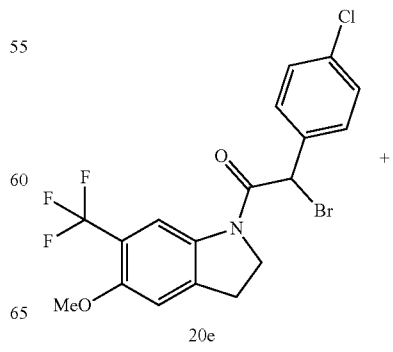

20e

+

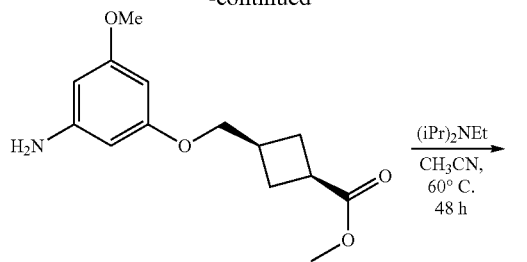

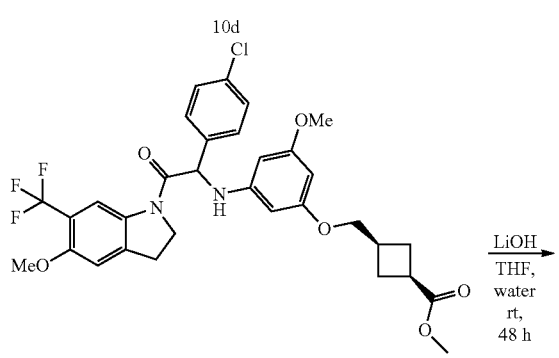

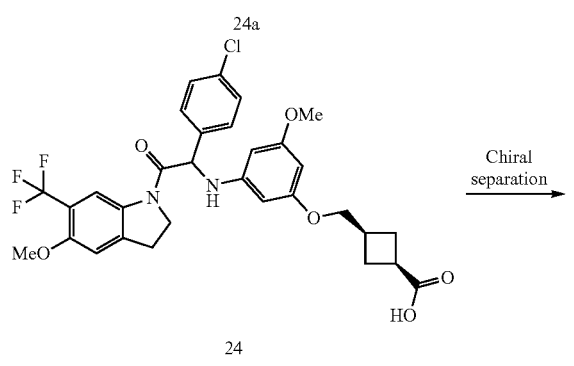

Enantiomers 24A and 24B

Synthesis of Compound 24 and Chiral Separation into Enantiomers 24A and 24B:

Compound 24 (550 mg) was synthesized from intermediate 20e using the procedures described for the synthesis of Compound 10. The two enantiomers were separated via chiral SFC (Stationary phase: Whelk® O1 (S,S) 5 μm 250×21.1 mm, mobile phase: 50% CO$_2$, 50% MeOH) to give, after solidification from Et$_2$O, the first eluted Enantiomer 24A (190 mg) and the second eluted Enantiomer 24B (177 mg).

Compound 24:
$^1$H NMR (500 MHz, DMSO-d$_6$) δ ppm 1.93 (br q, J=9.77 Hz, 2H) 2.11-2.32 (m, 2H) 2.53-2.60 (m, 1H) 2.97 (quin, J=8.91 Hz, 1H) 3.16-3.30 (m, 2H) 3.62 (s, 3H) 3.74-3.82 (m, 2H) 3.85 (s, 3H) 3.96-4.06 (m, 1H) 4.51 (td, J=10.25, 5.99 Hz, 1H) 5.55 (d, J=8.83 Hz, 1H) 5.74 (s, 1H) 5.94 (br s, 2H) 6.39 (d, J=8.51 Hz, 1H) 7.23 (s, 1H) 7.44 (d, J=8.51 Hz, 2H) 7.55 (d, J=8.51 Hz, 2H) 8.34 (s, 1H) 12.07 (br s, 1H)
LC/MS (method LC-C): R$_t$ 2.91 min, MH$^+$ 619

Enantiomer 24A:
$^1$H NMR (500 MHz, DMSO-d$_6$) δ ppm 1.87-2.02 (m, 2H) 2.15-2.30 (m, 2H) 2.52-2.59 (m, 1H) 2.95 (qt J=8.83 Hz, 1H) 3.07-3.29 (m, 2H) 3.61 (s, 3H) 3.77 (br d, J=6.31 Hz, 2H) 3.84 (s, 3H) 3.95-4.07 (m, 1H) 4.42-4.56 (m, 1H) 5.54 (d, J=8.83 Hz, 1H) 5.74 (t, J=2.05 Hz, 1H) 5.81-6.01 (m, 2H) 6.38 (d, J=8.83 Hz, 1H) 7.23 (s, 1H) 7.43 (d, J=8.51 Hz, 2H) 7.55 (d, J=8.51 Hz, 2H) 8.33 (s, 1H) 12.11 (br s, 1H)
LC/MS (method LC-C): R$_t$ 2.89 min, MH$^+$ 619
[α]$_D^{20}$: −41.5° (c 0.224, DMF)
Chiral SFC (method SFC-T): R$_t$ 1.81 min, no MH$^+$, chiral purity 100%.

Enantiomer 24B:
$^1$H NMR (500 MHz, DMSO-d$_6$) δ ppm 1.91 (q, J=9.35 Hz, 2H) 2.17-2.26 (m, 2H) 2.53-2.61 (m, 1H) 2.94 (quin, J=8.91 Hz, 1H) 3.13-3.27 (m, 2H) 3.61 (s, 3H) 3.72-3.79 (m, 2H) 3.84 (s, 3H) 3.90-4.06 (m, 1H) 4.50 (td, J=10.32, 6.46 Hz, 1H) 5.54 (d, J=8.83 Hz, 1H) 5.72-5.75 (m, 1H) 5.91-5.95 (m, 2H) 6.38 (d, J=8.83 Hz, 1H) 7.23 (s, 1H) 7.43 (d, J=8.51 Hz, 2H) 7.55 (d, J=8.20 Hz, 2H) 8.33 (s, 1H) 12.07 (br s, 1H)
LC/MS (method LC-C): R$_t$ 2.89 min, MH$^+$ 619
[α]$_D^{20}$: +36.6° (c 0.232, DMF)
Chiral SFC (method SFC-T): R$_t$ 2.26 min, no MH$^+$, chiral purity 98.71%.

Example 25: Synthesis of (1r,3r)-3-((3-((1-(4-chlorophenyl)-2-(5-methoxy-6-(trifluoromethyl)indolin-1-yl)-2-oxoethyl)amino)-5-methoxyphenoxy)methyl)-cyclobutanecarboxylic Acid (Compound 25) and Chiral Separation into Enantiomers 25A and 25B

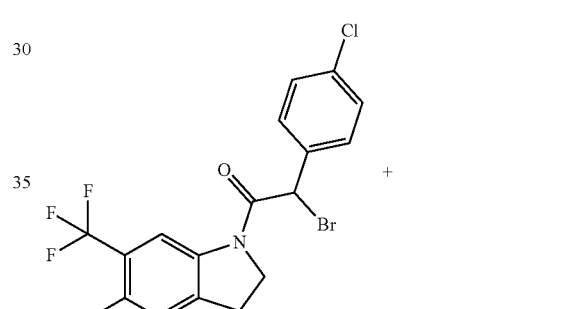

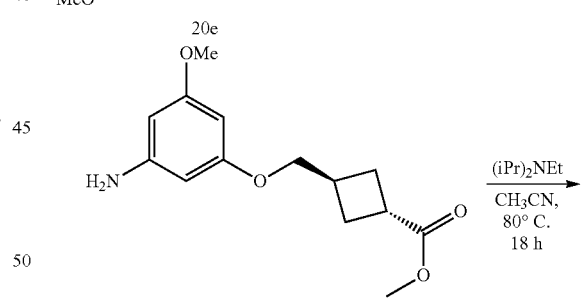

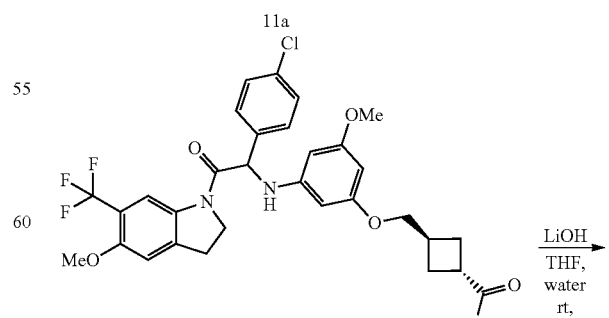

-continued

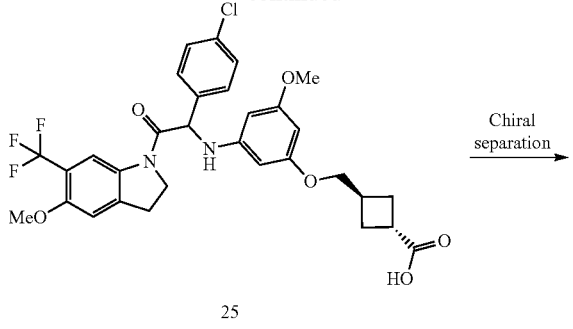

Enantiomers 25A and 25B

Synthesis of Compound 25 and Chiral Separation into Enantiomers 25A and 25B:

Compound 25 (310 mg) was synthesized from intermediate 20e using the procedures described for the synthesis of Compound 11. The two enantiomers were separated via chiral SFC (Stationary phase: Whelk® O1 (S,S) 5 μm 250×21.1 mm, mobile phase: 50% $CO_2$, 50% MeOH) to give, after solidification from $Et_2O$/pentane, the first eluted Enantiomer 25A (94 mg) and the second eluted Enantiomer 25B (105 mg).

Compound 25:

$^1$H NMR (400 MHz, DMSO-$d_6$) δ ppm 1.80-2.04 (m, 2H) 2.22-2.31 (m, 2H) 2.56-2.64 (m, 1H) 3.09 (br qt, J=7.33 Hz, 1H) 3.14-3.28 (m, 2H) 3.62 (s, 3H) 3.84 (s, 3H) 3.87 (d, J=6.57 Hz, 2H) 3.93-4.06 (m, 1H) 4.45-4.56 (m, 1H) 5.54 (d, J=8.59 Hz, 1H) 5.77 (s, 1H) 5.94 (s, 1H) 5.96 (s, 1H) 6.38 (d, J=9.09 Hz, 1H) 7.23 (s, 1H) 7.43 (d, J=8.59 Hz, 2H) 7.55 (d, J=8.59 Hz, 2H) 8.33 (s, 1H) 12.10 (br s, 1H)

LC/MS (method LC-C): $R_t$ 2.87 min, MH$^+$ 619

Enantiomer 25A:

$^1$H NMR (400 MHz, DMSO-$d_6$) δ ppm 1.91-2.03 (m, 2H) 2.18-2.29 (m, 2H) 2.55-2.62 (m, 1H) 3.01-3.11 (m, 1H) 3.14-3.28 (m, 2H) 3.62 (s, 3H) 3.84 (s, 3H) 3.86 (d, J=7.07 Hz, 2H) 3.93-4.05 (m, 1H) 4.42-4.58 (m, 1H) 5.54 (d, J=8.59 Hz, 1H) 5.77 (s, 1H) 5.92-5.95 (m, 1H) 5.95-5.98 (m, 1H) 6.38 (d, J=8.59 Hz, 1H) 7.23 (s, 1H) 7.43 (d, J=8.08 Hz, 2H) 7.55 (d, J=8.08 Hz, 2H) 8.33 (s, 1H)

LC/MS (method LC-C): $R_t$ 2.90 min, MH$^+$ 619

$[\alpha]_D^{20}$: −41.1° (c 0.28, DMF)

Chiral SFC (method SFC-T): $R_t$ 1.91 min, no MH$^+$, chiral purity 100%.

Enantiomer 25B:

$^1$H NMR (400 MHz, DMSO-$d_6$) δ ppm 1.90-2.04 (m, 2H) 2.19-2.29 (m, 2H) 2.55-2.60 (m, 1H) 3.00-3.30 (m, 3H) 3.62 (s, 3H) 3.84 (s, 3H) 3.86 (br d, J=7.07 Hz, 2H) 3.94-4.04 (m, 1H) 4.45-4.55 (m, 1H) 5.54 (d, J=8.59 Hz, 1H) 5.77 (s, 1H) 5.88-5.95 (m, 1H) 5.95-5.98 (m, 1H) 6.38 (br d, J=8.59 Hz, 1H) 7.23 (s, 1H) 7.43 (d, J=8.59 Hz, 2H) 7.55 (d, J=8.08 Hz, 2H) 8.33 (s, 1H)

LC/MS (method LC-C): $R_t$ 2.90 min, MH$^+$ 619

$[\alpha]_D^{20}$: +40.6° (c 0.32, DMF)

Chiral SFC (method SFC-T): $R_t$ 2.48 min, no MH$^+$, chiral purity 98.68%.

Example 26A: Synthesis of (1R*,2R*)-2-((3-((1-(4-chlorophenyl)-2-(5-fluoro-6-(trifluoromethoxy)indolin-1-yl)-2-oxoethyl)amino)-5-methoxyphenoxy) methyl)-cyclopropanecarboxylic Acid (Compound 26A)

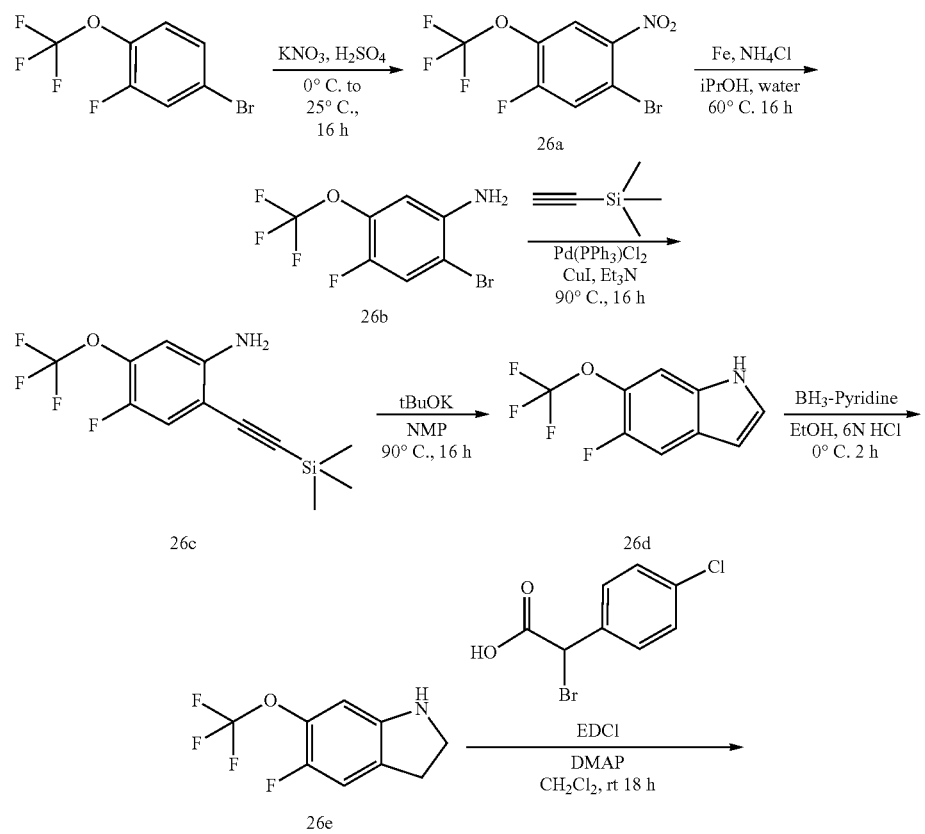

-continued

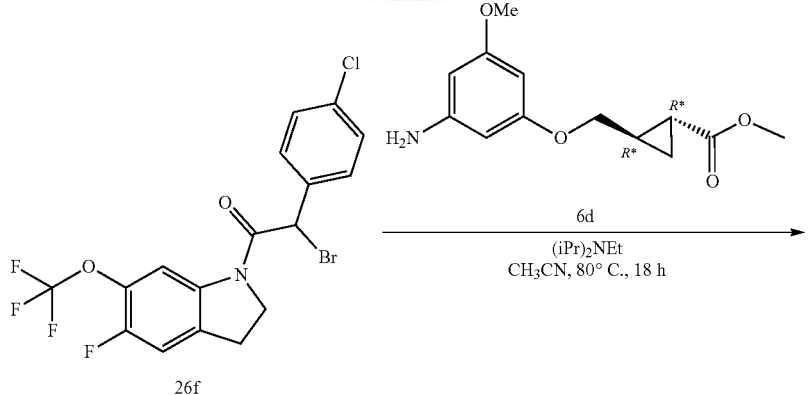

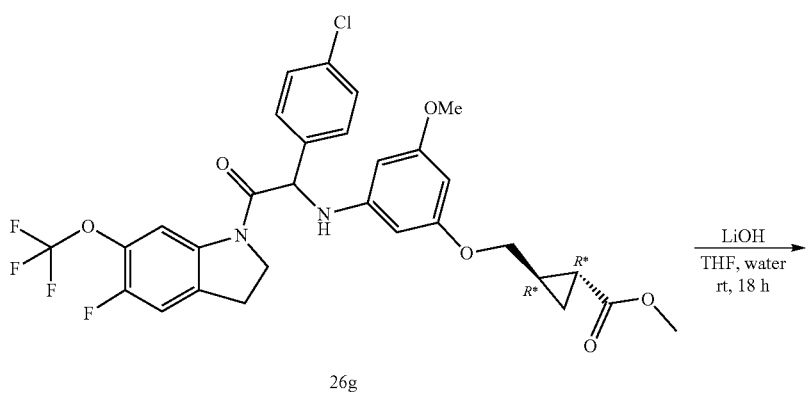

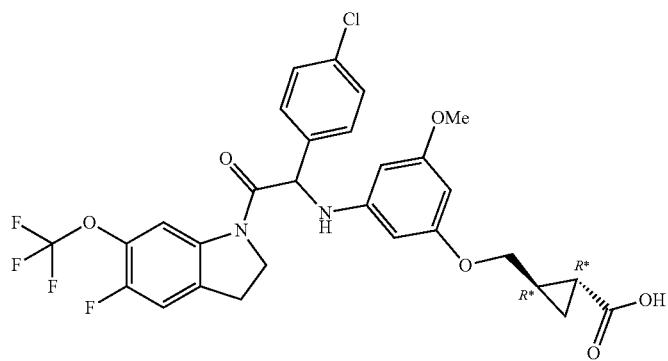

Synthesis of Intermediate 26a:

A solution of 4-bromo-2-fluoro-1-(trifluoromethoxy)benzene [CAS 105529-58-6] (98.7 g, 381.1 mmol) in concentrated H$_2$SO$_4$ (98%, 200 mL), was cooled to 0° C. with an ice-bath. KNO$_3$ (43.0 g, 425.3 mmol) was added in portions. After addition, the ice-bath was removed and the mixture was stirred at room temperature for 16 h. The reaction mixture was poured out into ice-water (2 L) while stirring. The mixture was extracted with CH$_2$Cl$_2$ (3×500 mL). The combined organic layers were washed with a saturated aqueous NaHCO$_3$ solution (2×500 mL), brine (500 mL), dried over MgSO$_4$, filtered and concentrated under reduced pressure to afford 1-bromo-5-fluoro-2-nitro-4-(trifluoromethoxy)benzene 26a (117.2 g), which was used in the next step without further purification.

Synthesis of Intermediate 26b:

To a stirred suspension of 1-bromo-5-fluoro-2-nitro-4-(trifluoromethoxy)benzene 26a (70.0 g, 230 mmol) and NH$_4$Cl (123.2 g, 2.30 mol) in iPrOH (1 L) and water (330 mL) was added reductive iron powder (64.3 g, 1.15 mol)

under $N_2$-atmosphere. The reaction mixture was stirred at 60° C. for 16 h. The reaction mixture was diluted with EtOAc (1 L) and filtered through Celite®. The filtrate was concentrated under reduced pressure. The residue was partitioned between EtOAc (1 L) and water (800 mL). The layers were separated and the organic phase was washed with brine (1 L), dried over $MgSO_4$, filtered and concentrated under reduced pressure. The residue was purified by distillation under reduced pressure (oil pump, b.p. 60~64° C.). 2-Bromo-4-fluoro-5-(trifluoromethoxy)aniline 26b (47.3 g) was obtained as a yellow oil.

Synthesis of Intermediate 26c:

To a mixture of 2-bromo-4-fluoro-5-(trifluoromethoxy) aniline 26b (18.4 g, 67.2 mmol) and ethynyl(trimethyl)silane (19.9 g, 202.4 mmol, 28.00 mL) in $Et_3N$ (300 mL) was added CuI (1.28 g, 6.72 mmol) and $Pd(PPh_3)_2Cl_2$ (2.40 g, 3.42 mmol). The reaction mixture was heated under $N_2$-atmosphere at 90° C. for 16 h. After cooling to room temperature, the mixture was diluted with MTBE (300 mL) and filtered through Celite®. The filtrate was concentrated under reduced pressure. The residue was purified by flash chromatography on silica gel (ISCO®, 220 g SepaFlash® Silica Flash Column, eluent: gradient of 0 to 5% EtOAc in petroleum ether @100 mL/min). 4-Fluoro-5-(trifluoromethoxy)-2-((trimethylsilyl)ethynyl)aniline 26c (16.1 g, 90% purity) was obtained as a brown oil.

Synthesis of Intermediate 26d:

A mixture of 4-fluoro-5-(trifluoromethoxy)-2-((trimethylsilyl)ethynyl)aniline 26c (16.1 g, 55.3 mmol) and tBuOK (18.6 g, 165.8 mmol) in NMP (220.00 mL) was heated at 90° C. for 16 h under $N_2$-atmosphere. After cooling to room temperature, the reaction mixture was poured out into ice-water (1 L) and extracted with MTBE (3×300 mL). The combined organic phases were washed with water (2×200 mL), brine (300 mL), dried over $MgSO_4$, filtered and concentrated under reduced pressure. The residue was purified by flash chromatography on silica gel (ISCO®, 120 g SepaFlash® Silica Flash Column, eluent: gradient of 0 to 5% EtOAc in petroleum ether, flow rate=85 mL/min) to afford 5-fluoro-6-(trifluoromethoxy)-1H-indole 26d (11 g) product as a dark-green oil. The residue was combined with another fraction (total amount=17.2 g) and further purified by distillation under reduced pressure (oil pump, b.p. 60~64° C.) to provide 5-fluoro-6-(trifluoromethoxy)-1H-indole 26d (14.7 g, 95% purity) as a colorless oil.

Synthesis of Intermediate 26e:

At 0° C., $BH_3$—Pyridine (1.2 mL, 11 mmol) was added slowly to a solution of 5-fluoro-6-(trifluoromethoxy)-1H-indole 26d (500 mg, 2.3 mmol) in EtOH (3.2 mL). 6N HCl (7.6 mL) was slowly added while maintaining the temperature below 10° C. The mixture was stirred at 0° C. for 2 h. Water (100 mL) was added and the mixture was basified to pH 14 with concentrated NaOH (temperature was kept below 20° C.). $CH_2Cl_2$ was added. The organic layer was separated, dried over $MgSO_4$, filtered and the solvent was evaporated under reduced pressure to give 5-fluoro-6-(trifluoromethoxy)indoline 26e (550 mg). The compound was used in the next step without further purification.

Synthesis of Intermediate 26f:

To a mixture of 2-bromo-2-(4-chlorophenyl)acetic acid [CAS 3381-73-5] (0.61 g, 2.4 mmol), 5-fluoro-6-(trifluoromethoxy)indoline 26e (0.55 g, 2.2 mmol, 89% purity) and DMAP (0.027 g, 0.22 mmol) in $CH_2Cl_2$ (14 mL) was added EDCl (0.51 g, 2.7 mmol). The mixture was stirred at room temperature for 18 h. The mixture was diluted with a 10% $K_2CO_3$ solution in water. The layers were decanted. The organic layer was washed with water, dried over $MgSO_4$, filtered and the solvent was concentrated under reduced pressure to give 2-bromo-2-(4-chlorophenyl)-1-(5-fluoro-6-(trifluoromethoxy)indolin-1-yl)ethanone 26f (1.1 g, purple oil). The compound was used in the next step without further purification.

Synthesis of Compound 26A:

Compound 26A (135 mg) was synthesized from intermediate 26f using the procedures described for the synthesis of Compound 6A.

Compound 26A:

$^1$H NMR (500 MHz, DMSO-$d_6$) δ ppm 0.87-0.94 (m, 1H) 1.01-1.07 (m, 1H) 1.55 (dq, J=8.55, 4.40 Hz, 1H) 1.60~1.68 (m, 1H) 3.12-3.30 (m, 2H) 3.61 (s, 3H) 3.68 (dd, J=10.40, 7.57 Hz, 1H) 3.85 (dd, J=10.40, 6.31 Hz, 1H) 4.01-4.08 (m, 1H) 4.48-4.55 (m, 1H) 5.57 (d, J=8.83 Hz, 1H) 5.75 (s, 1H) 5.94 (br s, 1H) 5.95 (br s, 1H) 6.46 (br d, J=8.83 Hz, 1H) 7.40-7.48 (m, 3H) 7.54 (d, J=8.51 Hz, 2H) 8.16 (br d, J=6.94 Hz, 1H) 12.22 (br s, 1H)

LC/MS (method LC-C): $R_t$ 2.97 min, MH$^+$ 609

MP=120° C.

Example 26B: Synthesis of (1 S*,2S*)-2-((3-((1-(4-chlorophenyl)-2-(5-fluoro-6-(trifluoromethoxy)indolin-1-yl)-2-oxoethyl)amino)-5-methoxyphenoxy) methyl)-cyclopropanecarboxylic Acid (Compound 26B)

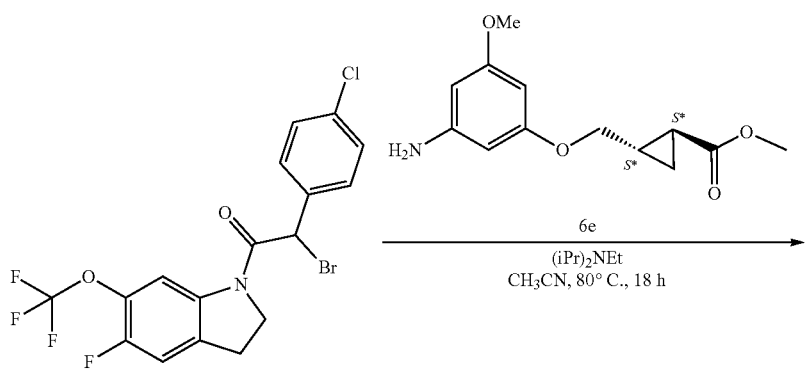

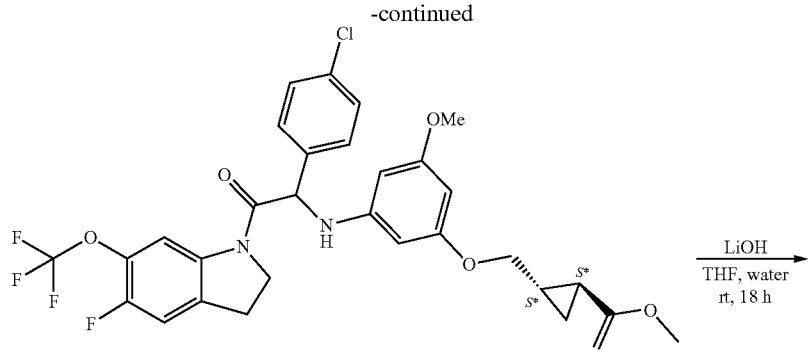

26h

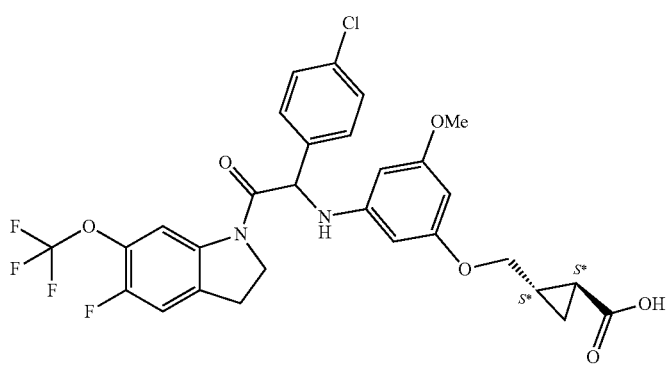

26B

Synthesis of Compound 26B:

Compound 26B (150 mg) was synthesized from intermediate 26f using the procedure described for the synthesis of Compound 6B.

Compound 26B:

¹H NMR (500 MHz, DMSO-d₆) δ ppm 0.86-0.94 (m, 1H) 1.04 (dq, J=8.20, 4.31 Hz, 1H) 1.55 (dq, J=8.43, 4.33 Hz, 1H) 1.58-1.67 (m, 1H) 3.12-3.30 (m, 2H) 3.61 (s, 3H) 3.68 (dd, J=10.40, 7.57 Hz, 1H) 3.85 (dd, J=10.25, 6.15 Hz, 1H) 4.04 (q, J=8.72 Hz, 1H) 4.47-4.55 (m, 1H) 5.57 (d, J=8.83 Hz, 1H) 5.75 (s, 1H) 5.94 (br s, 1H) 5.95 (br s, 1H) 6.46 (br d, J=8.51 Hz, 1H) 7.40-7.48 (m, 3H) 7.54 (d, J=8.51 Hz, 2H) 8.16 (br d, J=6.94 Hz, 1H) 12.21 (br s, 1H)

LC/MS (method LC-C): R$_t$ 2.97 min, MH⁺ 609

MP=126C

Example 27: Synthesis of ((1s,3s)-3-(3-((1-(4-chlorophenyl)-2-(5-fluoro-6-(trifluoromethoxy)indolin-1-yl)-2-oxoethyl)amino)-5-methoxyphenoxy)cyclobutene-carboxylic Acid (Compound 27) and Separation into Enantiomers 27A and 27B

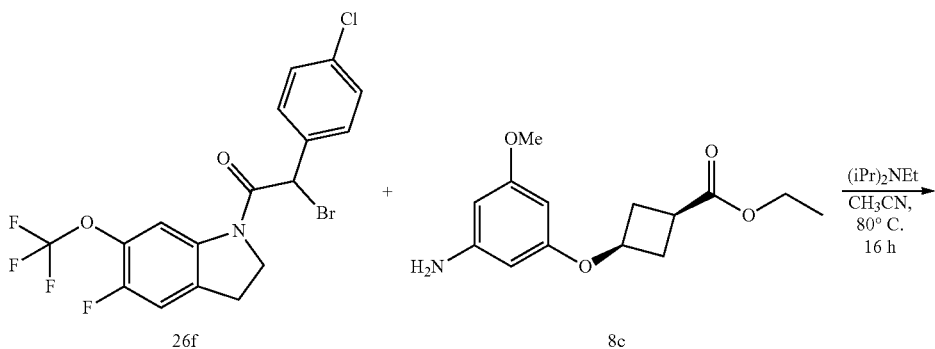

26f  +  8c

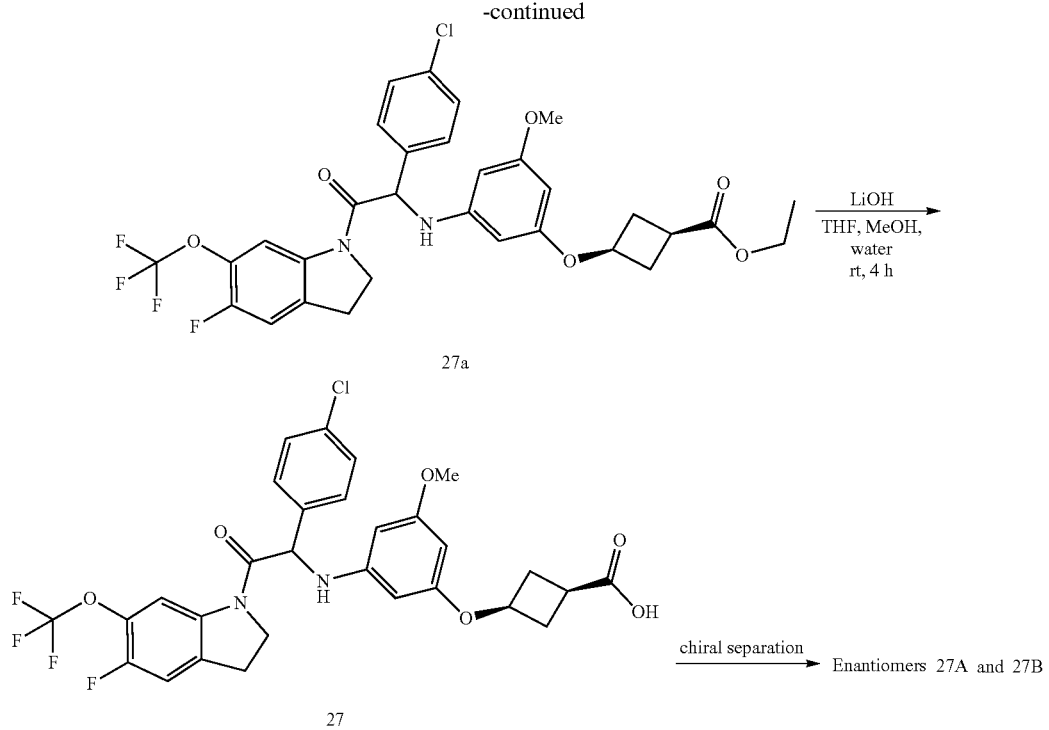

Synthesis of Compound 27 and Chiral Separation into Enantiomers 27A and 27B:

Compound 27 (175 mg) was synthesized from intermediate 26f using the procedure described for the synthesis of Compound 8. The two enantiomers were separated via chiral SFC (Stationary phase: Chiralcel® OD-H 5 µm 250×20 mm, mobile phase: 55% CO₂, 45% EtOH) to give, after solidification from heptane/diisopropyl ether, the first eluted Enantiomer 27A (33 mg) and the second eluted Enantiomer 27B (35 mg).

Compound 27:

$^1$H NMR (500 MHz, DMSO-d$_6$) δ ppm 2.01-2.17 (m, 2H) 2.57-2.65 (m, 2H) 2.66-2.77 (m, 1H) 3.08-3.28 (m, 2H) 3.61 (s, 3H) 3.99-4.10 (m, 1H) 4.43-4.57 (m, 2H) 5.54 (d, J=8.5 Hz, 1H) 5.66 (s, 1H) 5.86 (s, 1H) 5.93 (s, 1H) 6.49 (br d, J=8.5 Hz, 1H) 7.45 (d, J=8.5 Hz, 3H) 7.55 (d, J=8.5 Hz, 2H) 8.16 (br d, J=6.9 Hz, 1H) 12.06-12.47 (m, 1H)

LC/MS (method LC-C): R$_t$ 2.88 min, MH⁺ 609

Enantiomer 27A:

$^1$H NMR (500 MHz, DMSO-d$_6$) δ ppm 2.00-2.12 (m, 2H) 2.57-2.65 (m, 3H) 3.11-3.25 (m, 2H) 3.60 (s, 3H) 4.04 (br d, J=7.3 Hz, 1H) 4.40-4.48 (m, 1H) 4.48-4.57 (m, 1H) 5.53 (br d, J=8.5 Hz, 1H) 5.65 (s, 1H) 5.85 (s, 1H) 5.92 (s, 1H) 6.48 (br d, J=8.5 Hz, 1H) 7.44 (br d, J=8.5 Hz, 3H) 7.54 (br d, J=8.5 Hz, 2H) 8.16 (br d, J=6.9 Hz, 1H)

LC/MS (method LC-D): R$_t$ 2.79 min, MH⁺ 609

[α]$_D^{20}$: −40.5° (c 0.252, DMF)

Chiral SFC (method SFC-I): R$_t$ 1.18 min, no MH⁺, chiral purity 100%.

Enantiomer 27B:

$^1$H NMR (500 MHz, DMSO-d$_6$) δ ppm 2.00-2.13 (m, 2H) 2.54-2.67 (m, 3H) 3.10-3.27 (m, 2H) 3.60 (s, 3H) 3.99-4.10 (m, 1H) 4.40-4.48 (m, 1H) 4.48-4.56 (m, 1H) 5.54 (br d, J=8.5 Hz, 1H) 5.66 (s, 1H) 5.86 (s, 1H) 5.92 (s, 1H) 6.48 (br d, J=8.5 Hz, 1H) 7.44 (br d, J=8.5 Hz, 3H) 7.54 (br d, J=8.5 Hz, 2H) 8.16 (br d, J=6.9 Hz, 1H)

LC/MS (method LC-D): R$_t$ 2.79 min, MH⁺ 609

[α]$_D^{20}$: +37.5° (c 0.333, DMF)

Chiral SFC (method SFC-I): R$_t$ 2.56 min, no MH⁺, chiral purity 100%.

Example 28: Synthesis of (1R*,2S*)-2-((3-((1-(4-chlorophenyl)-2-oxo-2-(6-(trifluoromethoxy)indolin-1-yl)ethyl)amino)-5-methoxyphenoxy)methyl)-2-fluorocyclopropanecarboxylic Acid (Compound 28A) and Separation into Stereoisomers 28AA and 28AB and synthesis of (1S*,2R*)-2-((3-((1-(4-chlorophenyl)-2-oxo-2-(6-(trifluoromethoxy)indolin-1-yl)ethyl)amino)-5-methoxyphenoxy)methyl)-2-fluorocyclopropanecarboxylic Acid (Compound 28B) and Separation into Stereoisomers 28BA and 28BB

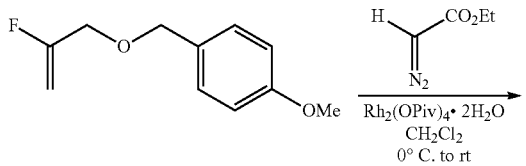

-continued
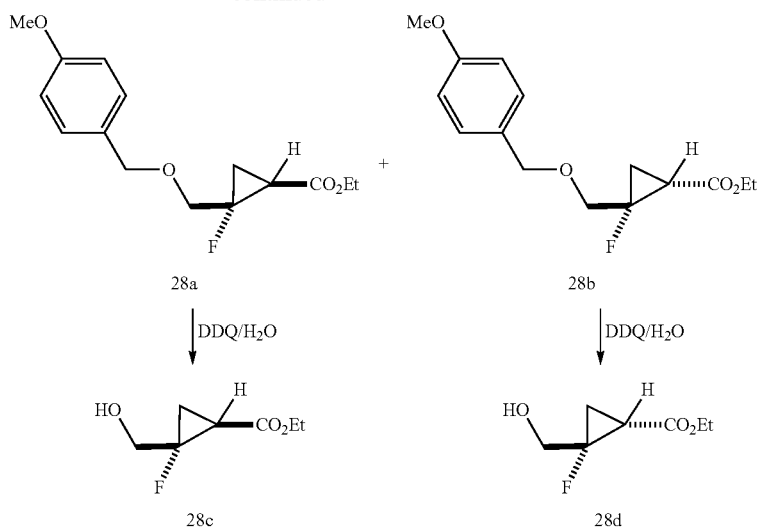
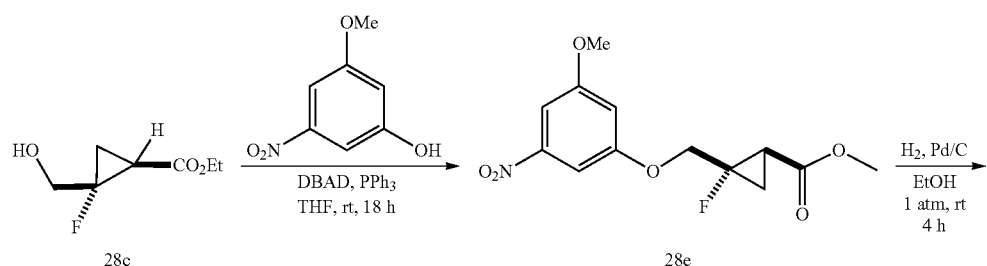
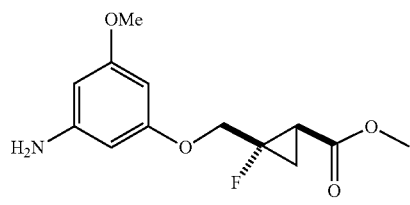
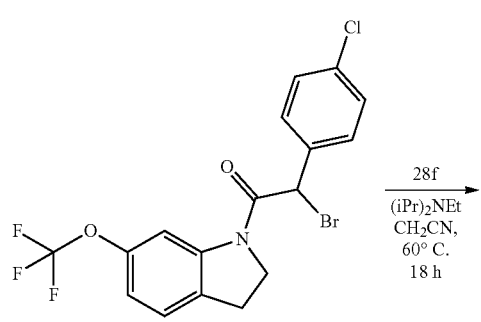

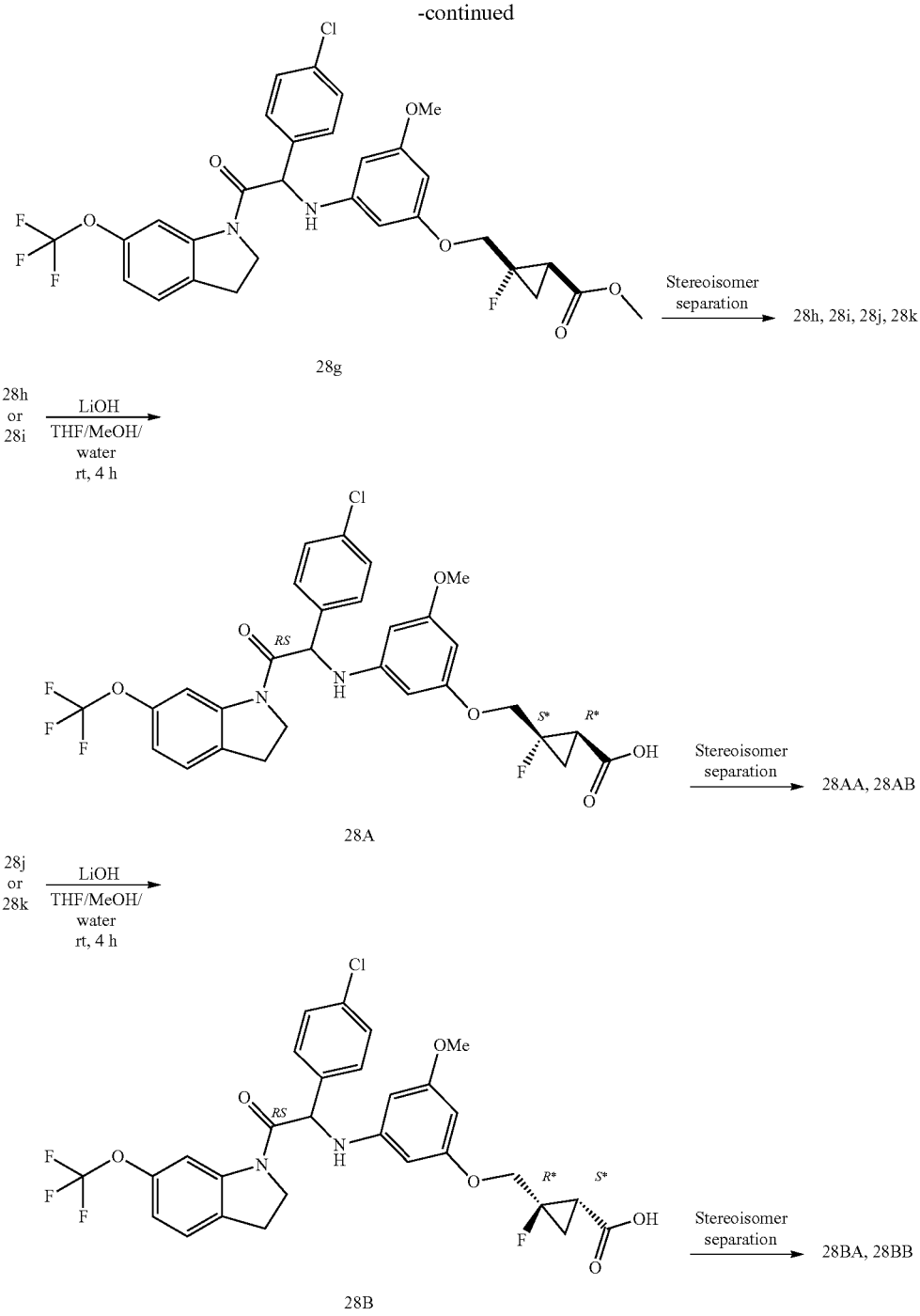

Synthesis of Intermediates 28a and 28b:

Rh₂(OPiv)₄.2H₂O (2 mol %, 0.599 mmol, 387 mg) was added to a solution of 1-(((2-fluoroallyl)oxy)methyl)-4-methoxybenzene [CAS 1673563-84-2] (29.9 mmol) in anhydrous CH₂Cl₂ (86 mL) in a three-necked round bottom flask equipped with a bubble room. After cooling the solution to 0° C., a solution of the commercially available diazo ethylacetate 83% in dichloromethane (3 equiv., 89.85 mmol) in anhydrous CH₂Cl₂ (86 mL) was slowly added using a micro pump with a flow rate of 24 mL/h. The mixture was stirred at room temperature until completion of the reaction (indicated by TLC and ¹⁹F NMR analysis) and concentrated under reduced pressure. The crude residue was purified by column chromatography on silica gel (petroleum ether/EtOAc, 9/1 to 7/3) to give in 60% yield a mixture of diastereomers (dr 53:47). The diastereomers were separated by column chromatography on silica gel (petroleum ether/EtOAc, from 100/0 to 80/20) to give trans-ethyl 2-fluoro-2-(((4-methoxybenzyl)oxy)methyl)cyclopropanecarboxylate 28a and cis-ethyl 2-fluoro-2-(((4-methoxybenzyl)oxy)methyl)cyclopropanecarboxylate 28b.

Synthesis of Intermediate 28c:

DDQ (1.5 equiv., 27.9 mmol, 6.33 g) was added to a solution of trans-ethyl 2-fluoro-2-(((4-methoxybenzyl)oxy)

methyl)cyclopropanecarboxylate 28a (1 equiv., 18.6 mmol, 5.25 g) in dichloromethane (340 mL) and water (30 mL) at 0° C. The mixture was stirred for 20 h. A solution of saturated aqueous NaHCO$_3$ was added and the mixture was stirred for 30 minutes. The aqueous layer was extracted three times with CH$_2$Cl$_2$. The combined organic layers were washed with a saturated NaHCO$_3$ solution and brine. The organic layer was evaporated under reduced pressure and the crude residue was purified by chromatography on silica gel (petroleum ether/EtOAc, 9/1 to 6/4) to give trans-ethyl 2-fluoro-2-(hydroxymethyl)-cyclopropanecarboxylate 28c (876 mg).

Synthesis of Intermediate 28d:

DDQ (1.5 equiv., 15.8 mmol, 3.6 g) was added to a solution of cis-ethyl 2-fluoro-2-(((4-methoxybenzyl)oxy) methyl)cyclopropanecarboxylate 28b (1 equiv., 10.6 mmol, 2.98 g) in dichloromethane (193 mL) and water (17 mL) at 0° C. The mixture was stirred for 20 h. A solution of saturated aqueous NaHCO$_3$ was added and the mixture was stirred for 30 minutes. The aqueous layer was extracted three times with CH$_2$Cl$_2$. The combined organic layers were washed with a saturated NaHCO$_3$ solution and brine. The organic layer was evaporated under reduced pressure and the crude residue was purified by chromatography on silica gel (petroleum ether/EtOAc, 9/1 to 6/4) to give cis-ethyl 2-fluoro-2-(hydroxymethyl)cyclopropane-carboxylate (876 mg).

Synthesis of Intermediate 28e:

Under a N$_2$ flow at 10° C., di-tert-butyl azodicarboxylate (948 mg, 4.118 mmol) was added portionwise to a solution of 3-methoxy-5-nitrophenol [7145-49-5] (633 mg, 3.743 mmol), trans-ethyl 2-fluoro-2-(hydroxymethyl)cyclopropanecarboxylate 28c (607 mg, 3.743 mmol), and PPh$_3$ (1.08 g; 4.118 mmol) in THF (30 mL). The reaction was stirred at room temperature under N$_2$ for 18 h. The solution was concentrated under reduced pressure. The crude residue was purified by column chromatography on silica gel (15-40 µm, 80 g, heptane/EtOAc from 95/5 to 80/20). The pure fractions were combined and concentrated under reduced pressure to give trans-methyl 2-fluoro-2-((3-methoxy-5-nitrophenoxy) methyl)cyclopropane-carboxylate 28e (930 mg).

Synthesis of Intermediate 28f:

A solution of trans-methyl 2-fluoro-2-((3-methoxy-5-nitrophenoxy)methyl)-cyclopropanecarboxylate 28e (810 mg, 2.586 mmol) in EtOH (20 mL) and THF (10 mL) containing a catalytic amount of 10% Pd/C (275 mg, 0.259 mmol) was hydrogenated under atmospheric pressure of H$_2$ at room temperature for 4 h. The catalyst was removed by filtration over a short pad of Celite® and the filter cake was rinsed several times with EtOH. The combined filtrates were evaporated under reduced pressure to give trans-methyl 2-((3-amino-5-methoxyphenoxy)-methyl)-2-fluorocyclopropanecarboxylate 28f (710 mg), which was used in the next step without further purification.

Synthesis of Intermediate 28g and Separation into Stereoisomers 28h, 28i, 28j and 28k:

A mixture of 2-bromo-2-(4-chlorophenyl)-1-(6-(trifluoromethoxy)indolin-1-yl)ethanone 1c (927 mg, 2.133 mmol), trans-methyl 2-((3-amino-5-methoxyphenoxy)methyl)-2-fluorocyclopropanecarboxylate 28f (725 mg, 2.559 mmol) and diisopropylethylamine (735 µL, 4.265 mmol) in CH$_3$CN (4 mL) was stirred at 80° C. for 12 h. The solvent was concentrated under reduced pressure. The residue was taken up with EtOAc. The organic layer was washed with 1N HCl, water, dried over MgSO$_4$, filtered, and concentrated under reduced pressure. The residue was purified by column chromatography on silica gel (15-40 µm, 40 g, heptane/ EtOAc from 95/5 to 80/20). The pure fractions were combined and evaporated under reduced pressure to give methyl 2-((3-((1-(4-chlorophenyl)-2-oxo-2-(6-(trifluoromethoxy) indolin-1-yl)ethyl)amino)-5-methoxyphenoxy)methyl)-trans-2-fluorocyclopropanecarboxylate 28g (550 mg). The four stereoisomers were separated via chiral SFC (Stationary phase: Chiralcel® OD-H 5 µm 250×20 mm, mobile phase: 70% CO$_2$, 30% EtOH) to give 28h (118 mg), 28i (114 mg), 28j (158 mg) and 28k (165 mg).

Synthesis of Compound 28A and Separation into Stereoisomers 28AA and 28AB:

LiOH monohydrate (23.3 mg, 0.556 mmol) was added dropwise to a solution of stereoisomer 28h (118 mg, 0.185 mmol) in THF/MeOH/water (1/1/1) (2 mL). The reaction mixture was stirred at room temperature for 4 h. The mixture was diluted with water and ice, slowly acidified with 1N HCl and extracted with EtOAc. The combined organic layers were washed with water, dried over MgSO$_4$, filtered, and concentrated under reduced pressure to give, after crystallization from heptane/diisopropyl ether, (1R*,2S*)-2-((3-((1-(4-chlorophenyl)-2-oxo-2-(6-(trifluoromethoxy)indolin-1-yl)ethyl)amino)-5-methoxyphenoxy)methyl)-2-fluorocyclopropanecarboxylic acid 28A (110 mg) (during this reaction, full racemization occurred on the central chiral center).

A second batch of Compound 28A (100 mg) was obtained similarly starting from stereoisomer 28i. The two batches were combined. The two stereoisomers were separated via chiral SFC (Stationary phase: Chiralcel® OD-H 5 µm 250× 20 mm, mobile phase: 65% CO$_2$, 35% EtOH) to give the first eluted stereoisomer (94 mg) and the second eluted stereoisomer (80 mg). The first eluted stereoisomer was solidified from diisopropyl ether to give Stereoisomer 28AA (47 mg). The second eluted stereoisomer was solidified from heptane to give Stereoisomer 28AB (37 mg).

Synthesis of Compound 28B and Separation into Stereoisomers 28BA and 28BB:

LiOH monohydrate (31.2 mg, 0.744 mmol) was added dropwise to a solution of stereoisomer 28j (158 mg, 0.248 mmol) in THF/MeOH/water (1/1/1) (2 mL). The reaction mixture was stirred at room temperature for 4 h. The mixture was diluted with water and ice, slowly acidified with 1N HCl and extracted with EtOAc. The combined organic layers were washed with water, dried over MgSO$_4$, filtered, and concentrated under reduced pressure to give, after crystallization from MeOH/water, (1 S*,2R*)-2-((3-((1-(4-chlorophenyl)-2-oxo-2-(6-(trifluoromethoxy)-indolin-1-yl)ethyl) amino)-5-methoxyphenoxy)methyl)-2-fluorocyclopropanecarboxylic acid 28B (100 mg) (during this reaction, full racemization occurred on the central chiral center).

A second batch of 28A (105 mg) was obtained similarly starting from stereoisomer 28k.

The two stereoisomers were separated via chiral SFC (Stationary phase: Chiralcel® OD-H 5 µm 250×30 mm, mobile phase: 60% CO$_2$, 30% MeOH) to give the first eluted stereoisomer (88 mg) and the second eluted stereoisomer (78 mg). The first eluted stereoisomer was solidified from heptane/diisopropyl ether to give Stereoisomer 28BA (54 mg). The second eluted stereoisomer was solidified from heptane/ diisopropyl ether to give Stereoisomer 28BB (60 mg).

Stereoisomer 28AA:

$^1$H NMR (500 MHz, DMSO-d$_6$) δ ppm 1.37 (dt, J=11.7, 7.1 Hz, 1H) 1.62-1.76 (m, 1H) 2.18-2.31 (m, 1H) 3.07-3.23 (m, 2H) 3.62 (s, 3H) 3.98-4.10 (m, 1H) 4.15-4.29 (m, 1H) 4.43 (dd, J=18.9, 12.0 Hz, 1H) 4.48-4.57 (m, 1H) 5.58 (d, J=8.8 Hz, 1H) 5.78 (s, 1H) 5.97 (s, 1H) 5.99 (s, 1H) 6.49 (br d, J=8.8 Hz, 1H) 7.01 (br d, J=7.9 Hz, 1H) 7.33 (d, J=8.2 Hz, 1H) 7.44 (d, J=8.5 Hz, 2H) 7.55 (d, J=8.2 Hz, 2H) 8.03 (s, 1H) 12.71 (br s, 1H)

LC/MS (method LC-C): $R_t$ 2.83 min, $MH^+$ 609
$[\alpha]_D^{20}$: −43.3° (c 0.3, DMF)
Chiral SFC (method SFC-F): $R_t$ 1.98 min, no $MH^+$, chiral purity 100%.

Stereoisomer 28AB:
$^1$H NMR (500 MHz, DMSO-$d_6$) δ ppm 1.32-1.42 (m, 1H) 1.62-1.75 (m, 1H) 2.24 (dt, J=18.5, 9.2 Hz, 1H) 3.08-3.25 (m, 2H) 3.62 (s, 3H) 3.99-4.08 (m, 1H) 4.13-4.26 (m, 1H) 4.39-4.57 (m, 2H) 5.58 (br d, J=8.8 Hz, 1H) 5.78 (s, 1H) 5.96 (br s, 1H) 5.99 (br s, 1H) 6.49 (br d, J=8.8 Hz, 1H) 7.01 (br d, J=7.6 Hz, 1H) 7.33 (br d, J=8.2 Hz, 1H) 7.44 (br d, J=8.2 Hz, 2H) 7.55 (br d, J=8.2 Hz, 2H) 8.03 (br s, 1H) 12.71 (br s, 1H)

LC/MS (method LC-C): $R_t$ 2.84 min, $MH^+$ 609
$[\alpha]_D^{20}$: +52.5° (c 0.301, DMF)
Chiral SFC (method SFC-F): $R_t$ 3.29 min, no $MH^+$, chiral purity 100%.

Stereoisomer 28BA:
$^1$H NMR (500 MHz, DMSO-$d_6$) δ ppm 1.32-1.42 (m, 1H) 1.62-1.72 (m, 1H) 2.18-2.29 (m, 1H) 3.08-3.23 (m, 2H) 3.62 (s, 3H) 4.04 (td, J=10.4, 7.3 Hz, 1H) 4.15-4.26 (m, 1H) 4.45 (dd, J=18.8, 11.8 Hz, 1H) 4.52 (td, J=10.5, 6.1 Hz, 1H) 5.58 (d, J=8.8 Hz, 1H) 5.78 (t, J=2.0 Hz, 1H) 5.96 (s, 1H) 5.99 (s, 1H) 6.49 (d, J=9.1 Hz, 1H) 7.01 (dd, J=8.2, 1.6 Hz, 1H) 7.33 (d, J=8.2 Hz, 1H) 7.44 (d, J=8.5 Hz, 2H) 7.55 (d, J=8.5 Hz, 2H) 8.03 (s, 1H) 12.76 (br s, 1H)

LC/MS (method LC-D): $R_t$ 2.71 min, $MH^+$ 609
$[\alpha]_D^{20}$: −57.1 (c 0.31, DMF)
Chiral SFC (method SFC-F): $R_t$ 2.26 min, no $MH^+$, chiral purity 100%.

Stereoisomer 28BB:
$^1$H NMR (500 MHz, DMSO-$d_6$) δ ppm 1.35 (dt, J=11.7, 7.1 Hz, 1H) 1.59-1.71 (m, 1H) 2.17-2.28 (m, 1H) 3.08-3.25 (m, 2H) 3.62 (s, 3H) 4.04 (td, J=10.5, 7.1 Hz, 1H) 4.17-4.29 (m, 1H) 4.43 (dd, J=19.5, 11.7 Hz, 1H) 4.52 (td, J=10.4, 6.3 Hz, 1H) 5.59 (d, J=9.1 Hz, 1H) 5.78 (t, J=1.9 Hz, 1H) 5.96 (s, 1H) 5.99 (s, 1H) 6.49 (d, J=8.8 Hz, 1H) 7.01 (dd, J=8.0, 1.4 Hz, 1H) 7.33 (d, J=8.2 Hz, 1H) 7.44 (d, J=8.5 Hz, 2H) 7.55 (d, J=8.2 Hz, 2H) 8.03 (s, 1H) 12.79 (br s, 1H)

LC/MS (method LC-D): $R_t$ 2.70 min, $MH^+$ 609
$[\alpha]_D^{20}$: +38.1 (c 0.289, DMF)
Chiral SFC (method SFC-F): $R_t$ 3.68 min, no $MH^+$, chiral purity 100%.

Example 29: Synthesis of (1 S*,2S*)-2-((3-((1-(4-chlorophenyl)-2-oxo-2-(6-(trifluoromethoxy)indolin-1-yl)ethyl)amino)-5-methoxyphenoxy)methyl)-2-fluorocyclopropanecarboxylic Acid (Compound 29A) and Separation into Stereoisomers 29AA and 29AB and synthesis of (1R*,2R*)-2-((3-((1-(4-chlorophenyl)-2-oxo-2-(6-(trifluoromethoxy)indolin-1-yl)ethyl)amino)-5-methoxyphenoxy)methyl)-2-fluorocyclopropanecarboxylic Acid (Compound 29B) and Separation into Stereoisomers 29BA and 29BB

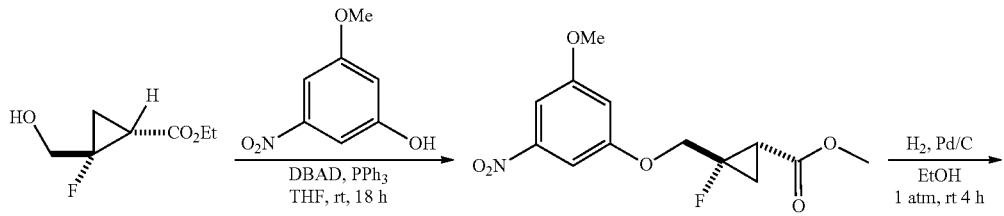

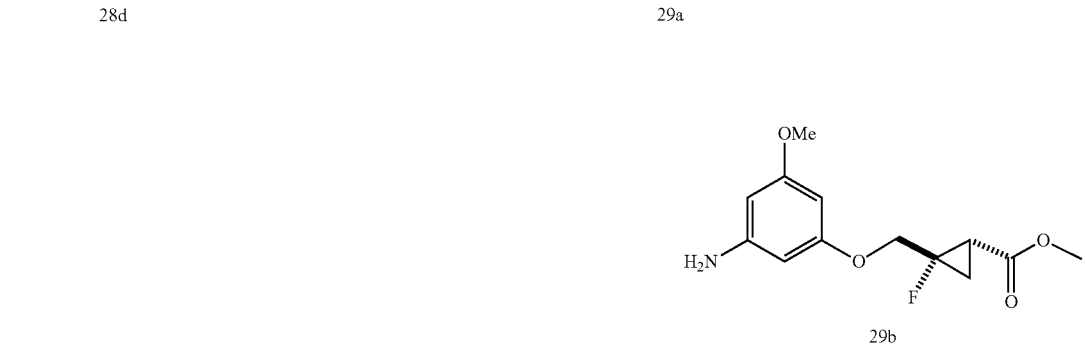

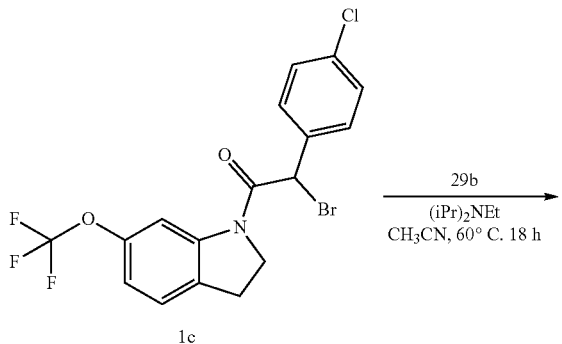

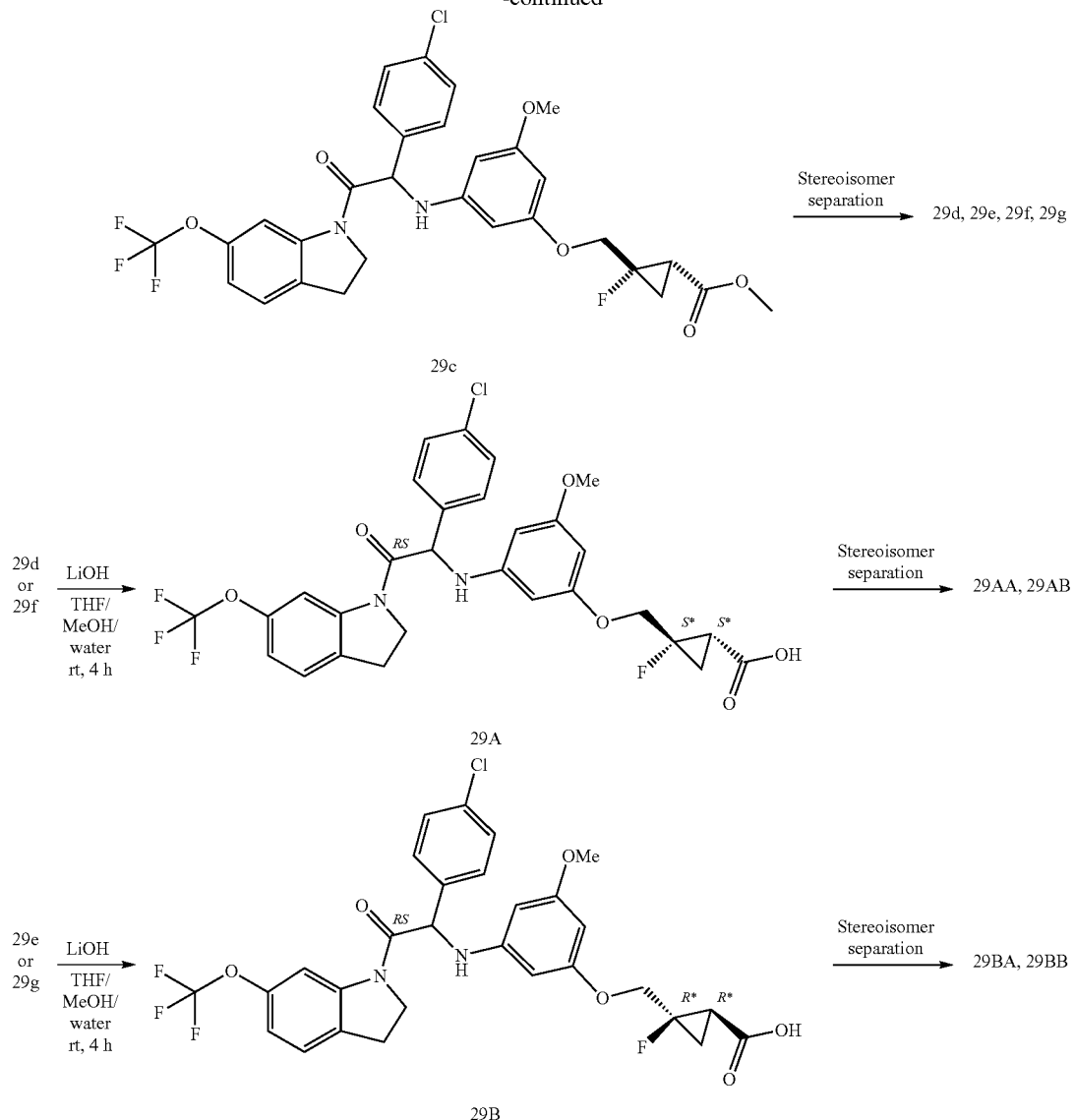

Synthesis of Intermediate 29a:

Under a N₂ flow at 10° C., di-tert-butyl azodicarboxylate (750 mg, 3.256 mmol) was added portionwise to a solution of 3-methoxy-5-nitrophenol [7145-49-5] (501 mg, 2.96 mmol), cis-ethyl 2-fluoro-2-(hydroxymethyl)cyclopropanecarboxylate 28d (480 mg, 2.96 mmol), and PPh₃ (854 mg, 3.256 mmol) in THF (23 mL). The reaction was stirred at room temperature under N₂ for 18 h. The solution was concentrated under reduced pressure. The crude residue was purified by column chromatography on silica gel (15-40 μm, 80 g, heptane/EtOAc 70/30). The pure fractions were combined and concentrated under reduced pressure to give cis-methyl 2-fluoro-2-((3-methoxy-5-nitrophenoxy)methyl) cyclopropanecarboxylate 29a (660 mg).

Synthesis of Intermediate 29b:

A solution of cis-methyl 2-fluoro-2-((3-methoxy-5-nitrophenoxy)methyl)-cyclopropanecarboxylate 29a (610 mg, 1.947 mmol) in EtOH (15 mL) and THF (7.5 mL) containing a catalytic amount of 10% Pd/C (207 mg, 0.195 mmol) was hydrogenated under atmospheric pressure of H₂ at room temperature for 4 h. The catalyst was removed by filtration over a short pad of Celite® and the filter cake was rinsed several times with EtOH. The combined filtrates were evaporated to give cis-methyl 2-((3-amino-5-methoxyphenoxy)methyl)-2-fluorocyclopropanecarboxylate 29b (560 mg), which was used in the next step without further purification.

Synthesis of Intermediate 29c and Separation into Stereoisomers 29d, 29e, 29f and 29g:

A mixture of 2-bromo-2-(4-chlorophenyl)-1-(6-(trifluoromethoxy)indolin-1-yl)ethanone 1c (716 mg, 1.647 mmol), cis-methyl 2-((3-amino-5-methoxy-phenoxy)methyl)-2-fluorocyclopropanecarboxylate 29b (560 mg, 1.977 mmol) and diisopropylethylamine (568 μL, 3.295 mmol) in CH₃CN (3.5 mL) was stirred at 80° C. for 12 h. The solvent was concentrated under reduced pressure. The residue was taken up with EtOAc. The organic layer was washed with 1N HCl, water, dried over MgSO₄, filtered, and concentrated under reduced pressure. The residue was purified by column chromatography on silica gel (15-40 μm, 40 g, heptane/EtOAc from 95/5 to 80/20). The pure fractions were combined and evaporated under reduced pressure to give methyl 2-((3-((1-(4-chlorophenyl)-2-oxo-2-(6-(trifluoromethoxy)indolin-1-yl)ethyl)amino)-5-methoxyphenoxy)methyl)-cis-2-fluorocyclopropanecarboxylate 29c (500 mg). The four stereoisomers were separated via chiral SFC (Stationary phase: Chiralpak® AD-H 5 μm 250×30 mm, mobile phase: 65% $CO_2$, 35% EtOH) to give a mixture of 29d+29e (250 mg), 29f (125 mg), and 29g (114 mg). The mixture of 29d+29e was further separated via chiral SFC (Stationary phase: Chiralpak® AD-H 5 μm 250×30 mm, mobile phase: 75% $CO_2$, 25% EtOH) to give 29d (88 mg) and 29e (66 mg).

Synthesis of Compound 29A and Separation into Stereoisomers 29AA and 29AB:

LiOH monohydrate (17.4 mg, 0.414 mmol) was added dropwise to a solution of stereoisomers 29d (88 mg, 0.138 mmol) in THF/MeOH/water (1/1/1) (1 mL). The reaction mixture was stirred at room temperature for 4 h. The mixture was diluted with water and ice, slowly acidified with 1N HCl and extracted with EtOAc. The combined organic layers were washed with water, dried over $MgSO_4$, filtered, and concentrated under reduced pressure to give, (1S*,2S*)-2-((3-((1-(4-chlorophenyl)-2-oxo-2-(6-(trifluoromethoxy)indolin-1-yl)ethyl)amino)-5-methoxyphenoxy)methyl)-2-fluorocyclopropanecarboxylic acid 29A (80 mg) (during this reaction, full racemization occurred on the central chiral center).

A second batch of 29A (90 mg) was obtained similarly starting from stereoisomer 29f. The two batches were combined. The two stereoisomers were separated via chiral SFC (Stationary phase: Chiralcel® OD-H 5 μm 250×20 mm, mobile phase: 65% $CO_2$, 35% MeOH) and further purified by flash chromatography on silica gel (15-40 μm, 4 g, $CH_2Cl_2$/MeOH 99/1) to give the first eluted stereoisomer (43 mg) and the second eluted stereoisomer (40 mg). The first eluted stereoisomer was solidified in heptane/diisopropyl ether to give stereoisomer 29AA (29 mg). The second eluted stereoisomer was solidified in heptane/diisopropyl ether to give stereoisomer 29AB (27 mg).

Synthesis of Compound 29B and separation into Stereoisomers 29BA and 29BB:

LiOH monohydrate (13 mg, 0.311 mmol) was added dropwise to a solution of stereoisomer 29e (66 mg, 0.104 mmol) in THF/MeOH/water (1/1/1) (1 mL). The reaction mixture was stirred at room temperature for 4 h. The mixture was diluted with water and ice, slowly acidified with 1N HCl and extracted with EtOAc. The combined organic layers were washed with water, dried over $MgSO_4$, filtered, and concentrated under reduced pressure to give, after crystallization from MeOH/water, (1R*,2R*)-2-((3-((1-(4-chlorophenyl)-2-oxo-2-(6-(trifluoromethoxy)-indolin-1-yl)ethyl)amino)-5-methoxyphenoxy)methyl)-2-fluorocyclopropanecarboxylic acid 29B (60 mg) (during this reaction, full racemization occurred on the central chiral center).

A second batch of 29A (100 mg) was obtained similarly starting from stereoisomer 29g. The two batches were combined. The two stereoisomers were separated via chiral SFC (Stationary phase: Chiralcel® OD-H 5 μm 250×20 mm, mobile phase: 70% $CO_2$, 30% MeOH) and further purified by flash chromatography on silica gel (15-40 μm, 4 g, $CH_2Cl_2$/MeOH 99/1) to give the first eluted stereoisomer (38 mg) and the second eluted stereoisomer (31 mg). The first eluted stereoisomer was solidified in heptane/diisopropyl ether to give stereoisomer 29BA (24 mg). The second eluted stereoisomer was solidified in heptane/diisopropyl ether to give stereoisomer 29BB (20 mg).

Stereoisomer 29AA:

$^1$H NMR (500 MHz, DMSO-$d_6$) δ ppm 1.30-1.37 (m, 1H) 1.69 (dt, J=19.7, 6.9 Hz, 1H) 1.98-2.06 (m, 1H) 3.08-3.24 (m, 2H) 3.63 (s, 3H) 4.01-4.09 (m, 1H) 4.10-4.23 (m, 2H) 4.48-4.57 (m, 1H) 5.59 (d, J=8.8 Hz, 1H) 5.81 (s, 1H) 5.99 (br d, J=5.7 Hz, 2H) 6.49 (br d, J=8.8 Hz, 1H) 7.01 (br d, J=7.9 Hz, 1H) 7.33 (d, J=7.9 Hz, 1H) 7.44 (d, J=8.5 Hz, 2H) 7.55 (d, J=8.2 Hz, 2H) 8.03 (br s, 1H) 12.58 (br s, 1H)

LC/MS (method LC-D): $R_t$ 2.67 min, MH$^+$ 609

$[α]_D^{20}$: −15.7° (c 0.242, DMF)

Chiral SFC (method SFC-P): $R_t$ 2.53 min, no MH$^+$, chiral purity 100%.

Stereoisomer 29AB:

$^1$H NMR (500 MHz, DMSO-$d_6$) δ ppm 1.29-1.38 (m, 1H) 1.69 (dt, J=19.5, 6.5 Hz, 1H) 1.97-2.10 (m, 1H) 3.08-3.25 (m, 2H) 3.63 (s, 3H) 4.00-4.10 (m, 1H) 4.10-4.23 (m, 2H) 4.52 (br d, J=6.0 Hz, 1H) 5.60 (br d, J=8.8 Hz, 1H) 5.82 (br s, 1H) 6.00 (br d, J=6.6 Hz, 2H) 6.50 (br d, J=8.5 Hz, 1H) 7.01 (br d, J=7.6 Hz, 1H) 7.34 (br d, J=7.9 Hz, 1H) 7.44 (br d, J=8.2 Hz, 2H) 7.55 (br d, J=8.2 Hz, 2H) 8.04 (br s, 1H) 12.58 (br s, 1H)

LC/MS (method LC-D): $R_t$ 2.67 min, MH$^+$ 609

$[α]_D^{20}$: +77.4° (c 0.323, DMF)

Chiral SFC (method SFC-P): $R_t$ 4.47 min, no MH$^+$, chiral purity 99.20%.

Stereoisomer 29BA:

$^1$H NMR (500 MHz, DMSO-$d_6$) δ ppm 1.33 (td, J=9.8, 6.6 Hz, 1H) 1.69 (dt, J=19.9, 6.9 Hz, 1H) 2.03 (ddd, J=9.5, 7.1, 3.0 Hz, 1H) 3.08-3.25 (m, 2H) 3.63 (s, 3H) 4.05 (td, J=10.3, 7.1 Hz, 1H) 4.10-4.23 (m, 2H) 4.52 (td, J=10.2, 6.3 Hz, 1H) 5.59 (d, J=8.8 Hz, 1H) 5.80-5.84 (m, 1H) 6.00 (br d, J=7.6 Hz, 2H) 6.49 (br d, J=8.8 Hz, 1H) 7.01 (dd, J=8.0, 1.4 Hz, 1H) 7.33 (d, J=8.2 Hz, 1H) 7.44 (d, J=8.5 Hz, 2H) 7.55 (d, J=8.2 Hz, 2H) 8.03 (s, 1H) 12.58 (br s, 1H)

LC/MS (method LC-D): $R_t$ 2.67 min, MH$^+$ 609

$[α]_D^{20}$: −74.2° (c 0.302, DMF)

Chiral SFC (method SFC-P): $R_t$ 2.37 min, no MH$^+$, chiral purity 100%.

Stereoisomer 29BB:

$^1$H NMR (500 MHz, DMSO-$d_6$) δ ppm 1.34 (td, J=9.8, 6.6 Hz, 1H) 1.69 (dt, J=19.9, 6.9 Hz, 1H) 2.02 (ddd, J=9.5, 7.1, 3.0 Hz, 1H) 3.09-3.25 (m, 2H) 3.63 (s, 3H) 4.05 (td, J=10.4, 7.3 Hz, 1H) 4.10-4.22 (m, 2H) 4.52 (td, J=10.3, 6.5 Hz, 1H) 5.59 (d, J=8.8 Hz, 1H) 5.81 (t, J=2.0 Hz, 1H) 5.96-6.03 (m, 2H) 6.49 (d, J=8.8 Hz, 1H) 7.01 (dd, J=8.2, 1.6 Hz, 1H) 7.33 (d, J=8.2 Hz, 1H) 7.44 (d, J=8.5 Hz, 2H) 7.55 (d, J=8.2 Hz, 2H) 8.03 (s, 1H) 12.58 (br s, 1H)

LC/MS (method LC-D): $R_t$ 2.70 min, MH$^+$ 609

$[α]_D^{20}$: +12.0° (c 0.3, DMF)

Chiral SFC (method SFC-P): $R_t$ 3.73 min, no MH$^+$, chiral purity 99.14%.

Example 30: Synthesis of (1s,3s)-3-((3-((1-(4-chlorophenyl)-2-(5-fluoro-6-(trifluoromethoxy)indolin-1-yl)-2-oxoethyl)amino)-5-methoxyphenoxy)methyl)-cyclobutanecarboxylic Acid (Compound 30) and Chiral Separation into Enantiomers 30A and 30B
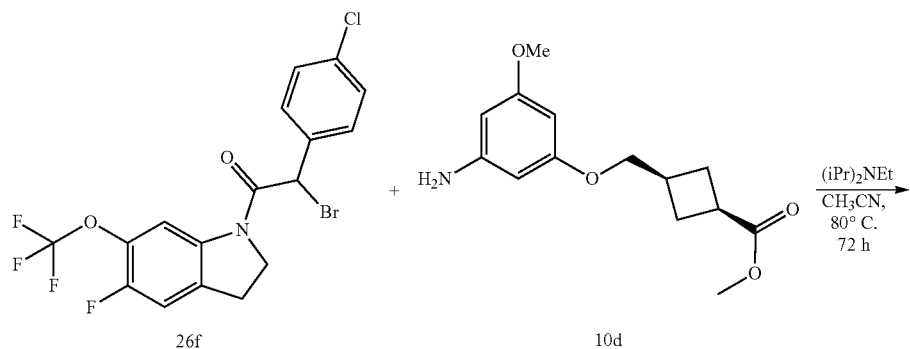
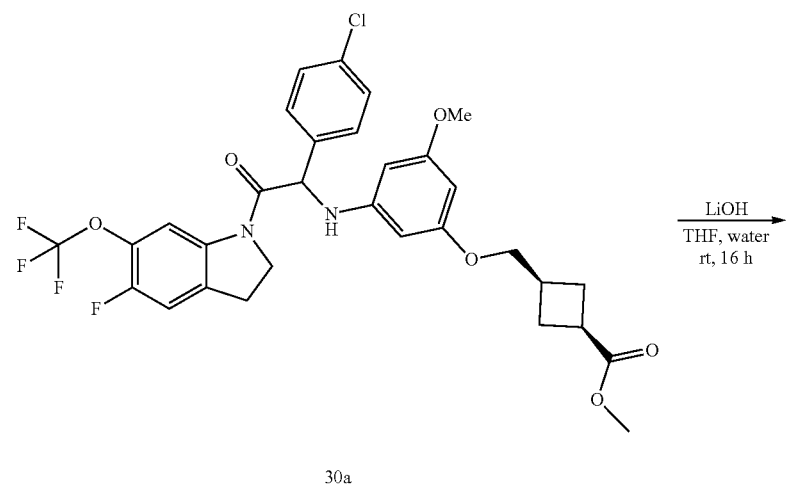
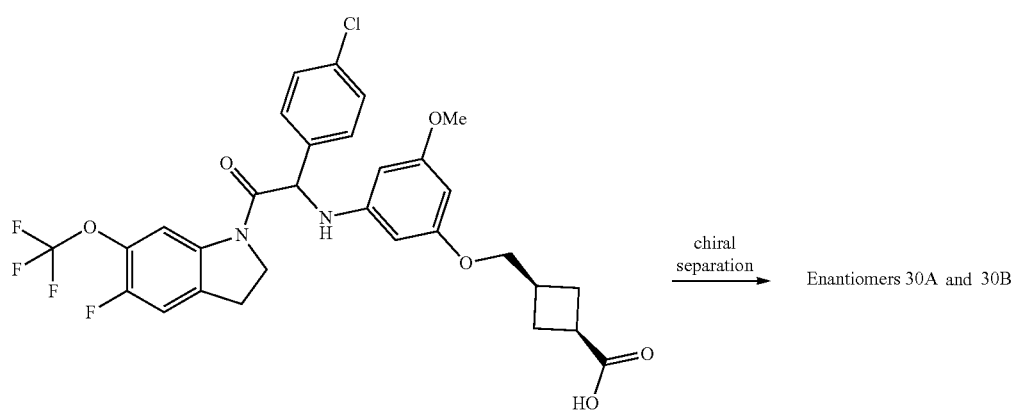

Synthesis of Compound 30 and Chiral Separation into Enantiomers 30A and 30B:

Compound 30 (105 mg) was synthesized from intermediate 26f using the procedures described for the synthesis of Compound 10. The two enantiomers were separated via chiral SFC (Stationary phase: Chiralcel® OJ-H 5 μm 250× 20 mm, mobile phase: 70% $CO_2$, 30% MeOH) to give, after lyophilization in $CH_3CN$/water, the first eluted Enantiomer 30A (43 mg) and the second eluted Enantiomer 30B (47 mg).

Enantiomer 30A:

$^1$H NMR (500 MHz, DMSO-$d_6$) δ ppm 1.85-1.98 (m, 2H) 2.17-2.28 (m, 2H) 2.53-2.59 (m, 1H) 2.96 (quin, J=8.9 Hz, 1H) 3.09-3.23 (m, 2H) 3.61 (s, 3H) 3.72-3.81 (m, 2H) 4.05 (td, J=10.3, 7.4 Hz, 1H) 4.51 (td, J=10.2, 6.5 Hz, 1H) 5.56 (d, J=8.8 Hz, 1H) 5.74 (s, 1H) 5.93 (s, 2H) 6.45 (br d, J=8.5 Hz, 1H) 7.44 (d, J=8.5 Hz, 3H) 7.54 (d, J=8.5 Hz, 2H) 8.16 (br d, J=6.9 Hz, 1H) 11.24-13.06 (m, 1H)

LC/MS (method LC-C): $R_t$ 3.08 min, $MH^+$ 623

$[α]_D^{20}$: +42.6° (c 0.298, DMF)

Chiral SFC (method SFC-F): $R_t$ 2.91 min, no $MH^+$, chiral purity 100%.

Enantiomer 30B:

$^1$H NMR (500 MHz, DMSO-$d_6$) δ ppm 1.87-1.99 (m, 2H) 2.16-2.29 (m, 2H) 2.53-2.59 (m, 1H) 2.96 (br t, J=8.8 Hz, 1H) 3.11-3.23 (m, 2H) 3.61 (s, 3H) 3.77 (br d, J=6.0 Hz, 2H) 4.05 (td, J=10.2, 7.3 Hz, 1H) 4.51 (td, J=10.3, 6.5 Hz, 1H) 5.56 (d, J=8.8 Hz, 1H) 5.74 (s, 1H) 5.93 (s, 2H) 6.45 (br d, J=8.8 Hz, 1H) 7.44 (br d, J=8.2 Hz, 3H) 7.54 (d, J=8.5 Hz, 2H) 8.16 (br d, J=6.9 Hz, 1H) 11.43-12.72 (m, 1H)

LC/MS (method LC-C): $R_t$ 3.07 min, $MH^+$ 623

$[α]_D^{20}$: −44.2° (c 0.217, DMF)

Chiral SFC (method SFC-F): $R_t$ 4.10 min, no $MH^+$, chiral purity 99.09%.

Example 31: Synthesis of (1r,3r)-3-((3-((1-(4-chlorophenyl)-2-(5-fluoro-6-(trifluoromethoxy)indolin-1-yl)-2-oxoethyl)amino)-5-methoxyphenoxy)methyl)cyclobutanecarboxylic Acid (Compound 31) and Chiral Separation into Enantiomers 31A and 31B

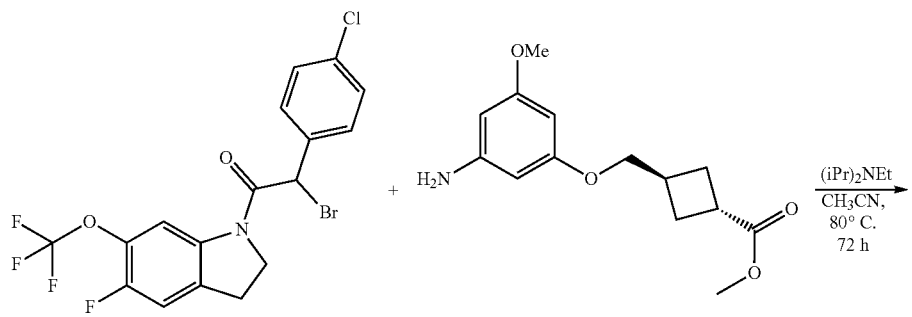

11a

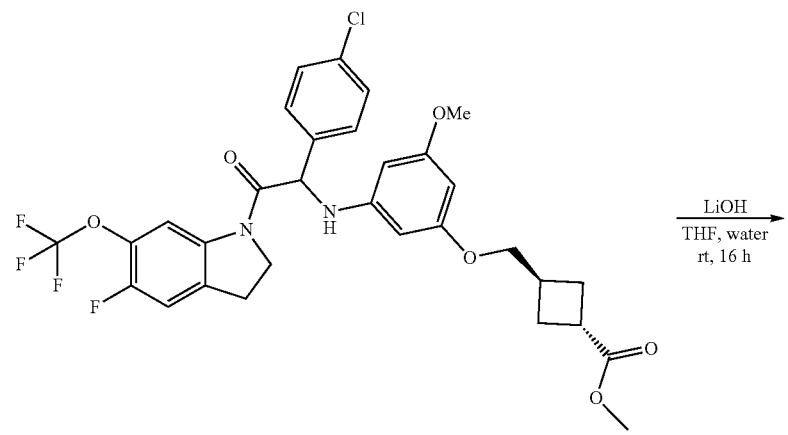

31a

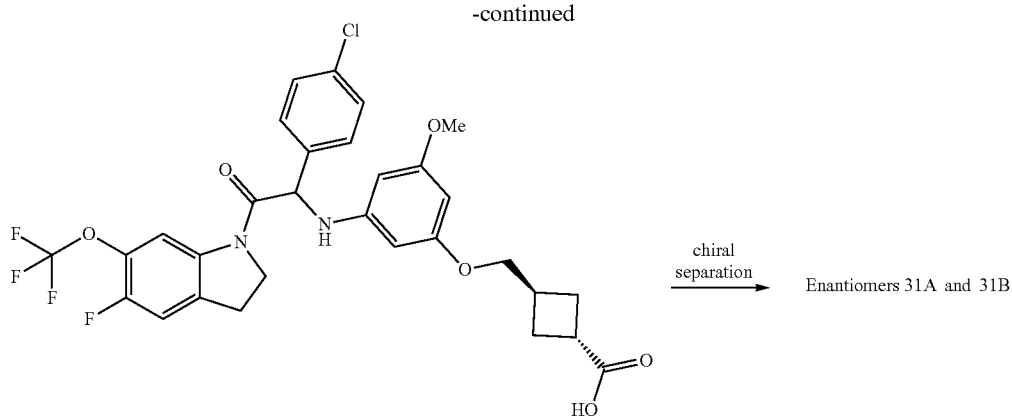

31

Synthesis of Compound 31 and Chiral Separation into Enantiomers 31A and 31B:

Compound 31 (75 mg) was synthesized from intermediate 26f using the procedure described for the synthesis of Compound 11. The two enantiomers were separated via chiral SFC (Stationary phase: Chiralcel® OJ-H 5 μm 250× 20 mm, mobile phase: 70% $CO_2$, 30% MeOH) to give, after lyophilization in $CH_3CN$/water, the first eluted Enantiomer 31A (23 mg) and the second eluted Enantiomer 31B (24 mg).

Enantiomer 31A:
$^1$H NMR (500 MHz, DMSO-$d_6$) δ ppm 1.90-2.03 (m, 2H) 2.20-2.30 (m, 2H) 2.55-2.62 (m, 1H) 3.07 (br t, J=7.7 Hz, 1H) 3.12-3.24 (m, 2H) 3.62 (s, 3H) 3.87 (br d, J=6.9 Hz, 2H) 4.05 (td, J=10.3, 7.1 Hz, 1H) 4.51 (td, J=10.4, 6.6 Hz, 1H) 5.57 (d, J=8.8 Hz, 1H) 5.78 (s, 1H) 5.94 (s, 1H) 5.96 (s, 1H) 6.45 (d, J=8.8 Hz, 1H) 7.44 (d, J=8.5 Hz, 3H) 7.54 (d, J=8.5 Hz, 2H) 8.16 (br d, J=6.9 Hz, 1H)
LC/MS (method LC-C): $R_t$ 3.07 min, MH$^+$ 623
$[α]_D^{20}$: +43.1 (c 0.255, DMF)
Chiral SFC (method SFC-F): $R_t$ 3.25 min, no MH$^+$, chiral purity 100%.

Enantiomer 31B:
$^1$H NMR (500 MHz, DMSO-$d_6$) δ ppm 1.90-2.03 (m, 2H) 2.19-2.31 (m, 2H) 2.55-2.62 (m, 1H) 3.01-3.10 (m, 1H) 3.12-3.23 (m, 2H) 3.62 (s, 3H) 3.86 (br d, J=6.9 Hz, 2H) 4.05 (td, J=10.2, 7.3 Hz, 1H) 4.51 (td, J=10.3, 6.5 Hz, 1H) 5.57 (d, J=8.8 Hz, 1H) 5.78 (s, 1H) 5.94 (s, 1H) 5.95 (s, 1H) 6.45 (br d, J=8.8 Hz, 1H) 7.44 (d, J=8.5 Hz, 3H) 7.54 (d, J=8.2 Hz, 2H) 8.15 (br d, J=6.6 Hz, 1H)
LC/MS (method LC-C): $R_t$ 3.07 min, MH$^+$ 623
$[α]_D^{20}$: −43.4° (c 0.244, DMF)
Chiral SFC (method SFC-F): $R_t$ 4.85 min, no MH$^+$, chiral purity 99.09%.

Example 32: Synthesis of (1s,3s)-3-(3-((2-(6-chloro-5-methoxyindolin-1-yl)-1-(4-chlorophenyl)-2-oxoethyl)amino)-5-methoxyphenoxy)cyclobutanecarboxylic Acid (Compound 32) and Chiral Separation into Enantiomers 32A and 32B

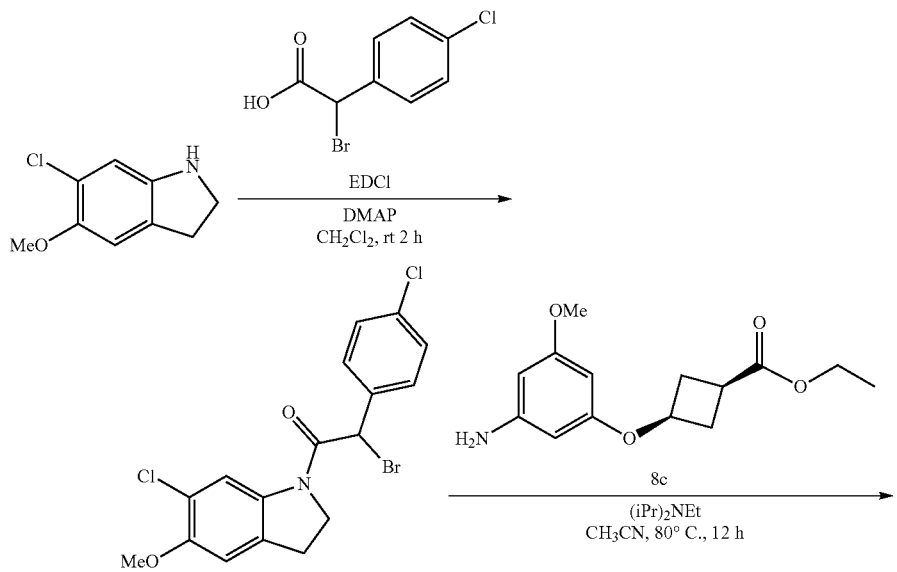

32a

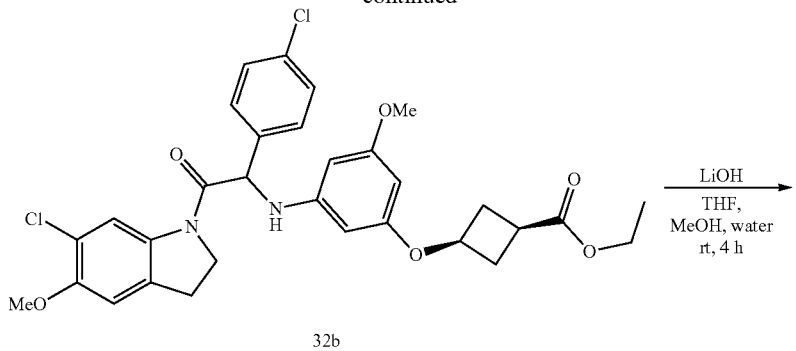

32b

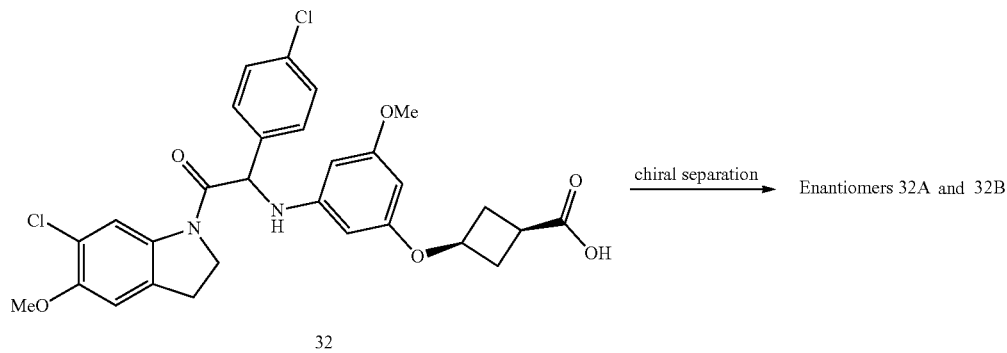

32

Synthesis of Intermediate 32a:

Intermediate 32a (3.58 g) was synthesized from 6-chloro-5-methoxyindoline [CAS 1369041-89-3] using the procedure described for the synthesis of intermediate 26f.

Synthesis of Intermediate 32b:

Intermediate 32b (210 mg) was synthesized from intermediate 32a using the procedure described for the synthesis of intermediate 8d.

Synthesis of Compound 32 and Chiral Separation into Enantiomers 32A and 32B:

Compound 32 (165 mg) was synthesized from intermediate 32b using the procedure described for the synthesis of Compound 28. The two enantiomers were separated via chiral SFC (Stationary phase: Chiralcel® OD-H 5 μm 250×30 mm, mobile phase: 50% $CO_2$, 50% EtOH) to give, after purification via flash chromatography on silica gel (15-40 μm; 4 g, $CH_2Cl_2/CH_3OH$ 97/3) and solidification from heptane/diisopropyl ether, the first eluted Enantiomer 32A (26 mg) and the second eluted Enantiomer 32B (31 mg).

Compound 32:

$^1$H NMR (500 MHz, DMSO-$d_6$) δ ppm 2.03-2.15 (m, 2H) 2.57-2.66 (m, 2H) 2.66-2.75 (m, 1H) 3.06-3.23 (m, 2H) 3.61 (s, 3H) 3.80 (s, 3H) 3.95 (td, J=10.4, 7.3 Hz, 1H) 4.43-4.52 (m, 2H) 5.50 (d, J=8.5 Hz, 1H) 5.65 (t, J=1.9 Hz, 1H) 5.86 (s, 1H) 5.93 (s, 1H) 6.40 (d, J=8.5 Hz, 1H) 7.10 (s, 1H) 7.44 (d, J=8.5 Hz, 2H) 7.54 (d, J=8.5 Hz, 2H) 8.11 (s, 1H) 12.26 (br s, 1H)

LC/MS (method LC-C): $R_t$ 2.66 min, MH$^+$ 569

Enantiomer 32A:

$^1$H NMR (500 MHz, DMSO-$d_6$) δ ppm 2.03-2.15 (m, 2H) 2.57-2.66 (m, 2H) 2.66-2.76 (m, 1H) 3.04-3.24 (m, 2H) 3.57-3.64 (m, 3H) 3.80 (s, 3H) 3.89-4.00 (m, 1H) 4.42-4.54 (m, 2H) 5.50 (br d, J=8.8 Hz, 1H) 5.65 (s, 1H) 5.86 (s, 1H) 5.93 (s, 1H) 6.40 (br d, J=8.5 Hz, 1H) 7.10 (s, 1H) 7.44 (d, J=8.2 Hz, 2H) 7.54 (br d, J=8.2 Hz, 2H) 8.11 (s, 1H) 12.26 (br s, 1H)

LC/MS (method LC-D): $R_t$ 2.56 min, MH$^+$ 569

$[α]_D^{20}$: −55.4° (c 0.332, DMF)

Chiral SFC (method SFC-R): $R_t$ 1.73 min, no MH$^+$, chiral purity 100%.

Enantiomer 32B:

$^1$H NMR (500 MHz, DMSO-$d_6$) δ ppm 2.02-2.14 (m, 2H) 2.58-2.65 (m, 2H) 2.66-2.74 (m, 1H) 3.04-3.24 (m, 2H) 3.61 (s, 3H) 3.80 (s, 3H) 3.95 (td, J=10.4, 7.3 Hz, 1H) 4.42-4.53 (m, 2H) 5.50 (d, J=8.5 Hz, 1H) 5.65 (t, J=2.0 Hz, 1H) 5.86 (s, 1H) 5.93 (s, 1H) 6.40 (d, J=8.5 Hz, 1H) 7.10 (s, 1H) 7.44 (d, J=8.5 Hz, 2H) 7.54 (d, J=8.5 Hz, 2H) 8.11 (s, 1H) 12.26 (br s, 1H)

LC/MS (method LC-D): $R_t$ 2.56 min, MH$^+$ 569

$[α]_D^{20}$: +53.4° (c 0.35, DMF)

Chiral SFC (method SFC-R): $R_t$ 3.16 min, no MH$^+$, chiral purity 99.59%.

Example 33: Synthesis of 3-((3-((1-(4-chlorophenyl)-2-oxo-2-(6-(trifluoromethoxy)indolin-1-yl)ethyl)amino)-5-methoxyphenyl)amino)-cyclobutanecarboxylic Acid (Compound 33) and Chiral Separation into Stereoisomers 33A, 33B, 33C and 33D
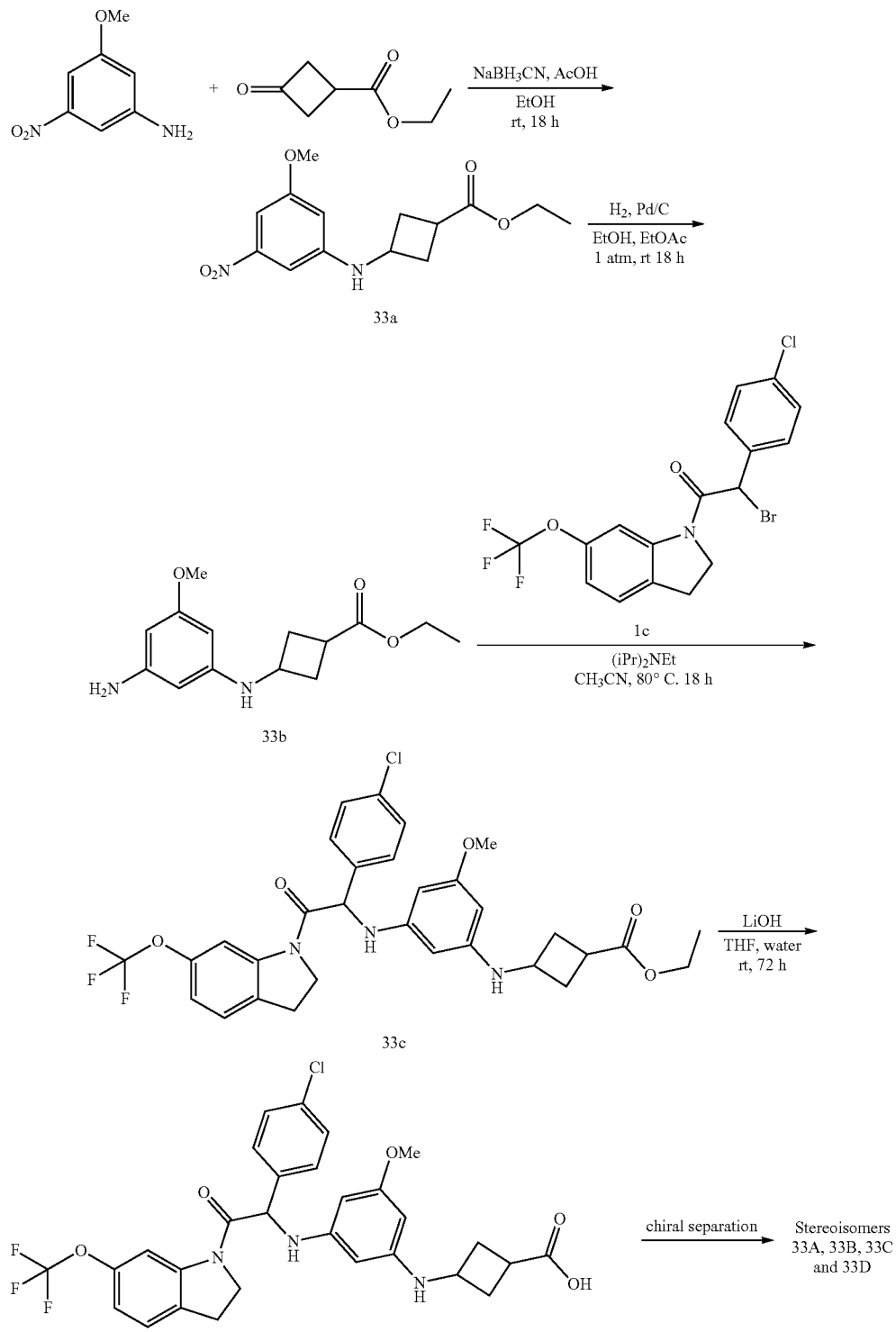

Synthesis of Intermediate 33a:

Under nitrogen, a mixture of 3-methoxy-5-nitroaniline [CAS 586-10-7] (0.50 g, 2.973 mmol), ethyl 3-oxocyclobutanecarboxylate [CAS 87121-89-9] (1.27 g, 8.92 mmol), and acetic acid (0.34 mL, 5.947 mmol) in dry EtOH (26 mL) was stirred at room temperature for 30 min. NaBH$_3$CN (0.374 g, 5.947 mmol) was added and the mixture was stirred at room temperature for 18 h. Brine was added and the mixture was extracted twice with CH$_2$Cl$_2$. The combined organic layers were dried over MgSO$_4$, filtered and concentrated under reduced pressure. The residue was purified by flash chromatography on silica gel (30 µm, 24 g, heptane/EtOAc from 85/15 to 75/25). The pure fractions were combined and concentrated under reduced pressure to give ethyl 3-((3-methoxy-5-nitrophenyl)amino)cyclobutanecarboxylate 33a (820 mg). The compound was used in the next step without further purification.

Synthesis of Intermediate 33b:

A solution of ethyl 3-((3-methoxy-5-nitrophenyl)amino)cyclobutanecarboxylate 33a (820 mg, 2.8 mmol) in EtOH (16 mL) and EtOAc (14 mL) containing a catalytic amount of 10% Pd/C (300 mg, 0.28 mmol) was hydrogenated under atmospheric pressure of H$_2$ at room temperature for 18 h. The catalyst was removed by filtration over a short pad of Celite® and the filter cake was rinsed several times with EtOAc. The combined filtrates were evaporated under reduced pressure to give ethyl 3-((3-amino-5-methoxyphenyl)amino)cyclobutanecarboxylate 33b (800 mg), which was used in the next step without further purification.

Synthesis of Intermediate 33c:

A mixture of 2-bromo-2-(4-chlorophenyl)-1-(6-(trifluoromethoxy)indolin-1-yl)ethanone 1c (0.936 g, 2.154 mmol), ethyl 3-((3-amino-5-methoxyphenyl)amino)cyclobutanecarboxylate 33b (0.74 g, 2.8 mmol) and diisopropylethylamine (0.742 mL, 4.307 mmol) in CH$_3$CN (11 mL) was stirred at 80° C. for 18 h. The mixture was concentrated under reduced pressure. Purification was performed by flash chromatography on silica gel (30 µm, 40 g, heptane/EtOAc from 85/15 to 70/30) The pure fractions were combined and evaporated to dryness to give ethyl 3-((3-((1-(4-chlorophenyl)-2-oxo-2-(6-(trifluoromethoxy)indolin-1-yl)ethyl)amino)-5-methoxyphenyl)amino)cyclobutanecarboxylate 33c (600 mg).

Synthesis of Compound 33 and Chiral Separation into Stereoisomers 33A, 33B, 33C and 33D:

A solution of LiOH monohydrate (0.407 g, 9.71 mmol) in water (5.3 mL) was added to a solution of ethyl 3-((3-((1-(4-chlorophenyl)-2-oxo-2-(6-(trifluoromethoxy)-indolin-1-yl)ethyl)amino)-5-methoxyphenyl)amino)cyclobutanecarboxylate 33c (600 mg, 0.971 mmol) in THF (12 mL). The mixture was stirred at room temperature for 72 h, acidified with AcOH, concentrated under reduced pressure, and co-evaporated twice with toluene. Purification was performed by flash chromatography on silica gel (30 µm, 24 g, CH$_2$Cl$_2$/MeOH from 99/1 to 96/4). The pure fractions were combined and evaporated to dryness. A second purification was performed via Reverse Phase chromatography (Stationary phase: YMC-actus Triart-C18 10 µm 30×150 mm, mobile phase: Gradient from 65% aqueous NH$_4$HCO$_3$ 0.2%, 35% CH$_3$CN to 25% aqueous NH$_4$HCO$_3$ 0.2%, 75% CH$_3$CN). The pure fractions were combined and evaporated to dryness to give 3-((3-((1-(4-chlorophenyl)-2-oxo-2-(6-(trifluoromethoxy)indolin-1-yl)ethyl)amino)-5-methoxyphenyl) amino)cyclobutanecarboxylic acid (Compound 33, 80 mg). The stereoisomers were separated via chiral SFC (Stationary phase: Chiralcel® OD-H 5 µm 250×20 mm, mobile phase: 60% CO$_2$, 40% EtOH) to give 4 fractions which were freezedried from CH$_3$CN/water to give Stereoisomer 33A (19 mg), Stereoisomer 33B (24 mg), Stereoisomer 33C (19 mg) and Stereoisomer 33D (26 mg).

Stereoisomer 33A:

$^1$H NMR (500 MHz, DMSO-d$_6$) δ ppm 1.94-2.02 (m, 2H) 2.43 (ddd, J=11.8, 7.7, 4.1 Hz, 2H) 2.91 (dt, J=9.5, 4.7 Hz, 1H) 3.07-3.21 (m, 2H) 3.56 (s, 3H) 3.78-3.88 (m, 1H) 4.05 (td, J=10.4, 7.3 Hz, 1H) 4.50 (td, J=10.3, 6.8 Hz, 1H) 5.38 (d, J=1.9 Hz, 1H) 5.43 (d, J=8.5 Hz, 1H) 5.46 (s, 1H) 5.60 (s, 1H) 5.63 (d, J=6.3 Hz, 1H) 6.19 (d, J=8.5 Hz, 1H) 7.00 (dd, J=8.2, 1.6 Hz, 1H) 7.33 (d, J=8.2 Hz, 1H) 7.43 (d, J=8.5 Hz, 2H) 7.54 (d, J=8.5 Hz, 2H) 8.03 (s, 1H)

LC/MS (method LC-C): R$_t$ 2.86 min, MH$^+$ 590

[α]$_D^{20}$: −26.2° (c 0.248, DMF)

Chiral SFC (method SFC-I): R$_t$ 1.48 min, no MH$^+$, chiral purity 100%.

Stereoisomer 33B:

$^1$H NMR (500 MHz, DMSO-d$_6$) δ ppm 1.82-1.95 (m, 2H) 2.41-2.47 (m, 2H) 2.68 (br t, J=8.5 Hz, 1H) 3.08-3.21 (m, 2H) 3.56 (s, 3H) 3.62 (br dd, J=15.4, 8.2 Hz, 1H) 4.06 (td, J=10.3, 7.1 Hz, 1H) 4.46-4.56 (m, 1H) 5.41 (s, 1H) 5.43 (br d, J=8.5 Hz, 1H) 5.50 (s, 1H) 5.60 (s, 2H) 6.14 (br d, J=8.8 Hz, 1H) 7.01 (br d, J=8.2 Hz, 1H) 7.33 (d, J=8.2 Hz, 1H) 7.43 (d, J=8.5 Hz, 2H) 7.54 (d, J=8.5 Hz, 2H) 8.03 (s, 1H)

LC/MS (method LC-C): R$_t$ 2.84 min, MH$^+$ 590

[α]$_D^{20}$: −27.9° (c 0.248, DMF)

Chiral SFC (method SFC-I): R$_t$ 2.20 min, no MH$^+$, chiral purity 100%.

Stereoisomer 33C:

$^1$H NMR (500 MHz, DMSO-d$_6$) δ ppm 1.93-2.03 (m, 2H) 2.41-2.46 (m, 2H) 2.82-2.95 (m, 1H) 3.07-3.21 (m, 2H) 3.56 (s, 3H) 3.78-3.88 (m, 1H) 4.00-4.11 (m, 1H) 4.45-4.56 (m, 1H) 5.37 (s, 1H) 5.40-5.49 (m, 2H) 5.58-5.66 (m, 2H) 6.19 (br d, J=8.5 Hz, 1H) 7.00 (br d, J=6.6 Hz, 1H) 7.32 (br d, J=8.2 Hz, 1H) 7.43 (d, J=8.5 Hz, 2H) 7.54 (d, J=8.2 Hz, 2H) 8.02 (br s, 1H)

LC/MS (method LC-C): R$_t$ 2.86 min, MH$^+$ 590

[α]$_D^{20}$: +26.7° (c 0.221, DMF)

Chiral SFC (method SFC-I): R$_t$ 2.91 min, no MH$^+$, chiral purity 100%.

Stereoisomer 33D:

$^1$H NMR (500 MHz, DMSO-d$_6$) δ ppm 1.78-1.96 (m, 2H) 2.40-2.47 (m, 2H) 2.65-2.71 (m, 1H) 3.08-3.21 (m, 2H) 3.56 (s, 3H) 3.58-3.67 (m, 1H) 4.06 (td, J=10.2, 7.3 Hz, 1H) 4.44-4.56 (m, 1H) 5.38-5.46 (m, 2H) 5.50 (s, 1H) 5.60 (s, 2H) 6.14 (br d, J=8.8 Hz, 1H) 7.00 (br d, J=6.9 Hz, 1H) 7.33 (d, J=8.2 Hz, 1H) 7.43 (d, J=8.5 Hz, 2H) 7.54 (d, J=8.5 Hz, 2H) 8.03 (s, 1H)

LC/MS (method LC-C): R$_t$ 2.84 min, MH$^+$ 590

[α]$_D^{20}$: +23.4° (c 0.295, DMF)

Chiral SFC (method SFC-I): R$_t$ 5.35 min, no MH$^+$, chiral purity 100%.

TABLE

| compounds prepared as described above | | |
| --- | --- | --- |
| Compound | Structure | Optical rotation |
| 1 | | racemic |
| 1A | | $[\alpha]_D^{20} = -37.6°$ |
| 1B | | $[\alpha]_D^{20} = -65.3°$ |
| 1C | | $[\alpha]_D^{20} = +35.2°$ |

TABLE-continued compounds prepared as described above

| Compound | Structure | Optical rotation |
|---|---|---|
| 1D | 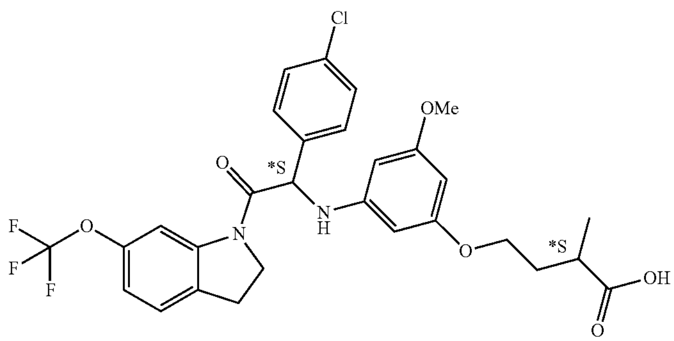 [SMILES: COc1cc(NC(C(=O)N2CCc3ccc(OC(F)(F)F)cc32)c2ccc(Cl)cc2)cc(OCCC(C)C(=O)O)c1] | $[\alpha]_D^{20} = +64.3°$ |
| 2 | 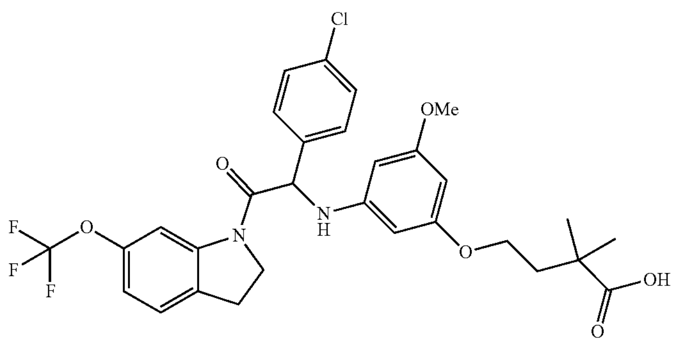 [SMILES: COc1cc(NC(C(=O)N2CCc3ccc(OC(F)(F)F)cc32)c2ccc(Cl)cc2)cc(OCCC(C)(C)C(=O)O)c1] | racemic |
| 2A | 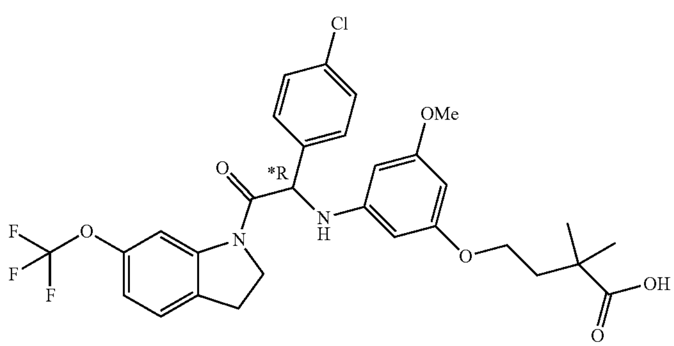 [SMILES: COc1cc(NC(C(=O)N2CCc3ccc(OC(F)(F)F)cc32)c2ccc(Cl)cc2)cc(OCCC(C)(C)C(=O)O)c1] | $[\alpha]_D^{20} = +49.6°$ |
| 2B | 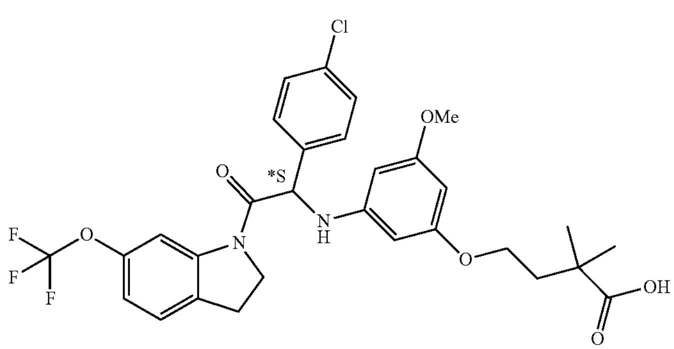 [SMILES: COc1cc(NC(C(=O)N2CCc3ccc(OC(F)(F)F)cc32)c2ccc(Cl)cc2)cc(OCCC(C)(C)C(=O)O)c1] | $[\alpha]_D^{20} = -49.2°$ |

TABLE-continued compounds prepared as described above

| Compound | Structure | Optical rotation |
|---|---|---|
| 3 | 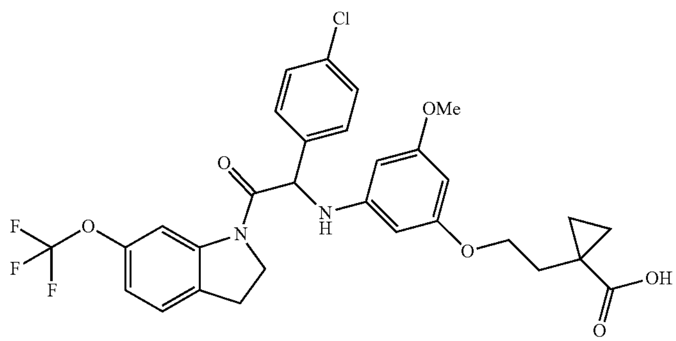 [SMILES: COc1cc(NC(C(=O)N2CCc3ccc(OC(F)(F)F)cc32)c2ccc(Cl)cc2)cc(OCCC2(C(=O)O)CC2)c1] | racemic |
| 4 | 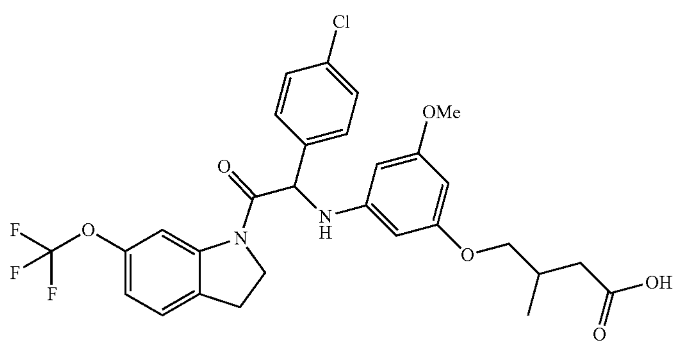 [SMILES: COc1cc(NC(C(=O)N2CCc3ccc(OC(F)(F)F)cc32)c2ccc(Cl)cc2)cc(OCC(C)CC(=O)O)c1] | racemic |
| 4A | 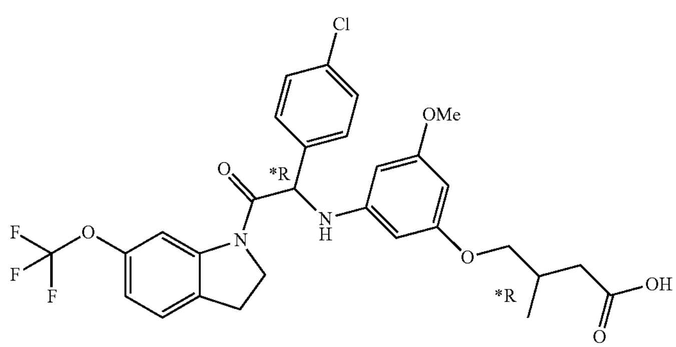 [SMILES: COc1cc(NC(C(=O)N2CCc3ccc(OC(F)(F)F)cc32)c2ccc(Cl)cc2)cc(OCC(C)CC(=O)O)c1] | $[\alpha]_D^{20} = -59.6°$ |
| 4B | 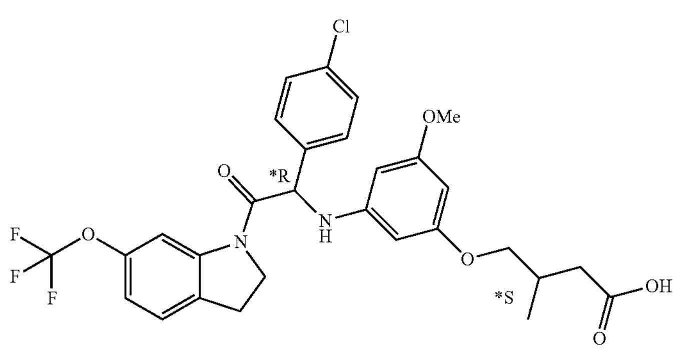 [SMILES: COc1cc(NC(C(=O)N2CCc3ccc(OC(F)(F)F)cc32)c2ccc(Cl)cc2)cc(OCC(C)CC(=O)O)c1] | $[\alpha]_D^{20} = -47.5°$ |

TABLE-continued compounds prepared as described above

| Compound | Structure | Optical rotation |
|---|---|---|
| 4C | 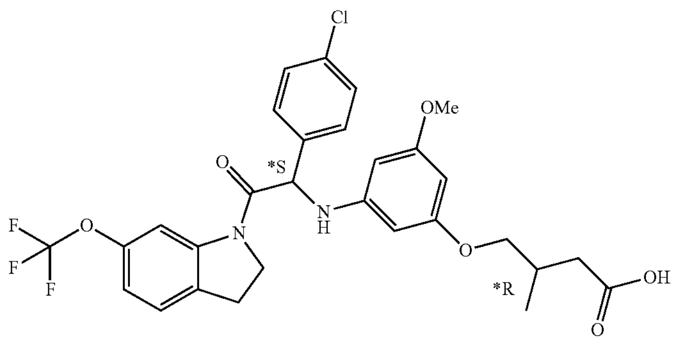 [SMILES: COc1cc(NC(C(=O)N2CCc3ccc(OC(F)(F)F)cc32)c2ccc(Cl)cc2)cc(OCC(C)CC(=O)O)c1] | $[\alpha]_D^{20} = +47.7°$ |
| 4D | 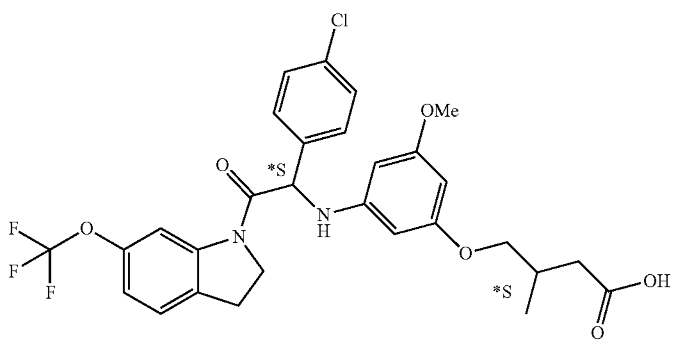 [SMILES: COc1cc(NC(C(=O)N2CCc3ccc(OC(F)(F)F)cc32)c2ccc(Cl)cc2)cc(OCC(C)CC(=O)O)c1] | $[\alpha]_D^{20} = +60.7°$ |
| 5 | 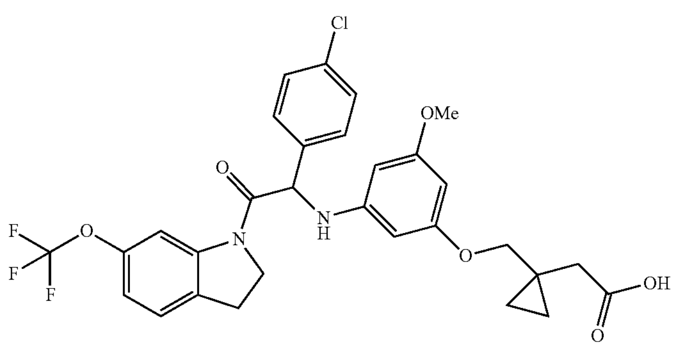 [SMILES: COc1cc(NC(C(=O)N2CCc3ccc(OC(F)(F)F)cc32)c2ccc(Cl)cc2)cc(OCC2(CC(=O)O)CC2)c1] | racemic |
| 5A | 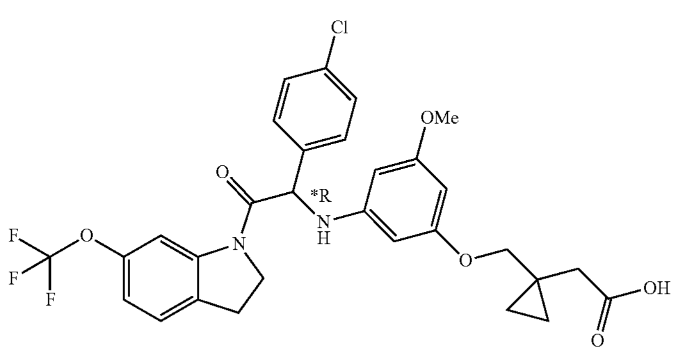 [SMILES: COc1cc(NC(C(=O)N2CCc3ccc(OC(F)(F)F)cc32)c2ccc(Cl)cc2)cc(OCC2(CC(=O)O)CC2)c1] | $[\alpha]_D^{20} = +37.0°$ |

TABLE-continued
compounds prepared as described above
| Compound | Structure | Optical rotation |
| --- | --- | --- |
| 5B | 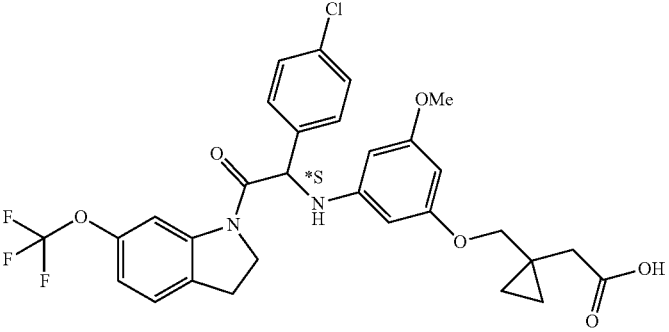 [SMILES: COc1cc(NC(C(=O)N2CCc3ccc(OC(F)(F)F)cc32)c2ccc(Cl)cc2)cc(OCC2(CC(=O)O)CC2)c1] | $[\alpha]_D^{20} = -48.8°$ |
| 6AA | 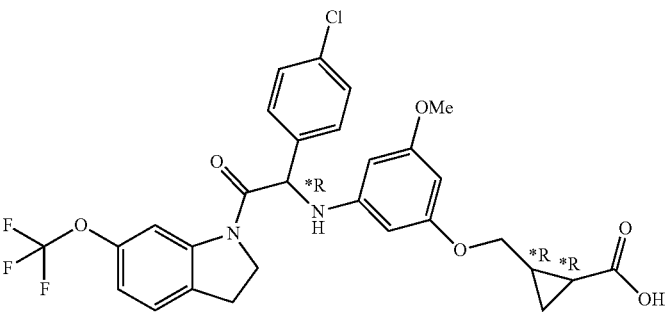 [SMILES: COc1cc(NC(C(=O)N2CCc3ccc(OC(F)(F)F)cc32)c2ccc(Cl)cc2)cc(OCC2CC2C(=O)O)c1] | $[\alpha]_D^{20} = -78.0°$ |
| 6AB | 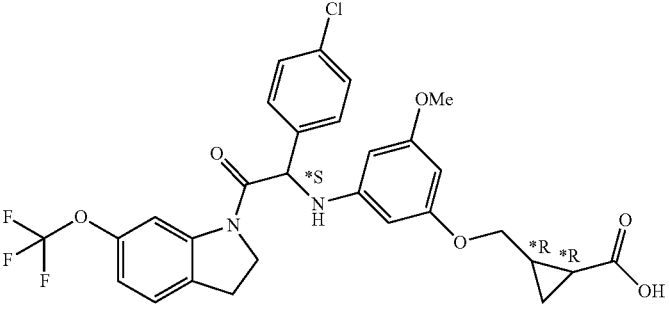 [SMILES: COc1cc(NC(C(=O)N2CCc3ccc(OC(F)(F)F)cc32)c2ccc(Cl)cc2)cc(OCC2CC2C(=O)O)c1] | $[\alpha]_D^{20} = +12.9°$ |
| 6BA | 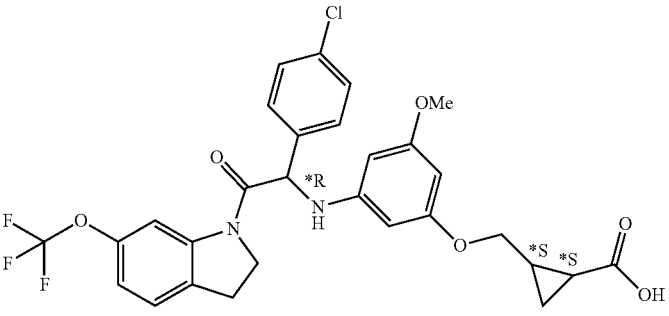 [SMILES: COc1cc(NC(C(=O)N2CCc3ccc(OC(F)(F)F)cc32)c2ccc(Cl)cc2)cc(OCC2CC2C(=O)O)c1] | $[\alpha]_D^{20} = -12.5°$ |

TABLE-continued compounds prepared as described above

| Compound | Structure | Optical rotation |
|---|---|---|
| 6BB | 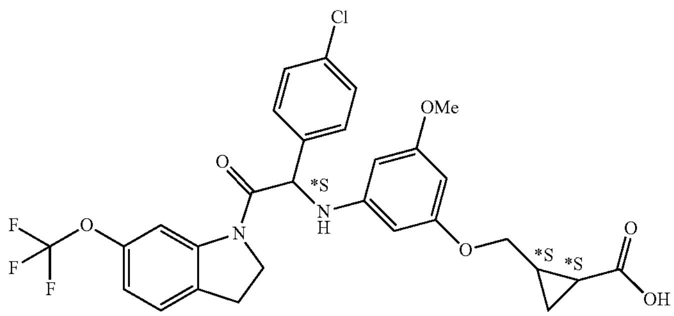 [SMILES: COc1cc(NC(C(=O)N2CCc3ccc(OC(F)(F)F)cc32)c2ccc(Cl)cc2)cc(OCC2CC2C(=O)O)c1] | $[\alpha]_D^{20}$ = +81.4° |
| 7 | 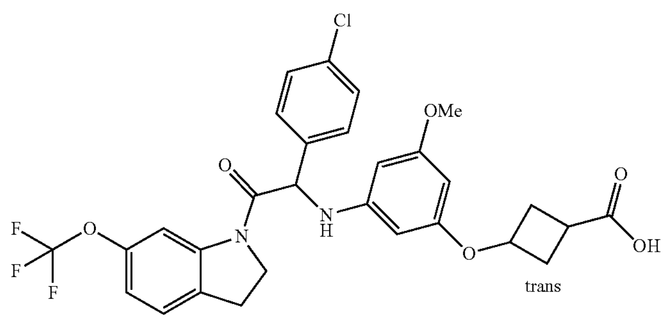 [SMILES: COc1cc(NC(C(=O)N2CCc3ccc(OC(F)(F)F)cc32)c2ccc(Cl)cc2)cc(OC2CC(C(=O)O)C2)c1] | — |
| 7A | 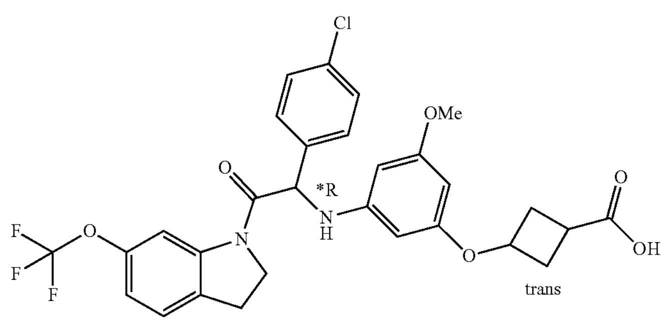 [SMILES: COc1cc(NC(C(=O)N2CCc3ccc(OC(F)(F)F)cc32)c2ccc(Cl)cc2)cc(OC2CC(C(=O)O)C2)c1] | $[\alpha]_D^{20}$ = −41.6° |
| 7B | 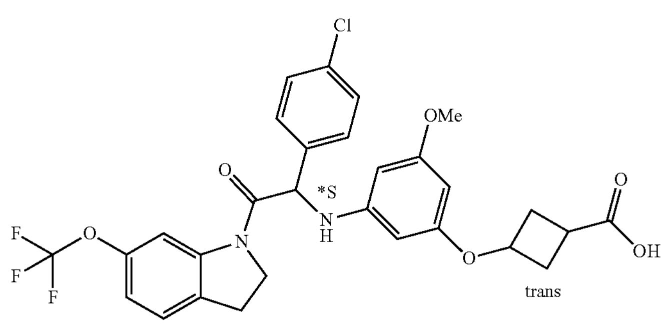 [SMILES: COc1cc(NC(C(=O)N2CCc3ccc(OC(F)(F)F)cc32)c2ccc(Cl)cc2)cc(OC2CC(C(=O)O)C2)c1] | $[\alpha]_D^{20}$ = +43.7° |

TABLE-continued
compounds prepared as described above
| Compound | Structure | Optical rotation |
|---|---|---|
| 8 | 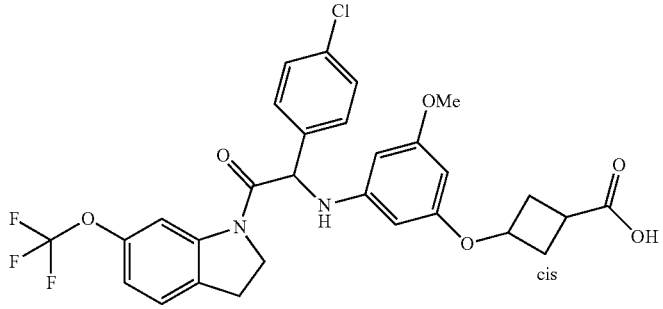 [SMILES: COc1cc(NC(C(=O)N2CCc3ccc(OC(F)(F)F)cc32)c2ccc(Cl)cc2)cc(OC2CC(C(=O)O)C2)c1] | — |
| 8A | 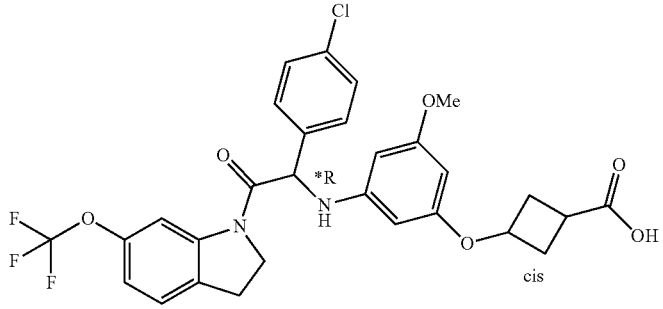 [SMILES: COc1cc(NC(C(=O)N2CCc3ccc(OC(F)(F)F)cc32)c2ccc(Cl)cc2)cc(OC2CC(C(=O)O)C2)c1] | $[\alpha]_D^{20} = -47.1°$ |
| 8B | 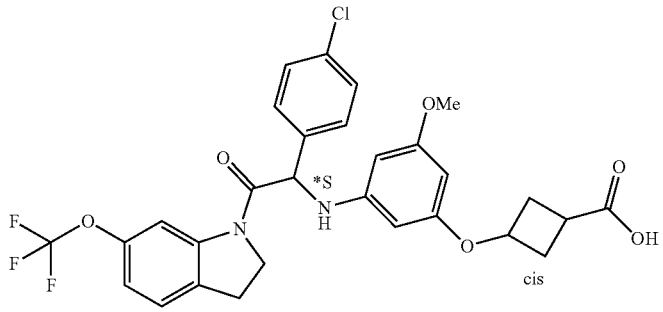 [SMILES: COc1cc(NC(C(=O)N2CCc3ccc(OC(F)(F)F)cc32)c2ccc(Cl)cc2)cc(OC2CC(C(=O)O)C2)c1] | $[\alpha]_D^{20} = +40.0°$ |
| 9 | 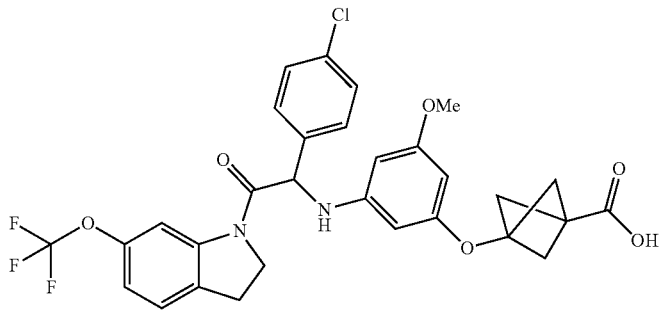 [SMILES: COc1cc(NC(C(=O)N2CCc3ccc(OC(F)(F)F)cc32)c2ccc(Cl)cc2)cc(OC23CC(C(=O)O)(C2)C3)c1] | racemic |

TABLE-continued compounds prepared as described above

| Compound | Structure | Optical rotation |
|---|---|---|
| 9A | 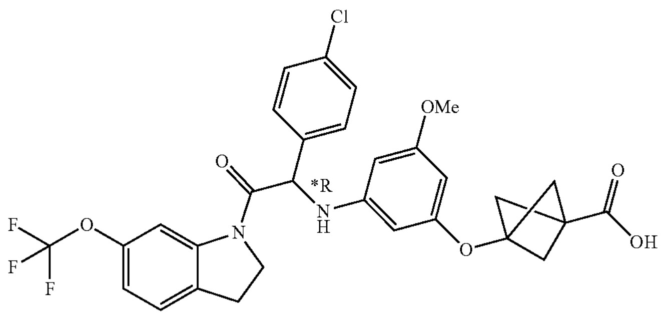 [SMILES: COc1cc(NC(C(=O)N2CCc3ccc(OC(F)(F)F)cc32)c2ccc(Cl)cc2)cc(OC23CC(C(=O)O)(C2)C3)c1] | $[\alpha]_D^{20} = -43.6°$ |
| 9B | 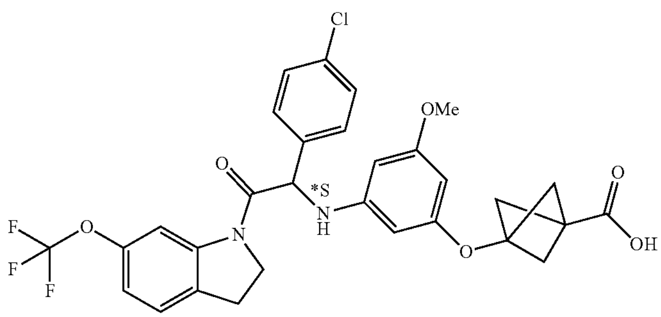 [SMILES: COc1cc(NC(C(=O)N2CCc3ccc(OC(F)(F)F)cc32)c2ccc(Cl)cc2)cc(OC23CC(C(=O)O)(C2)C3)c1] | $[\alpha]_D^{20} = +42.2°$ |
| 10 | 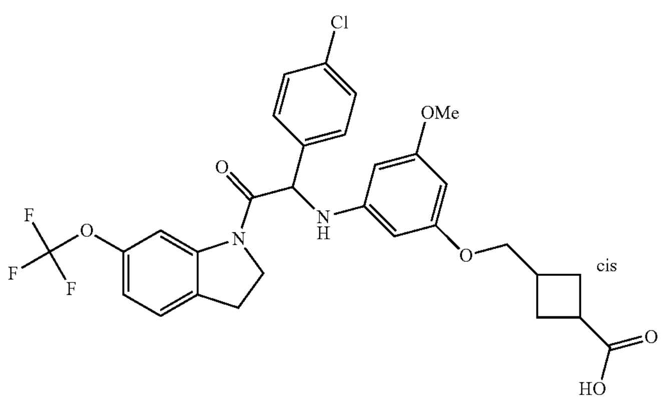 [SMILES: COc1cc(NC(C(=O)N2CCc3ccc(OC(F)(F)F)cc32)c2ccc(Cl)cc2)cc(OCC2CC(C(=O)O)C2)c1] | — |
| 10A | 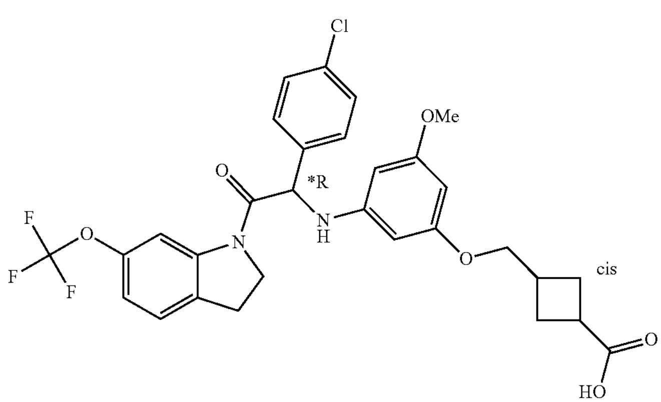 [SMILES: COc1cc(NC(C(=O)N2CCc3ccc(OC(F)(F)F)cc32)c2ccc(Cl)cc2)cc(OCC2CC(C(=O)O)C2)c1] | $[\alpha]_D^{20} = -44.0°$ |

TABLE-continued compounds prepared as described above

| Compound | Structure | Optical rotation |
|---|---|---|
| 10B | 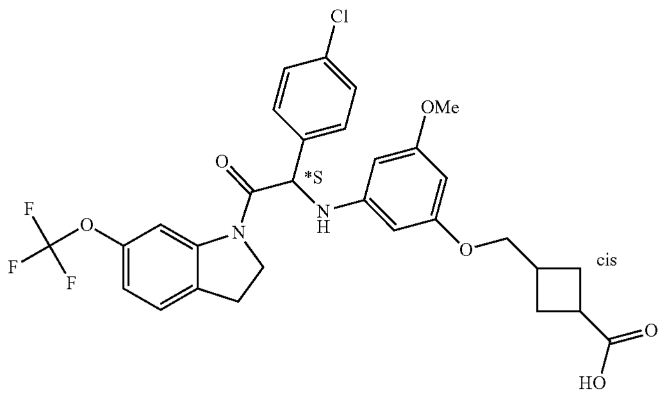 [SMILES: COc1cc(NC(C(=O)N2CCc3ccc(OC(F)(F)F)cc32)c2ccc(Cl)cc2)cc(OCC2CC(C(=O)O)C2)c1] | $[\alpha]_D^{20} = +45.5°$ |
| 11 | 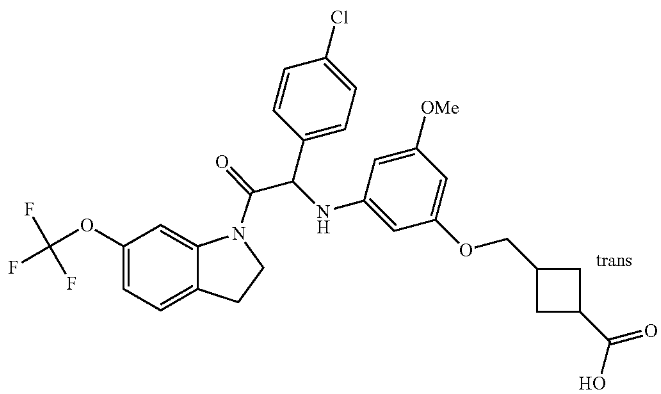 [SMILES: COc1cc(NC(C(=O)N2CCc3ccc(OC(F)(F)F)cc32)c2ccc(Cl)cc2)cc(OCC2CC(C(=O)O)C2)c1] | — |
| 11A | 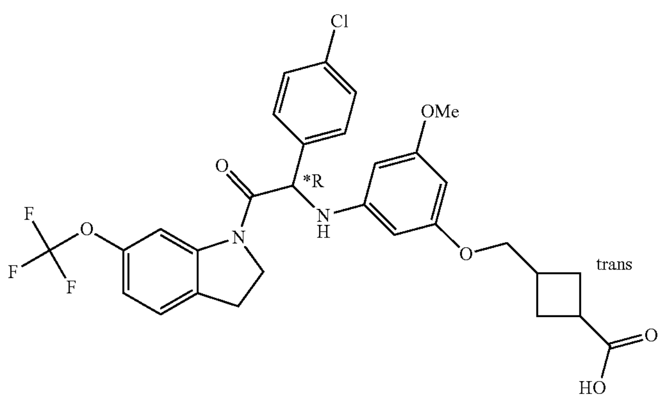 [SMILES: COc1cc(NC(C(=O)N2CCc3ccc(OC(F)(F)F)cc32)c2ccc(Cl)cc2)cc(OCC2CC(C(=O)O)C2)c1] | $[\alpha]_D^{20} = -43.3°$ |
| 11B | 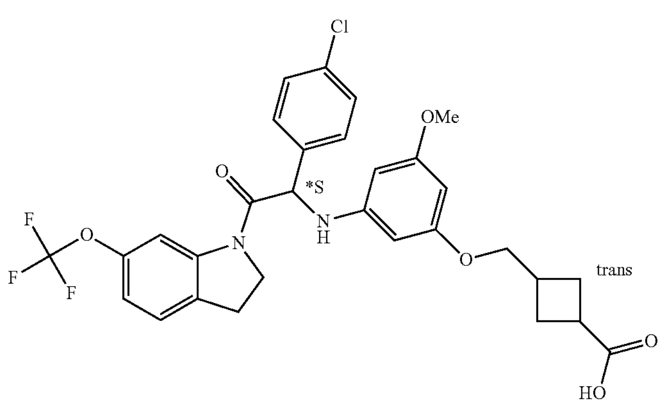 [SMILES: COc1cc(NC(C(=O)N2CCc3ccc(OC(F)(F)F)cc32)c2ccc(Cl)cc2)cc(OCC2CC(C(=O)O)C2)c1] | $[\alpha]_D^{20} = +45.5°$ |

TABLE-continued compounds prepared as described above

| Compound | Structure | Optical rotation |
|---|---|---|
| 12 | 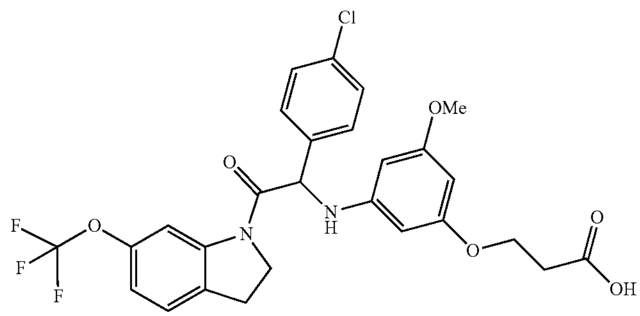 [SMILES: COc1cc(NC(C(=O)N2CCc3ccc(OC(F)(F)F)cc32)c2ccc(Cl)cc2)cc(OCCC(=O)O)c1] | racemic |
| 12A | 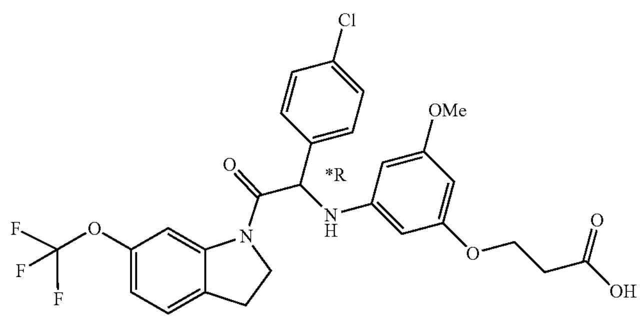 [SMILES: COc1cc(NC(C(=O)N2CCc3ccc(OC(F)(F)F)cc32)c2ccc(Cl)cc2)cc(OCCC(=O)O)c1] | $[\alpha]_D^{20} = -47.3°$ |
| 12B | 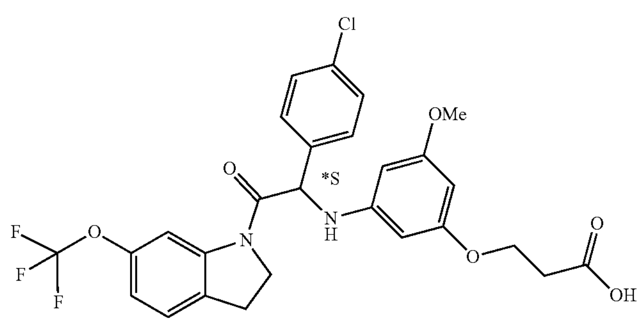 [SMILES: COc1cc(NC(C(=O)N2CCc3ccc(OC(F)(F)F)cc32)c2ccc(Cl)cc2)cc(OCCC(=O)O)c1] | $[\alpha]_D^{20} = +41.8°$ |
| 13 | 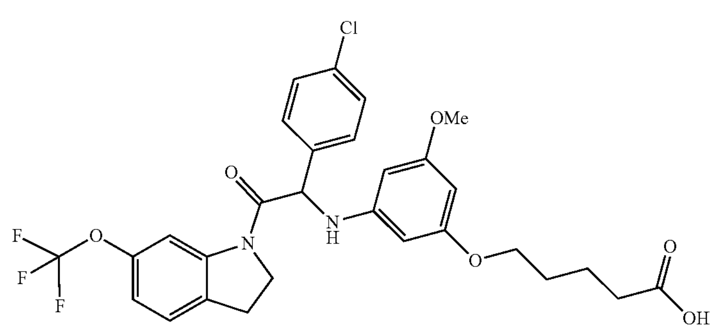 [SMILES: COc1cc(NC(C(=O)N2CCc3ccc(OC(F)(F)F)cc32)c2ccc(Cl)cc2)cc(OCCCCC(=O)O)c1] | racemic |

TABLE-continued
compounds prepared as described above
| Compound | Structure | Optical rotation |
|---|---|---|
| 13A | 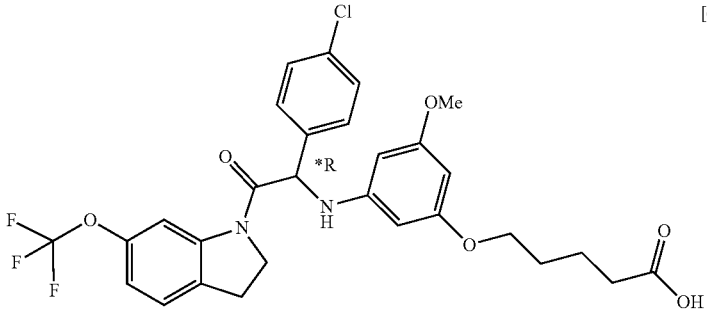 [SMILES: COc1cc(NC(C(=O)N2CCc3ccc(OC(F)(F)F)cc32)c2ccc(Cl)cc2)cc(OCCCCC(=O)O)c1] | $[\alpha]_D^{20} = -48.6°$ |
| 13B | 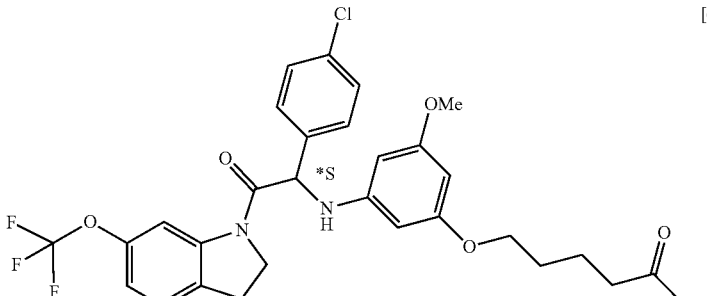 | $[\alpha]_D^{20} = +48.3°$ |
| 14 | 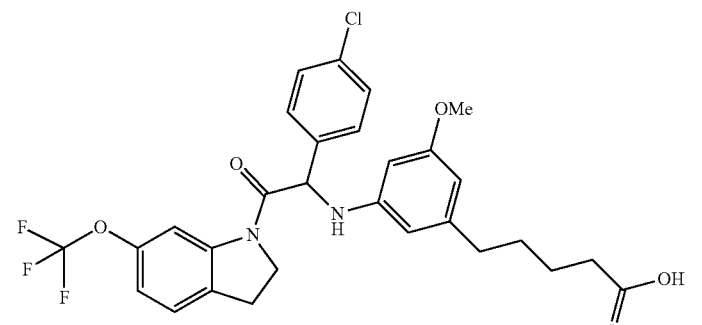 | racemic |
| 14A | 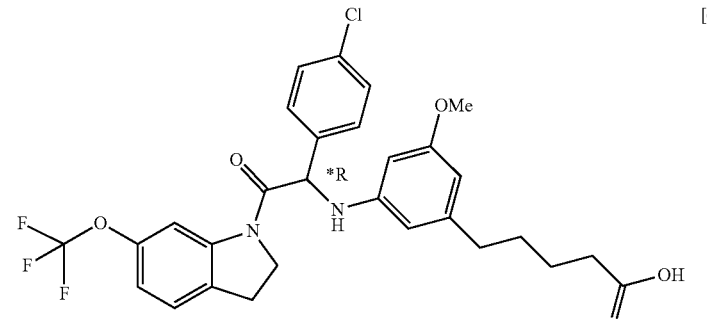 | $[\alpha]_D^{20} = +55.8°$ |

TABLE-continued compounds prepared as described above

| Compound | Structure | Optical rotation |
|---|---|---|
| 14B | 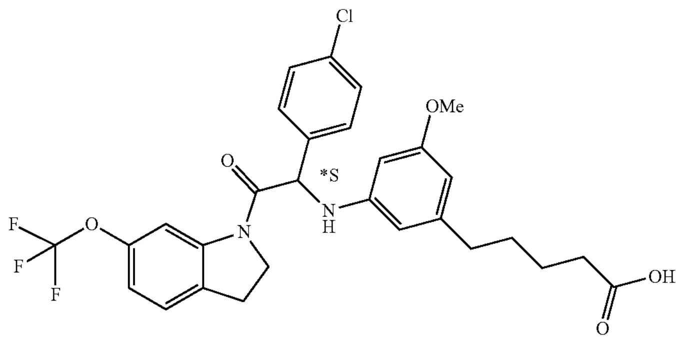 | $[\alpha]_D^{20} = -53.7°$ |
| 15 | 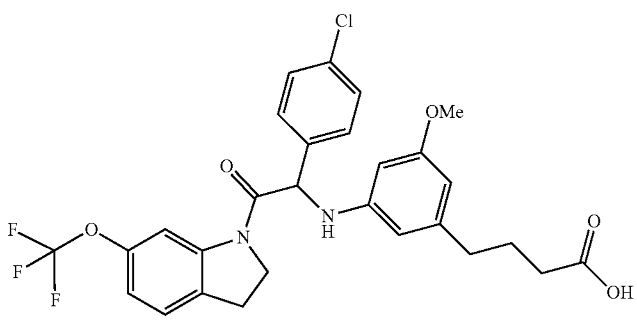 | racemic |
| 15A | 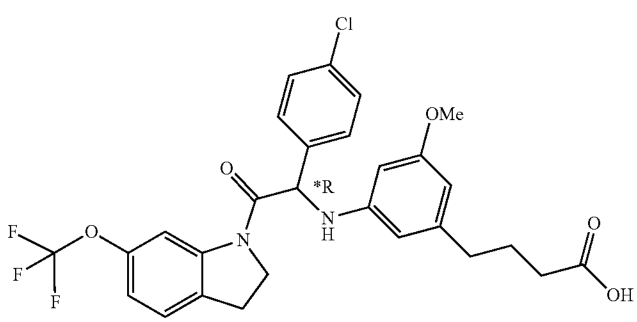 [SMILES: COc1cc(CCCC(=O)O)cc(NC(C(=O)N2CCc3ccc(OC(F)(F)F)cc32)c2ccc(Cl)cc2)c1] | $[\alpha]_D^{20} = -59.0°$ |
| 15B | 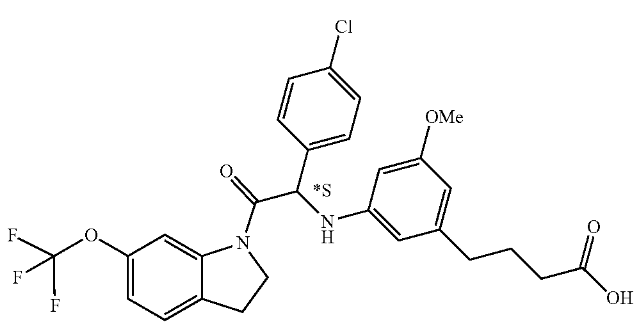 | $[\alpha]_D^{20} = +48.0°$ |

TABLE-continued compounds prepared as described above

| Compound | Structure | Optical rotation |
|---|---|---|
| 16 | 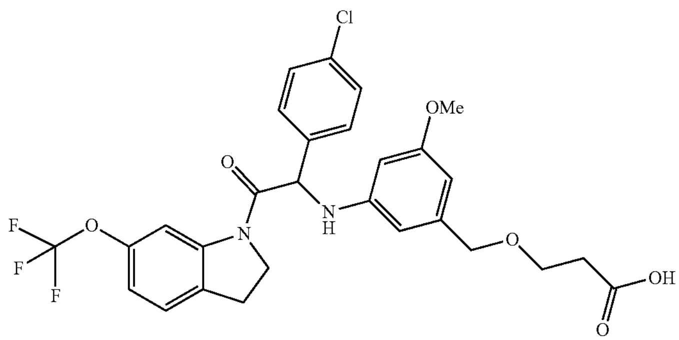 [SMILES: COc1cc(COCCC(=O)O)cc(NC(C(=O)N2CCc3ccc(OC(F)(F)F)cc32)c2ccc(Cl)cc2)c1] | racemic |
| 17 | 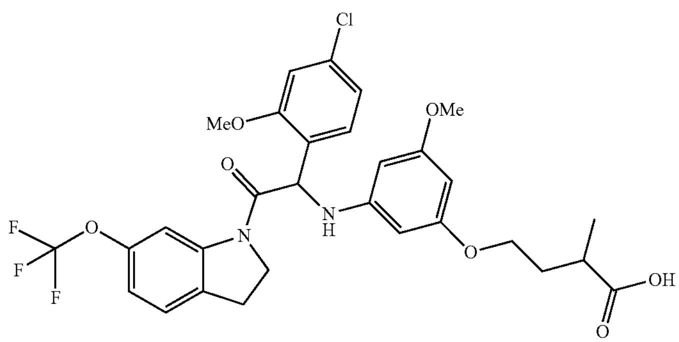 [SMILES: COc1cc(NC(C(=O)N2CCc3ccc(OC(F)(F)F)cc32)c2ccc(Cl)cc2OC)cc(OCCC(C)C(=O)O)c1] | racemic |
| 17A | 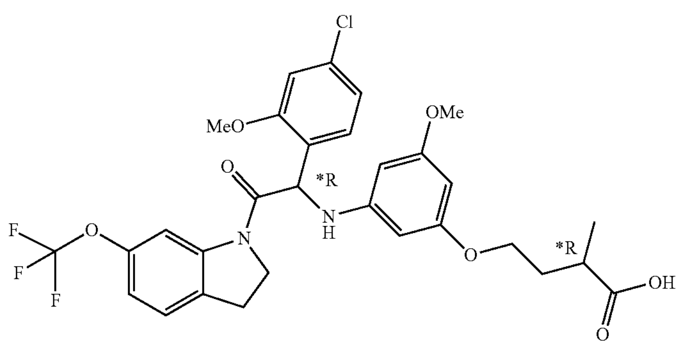 [SMILES: COc1cc(NC(C(=O)N2CCc3ccc(OC(F)(F)F)cc32)c2ccc(Cl)cc2OC)cc(OCCC(C)C(=O)O)c1] | $[\alpha]_D^{20} = -18.4°$ |
| 17B | 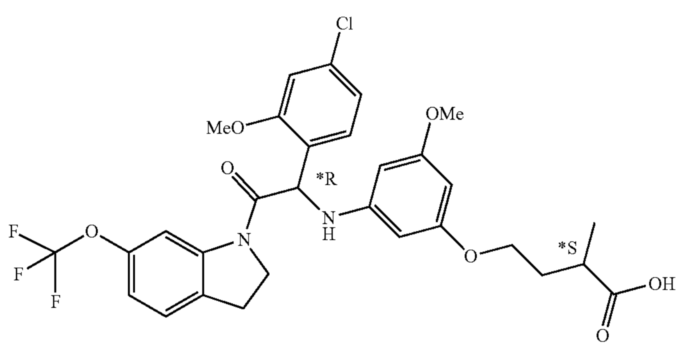 [SMILES: COc1cc(NC(C(=O)N2CCc3ccc(OC(F)(F)F)cc32)c2ccc(Cl)cc2OC)cc(OCCC(C)C(=O)O)c1] | $[\alpha]_D^{20} = -51.0°$ |

TABLE-continued
compounds prepared as described above
| Compound | Structure | Optical rotation |
|---|---|---|
| 17C | 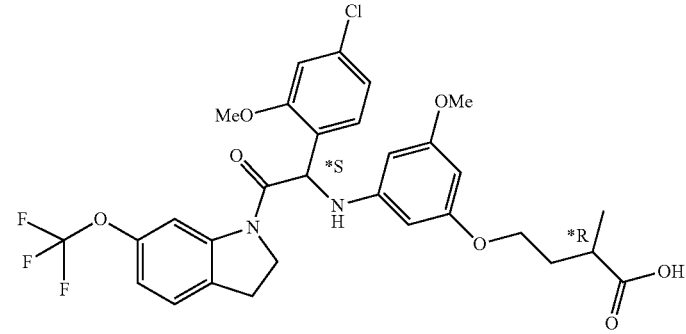 [SMILES: COc1cc(NC(C(=O)N2CCc3ccc(OC(F)(F)F)cc32)c2ccc(Cl)cc2OC)cc(OCCC(C)C(=O)O)c1] | $[\alpha]_D^{20} = +41.6°$ |
| 17D | 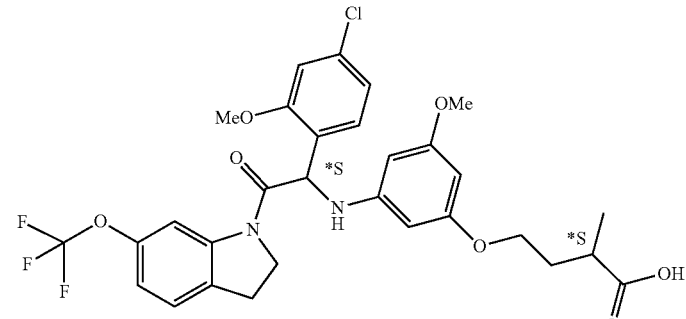 | $[\alpha]_D^{20} = +15.8°$ |
| 18 | 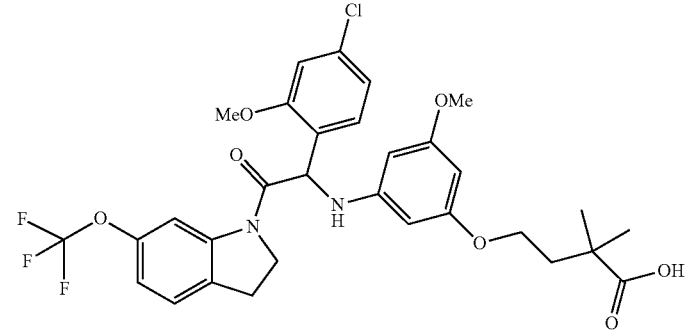 [SMILES: COc1cc(NC(C(=O)N2CCc3ccc(OC(F)(F)F)cc32)c2ccc(Cl)cc2OC)cc(OCCC(C)(C)C(=O)O)c1] | racemic |
| 18A | 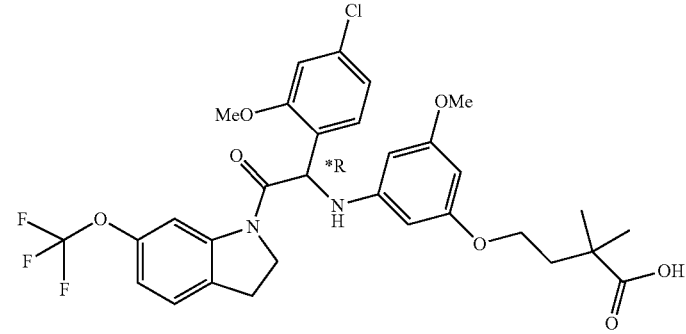 [SMILES: COc1cc(NC(C(=O)N2CCc3ccc(OC(F)(F)F)cc32)c2ccc(Cl)cc2OC)cc(OCCC(C)(C)C(=O)O)c1] | $[\alpha]_D^{20} = -30.2°$ |

TABLE-continued compounds prepared as described above

| Compound | Structure | Optical rotation |
|---|---|---|
| 18B | 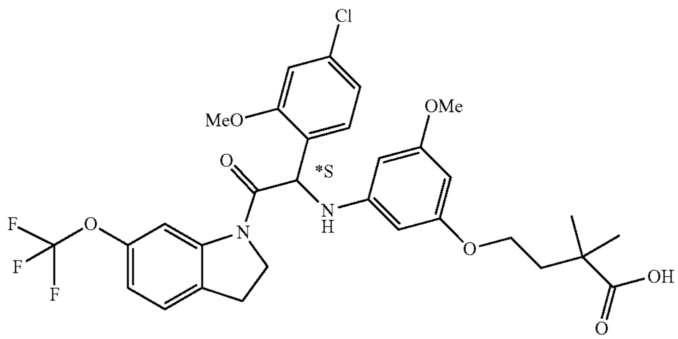 [SMILES: COc1cc(NC(C(=O)N2CCc3ccc(OC(F)(F)F)cc32)c2ccc(Cl)cc2OC)cc(OCCC(C)(C)C(=O)O)c1] | $[\alpha]_D^{20} = +28.0°$ |
| 19AA | 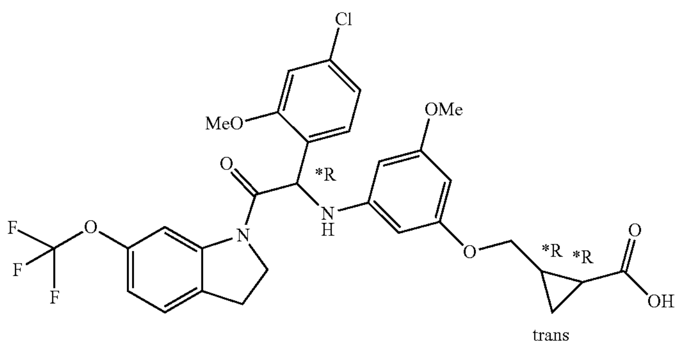 [SMILES: COc1cc(NC(C(=O)N2CCc3ccc(OC(F)(F)F)cc32)c2ccc(Cl)cc2OC)cc(OCC2CC2C(=O)O)c1] | $[\alpha]_D^{20} = -65.6°$ |
| 19AB | 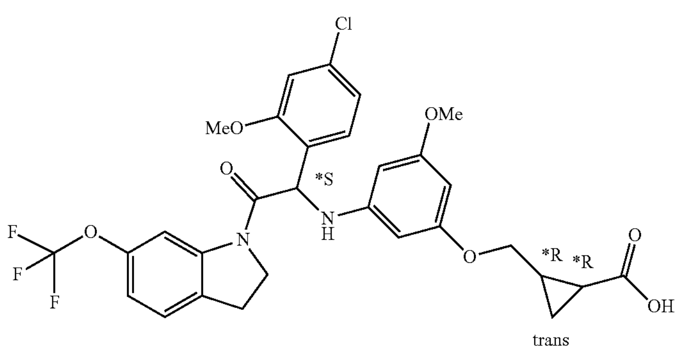 [SMILES: COc1cc(NC(C(=O)N2CCc3ccc(OC(F)(F)F)cc32)c2ccc(Cl)cc2OC)cc(OCC2CC2C(=O)O)c1] | $[\alpha]_D^{20} = +37.1°$ |
| 19BA | 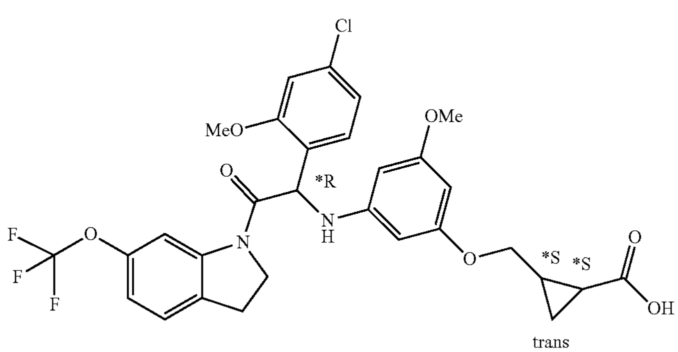 [SMILES: COc1cc(NC(C(=O)N2CCc3ccc(OC(F)(F)F)cc32)c2ccc(Cl)cc2OC)cc(OCC2CC2C(=O)O)c1] | $[\alpha]_D^{20} = -47.6°$ |

TABLE-continued compounds prepared as described above

| Compound | Structure | Optical rotation |
|---|---|---|
| 19BB | 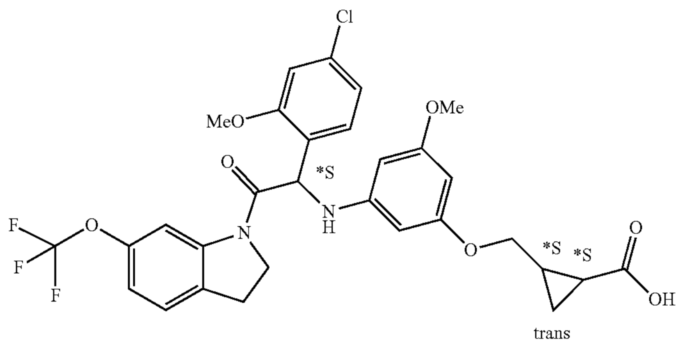 [SMILES: COc1cc(NC(C(=O)N2CCc3ccc(OC(F)(F)F)cc32)c2ccc(Cl)cc2OC)cc(OCC2CC2C(=O)O)c1] | $[\alpha]_D^{20} = +56.8°$ |
| 20A | 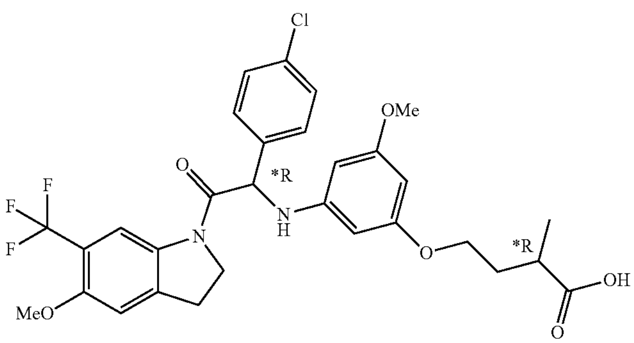 [SMILES: COc1cc(NC(C(=O)N2CCc3cc(OC)c(C(F)(F)F)cc32)c2ccc(Cl)cc2)cc(OCCC(C)C(=O)O)c1] | $[\alpha]_D^{20} = -40.9°$ |
| 20B | 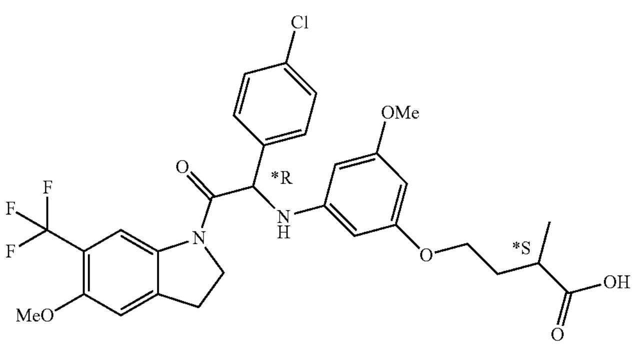 [SMILES: COc1cc(NC(C(=O)N2CCc3cc(OC)c(C(F)(F)F)cc32)c2ccc(Cl)cc2)cc(OCCC(C)C(=O)O)c1] | $[\alpha]_D^{20} = -50.0°$ |
| 20C | 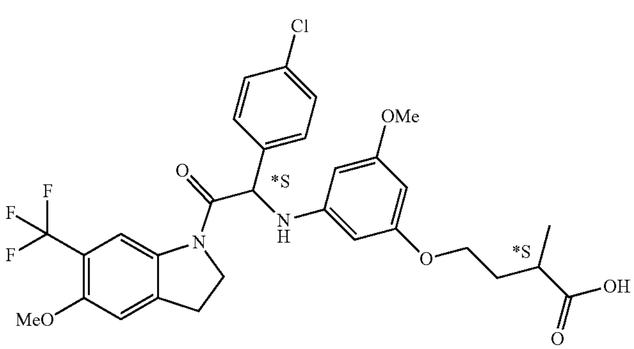 [SMILES: COc1cc(NC(C(=O)N2CCc3cc(OC)c(C(F)(F)F)cc32)c2ccc(Cl)cc2)cc(OCCC(C)C(=O)O)c1] | $[\alpha]_D^{20} = +26.0°$ |

TABLE-continued compounds prepared as described above

| Compound | Structure | Optical rotation |
|---|---|---|
| 20D | 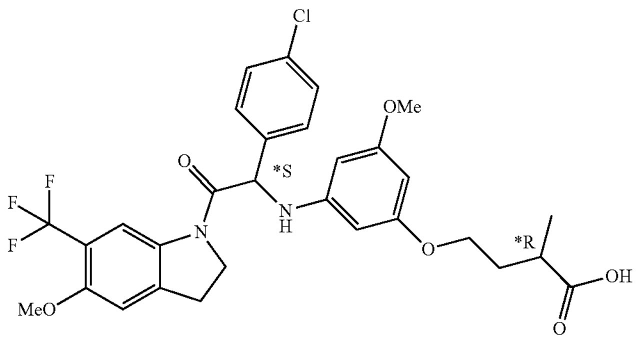 [SMILES: COc1cc(NC(C(=O)N2CCc3cc(OC)c(C(F)(F)F)cc32)c2ccc(Cl)cc2)cc(OCCC(C)C(=O)O)c1] | $[\alpha]_D^{20} = +57.4°$ |
| 21 | 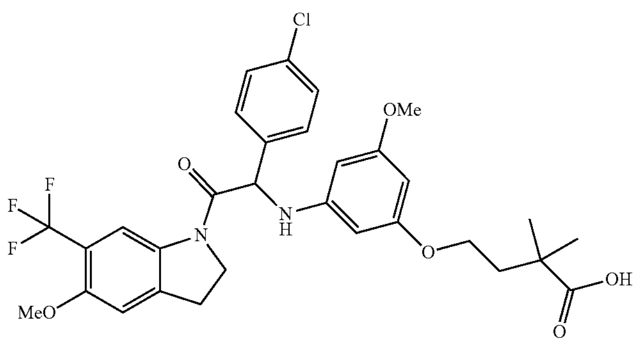 [SMILES: COc1cc(NC(C(=O)N2CCc3cc(OC)c(C(F)(F)F)cc32)c2ccc(Cl)cc2)cc(OCCC(C)(C)C(=O)O)c1] | racemic |
| 21A | 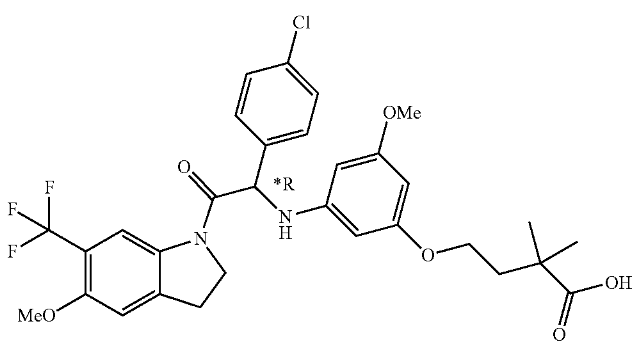 [SMILES: COc1cc(NC(C(=O)N2CCc3cc(OC)c(C(F)(F)F)cc32)c2ccc(Cl)cc2)cc(OCCC(C)(C)C(=O)O)c1] | $[\alpha]_D^{20} = -41.7°$ |
| 21B | 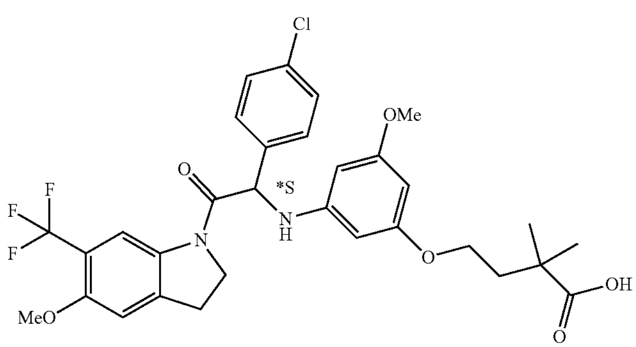 [SMILES: COc1cc(NC(C(=O)N2CCc3cc(OC)c(C(F)(F)F)cc32)c2ccc(Cl)cc2)cc(OCCC(C)(C)C(=O)O)c1] | $[\alpha]_D^{20} = +44.0°$ |

TABLE-continued
compounds prepared as described above
| Compound | Structure | Optical rotation |
|---|---|---|
| 22AA | 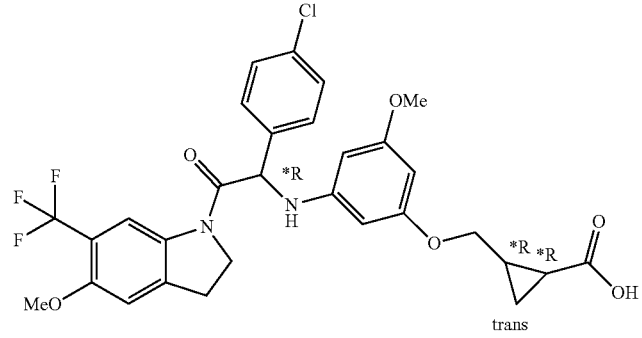 [SMILES: COc1cc(NC(C(=O)N2CCc3cc(OC)c(C(F)(F)F)cc32)c2ccc(Cl)cc2)cc(OCC2CC2C(=O)O)c1] | $[\alpha]_D^{20} = -75.0°$ |
| 22AB | 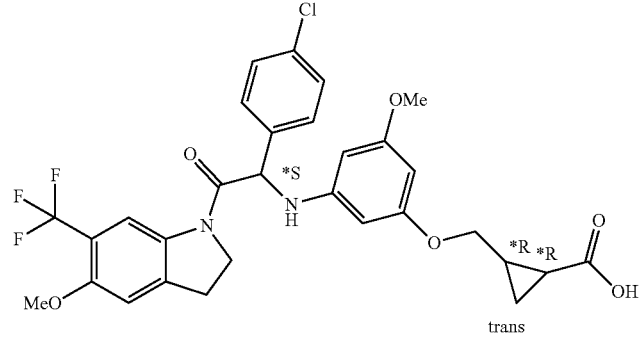 [SMILES: COc1cc(NC(C(=O)N2CCc3cc(OC)c(C(F)(F)F)cc32)c2ccc(Cl)cc2)cc(OCC2CC2C(=O)O)c1] | $[\alpha]_D^{20} = +10.0°$ |
| 22BA | 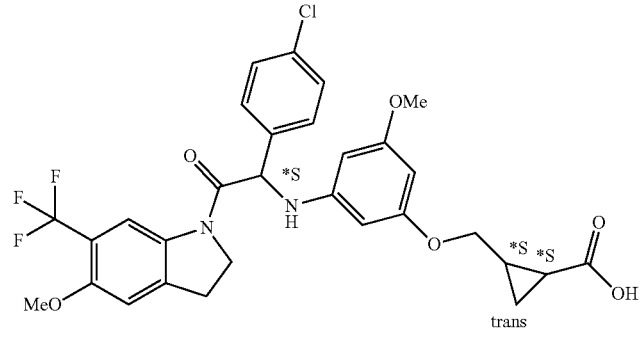 [SMILES: COc1cc(NC(C(=O)N2CCc3cc(OC)c(C(F)(F)F)cc32)c2ccc(Cl)cc2)cc(OCC2CC2C(=O)O)c1] | $[\alpha]_D^{20} = -9.3°$ |
| 22BB | 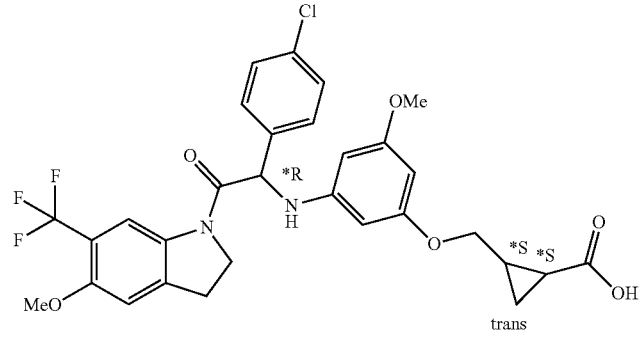 [SMILES: COc1cc(NC(C(=O)N2CCc3cc(OC)c(C(F)(F)F)cc32)c2ccc(Cl)cc2)cc(OCC2CC2C(=O)O)c1] | $[\alpha]_D^{20} = +80.0°$ |

TABLE-continued
compounds prepared as described above
| Compound | Structure | Optical rotation |
|---|---|---|
| 23 | 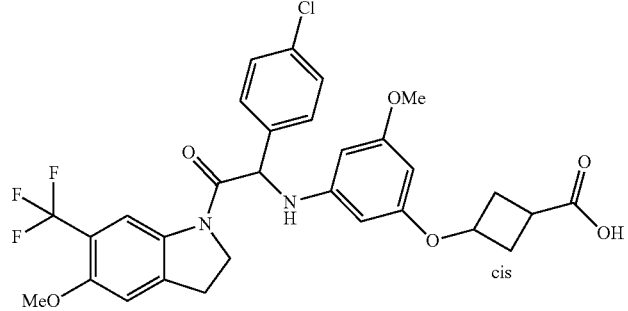 [SMILES: COc1cc(NC(C(=O)N2CCc3cc(OC)c(C(F)(F)F)cc32)c2ccc(Cl)cc2)cc(OC2CC(C(=O)O)C2)c1] | — |
| 23A | 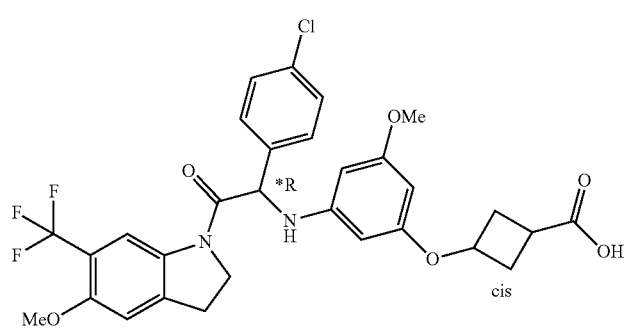 [SMILES: COc1cc(NC(C(=O)N2CCc3cc(OC)c(C(F)(F)F)cc32)c2ccc(Cl)cc2)cc(OC2CC(C(=O)O)C2)c1] | $[\alpha]_D^{20} = -38.1°$ |
| 23B | 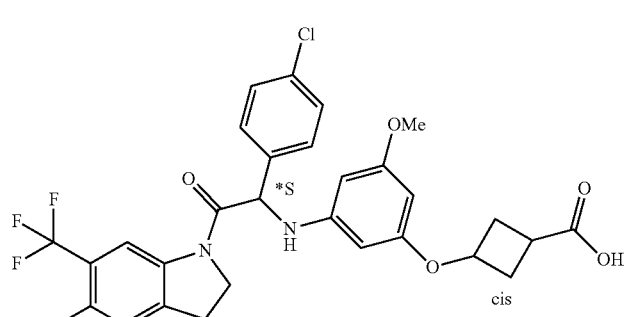 | $[\alpha]_D^{20} = +36.9°$ |
| 24 | 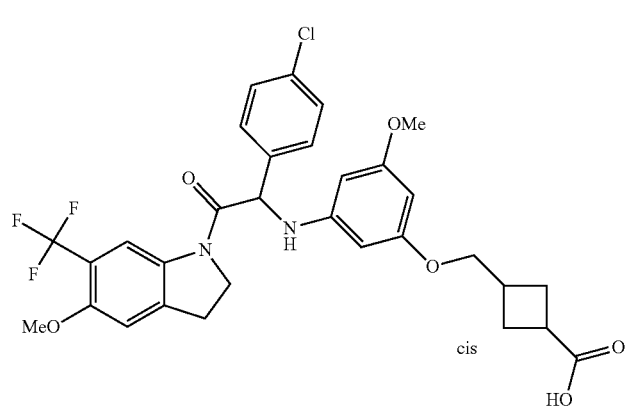 [SMILES: COc1cc(NC(C(=O)N2CCc3cc(OC)c(C(F)(F)F)cc32)c2ccc(Cl)cc2)cc(OCC2CC(C(=O)O)C2)c1] | — |

TABLE-continued compounds prepared as described above

| Compound | Structure | Optical rotation |
|---|---|---|
| 24A | (cis) | $[\alpha]_D^{20} = -41.5°$ |
| 24B | (cis) | $[\alpha]_D^{20} = +36.6°$ |
| 25 | (trans) | — |
| 25A | (trans) | $[\alpha]_D^{20} = -41.1°$ |

TABLE-continued
compounds prepared as described above
| Compound | Structure | Optical rotation |
|---|---|---|
| 25B | 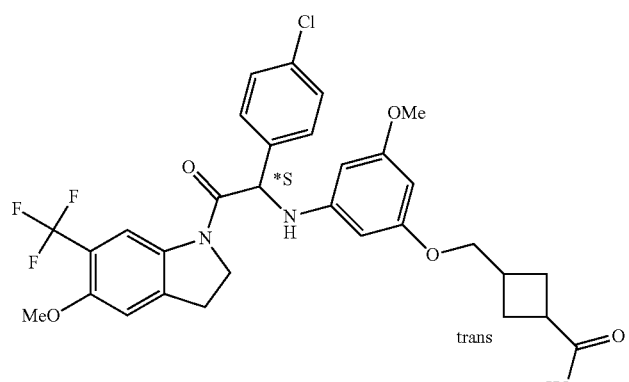 trans | $[\alpha]_D^{20} = +40.6°$ |
| 26A | 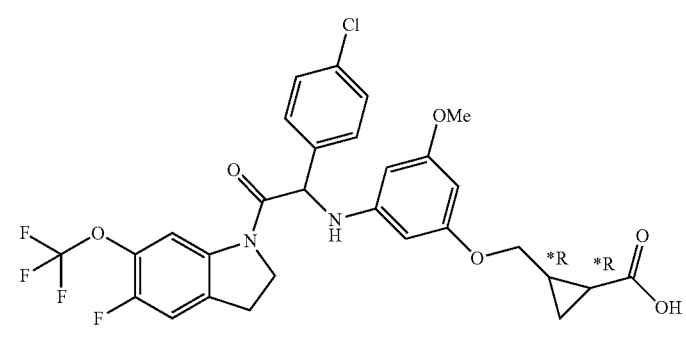 trans | — |
| 26B | 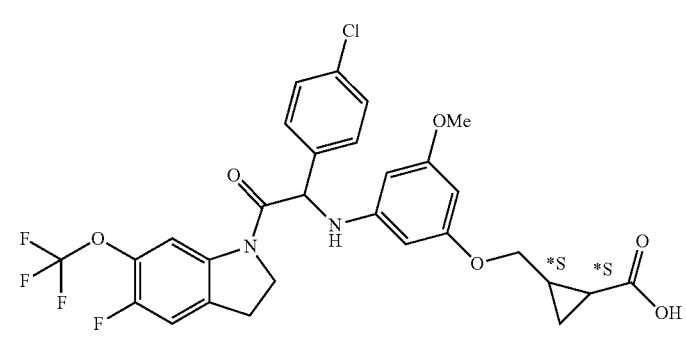 trans | — |
| 27 | 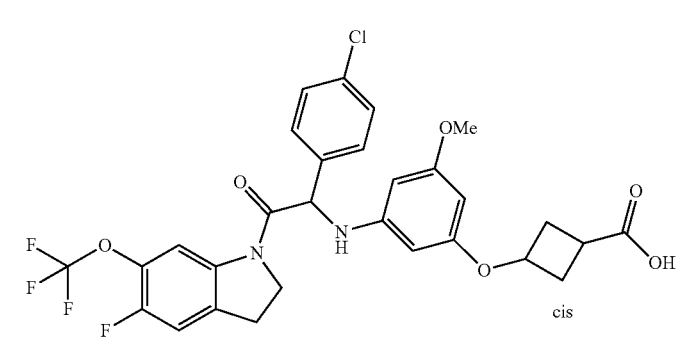 [SMILES: COc1cc(NC(C(=O)N2CCc3cc(F)c(OC(F)(F)F)cc32)c2ccc(Cl)cc2)cc(OC2CC(C(=O)O)C2)c1] cis | — |

TABLE-continued
compounds prepared as described above
| Compound | Structure | Optical rotation |
|---|---|---|
| 27A | 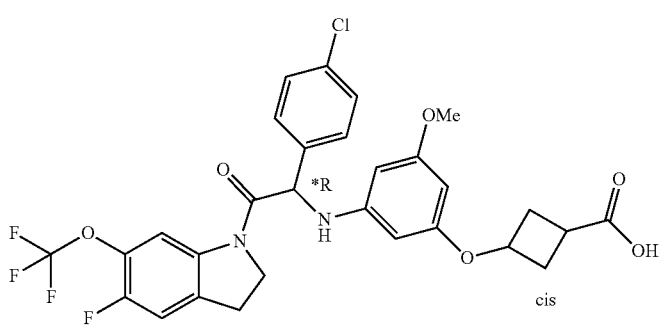 [SMILES: COc1cc(NC(C(=O)N2CCc3cc(F)c(OC(F)(F)F)cc32)c2ccc(Cl)cc2)cc(OC2CC(C(=O)O)C2)c1] cis | $[\alpha]_D^{20} = -40.5°$ |
| 27B | 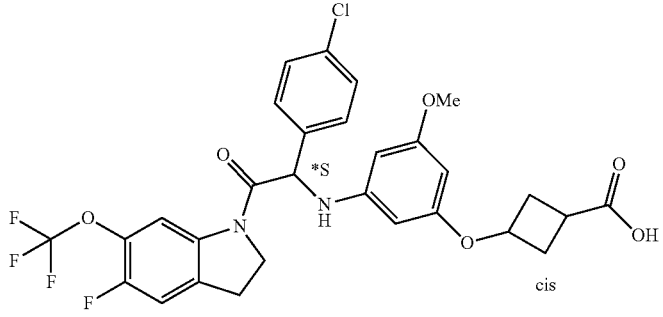 [SMILES: COc1cc(NC(C(=O)N2CCc3cc(F)c(OC(F)(F)F)cc32)c2ccc(Cl)cc2)cc(OC2CC(C(=O)O)C2)c1] cis | $[\alpha]_D^{20} = +37.5°$ |
| 28AA | 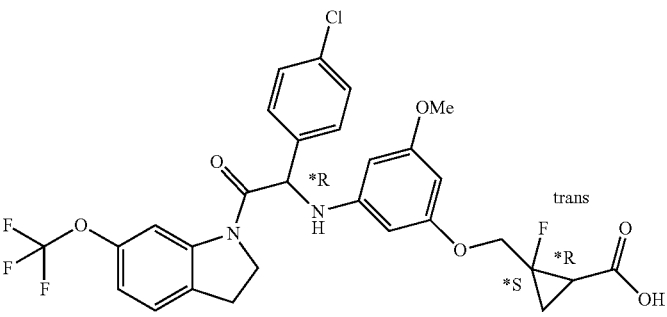 [SMILES: COc1cc(NC(C(=O)N2CCc3ccc(OC(F)(F)F)cc32)c2ccc(Cl)cc2)cc(OCC2(F)CC2C(=O)O)c1] trans | $[\alpha]_D^{20} = -43.3°$ |
| 28AB | 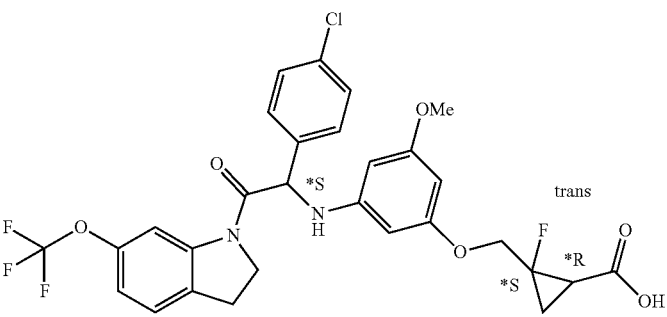 [SMILES: COc1cc(NC(C(=O)N2CCc3ccc(OC(F)(F)F)cc32)c2ccc(Cl)cc2)cc(OCC2(F)CC2C(=O)O)c1] trans | $[\alpha]_D^{20} = +52.5°$ |

TABLE-continued compounds prepared as described above

| Compound | Structure | Optical rotation |
|---|---|---|
| 28BA | 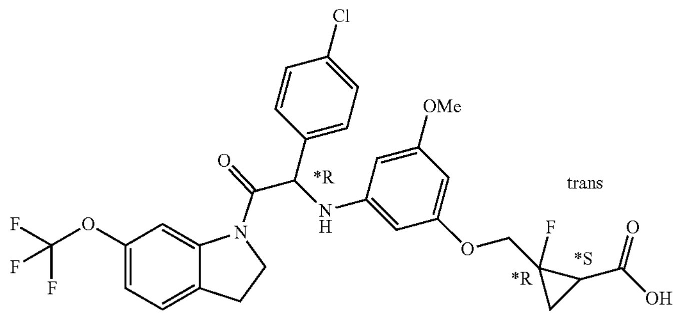 [SMILES: COc1cc(NC(C(=O)N2CCc3ccc(OC(F)(F)F)cc32)c2ccc(Cl)cc2)cc(OCC2(F)CC2C(=O)O)c1] | $[\alpha]_D^{20} = -57.1°$ |
| 28BB | 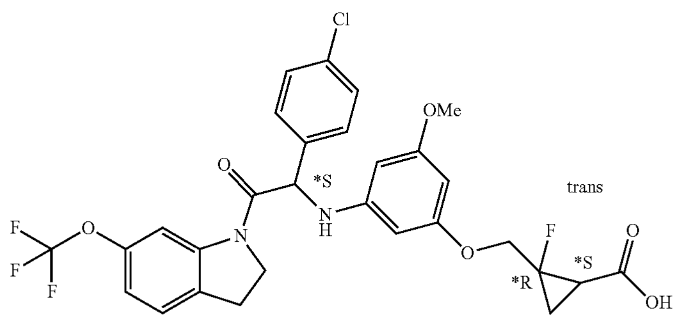 [SMILES: COc1cc(NC(C(=O)N2CCc3ccc(OC(F)(F)F)cc32)c2ccc(Cl)cc2)cc(OCC2(F)CC2C(=O)O)c1] | $[\alpha]_D^{20} = +38.1°$ |
| 29AA | 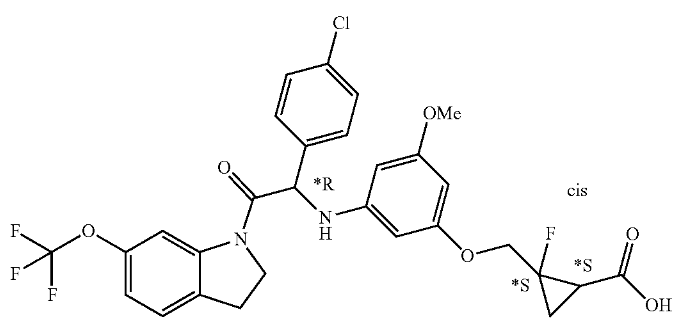 [SMILES: COc1cc(NC(C(=O)N2CCc3ccc(OC(F)(F)F)cc32)c2ccc(Cl)cc2)cc(OCC2(F)CC2C(=O)O)c1] | $[\alpha]_D^{20} = -15.7°$ |
| 29AB | 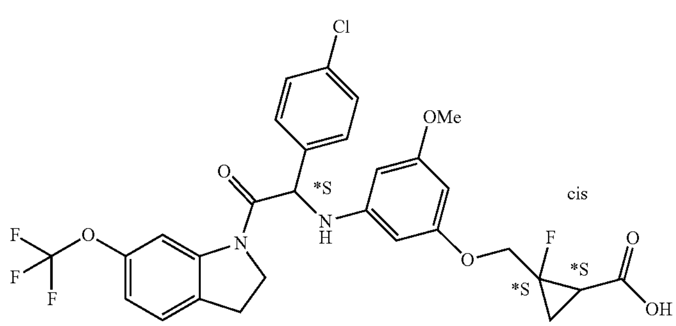 [SMILES: COc1cc(NC(C(=O)N2CCc3ccc(OC(F)(F)F)cc32)c2ccc(Cl)cc2)cc(OCC2(F)CC2C(=O)O)c1] | $[\alpha]_D^{20} = +77.4°$ |

TABLE-continued
compounds prepared as described above
| Compound | Structure | Optical rotation |
|---|---|---|
| 29BA | 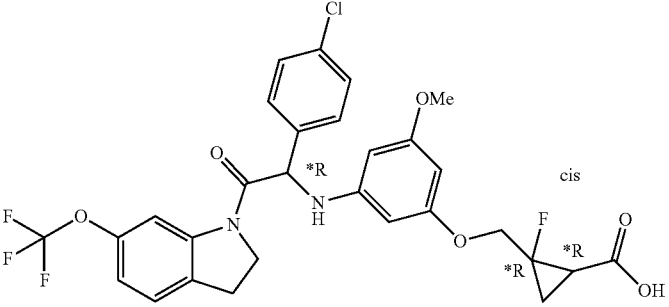 [SMILES: COc1cc(NC(C(=O)N2CCc3ccc(OC(F)(F)F)cc32)c2ccc(Cl)cc2)cc(OCC2(F)CC2C(=O)O)c1] | $[\alpha]_D^{20} = -74.2°$ |
| 29BB | 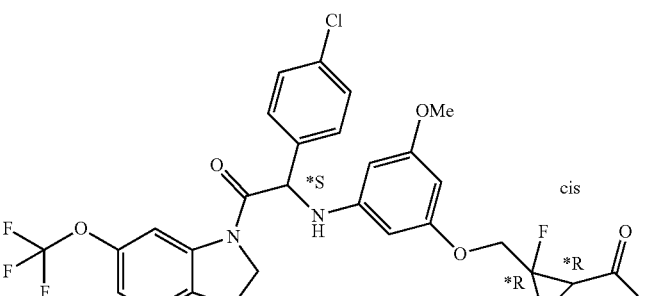 | $[\alpha]_D^{20} = +12.0°$ |
| 30A | 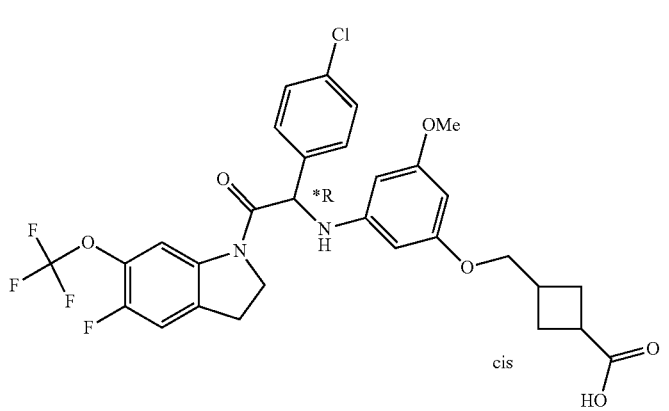 [SMILES: COc1cc(NC(C(=O)N2CCc3cc(F)c(OC(F)(F)F)cc32)c2ccc(Cl)cc2)cc(OCC2CC(C(=O)O)C2)c1] | $[\alpha]_D^{20} = +42.6°$ |
| 30B | 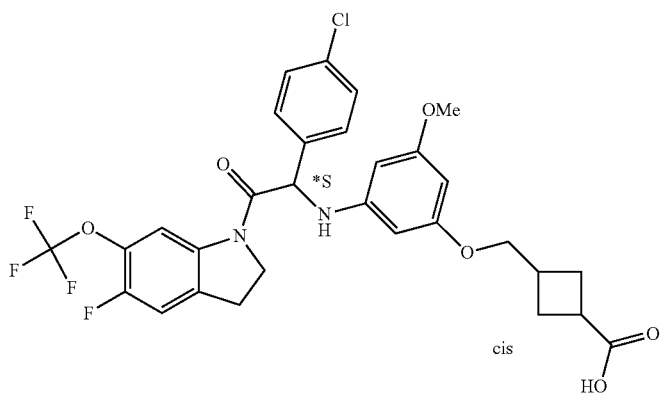 [SMILES: COc1cc(NC(C(=O)N2CCc3cc(F)c(OC(F)(F)F)cc32)c2ccc(Cl)cc2)cc(OCC2CC(C(=O)O)C2)c1] | $[\alpha]_D^{20} = -44.2°$ |

TABLE-continued
compounds prepared as described above
| Compound | Structure | Optical rotation |
|---|---|---|
| 31A | 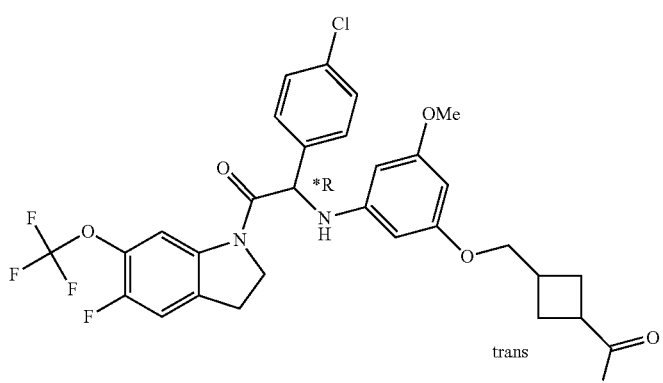 | $[\alpha]_D^{20} = +43.1°$ |
| 31B | 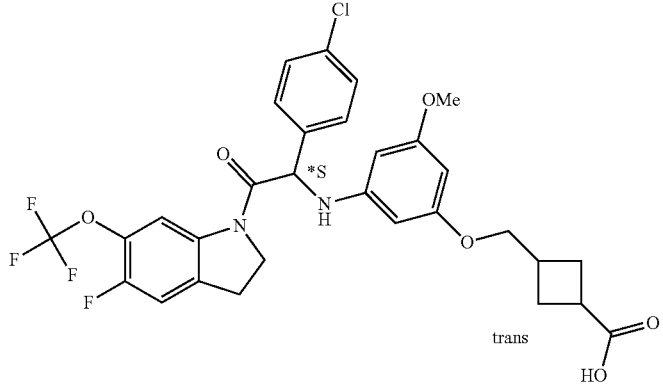 [SMILES: COc1cc(NC(C(=O)N2CCc3cc(F)c(OC(F)(F)F)cc32)c2ccc(Cl)cc2)cc(OCC2CC(C(=O)O)C2)c1] | $[\alpha]_D^{20} = -43.4°$ |
| 32 | 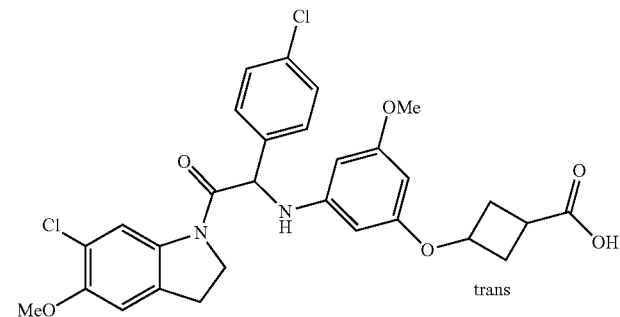 [SMILES: COc1cc(NC(C(=O)N2CCc3cc(OC)c(Cl)cc32)c2ccc(Cl)cc2)cc(OC2CC(C(=O)O)C2)c1] | — |
| 32A | 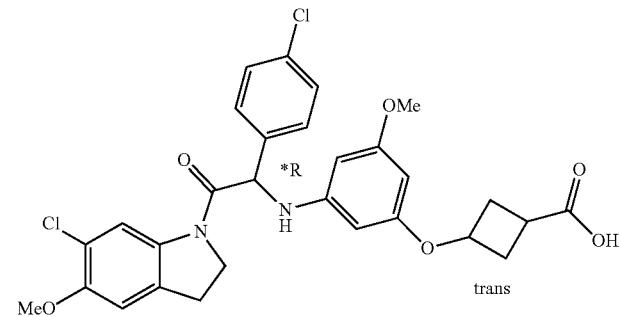 [SMILES: COc1cc(NC(C(=O)N2CCc3cc(OC)c(Cl)cc32)c2ccc(Cl)cc2)cc(OC2CC(C(=O)O)C2)c1] | $[\alpha]_D^{20} = -55.4°$ |

TABLE-continued
compounds prepared as described above
| Compound | Structure | Optical rotation |
|---|---|---|
| 32B | 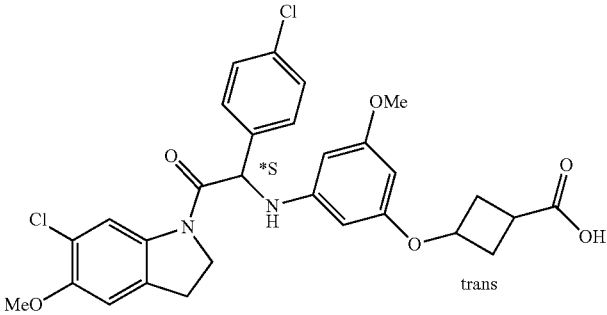 [SMILES: COc1cc(NC(C(=O)N2CCc3cc(OC)c(Cl)cc32)c2ccc(Cl)cc2)cc(OC2CC(C(=O)O)C2)c1] trans | $[\alpha]_D^{20} = +53.4°$ |
| 33A | 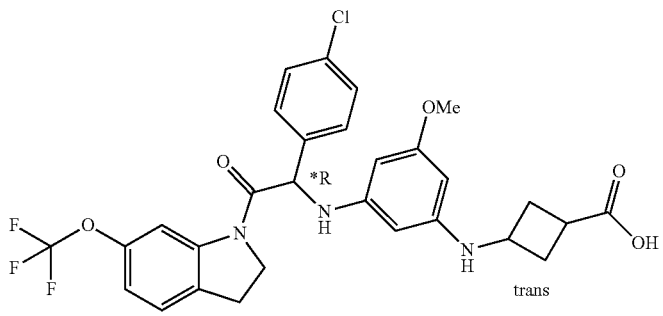 [SMILES: COc1cc(NC2CC(C(=O)O)C2)cc(NC(C(=O)N2CCc3ccc(OC(F)(F)F)cc32)c2ccc(Cl)cc2)c1] trans | $[\alpha]_D^{20} = -26.2°$ |
| 33B | 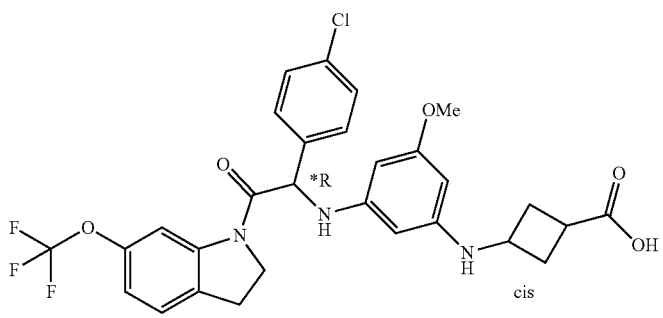 [SMILES: COc1cc(NC2CC(C(=O)O)C2)cc(NC(C(=O)N2CCc3ccc(OC(F)(F)F)cc32)c2ccc(Cl)cc2)c1] cis | $[\alpha]_D^{20} = -27.9°$ |
| 33C | 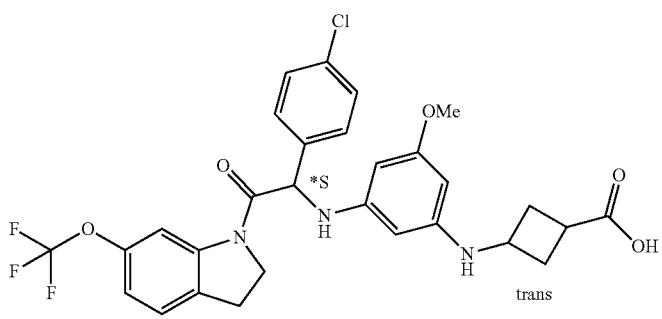 [SMILES: COc1cc(NC2CC(C(=O)O)C2)cc(NC(C(=O)N2CCc3ccc(OC(F)(F)F)cc32)c2ccc(Cl)cc2)c1] trans | $[\alpha]_D^{20} = +26.7°$ |

TABLE-continued compounds prepared as described above

| Compound | Structure | Optical rotation |
|---|---|---|
| 33D | (structure: 4-chlorophenyl, 6-trifluoromethoxy indoline attached via C(=O)-CH(*S)-NH to 3-methoxy-5-(cis-3-carboxycyclobutylamino)phenyl) | $[\alpha]_D^{20} = +23.4°$ |

Antiviral Activity of the Compounds of the Invention

DENV-2 Antiviral Assay

The antiviral activity of all the compounds of the invention was tested against the DENV-2 16681 strain which was labeled with enhanced green fluorescent protein (eGPF). The culture medium consists of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 25 µL was added to 384-well plates (2500 cells/well), which already contain the antiviral compounds. Typically, these plates contain a 5-fold serial dilution of 9 dilution steps of the test compound at 200 times the final concentration in 100% DMSO (200 nL). In addition, each compound concentration is tested in quadruplicate (final concentration range: 25 µM-0.000064 µM or 2.5 µM-0.0000064 µM for the most active compounds). Finally, each plate contains wells which are assigned as virus controls (containing cells and virus in the absence of compound), cell controls (containing cells in the absence of virus and compound) and medium controls (containing medium in the absence of cells, virus and compounds). To the wells assigned as medium control, 25 µL of culture medium was added instead of Vero cells. Once the cells are added to the plates, the plates were incubated for 30 minutes at room temperature to allow the cells to distribute evenly within the wells. Next, the plates were incubated in a fully humidified incubator (37° C., 5% $CO_2$) until the next day. Then, DENV-2 strain 16681, labeled with eGFP, was added at a multiplicity of infection (MOI) of 0.5. Therefore, 15 µL of virus suspension was added to all the wells containing test compound and to the wells assigned as virus control. In parallel, 15 µL of culture medium was added to the medium and cell controls. Next, the plates were incubated for 3 days in a fully humidified incubator (37° C., 5% $CO_2$). At the day of the read out, the eGFP fluorescence was measured using an automated fluorescence microscope at 488 nm (blue laser). Using an in-house LIMS system, inhibition dose response curves for each compound were calculated and the half maximal effective concentration ($EC_{50}$) was determined. Therefore, the percent inhibition (I) for every test concentration is calculated using the following formula: $I=100*(S_T-S_{CC})/(S_{VC}-S_{CC})$; $S_T$, $S_{CC}$ and $S_{VC}$ are the amount of eGFP signal in the test compound, cell control and virus control wells, respectively. The $EC_{50}$ represents the concentration of a compound at which the virus replication is inhibited with 50%, as measured by a 50% reduction of the eGFP fluorescent intensity compared to the virus control. The $EC_{50}$ is calculated using linear interpolation (Table 1).

In parallel, the toxicity of the compounds was assessed on the same plates. Once the read-out for the eGFP signal was done, 40 µL of ATPlite, a cell viability stain, was added to all wells of the 384-well plates. ATP is present in all metabolically active cells and the concentration declines very rapidly when the cells undergo necrosis or apoptosis. The ATPLite assay system is based on the production of light caused by the reaction of ATP with added luciferase and D-luciferin. The plates were incubated for 10 minutes at room temperature. Next, the plates were measured on a ViewLux. The half maximal cytotoxic concentration ($CC_{50}$) was also determined, defined as the concentration required to reduce the luminescent signal by 50% compared to that of the cell control wells. Finally, the selectivity index (SI) was determined for the compounds, which was calculated as followed: $SI=CC_{50}/EC_{50}$.

TABLE 1

$EC_{50}$, $CC_{50}$, and SI for the compounds of the invention in the DENV-2 antiviral assay

| compound# | $EC_{50}$ (µM) | N | $CC_{50}$ (µM) | N | SI | N |
|---|---|---|---|---|---|---|
| 1 | 0.00050 | 3 | 11 | 3 | 24400 | 3 |
| 1A | 0.018 | 3 | 9.6 | 3 | 523 | 3 |
| 1B | 0.018 | 4 | 10 | 4 | 579 | 4 |
| 1C | 0.000094 | 3 | 12 | 3 | 131193 | 3 |
| 1D | 0.00023 | 3 | 12 | 3 | 57700 | 3 |
| 2 | 0.00062 | 3 | 12 | 3 | 19200 | 3 |
| 2A | 0.00038 | 3 | 13 | 3 | 34500 | 3 |
| 2B | 0.019 | 3 | 11 | 4 | 565 | 3 |
| 3 | 0.00050 | 3 | 10 | 3 | 17700 | 3 |
| 4 | 0.00014 | 3 | 10 | 3 | 73900 | 3 |
| 4A | 0.0029 | 3 | 9.0 | 3 | 3090 | 3 |
| 4B | 0.011 | 3 | 10 | 3 | 935 | 3 |
| 4C | 0.00011 | 4 | 13 | 4 | 121878 | 4 |
| 4D | 0.00017 | 3 | 13 | 3 | 81200 | 3 |
| 5 | 0.00092 | 3 | 9.7 | 3 | 11300 | 3 |
| 5A | 0.00051 | 3 | 12 | 3 | 26300 | 3 |
| 5B | 0.011 | 3 | 10 | 3 | 921 | 3 |
| 6AA | 0.00074 | 3 | 8.3 | 3 | 8870 | 3 |
| 6AB | 0.000016 | 6 | 12 | 7 | >199223 | 6 |
| 6BA | 0.012 | 3 | 8.7 | 3 | 703 | 3 |
| 6BB | 0.00018 | 3 | 12 | 3 | 83800 | 3 |
| 7 | 0.00049 | 3 | 12 | 3 | 14600 | 3 |
| 7A | 0.0091 | 3 | 10 | 3 | 1130 | 3 |
| 7B | 0.00012 | 3 | 13 | 3 | 121027 | 3 |
| 8 | 0.000048 | 5 | 13 | 5 | >126733 | 5 |

TABLE 1-continued

EC$_{50}$, CC$_{50}$, and SI for the compounds of the invention in the DENV-2 antiviral assay

| compound# | EC$_{50}$ (μM) | N | CC$_{50}$ (μM) | N | SI | N |
|---|---|---|---|---|---|---|
| 8A | 0.00086 | 3 | 12 | 3 | 11600 | 3 |
| 8B | 0.000023 | 10 | 14 | 10 | >102836 | 10 |
| 9 | 0.00070 | 3 | 9.8 | 3 | 14700 | 3 |
| 9A | 0.090 | 3 | 11 | 3 | 125 | 3 |
| 9B | 0.00039 | 3 | 12 | 4 | 32500 | 3 |
| 10 | 0.00027 | 3 | 12 | 3 | 44900 | 3 |
| 10A | 0.0027 | 3 | 10 | 3 | 3790 | 3 |
| 10B | 0.00011 | 3 | 11 | 3 | 109987 | 3 |
| 11 | 0.00013 | 4 | 12 | 4 | 97100 | 4 |
| 11A | 0.0038 | 3 | 10 | 3 | 2710 | 3 |
| 11B | 0.00011 | 4 | 11 | 4 | 118692 | 4 |
| 12 | 0.0011 | 3 | 11 | 3 | 9440 | 3 |
| 12A | 0.038 | 3 | 10 | 3 | 267 | 3 |
| 12B | 0.00069 | 3 | 14 | 3 | 21500 | 3 |
| 13 | 0.00025 | 3 | 12 | 4 | 38100 | 3 |
| 13A | 0.0014 | 6 | 9.1 | 7 | 5720 | 6 |
| 13B | 0.00013 | 4 | 12 | 4 | 88200 | 4 |
| 14 | 0.00023 | 3 | 9.6 | 3 | 50200 | 3 |
| 14A | 0.00011 | 3 | 16 | 3 | 151558 | 3 |
| 14B | 0.060 | 3 | 9.3 | 3 | 156 | 3 |
| 15 | 0.00042 | 3 | 8.3 | 3 | 25500 | 3 |
| 15A | 0.049 | 3 | 8.4 | 3 | 171 | 3 |
| 15B | 0.00045 | 3 | 12 | 5 | 24900 | 3 |
| 16 | 0.00033 | 4 | 16 | 5 | 56100 | 4 |
| 17 | 0.00018 | 3 | 13 | 3 | 100043 | 3 |
| 17A | 0.076 | 3 | 11 | 3 | 147 | 3 |
| 17B | 0.18 | 3 | 11 | 3 | 59 | 3 |
| 17C | 0.00023 | 3 | 12 | 3 | 39300 | 3 |
| 17D | 0.00012 | 4 | 14 | 4 | >9720 | 4 |
| 18 | 0.00049 | 3 | 11 | 3 | 26100 | 3 |
| 18A | 0.0099 | 3 | 12 | 4 | 1160 | 3 |
| 18B | 0.00028 | 3 | 12 | 3 | 62700 | 3 |
| 19AA | 0.010 | 3 | 11 | 4 | 1030 | 3 |
| 19AB | 0.000012 | 8 | 12 | 9 | >390600 | 8 |
| 19BA | 0.016 | 3 | 11 | 3 | 707 | 3 |
| 19BB | 0.000038 | 5 | 8.8 | 5 | >148612 | 5 |
| 20A | 0.44 | 3 | 12 | 3 | 27 | 3 |
| 20B | 0.18 | 3 | 12 | 3 | 69 | 3 |
| 20C | 0.00017 | 3 | 12 | 3 | 59500 | 3 |
| 20D | 0.00023 | 3 | 13 | 3 | 53400 | 3 |
| 21 | 0.0011 | 3 | 15 | 3 | 11000 | 3 |
| 21A | 0.016 | 3 | 11 | 3 | 687 | 3 |
| 21B | 0.00032 | 3 | 12 | 3 | 45200 | 3 |
| 22AA | 0.016 | 4 | 13 | 4 | 798 | 4 |
| 22AB | 0.000034 | 6 | 12 | 7 | >196427 | 6 |
| 22BA | 0.015 | 3 | 12 | 3 | 786 | 3 |
| 22BB | 0.00046 | 3 | 14 | 3 | 27600 | 3 |
| 23 | 0.000093 | 4 | 12 | 4 | 116424 | 4 |
| 23A | 0.034 | 3 | 11 | 3 | 321 | 3 |
| 23B | 0.000062 | 7 | 12 | 8 | >88755 | 7 |
| 24 | 0.00064 | 4 | 12 | 4 | 18300 | 4 |
| 24A | 0.024 | 3 | 11 | 3 | 469 | 3 |
| 24B | 0.00034 | 3 | 12 | 3 | 43100 | 3 |
| 25 | 0.00045 | 4 | 12 | 4 | 26800 | 4 |
| 25A | 0.0071 | 3 | 12 | 3 | 1640 | 3 |
| 25B | 0.00028 | 3 | 13 | 3 | 52900 | 3 |
| 26A | 0.00010 | 4 | 14 | 4 | >12200 | 4 |
| 26B | 0.00094 | 4 | 12 | 4 | 10600 | 4 |
| 27 | 0.000067 | 4 | 13 | 4 | 149640 | 4 |
| 27A | 0.00041 | 3 | 11 | 3 | 14300 | 3 |
| 27B | 0.000022 | 6 | 13 | 7 | >205482 | 6 |
| 28AA | 0.33 | 3 | 11 | 3 | 34 | 3 |
| 28AB | 0.00068 | 3 | 13 | 3 | 19000 | 3 |
| 28BA | 0.017 | 3 | 10.0 | 3 | 574 | 3 |
| 28BB | 0.00020 | 3 | 12 | 3 | 70600 | 3 |
| 29AA | 0.061 | 3 | 9.2 | 3 | 151 | 3 |
| 29AB | 0.00053 | 3 | 12 | 3 | 22300 | 3 |
| 29BA | 0.0034 | 3 | 9.8 | 3 | 2890 | 3 |
| 29BB | 0.000069 | 3 | 12 | 4 | 124722 | 3 |
| 30A | 0.00024 | 3 | 13 | 4 | 47400 | 3 |
| 30B | 0.0059 | 3 | 11 | 3 | 1800 | 3 |
| 31A | 0.00020 | 3 | 12 | 3 | 70300 | 3 |
| 31B | 0.0026 | 3 | 12 | 3 | 4400 | 3 |
| 32 | 0.00013 | 3 | 15 | 3 | 130935 | 3 |
| 32A | 0.063 | 3 | 13 | 3 | 205 | 3 |
| 32B | 0.000081 | 5 | 14 | 5 | >230623 | 5 |
| 33A | 0.013 | 3 | 17 | 4 | 1110 | 3 |
| 33B | 0.0079 | 3 | 14 | 3 | 1760 | 3 |
| 33C | 0.0032 | 3 | 19 | 3 | 5930 | 3 |
| 33D | 0.00052 | 3 | 18 | 3 | 39000 | 3 |

N = the number of independent experiments in which the compounds were tested.

Tetravalent Reverse Transcriptase Quantitative-PCR (RT-qPCR) Assay

The antiviral activity of the compounds of the invention was tested against DENV-1 strain TC974#666 (NCPV), DENV-2 strain 16681, DENV-3 strain H87 (NCPV) and DENV-4 strain H241 (NCPV) in a RT-qPCR assay. Therefore, Vero cells were infected with either DENV-1, or -2, or -3, or -4 in the presence or absence of test compounds. At day 3 post-infection, the cells were lysed and cell lysates were used to prepare cDNA of both a viral target (the 3'UTR of DENV; Table 2) and a cellular reference gene (β-actin, Table 2). Subsequently, a duplex real time PCR was performed on a Lightcycler480 instrument. The generated Cp value is inversely proportional to the amount of RNA expression of these targets. Inhibition of DENV replication by a test compound results in a shift of Cp's for the 3'UTR gene. On the other hand, if a test compound is toxic to the cells, a similar effect on β-actin expression will be observed. The comparative ΔΔCp method is used to calculate ECs$_{50}$, which is based on the relative gene expression of the target gene (3'UTR) normalized with the cellular housekeeping gene (β-actin). In addition, CC$_{50}$ values are determined based on the $C_p$ values acquired for the housekeeping gene β-actin.

TABLE 2

Primers and probes used for the real-time, quantitative RT-PCR.

| Primer/probe | Target | Sequence$^{a,b}$ |
|---|---|---|
| F3utr258 | DENV 3'-UTR | 5'-CGGTTAGAGGAGACCCCTC-3' |
| R3utr425 | DENV 3'-UTR | 5'-GAGACAGCAGGATCTCTGGTC-3' |
| P3utr343 | DENV 3'-UTR | FAM--5'-AAGGACTAG-ZEN-AGGTTAGAGGAGACCCCCC-3'-IABkFQ |

TABLE 2-continued

Primers and probes used for the real-time, quantitative RT-PCR.

| Primer/probe | Target | Sequence[a,b] |
|---|---|---|
| Factin743 | β-actin | 5'-GGCCAGGTCATCACCATT-3' |
| Ractin876 | β-actin | 5'-ATGTCCACGTCACACTTCATG-3' |
| Pactin773 | β-actin | HEX--5'-TTCCGCTGC-*ZEN*ZEN-CCTGAGGCTCTC-3'-*IABkFQ* |

[a]Reporter dyes (FAM, HEX) and quenchers (ZEN and IABkFQ) elements are indicated in bold and italics.
[b]The nucleotide sequence of the primers and probes were selected from the conserved region in the 3'UTR region of the dengue virus genome, based on the alignment of 300 nucleotide sequences of the four dengue serotypes deposited in Genbank (Gong et al., 2013, Methods Mol Biol, Chapter 16).

The culture medium consisted of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 75 µL/well was added in 96-well plates (10000 cells/well), which already contain the antiviral compounds. Typically, these plates contain a 5-fold serial dilution of 9 dilution steps of the test compound at 200 times the final concentration in 100% DMSO (500 nL; final concentration range: 25 µM-0.000064 µM or 2.5 µM-0.0000064 µM for the most active compounds). In addition, each plate contains wells which are assigned as virus controls (containing cells and virus in the absence of compound) and cell controls (containing cells in the absence of virus and compound). Once the cells were added in the plates, the plates were incubated in a fully humidified incubator (37° C., 5% $CO_2$) until the next day. Dengue viruses serotype-1, 2, 3 and 4 were diluted in order to obtain a Cp of ~22-24 in the assay. Therefore, 25 µL of virus suspension was added to all the wells containing test compound and to the wells assigned as virus control. In parallel, 25 µL of culture medium was added to the cell controls. Next, the plates were incubated for 3 days in a fully humidified incubator (37° C., 5% $CO_2$). After 3 days, the supernatant was removed from the wells and the cells were washed twice with ice-cold PBS (~100 µL). The cell pellets within the 96-well plates were stored at −80° C. for at least 1 day. Next, RNA was extracted using the Cells-to-CT™ lysis kit, according to the manufacturer's guideline (Life Technologies). The cell lysates can be stored at −80C or immediately used in the reverse transcription step.

In preparation of the reverse transcription step, mix A (table 3A) was prepared and 7.57 µL/well was dispensed in a 96-well plate. After addition of 5 µL of the cell lysates, a five minute denaturation step at 75° C. was performed (table 3B). Afterwards, 7.43 µL of mix B was added (table 3C) and the reverse transcription step was initiated (table 3D) to generate cDNA.

Finally, a RT-qPCR mix was prepared, mix C (table 4A), and 22.02 µL/well was dispensed in 96-well LightCycler qPCR plates to which 3 µL of cDNA was added and the qPCR was performed according to the conditions in table 4B on a LightCycler 480.

Using the LightCycler software and an in-house LIMS system, dose response curves for each compound were calculated and the half maximal effective concentration ($EC_{50}$) and the half maximal cytotoxic concentration ($CC_{50}$) were determined (Tables 5-8).

TABLE 3 cDNA synthesis using Mix A, denaturation, Mix B and reverse transcription.

A Mix A
Plates 8
Samples 828

| | | Concentration | | Reaction Vol. (µl) 20 Volume for (µl) | |
|---|---|---|---|---|---|
| Mix Item | Unit | Stock | Final | 1 sample | x samples |
| Milli-Q $H_2O$ | | | | 7.27 | 6019.56 |
| R3utr425 | µM | 20 | 0.27 | 0.15 | 124.20 |
| Ractin876 | µM | 20 | 0.27 | 0.15 | 124.20 |
| | | | Volume mix/well (µl) | 7.57 | |
| | | | Cell lysates | 5.00 | |

| B Denaturation step: | | |
|---|---|---|
| Step | Temp | Time |
| Denaturation | 75° C. | 5' |
| Hold | 4° C. | hold |

TABLE 3-continued cDNA synthesis using Mix A, denaturation, Mix B and reverse transcription.

C Mix B Samples 864

| Mix Item | Unit | Concentration Stock | Concentration Final | Volume for (µl) 1 sample | Volume for (µl) x samples |
|---|---|---|---|---|---|
| Expand HIFI buffer 2 | X | 10.00 | 1.00 | 2.00 | 1728.0 |
| $MgCl_2$ | mM | 25.00 | 3.50 | 2.80 | 2419.2 |
| dNTPs | mM | 10.00 | 1.00 | 2.00 | 1728.0 |
| Rnase inhibitor | U/µl | 40.00 | 1.00 | 0.50 | 432.0 |
| Expand RT | U/µl | 50.00 | 0.33 | 0.13 | 112.3 |
| | | Total Volume Mix (µl) | | 7.43 | |

D Protocol cDNA synthesis

| Step | Temp | Time |
|---|---|---|
| Rev transc | 42° C. | 30' |
| Denaturation | 99° C. | 5' |
| Hold | 4° C. | hold |

TABLE 4 qPCR mix and protocol.

A Mix C Samples 833

| Mix Item | Unit | Concentration Stock | Concentration Final | Reaction Vol. (µl) 25 Volume for (µl) 1 sample | Reaction Vol. (µl) 25 Volume for (µl) x samples |
|---|---|---|---|---|---|
| $H_2O$ PCR grade Roche | | | | 7.74 | 6447.42 |
| Roche 2 × MM mix | X | 2 | 1 | 12.50 | 10412.50 |
| F3utr258 | µM | 20 | 0.3 | 0.38 | 316.54 |
| R3utr425 | µM | 20 | 0.3 | 0.38 | 316.54 |
| P3utr343 | µM | 20 | 0.1 | 0.13 | 108.29 |
| Factin743 | µM | 20 | 0.3 | 0.38 | 316.54 |
| Ractin876 | µM | 20 | 0.3 | 0.38 | 316.54 |
| Pactin773 | µM | 20 | 0.1 | 0.13 | 108.29 |
| | | Volume Mix/Tube (µl) | | 22.02 | |
| | | cDNA | | 3.00 | |

B Protocol qPCR3

| Step | Temp | Time | Ramp rate | |
|---|---|---|---|---|
| preincub/denat | 95° C. | 10 min | 4.4 | |
| Denaturation | 95° C. | 10 sec | 4.4 | 40 cycles |
| annealing | 58° C. | 1 min | 2.2 | |
| Elongation | 72° C. | 1 sec | 4.4 | |
| Cooling | 40° C. | 10 sec | 1.5 | |

TABLE 5

$EC_{50}$, $CC_{50}$, and SI for the compounds against serotype 1 in the RT-qPCR assays RT-qPCR serotype 1 TC974#666

| compound# | $EC_{50}$ (µM) | N | $CC_{50}$ (µM) | N | SI | N |
|---|---|---|---|---|---|---|
| 1C | 0.00023 | 3 | >2.5 | 3 | >11000 | 3 |
| 1D | 0.00027 | 3 | >2.5 | 3 | >11400 | 3 |
| 2A | 0.00057 | 3 | >2.5 | 3 | >7920 | 3 |
| 4C | 0.000066 | 4 | >1.0 | 4 | >61000 | 4 |
| 4D | 0.00023 | 4 | >1.0 | 4 | >7140 | 4 |
| 5A | 0.00058 | 3 | >1.0 | 3 | >1930 | 3 |
| 6AB | 0.000022 | 3 | >2.5 | 3 | >133413 | 3 |
| 6BB | 0.00013 | 3 | >2.5 | 2 | >24100 | 2 |
| 7B | 0.00015 | 3 | >2.5 | 3 | >23200 | 3 |
| 8B | 0.000032 | 3 | >1.0 | 3 | >38900 | 3 |
| 9B | 0.00081 | 3 | >1.0 | 3 | >2080 | 3 |
| 10B | 0.00027 | 3 | >2.5 | 3 | >18700 | 3 |
| 11B | 0.00020 | 4 | >2.5 | 4 | >11800 | 4 |
| 12B | 0.00047 | 3 | >2.5 | 3 | >8660 | 3 |
| 13B | 0.00019 | 3 | >2.5 | 3 | >10400 | 3 |
| 14A | 0.00026 | 3 | >1.0 | 3 | >6140 | 3 |
| 15B | 0.00024 | 3 | >1.0 | 2 | >6280 | 2 |
| 17C | 0.00019 | 3 | >1.0 | 3 | >8230 | 3 |
| 17D | 0.00021 | 3 | >1.0 | 3 | >15400 | 3 |
| 18B | 0.00055 | 3 | >1.0 | 3 | >2220 | 3 |
| 19AB | 0.000021 | 3 | >1.0 | 3 | >56300 | 3 |
| 19BB | 0.000091 | 3 | >1.0 | 3 | >13300 | 3 |
| 20C | 0.00030 | 4 | >1.0 | 4 | >4540 | 4 |
| 20D | 0.00089 | 4 | >1.0 | 4 | >1820 | 4 |
| 21B | 0.0010 | 3 | >2.5 | 3 | >1950 | 3 |
| 22AB | 0.000091 | 3 | >1.0 | 3 | >15700 | 3 |
| 22BB | 0.0015 | 3 | >2.5 | 1 | >1740 | 1 |
| 23B | 0.000092 | 5 | >1.0 | 5 | >18200 | 5 |
| 24B | 0.0022 | 4 | >1.0 | 4 | >898 | 4 |
| 25B | 0.0013 | 4 | >1.0 | 4 | >1210 | 4 |
| 27B | 0.000013 | 4 | >1.0 | 4 | >114234 | 4 |
| 28AB | 0.00041 | 4 | >1.0 | 4 | >4260 | 4 |
| 28BB | 0.00011 | 4 | >1.0 | 4 | >29800 | 4 |
| 29AB | 0.00023 | 4 | >1.0 | 4 | >5680 | 4 |
| 29BB | 0.000048 | 4 | >1.0 | 4 | >30400 | 4 |
| 30A | 0.000094 | 5 | >1.0 | 5 | >54900 | 5 |
| 31A | 0.00019 | 3 | >1.0 | 3 | >6090 | 3 |
| 32B | 0.00011 | 4 | >1.0 | 4 | >10300 | 4 |
| 33C | 0.00097 | 4 | >1.0 | 4 | >3500 | 4 |
| 33D | 0.00048 | 4 | >1.0 | 4 | >7130 | 4 |

N = the number of independent experiments in which the compounds were tested.

TABLE 6

EC$_{50}$, CC$_{50}$, and SI for the compounds against serotype 2 in the RT-qP assays RT-qPCR serotype 2 16681

| compound# | EC$_{50}$ (µM) | N | CC$_{50}$ (µM) | N | SI | N |
|---|---|---|---|---|---|---|
| 1C | 0.00018 | 3 | >2.5 | 3 | >15300 | 3 |
| 1D | 0.00023 | 3 | >2.5 | 3 | >9200 | 3 |
| 2A | 0.00048 | 3 | >2.5 | 3 | >6500 | 3 |
| 4C | 0.000060 | 4 | >1.0 | 4 | >51900 | 4 |
| 4D | 0.00013 | 4 | >1.0 | 4 | >15600 | 4 |
| 5A | 0.00042 | 3 | >1.0 | 3 | >3220 | 3 |
| 6AB | 0.000017 | 3 | >2.5 | 3 | >187753 | 3 |
| 6BB | 0.00012 | 3 | >2.5 | 3 | >23700 | 3 |
| 7B | 0.00012 | 3 | >2.5 | 3 | >30600 | 3 |
| 8B | 0.000025 | 3 | >1.0 | 3 | >54100 | 3 |
| 9B | 0.00050 | 3 | >1.0 | 3 | >2680 | 3 |
| 10B | 0.00011 | 3 | >2.5 | 3 | >27400 | 3 |
| 11B | 0.00010 | 3 | >2.5 | 3 | >22400 | 3 |
| 12B | 0.00053 | 3 | >2.5 | 3 | >8920 | 3 |
| 13B | 0.00012 | 3 | >2.5 | 3 | >23900 | 3 |
| 14A | 0.00020 | 3 | >1.0 | 3 | >5890 | 3 |
| 15B | 0.00023 | 4 | >1.0 | 3 | >4310 | 3 |
| 17C | 0.00011 | 3 | >1.0 | 3 | >13700 | 3 |
| 17D | 0.00010 | 3 | >1.0 | 3 | >24100 | 3 |
| 18B | 0.00034 | 4 | >1.0 | 3 | >4590 | 3 |
| 19AB | 0.000014 | 3 | >1.0 | 3 | >92300 | 3 |
| 19BB | 0.000078 | 3 | >1.0 | 3 | >14100 | 3 |
| 20C | 0.000071 | 4 | >1.0 | 4 | >19200 | 4 |
| 20D | 0.00019 | 4 | >1.0 | 4 | >7660 | 4 |
| 21B | 0.00016 | 3 | >2.5 | 3 | >12700 | 3 |
| 22AB | 0.000029 | 4 | >1.0 | 3 | >46400 | 3 |
| 22BB | 0.00033 | 3 | >2.5 | 2 | >9450 | 2 |
| 23B | 0.000034 | 5 | >1.0 | 4 | >51700 | 4 |
| 24B | 0.00026 | 4 | >1.0 | 4 | >11300 | 4 |
| 25B | 0.00027 | 4 | >1.0 | 3 | >6080 | 3 |
| 27B | 0.000014 | 4 | >1.0 | 4 | >92800 | 4 |
| 28AB | 0.00031 | 4 | >1.0 | 4 | >5530 | 4 |
| 28BB | 0.00010 | 4 | >1.0 | 4 | >19900 | 4 |
| 29AB | 0.00025 | 3 | >1.0 | 3 | >5180 | 3 |
| 29BB | 0.000025 | 4 | >1.0 | 4 | >60200 | 4 |
| 30A | 0.000076 | 4 | >1.0 | 4 | >65700 | 4 |
| 31A | 0.00011 | 3 | >1.0 | 3 | >11600 | 3 |
| 32B | 0.000033 | 4 | >1.0 | 3 | >35800 | 3 |
| 33C | 0.0010 | 4 | >1.0 | 4 | >4630 | 4 |
| 33D | 0.00066 | 4 | >1.0 | 4 | >6620 | 4 |

N = the number of independent experiments in which the compounds were tested.

TABLE 7

EC$_{50}$, CC$_{50}$, and SI for the compounds against serotype 3 in the RT-qPCR assays RT-qPCR serotype 3 H87

| compound# | EC$_{50}$ (µM) | N | CC$_{50}$ (µM) | N | SI | N |
|---|---|---|---|---|---|---|
| 1C | 0.0024 | 4 | >2.5 | 4 | >1300 | 4 |
| 1D | 0.0034 | 4 | >2.5 | 4 | >949 | 4 |
| 2A | 0.0061 | 4 | >2.5 | 4 | >390 | 4 |
| 4C | 0.00077 | 4 | >1.0 | 3 | >1660 | 3 |
| 4D | 0.0023 | 4 | >1.0 | 4 | >727 | 4 |
| 5A | 0.0081 | 3 | >1.0 | 3 | >170 | 3 |
| 6AB | 0.00013 | 3 | >2.5 | 3 | >15300 | 3 |
| 6BB | 0.0016 | 3 | >2.5 | 3 | >1320 | 3 |
| 7B | 0.0018 | 3 | >2.5 | 3 | >1810 | 3 |
| 8B | 0.00016 | 3 | >1.0 | 3 | >7020 | 3 |
| 9B | 0.0080 | 3 | >1.0 | 3 | >203 | 3 |
| 10B | 0.0029 | 3 | >2.5 | 3 | >1370 | 3 |
| 11B | 0.0018 | 3 | >2.5 | 3 | >1650 | 3 |
| 12B | 0.0047 | 4 | >2.5 | 4 | >401 | 4 |
| 13B | 0.0019 | 4 | >2.5 | 4 | >1350 | 4 |
| 14A | 0.0028 | 3 | >1.0 | 3 | >584 | 3 |
| 15B | 0.0028 | 3 | >1.0 | 2 | >525 | 2 |
| 17C | 0.0036 | 3 | >1.0 | 3 | >401 | 3 |
| 17D | 0.0027 | 3 | >1.0 | 3 | >541 | 3 |
| 18B | 0.0043 | 3 | >1.0 | 3 | >281 | 3 |
| 19AB | 0.00014 | 3 | >1.0 | 3 | >8790 | 3 |
| 19BB | 0.00085 | 5 | >1.0 | 5 | >1910 | 5 |
| 20C | 0.0034 | 4 | >1.0 | 3 | >249 | 3 |
| 20D | 0.0089 | 4 | >1.0 | 4 | >178 | 4 |
| 21B | 0.0065 | 3 | >2.5 | 3 | >357 | 3 |
| 22AB | 0.00049 | 3 | >1.0 | 3 | >4430 | 3 |
| 22BB | 0.0090 | 3 | >2.5 | 3 | >245 | 3 |
| 23B | 0.00033 | 5 | >1.0 | 5 | >6770 | 5 |
| 24B | 0.014 | 5 | >1.0 | 5 | >123 | 5 |
| 25B | 0.0063 | 5 | >1.0 | 5 | >190 | 5 |
| 27B | 0.000091 | 4 | >1.0 | 4 | >22600 | 4 |
| 28AB | 0.0053 | 3 | >1.0 | 3 | >277 | 3 |
| 28BB | 0.0012 | 3 | >1.0 | 3 | >1680 | 3 |
| 29AB | 0.0046 | 4 | >1.0 | 4 | >264 | 4 |
| 29BB | 0.00039 | 3 | >1.0 | 3 | >3050 | 3 |
| 30A | 0.0019 | 3 | >1.0 | 3 | >840 | 3 |
| 31A | 0.0015 | 4 | >1.0 | 4 | >791 | 4 |
| 32B | 0.00057 | 3 | >1.0 | 3 | >2870 | 3 |
| 33C | 0.011 | 4 | >1.0 | 4 | >185 | 4 |
| 33D | 0.0023 | 4 | >1.0 | 4 | >732 | 4 |

N = the number of independent experiments in which the compounds were tested.

TABLE 8

EC$_{50}$, CC$_{50}$, and SI for the compounds against serotype 4 in the RT-qPCR assays RT-qPCR serotype 4 H241

| compound# | EC$_{50}$ (µM) | N | CC$_{50}$ (µM) | N | SI | N |
|---|---|---|---|---|---|---|
| 1C | 0.016 | 3 | 8.7 | 3 | 427 | 3 |
| 1D | 0.024 | 3 | 7.3 | 3 | 280 | 3 |
| 2A | 0.027 | 3 | 2.2 | 3 | 125 | 3 |
| 4C | 0.015 | 3 | >1.0 | 2 | >73 | 2 |
| 4D | 0.026 | 3 | 3.2 | 3 | 73 | 3 |
| 5A | 0.058 | 3 | 8.0 | 3 | 206 | 3 |
| 6AB | 0.0029 | 3 | >1.0 | 2 | >425 | 2 |
| 6BB | 0.020 | 3 | 5.4 | 3 | 205 | 3 |
| 7B | 0.013 | 3 | 8.8 | 2 | 582 | 2 |
| 8B | 0.0013 | 3 | 8.7 | 2 | 8240 | 2 |
| 9B | 0.036 | 3 | 6.7 | 3 | 372 | 3 |
| 10B | 0.022 | 3 | >1.0 | 2 | >57 | 2 |
| 11B | 0.017 | 3 | 5.7 | 3 | 273 | 3 |
| 12B | 0.039 | 3 | 9.2 | 2 | 318 | 2 |
| 13B | 0.015 | 3 | 3.7 | 2 | 323 | 2 |
| 14A | 0.015 | 3 | 8.9 | 3 | 510 | 3 |
| 15B | 0.035 | 3 | 10.0 | 3 | 456 | 3 |
| 17C | 0.016 | 3 | 1.7 | 2 | 95 | 2 |
| 17D | 0.015 | 3 | 2.9 | 3 | 168 | 3 |
| 18B | 0.033 | 3 | 3.0 | 2 | 148 | 2 |
| 19AB | 0.00069 | 3 | 6.4 | 3 | 8200 | 3 |
| 19BB | 0.0068 | 3 | 5.2 | 3 | 905 | 3 |
| 20C | 0.020 | 3 | >1.0 | 2 | >60 | 2 |
| 20D | 0.055 | 3 | >1.0 | 1 | >21 | 1 |
| 21B | 0.048 | 3 | 9.0 | 3 | 115 | 3 |
| 22AB | 0.0033 | 3 | 9.1 | 2 | 2890 | 2 |
| 22BB | 0.071 | 3 | 8.2 | 3 | 126 | 3 |
| 23B | 0.0027 | 3 | 6.0 | 2 | 2230 | 2 |
| 24B | 0.066 | 3 | 7.8 | 3 | 115 | 3 |
| 25B | 0.055 | 3 | 9.9 | 2 | 202 | 2 |
| 27B | 0.00081 | 3 | 8.3 | 3 | 9330 | 3 |
| 28AB | 0.069 | 3 | 9.0 | 3 | 158 | 3 |
| 28BB | 0.018 | 3 | >1.0 | 2 | >58 | 2 |
| 29AB | 0.035 | 3 | 8.0 | 2 | 118 | 2 |

TABLE 8-continued

EC$_{50}$, CC$_{50}$, and SI for the compounds against serotype 4 in the RT-qPCR assays

| compound# | RT-qPCR serotype 4 H241 | | | | | |
|---|---|---|---|---|---|---|
| | EC$_{50}$ (μM) | N | CC$_{50}$ (μM) | N | SI | N |
| 29BB | 0.0028 | 3 | 8.3 | 3 | 2790 | 3 |
| 30A | 0.018 | 3 | 7.3 | 3 | 399 | 3 |
| 31A | 0.017 | 4 | 7.3 | 4 | 445 | 4 |
| 32B | 0.010 | 3 | 4.3 | 3 | 295 | 3 |
| 33C | 0.34 | 3 | 4.2 | 3 | 9.8 | 3 |
| 33D | 0.022 | 3 | 5.4 | 3 | 256 | 3 |

N = the number of independent experiments in which the compounds were tested.

The invention claimed is:

1. A compound of formula (I), including any stereochemically isomeric form thereof,

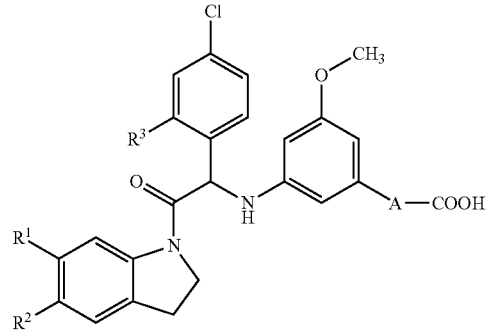
(I)

wherein
R$^1$ is trifluoromethyl, trifluoromethoxy, or chloro;
R$^2$ is hydrogen, fluoro, or methoxy;
R$^3$ is hydrogen, or methoxy;
A represents —(CH$_2$)$_n$— wherein n is 3 or 4;
—O—(CH$_2$)$_n$— wherein n is 2 or 4;

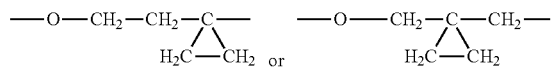

—CH$_2$—O—(CH$_2$)$_n$— wherein n is 2; or
—X—Y— wherein X is a —O—, —OCH$_2$—, or —NH—; and
Y is C$_{3-4}$cycloalkyl optionally substituted with fluoro, or
Y is bicyclo[1.1.1]pentanyl;
or a pharmaceutically acceptable salt, solvate or polymorph thereof.

2. The compound according to claim 1 wherein said compound is selected from the group consisting of:

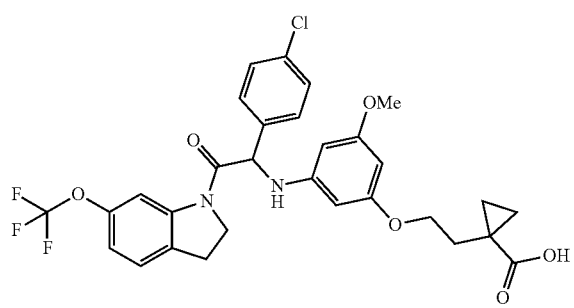

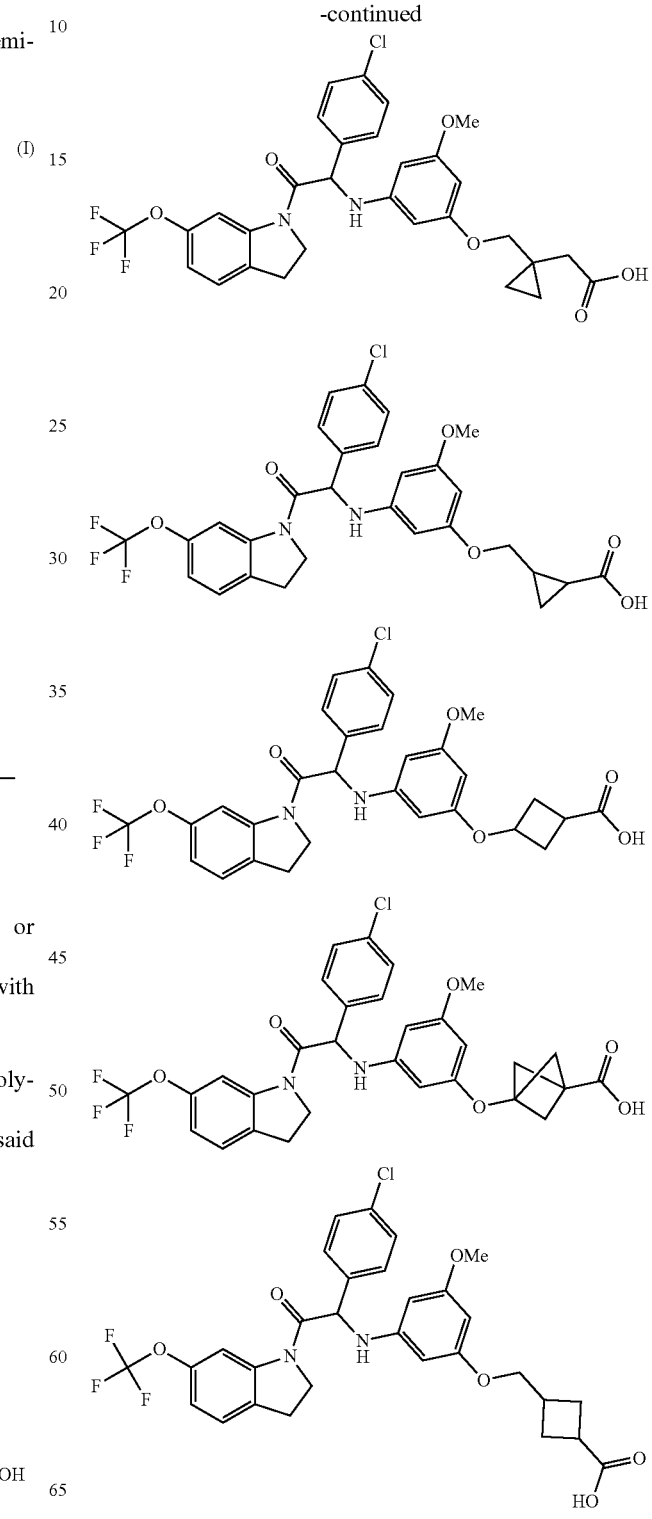

221
-continued
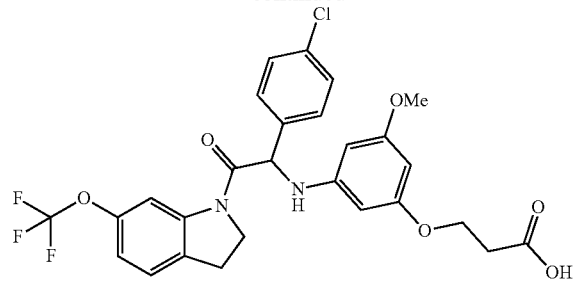
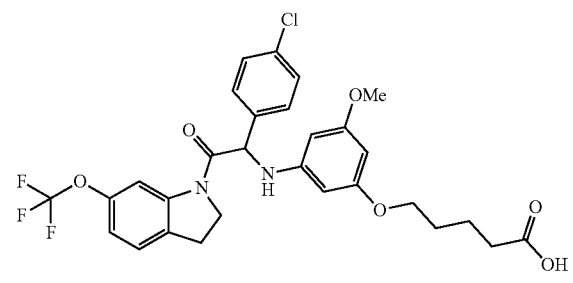
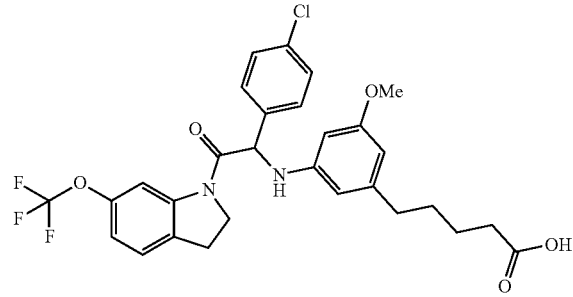
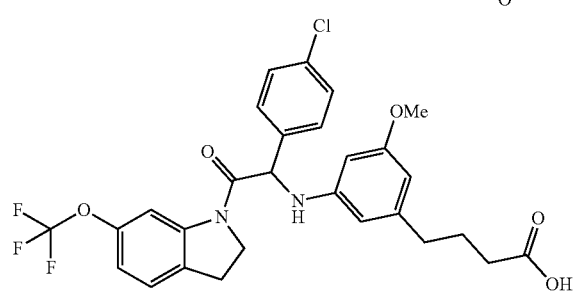
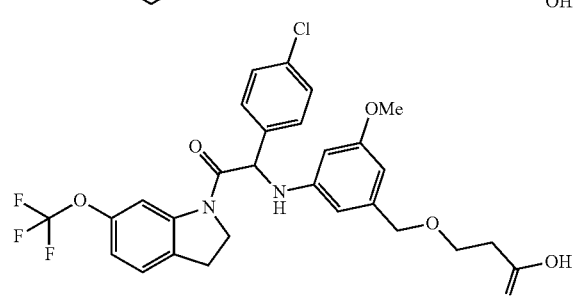
222
-continued
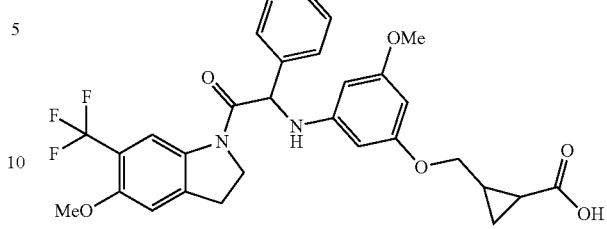
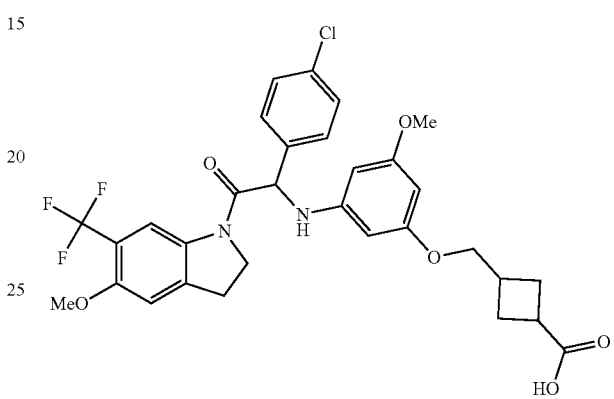
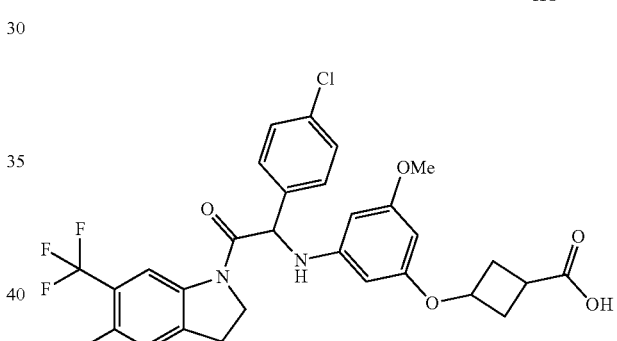
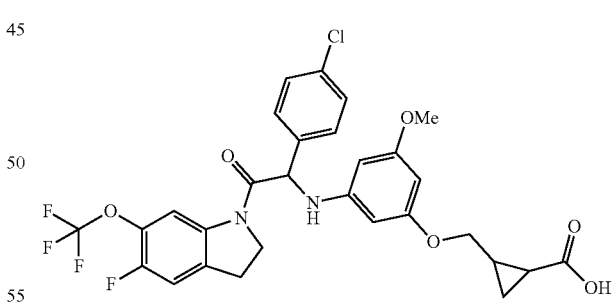
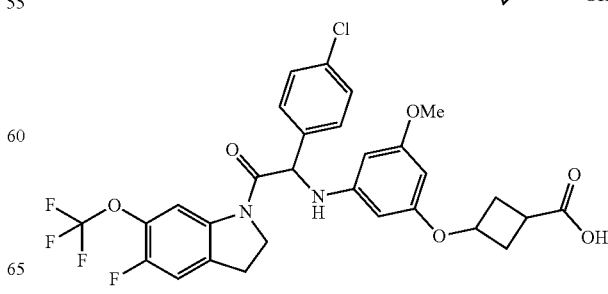

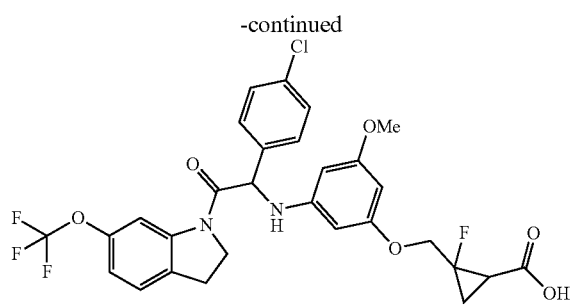
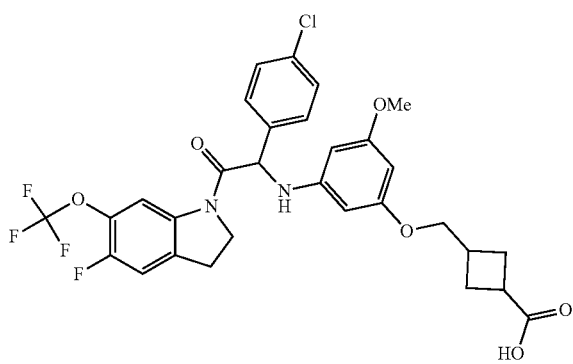
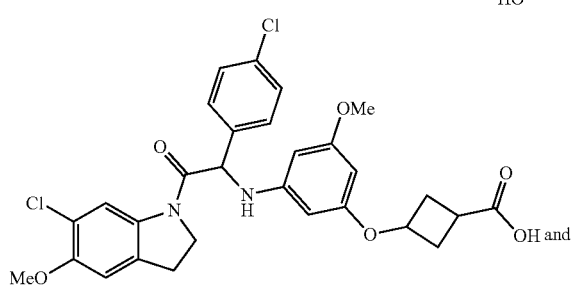
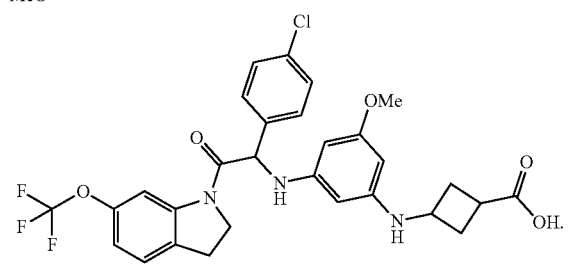
3. The compound according to claim 1 wherein said compound has the (+) specific rotation measured in DMF as solvent.
4. The compound according to claim 3 wherein said compound is selected from the group consisting of:
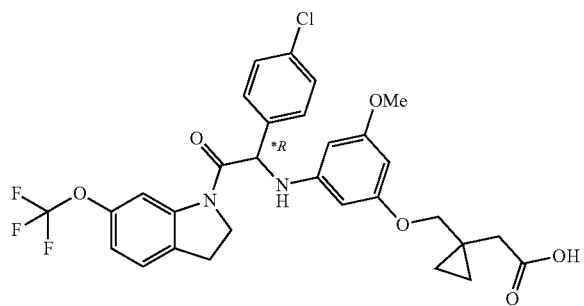
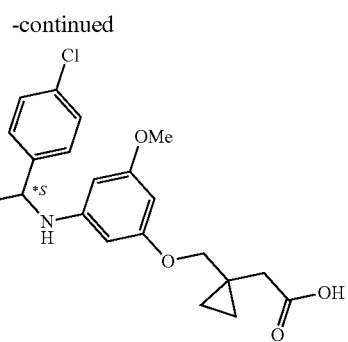
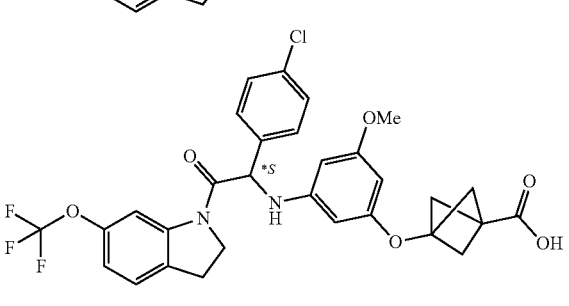

225
-continued
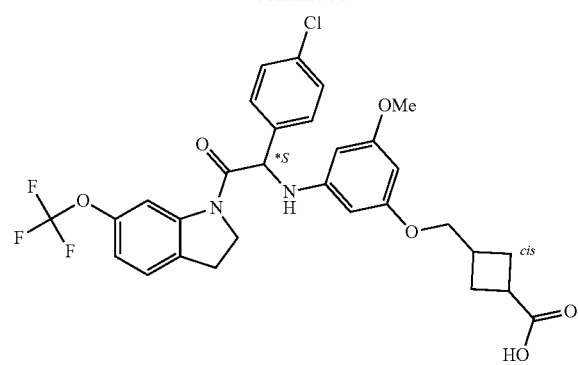
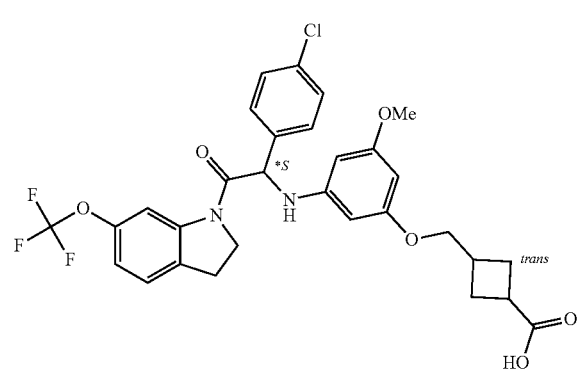
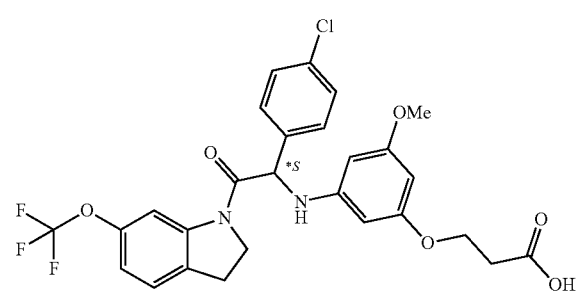
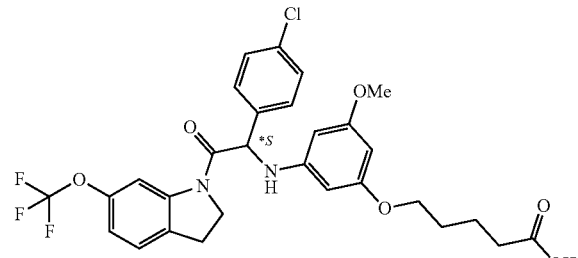
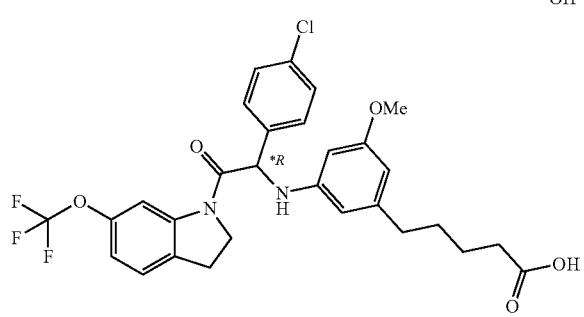
226
-continued
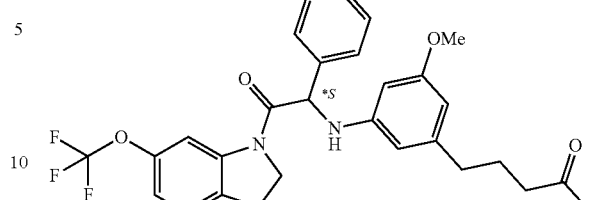
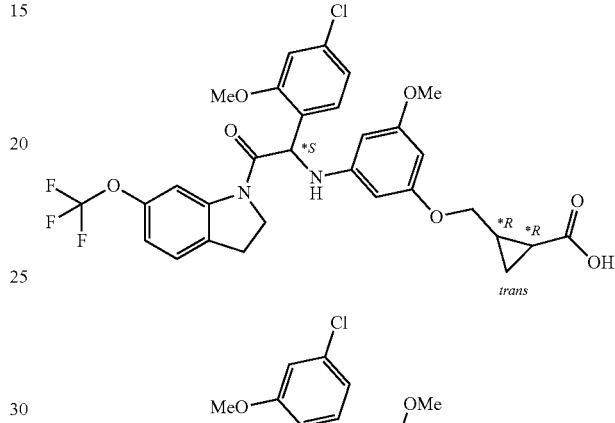
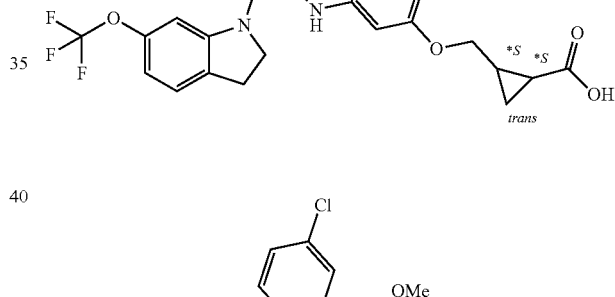
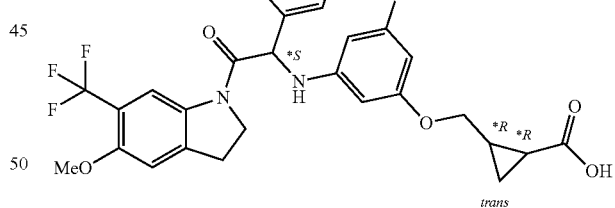
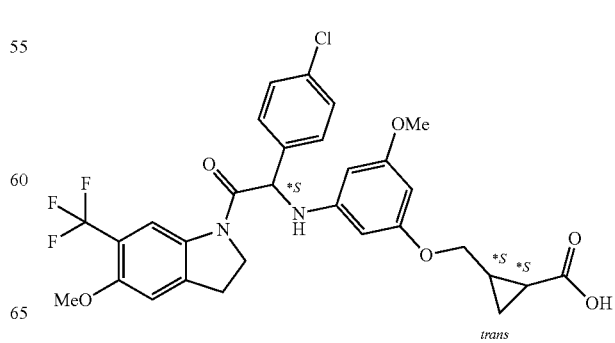

227
-continued
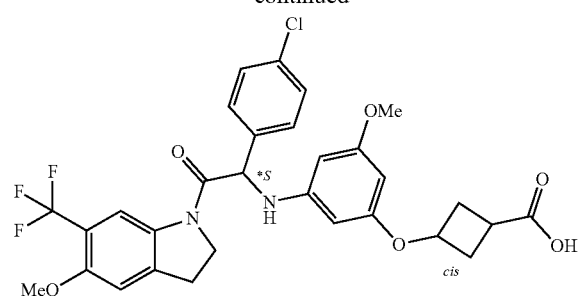
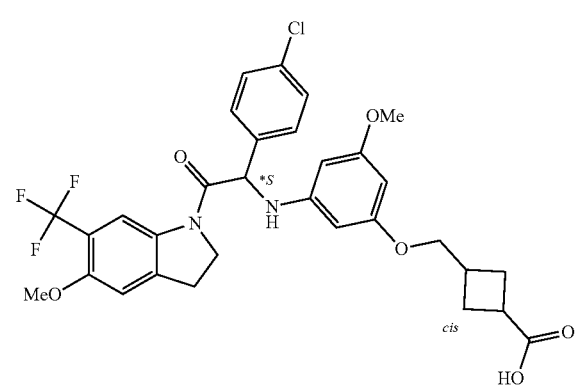
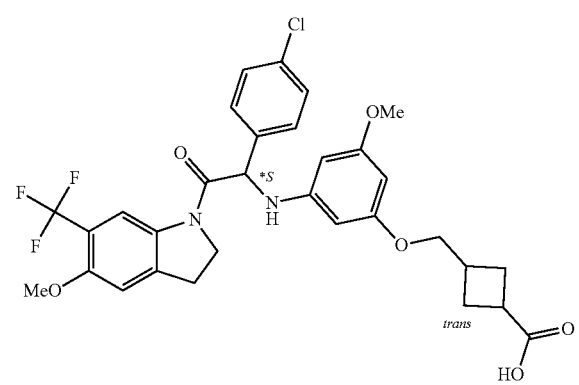
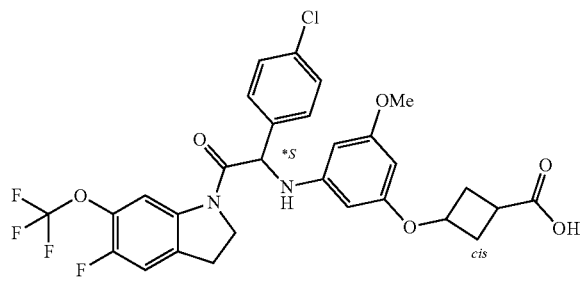
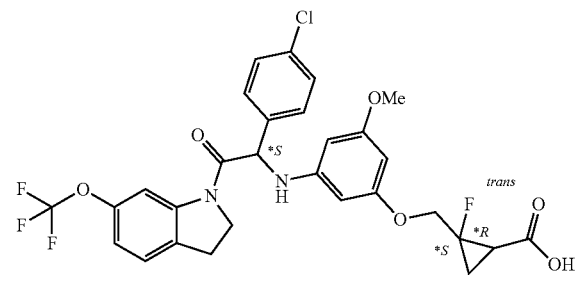
228
-continued
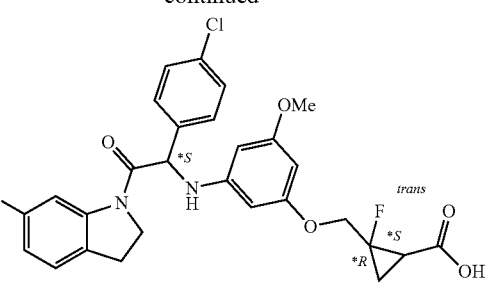
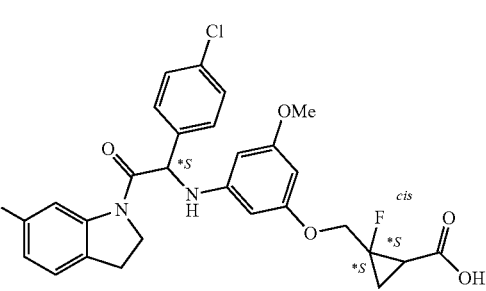
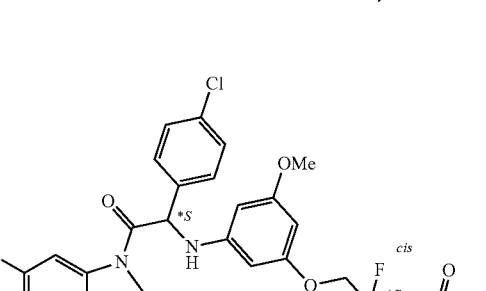
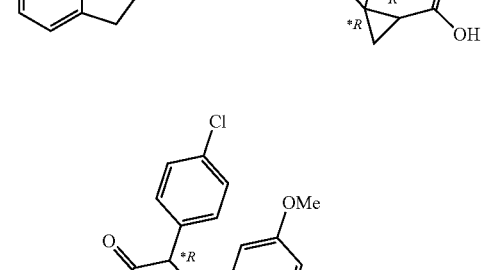
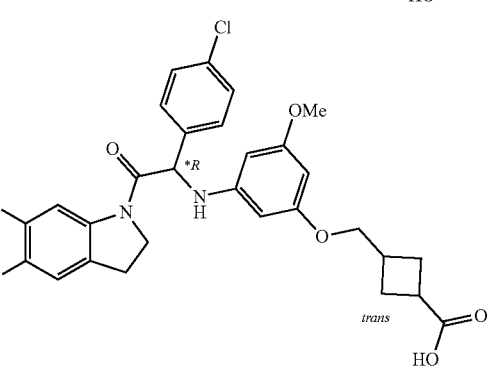

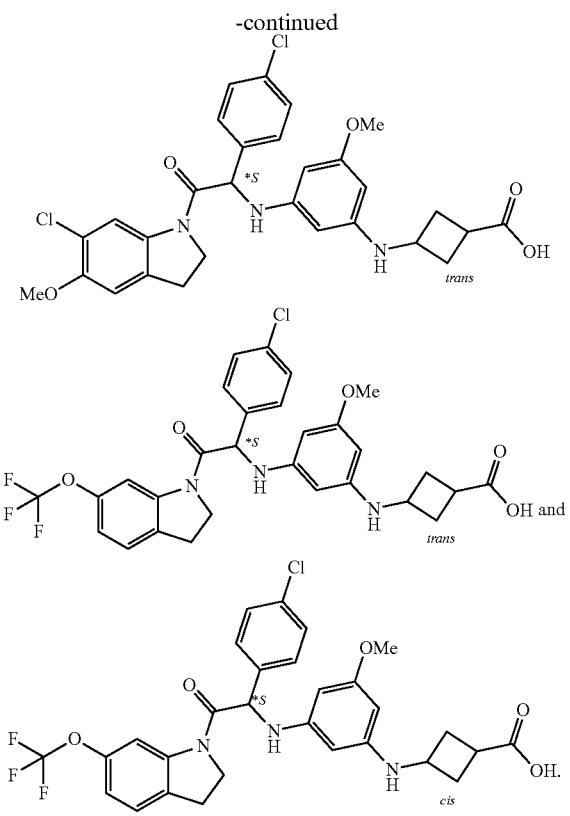

5. The compound as claimed in claim 1 wherein $R^1$ is trifluoromethoxy, $R^2$ is hydrogen, and $R^3$ is hydrogen.

6. The compound as claimed in claim 1 wherein A represents —(CH$_2$)$_n$— wherein n is 3 or 4.

7. The compound as claimed in claim 1 wherein A represents —O—(CH$_2$)$_n$— wherein n is 2 or 4.

8. The compound as claimed in claim 1 wherein A represents

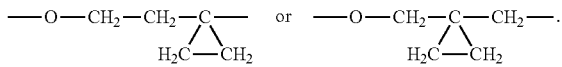

9. The compound as claimed in claim 1 wherein A represents —X—Y— wherein X is a —O—, —OCH$_2$—, or —NH—; and Y is C$_{3-4}$ cycloalkyl optionally substituted with fluoro.

10. A pharmaceutical composition comprising a compound according to claim 1 together with one or more pharmaceutically acceptable excipients, diluents or carriers.

11. The pharmaceutical composition according to claim 10 which comprises a second or further active ingredient.

12. The pharmaceutical composition according to claim 11 wherein the second or further active ingredient is an antiviral agent.

13. A method of treating Dengue infection or a disease associated with Dengue infection, comprising administering to a subject in need thereof an effective amount of the compound according to claim 1.

14. The method according to claim 13 wherein the Dengue infection is infection by viruses of the DENV-1, DENV-2, DENV-3 or DENV-4 strain.

15. The compound as claimed in claim 5, wherein A represents

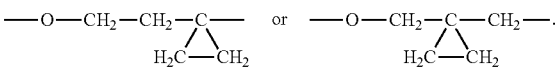

16. The compound as claimed in claim 5, wherein A represents —X—Y— wherein X is a —O—, —OCH$_2$—, or —NH—; and Y is C$_{3-4}$ cycloalkyl optionally substituted with fluoro.

17. The compound as claimed in claim 1, wherein $R^1$ is trifluoromethoxy, $R^2$ is fluoro or methoxy, and $R^3$ is hydrogen.

18. The compound as claimed in claim 17, wherein A represents

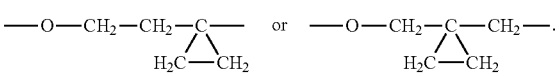

19. The compound as claimed in claim 17, wherein A represents —X—Y— wherein X is a —O—, —OCH$_2$—, or —NH—; and Y is C$_{3-4}$ cycloalkyl optionally substituted with fluoro.

20. A method of inhibiting Dengue virus replication in an animal cell, comprising administering to a subject in need thereof an effective amount of the compound according to claim 1.

21. The method according to claim 20 wherein the Dengue infection is infection by viruses of the DENV-1, DENV-2, DENV-3 or DENV-4 strain.

\* \* \* \* \*

SEQUENCE LISTING

<160> NUMBER OF SEQ ID NOS: 14

<210> SEQ ID NO 1
<211> LENGTH: 19
<212> TYPE: DNA
<213> ORGANISM: Dengue virus

<400> SEQUENCE: 1
cggttagagg agacccctc                                              19

<210> SEQ ID NO 2
<211> LENGTH: 21
<212> TYPE: DNA
<213> ORGANISM: Dengue virus

<400> SEQUENCE: 2
gagacagcag gatctctggt c                                           21

<210> SEQ ID NO 3
<211> LENGTH: 28
<212> TYPE: DNA
<213> ORGANISM: Dengue virus

<400> SEQUENCE: 3
aaggactaga ggttagagga gaccccccc                                   28

<210> SEQ ID NO 4
<211> LENGTH: 18
<212> TYPE: DNA
<213> ORGANISM: Dengue virus

<400> SEQUENCE: 4
ggccaggtca tcaccatt                                               18

<210> SEQ ID NO 5
<211> LENGTH: 21
<212> TYPE: DNA
<213> ORGANISM: Dengue virus

<400> SEQUENCE: 5
atgtccacgt cacacttcat g                                           21

<210> SEQ ID NO 6
<211> LENGTH: 21
<212> TYPE: DNA
<213> ORGANISM: Dengue virus

```
<400> SEQUENCE: 6
ttccgctgcc ctgaggctct c                                              21

<210> SEQ ID NO 7
<211> LENGTH: 20
<212> TYPE: DNA
<213> ORGANISM: Dengue virus

<400> SEQUENCE: 7
tcggagccgg agtttacaaa                                                20

<210> SEQ ID NO 8
<211> LENGTH: 20
<212> TYPE: DNA
<213> ORGANISM: Dengue virus

<400> SEQUENCE: 8
tcttaacgtc cgcccatgat                                                20

<210> SEQ ID NO 9
<211> LENGTH: 19
<212> TYPE: DNA
<213> ORGANISM: Dengue virus

<400> SEQUENCE: 9
attccacaca atgtggcat                                                 19

<210> SEQ ID NO 10
<211> LENGTH: 23
<212> TYPE: DNA
<213> ORGANISM: Dengue virus

<400> SEQUENCE: 10
ggatagacca gagatcctgc tgt                                            23

<210> SEQ ID NO 11
<211> LENGTH: 20
<212> TYPE: DNA
<213> ORGANISM: Dengue virus

<400> SEQUENCE: 11
cattccattt tctggcgttc                                                20

<210> SEQ ID NO 12
<211> LENGTH: 20
<212> TYPE: DNA
<213> ORGANISM: Dengue virus

<400> SEQUENCE: 12
caatccatct tgcggcgctc                                                20

<210> SEQ ID NO 13
<211> LENGTH: 20
<212> TYPE: DNA
<213> ORGANISM: Dengue virus

<400> SEQUENCE: 13
cagcatcatt ccaggcacag                                                20

<210> SEQ ID NO 14
<211> LENGTH: 20
<212> TYPE: DNA
```

```
<213> ORGANISM: Dengue virus

<400> SEQUENCE: 14
caacatcaat ccaggcacag                                            20
```